(12) United States Patent
Edmondson et al.

(10) Patent No.: US 8,354,403 B2
(45) Date of Patent: Jan. 15, 2013

(54) PYRROLIDINE DERIVED BETA 3 ADRENERGIC RECEPTOR AGONISTS

(75) Inventors: Scott D. Edmondson, Clark, NJ (US); Richard Berger, Princeton, NJ (US); Lehua Chang, Ramsey, NJ (US); Vincent J. Colandrea, North Brunswick, NJ (US); Jeffrey J. Hale, Westfield, NJ (US); Bart Harper, New York, NY (US); Nam Fung Kar, Brooklyn, NY (US); Bing Li, Towaco, NJ (US); Greg J. Morriello, Randolph, NJ (US); Christopher R. Moyes, Westfield, NJ (US); Deyou Sha, Yardley, PA (US); Dong-Ming Shen, Edison, NJ (US); Liping Wang, Cranbury, NJ (US); Harvey Wendt, Medford Lakes, NJ (US); Cheng Zhu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/392,662

(22) PCT Filed: Aug. 17, 2010

(86) PCT No.: PCT/US2010/045712
§ 371 (c)(1),
(2), (4) Date: Feb. 27, 2012

(87) PCT Pub. No.: WO2011/025690
PCT Pub. Date: Mar. 3, 2011

(65) Prior Publication Data
US 2012/0157432 A1 Jun. 21, 2012

Related U.S. Application Data

(60) Provisional application No. 61/237,391, filed on Aug. 27, 2009.

(51) Int. Cl.
*A61K 31/536* (2006.01)
*A61K 31/438* (2006.01)
*A61K 31/4245* (2006.01)
*C07D 265/12* (2006.01)
*C07D 221/20* (2006.01)
*C07D 413/14* (2006.01)

(52) U.S. Cl. ............... 514/230.5; 514/278; 514/364; 544/92; 546/16; 548/131

(58) Field of Classification Search .............. 514/248, 514/370, 367, 228.8, 342, 210.18, 406, 210.2, 514/422, 364, 409, 338, 265.1, 326, 278, 514/318, 230.5, 255.05, 252.03, 253.09; 548/194, 163, 364.7, 518, 131, 409; 544/237, 544/96, 408, 280, 92, 336, 238, 364; 546/270.7, 546/276.7, 208, 16, 194
See application file for complete search history.

(56) References Cited

U.S. PATENT DOCUMENTS
2002/0022605 A1 2/2002 Sum et al.
2003/0212063 A1 11/2003 Lafontaine et al.

OTHER PUBLICATIONS

Prathipati et al., "Characterization of B3-Adrenergic Receptor," Journal of Computer-Aided Molecular Design, vol. 19, p. 93-110 (2005).

*Primary Examiner* — Kristen Bianchi
(74) *Attorney, Agent, or Firm* — Patricia A. Shatynski; Valerie J. Camara

(57) ABSTRACT

The present invention provides compounds of Formula (I), pharmaceutical compositions thereof, and method of using the same in the treatment or prevention of diseases mediated by the activation of β3-adrenoceptor.

(I)

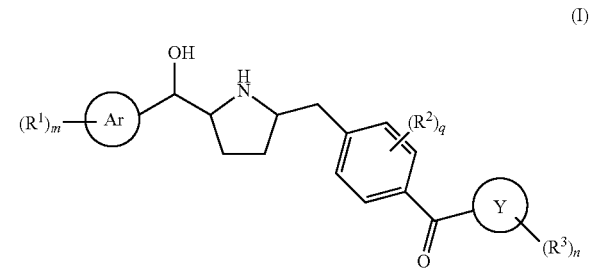

14 Claims, No Drawings

PYRROLIDINE DERIVED BETA 3 ADRENERGIC RECEPTOR AGONISTS

CROSS REFERENCE TO RELATED APPLICATIONS

This application is a U.S. National Phase application under 35 U.S.C. §371 of PCT Application No. PCT/US2010/045712, filed Aug. 17, 2010, which claims priority under 35 U.S.C. §119(e) from U.S. Provisional Application Ser. No. 61/237,391, filed Aug. 27, 2009.

BACKGROUND OF THE INVENTION

The function of the lower urinary tract is to store and periodically release urine. This requires the orchestration of storage and micturition reflexes which involve a variety of afferent and efferent neural pathways, leading to modulation of central and peripheral neuroeffector mechanisms, and resultant coordinated regulation of sympathetic and parasympathetic components of the autonomic nervous system as well as somatic motor pathways. These proximally regulate the contractile state of bladder (detrusor) and urethral smooth muscle, and urethral sphincter striated muscle.

β Adrenergic receptors (βAR) are present in detrusor smooth muscle of various species, including human, rat, guinea pig, rabbit, ferret, dog, cat, pig and non-human primate. However, pharmacological studies indicate there are marked species differences in the receptor subtypes mediating relaxation of the isolated detrusor; β1AR predominate in cats and guinea pig, β2AR predominate in rabbit, and β3AR contribute or predominate in dog, rat, ferret, pig, cynomolgus and human detrusor. Expression of βAR subtypes in the human and rat detrusor has been examined by a variety of techniques, and the presence of β3AR was confirmed using in situ hybridization and/or reverse transcription-polymerase chain reaction (RT-PCR). Real time quantitative PCR analyses of β1AR, β2AR and β3AR mRNAs in bladder tissue from patients undergoing radical cystectomy revealed a preponderance of β3AR mRNA (97%, cf 1.5% for β1AR mRNA and 1.4% for β2AR mRNA). Moreover, β3AR mRNA expression was equivalent in control and obstructed human bladders. These data suggest that bladder outlet obstruction does not result in downregulation of β3AR, or in alteration of βAR-mediated detrusor relaxation. β3AR responsiveness also has been compared in bladder strips obtained during cystectomy or enterocystoplasty from patients judged to have normal bladder function, and from patients with detrusor hyporeflexia or hyperreflexia. No differences in the extent or potency of β3AR agonist mediated relaxation were observed, consistent with the concept that the β3AR activation is an effective way of relaxing the detrusor in normal and pathogenic states.

Functional evidence in support of an important role for the β3AR in urine storage emanates from studies in vivo. Following intravenous administration to rats, the rodent selective β3AR agonist CL316243 reduces bladder pressure and in cystomeric studies increases bladder capacity leading to prolongation of micturition interval without increasing residual urine volume.

Overactive bladder is characterized by the symptoms of urinary urgency, with or without urgency urinary incontinence, usually associated with frequency and nocturia. The prevalence of OAB in the United States and Europe has been estimated at 16 to 17% in both women and men over the age of 18 years. Overactive bladder is most often classified as idiopathic, but can also be secondary to neurological condition, bladder outlet obstruction, and other causes. From a pathophysiologic perspective, the overactive bladder symptom complex, especially when associated with urge incontinence, is suggestive of detrusor overactivity. Urgency with or without incontinence has been shown to negatively impact both social and medical well-being, and represents a significant burden in terms of annual direct and indirect healthcare expenditures. Importantly, current medical therapy for urgency (with or without incontinence) is suboptimal, as many patients either do not demonstrate an adequate response to current treatments, and/or are unable to tolerate current treatments (for example, dry mouth associated with anticholinergic therapy). Therefore, there is need for new, well-tolerated therapies that effectively treat urinary frequency, urgency and incontinence, either as monotherapy or in combination with available therapies. Agents that relax bladder smooth muscle, such as β3AR agonists, are expected to be effective for treating such urinary disorders.

SUMMARY OF THE INVENTION

The present invention relates to novel β3AR agonists of Formula I,

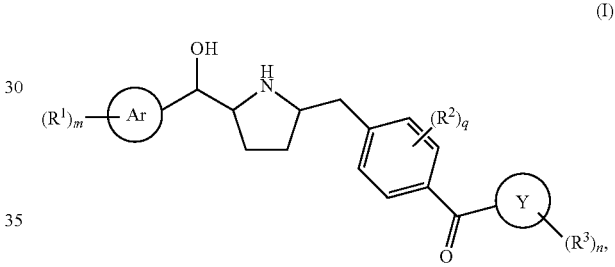

(I)

pharmaceutical compositions containing them, as well as methods for the treatment or prophylaxis of disorders mediated through the β3AR using such novel compounds.

DESCRIPTION OF THE INVENTION

Described herein are compounds of structural Formula I:

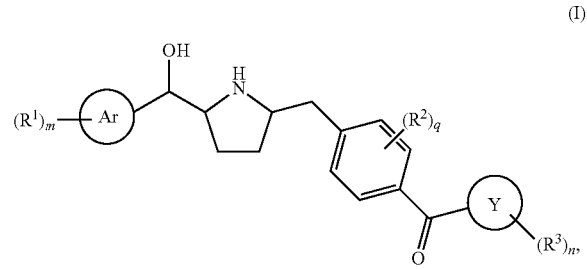

(I)

wherein m is 0, 1, 2, 3, 4, or 5;

n is 0, 1, 2, 3, 4, or 5;

p is 0, 1, or 2;

q is 0, 1, 2, 3, or 4;

Ar is phenyl or pyridyl;

Y is a ring system selected from the group consisting of:

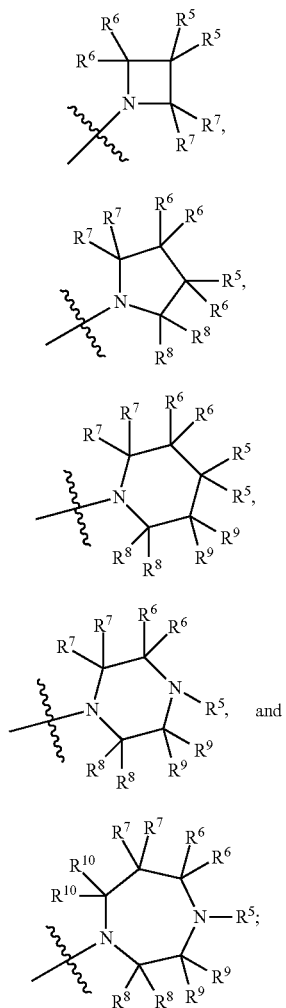

wherein $R^5$, $R^6$, $R^7$, $R^8$, $R^9$, and $R^{10}$ are each a hydrogen;
or two $R^5$ groups, two $R^6$ groups, or two $R^7$ groups, together with the carbon atom to which they are attached, form a 3- to 6-membered ring containing 0, 1, 2, or 3 hetero atoms independently selected from oxygen, sulfur, and nitrogen; wherein the 3- to 6-membered ring is optionally fused to a phenyl or a 4- to 6-membered heterocyclic ring with from 1 to 4 heteroatoms selected from oxygen, sulfur and nitrogen to form a fused ring; and wherein the 3- to 6-membered ring or the fused ring is optionally substituted with 1 to 5 $R^3$ groups;
or $R^5$ and $R^6$, $R^6$ and $R^7$, or $R^5$ and $R^9$, together with the nitrogen or carbon atoms to which they are attached, form a 5- to 6-membered ring containing 0, 1, 2, or 3 hetero atoms independently selected from oxygen and nitrogen; wherein the 5- to 6-membered ring is optionally fused to a phenyl or a 4- to 6-membered heterocyclic ring with from 1 to 4 heteroatoms selected from oxygen, sulfur and nitrogen to form a fused ring; and wherein the 5- to 6-membered ring or the fused ring is optionally substituted with 1 to 5 $R^3$ groups;
or $R^6$ and $R^9$ form a direct bond;
or $R^6$ and $R^8$ form a $C_1$-$C_4$ alkylene bridge; and wherein the alkylene bridge is optionally substituted with 1 to 3 $R^3$ groups;
or $R^6$ and $R^9$ form a $C_1$-$C_4$ alkylene bridge; and wherein the alkylene bridge is optionally substituted with 1 to 3 $R^3$ groups;
or $R^7$ and $R^8$ form a $C_1$-$C_4$ alkylene bridge; and wherein the alkylene bridge is optionally substituted with 1 to 3 $R^3$ groups;

Z is selected from the group consisting of:
(1) $C_5$-$C_{10}$ carbocyclic ring,
(2) 4- to 6-membered heterocyclic ring with from 1 to 4 heteroatoms selected from oxygen, sulfur and nitrogen,
(3) benzene ring fused to a $C_5$-$C_{10}$ carbocyclic ring,
(4) 5 or 6-membered heterocyclic ring with from 1 to 4 heteroatoms selected from oxygen, sulfur and nitrogen fused to a $C_5$-$C_{10}$ carbocyclic ring, and
(5) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;

each occurrence of $R^1$ is independently selected from the group consisting of:
(1) $C_1$-$C_6$ alkyl optionally substituted with 1 to 5 halogen atoms,
(2) $C_3$-$C_6$ cycloalkyl,
(3) halogen,
(4) —$OR^a$,
(5) oxo,
(6) cyano,
(7) —$C(O)R^a$,
(8) —$C(O)NR^aR^b$,
(9) —$NR^aR^b$,
(10) —$S(O)p$-$C_1$-$C_6$ alkyl, and
(11) Z optionally substituted with 1 to 5 halogen atoms;

each occurrence of $R^2$ is independently selected from the group consisting of:
(1) halogen,
(2) —$OR^a$, and
(3) $C_1$-$C_6$ alkyl optionally substituted with 1 to 5 halogen atoms;

each occurrence of $R^3$ is independently selected from the group consisting of:
(1) $C_1$-$C_6$ alkyl optionally substituted with 1 to 5 groups independently selected from:
  (a) halogen,
  (b) oxo,
  (c) cyano,
  (d) —$OR^a$,
  (e) —$C(O)R^a$,
  (f) —$CO_2R^a$,
  (g) —$C(O)R^c$,
  (h) —$C(O)NR^aR^b$,
  (i) —$NR^aR^b$,
  (j) —$N(R^a)C(O)R^a$,
  (k) —$S(O)p$-$C_1$-$C_6$ alkyl,
  (l) $C_3$-$C_6$ cycloalkyl optionally substituted with 1 to 5 groups independently selected from halogen, $C_1$-$C_6$ alkyl optionally substituted with 1 to 5 halogen atoms, —$OR^a$, and oxo, and
  (m) Z optionally substituted with 1 to 5 groups independently selected from halogen, $C_1$-$C_6$ alkyl optionally substituted with 1 to 5 halogen atoms, oxo, cyano, —$OR^a$, —$CO_2R^a$, $C_3$-$C_6$ cycloalkyl, and Z,
(2) $C_3$-$C_6$ cycloalkyl, optionally substituted with 1 to 5 groups independently selected from halogen, $C_1$-$C_6$ alkyl optionally substituted with 1 to 5 halogen atoms, oxo, —$OR^a$, and Z optionally substituted with 1 to 5 halogen atoms, (3) halogen,
(4) oxo,
(5) cyano,
(6) —OR$^a$,
(7) —C(O)R$^a$,
(8) —CO$_2$R$^a$,
(9) —C(O)NR$^a$R$^b$,
(10) —NR$^a$R$^b$,
(11) —N(R$^a$)C(O)R$^a$,
(12) —N(R$^a$)CO$_2$R$^a$,
(13) —N(R$^a$)C(O)NR$^a$R$^b$,
(14) =N—OR$^a$,
(15) —S(O)p-R$^a$, and
(16) Z optionally substituted with 1 to 5 groups independently selected from
  (a) C$_1$-C$_6$ alkyl optionally substituted with 1 to 5 groups independently selected from halogen, oxo, cyano, —OR$^a$, —CO$_2$R$^a$, C$_3$-C$_6$ cycloalkyl, and Z,
  (b) C$_3$-C$_6$ cycloalkyl optionally substituted with 1 to 5 groups independently selected from halogen, C$_1$-C$_6$ alkyl optionally substituted with 1 to 5 halogen atoms, oxo, —OR$^a$, —CO$_2$R$^a$, and Z,
  (c) halogen,
  (d) nitro,
  (e) oxo,
  (f) cyano,
  (g) —OR$^a$,
  (h) —C(O)R$^a$,
  (i) —CO$_2$R$^a$,
  (j) —C(O)NR$^a$R$^b$,
  (k) —NR$^a$R$^b$,
  (l) —S(O)p-C$_1$-C$_6$ alkyl, and
  (m) Z optionally substituted with 1 to 5 groups independently selected from halogen, C$_1$-C$_6$ alkyl optionally substituted with 1 to 5 halogen atoms, oxo, cyano, —OR$^a$, —CO$_2$R$^a$, and C$_3$-C$_6$ cycloalkyl;

each occurrence of R$^a$ is independently selected from the group consisting of:
(1) hydrogen,
(2) C$_1$-C$_6$ alkyl optionally substituted with 1 to 5 groups independently selected from:
  (a) halogen,
  (b) cyano,
  (c) —OR$^b$,
  (d) —C(O)R$^b$,
  (e) —CO$_2$R$^b$,
  (f) —C(O)NR$^b$R$^b$,
  (g) —S(O)$_p$—C$_1$-C$_6$ alkyl;
  (h) C$_3$-C$_6$ cycloalkyl optionally substituted with 1 to 5 groups independently selected from C$_1$-C$_6$ alkyl and —OR$^b$, and
  (i) Z optionally substituted with 1 to 5 groups independently selected from halogen, C$_1$-C$_6$ alkyl optionally substituted with 1 to 5 halogen atoms, oxo, cyano, —OR$^b$, —CO$_2$R$^b$, C$_3$-C$_6$ cycloalkyl, and Z,
(3) C$_3$-C$_6$ cycloalkyl optionally substituted with 1 to 5 groups independently selected from halogen, C$_1$-C$_6$ alkyl optionally substituted with 1 to 5 groups independently selected from halogen, oxo, —OR$^b$, and Z, and
(4) Z optionally substituted with 1 to 5 groups independently selected from:
  (a) halogen,
  (b) nitro,
  (c) cyano,
  (d) oxo,
  (e) —OR$^b$,
  (f) —C(O)R$^b$,
  (g) —CO$_2$R$^b$,
  (h) —C(O)NR$^b$R$^b$,
  (i) —NR$^b$R$^b$,
  (j) —S(O)$_p$—C$_1$-C$_6$ alkyl,
  (k) C$_1$-C$_6$ alkyl optionally substituted with 1 to 5 groups independently selected from halogen, oxo, cyano, —OR$^b$, —CO$_2$R$^b$, C$_3$-C$_6$ cycloalkyl, and Z,
  (l) C$_3$-C$_6$ cycloalkyl, and
  (m) Z optionally substituted with 1 to 5 groups independently selected from halogen, C$_1$-C$_6$ alkyl optionally substituted with 1 to 5 halogen atoms, oxo, cyano, —OR$^b$, —CO$_2$R$^b$, and C$_3$-C$_6$ cycloalkyl;

each occurrence of R$^b$ is independently selected from the group consisting of
(1) hydrogen,
(2) C$_1$-C$_6$ alkyl optionally substituted with 1 to 5 groups independently selected from halogen, C$_1$-C$_6$ alkyl optionally substituted with 1 to 5 groups independently selected from halogen, oxo, cyano, hydroxy, C$_1$-C$_6$ alkoxy, —C(O)NH$_2$, —CO$_2$H, C$_3$-C$_6$ cycloalkyl optionally substituted with 1 to 5 groups independently selected from hydroxy and C$_1$-C$_6$ alkyl, and Z optionally substituted with 1 to 5 groups independently selected from halogen, hydroxy, oxo, and C$_1$-C$_6$ alkyl,
(3) C$_3$-C$_6$ cycloalkyl optionally substituted with 1 to 5 groups independently selected from halogen, C$_1$-C$_6$ alkyl optionally substituted with 1 to 5 halogen atoms, hydroxy, C$_1$-C$_6$ alkoxy, and oxo, and
(4) Z optionally substituted with 1 to 5 groups independently selected from halogen, trifluoromethyl, C$_1$-C$_6$ alkyl, oxo, hydroxy, and C$_1$-C$_6$ alkoxy; and each occurrence of R$^c$ is independently selected from the group consisting of:

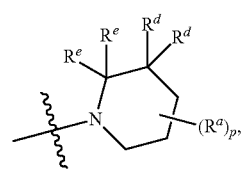

(1)

wherein R$^d$ and R$^e$ are each hydrogen or C$_1$-C$_6$ alkyl; or two R$^d$ groups or two R$^e$ groups together with the carbon atom to which they are attached form a 3- to 6-membered ring containing 0 or 1 hetero atom selected from oxygen and nitrogen; and wherein the 3- to 6-membered ring is optionally substituted with 1 to 5 R$^3$ groups:

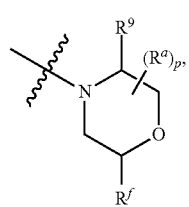

(2)

wherein R$^f$ and R$^g$ are each hydrogen or C$_1$-C$_6$ alkyl; or R$^f$ and R$^g$ form a C$_1$-C$_4$ alkylene bridge;

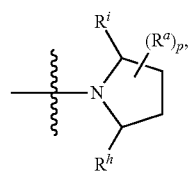
(3)

wherein $R^h$ and $R^i$ are each hydrogen or $C_1$-$C_6$ alkyl; or $R^h$ and $R^i$ form a $C_1$-$C_4$ alkylene bridge; and

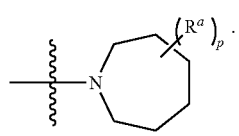
(4)

As used herein, the term "alkyl" means both branched- and straight-chain saturated aliphatic hydrocarbon groups having the specified number of carbon atoms. For example, $C_1$-$C_6$ alkyl includes, but is not limited to, methyl (Me), ethyl (Et), n-propyl (Pr), n-butyl (By), n-pentyl, n-hexyl, and the isomers thereof such as isopropyl (i-Pr), isobutyl (i-Bu), secbutyl (s-Bu), tert-butyl (t-Bu), isopentyl, sec-pentyl, tert-pentyl, isohexyl and the like.

The term "cycloalkyl" means a monocyclic saturated carbocyclic ring, having the specified number of carbon atoms, e.g., 3, 4, 5 or 6 carbon atoms. Non-limiting examples of $C_3$-$C_6$ cycloalkyl include cyclopropyl, cyclobutyl, cyclopentyl and cyclohexyl.

The term "alkanediyl" means a straight or branched divalent hydrocarbon radical having the specified number of carbon atoms. Non-limiting examples of $C_1$-$C_4$ "alkanediyl" include, but are not limited to, methylene (—$CH_2$—), ethylene (—$CH_2CH_2$—), 1,1-ethanediyl (—$CH(CH_3)$—), 1,2-propanediyl (—$CH(CH_3)CH_2$—), 2-methyl-1,1-propanediyl (—$CH[C(CH_3)_2]$—), 1,4-butanediyl (—$CH_2CH_2CH_2CH_2$—), 2,3-butanediyl (—$CH(CH_3)CH(CH_3)$—, and the like. Example of a halogen substituted alkanediyl is —$C(CH_3)(F)$—.

The term "optionally substituted" means "unsubstituted or substituted," and therefore, the generic structural Formulas described herein encompass compounds containing the specified optional substituent as well as compounds that do not contain the optional substituent. Each variable is independently defined each time it occurs within the generic structural formula definitions.

The terms "halo" or "halogen" are meant to include fluoro, chloro, bronco and iodo, unless otherwise noted.

The terms "carbocycle" or "carbocyclic" refer to saturated, partially unsaturated and aromatic rings having only ring carbon atoms. For examples, $C_1$-$C_4$ carbocyclic ring include, but are not limited to, cyclopentyl, cyclohexyl, cycloheptyl, cyclooctyl, cyclopentenyl, cyclohexenyl, cyclohexadienyl, and phenyl.

The term "aryl" refers to an aromatic carbocycle.

The terms "heterocycle" or "heterocyclic" refer to saturated, partially unsaturated and aromatic rings having at least one ring heteroatom and at least one ring carbon atom; the heterocycle may be attached to the rest of the molecule via a ring carbon atom or a ring hetero atom, for example, a ring nitrogen atom. The terms "heteroaryl" or "heteroaromatic" refer to an aromatic heterocycle. For example, within the definition for Z, the term "a 5- or 6-membered heterocyclic ring with from 1 to 4 heteroatoms selected from oxygen, sulfur and nitrogen" includes, but is not limited to, pyrrolyl, thienyl, furanyl, imidazolyl, pyrazolyl, oxazolyl, isoxazolyl, thiazolyl, isothiazolyl, triazolyl, tetrazolyl, oxadiazolyl, thiadiazolyl, pyrrolidinyl, tetrahydrofuranyl, pyridinyl, dihydropyridinyl, tetrahydropyridinyl, pyrimidinyl, dihydropyrimidinyl, tetrahydropyrimidinyl, pyrazinyl, dihydropyrazinyl, tetrahydropyrazinyl, pyridazinyl, dihydropyridazinyl, tetrahydropyridazinyl, piperidinyl, piperazinyl, morpholinyl, pyranyl, dihydropyranyl, tetrahydropyranyl, and the like.

Within the definition for Z, the term "a benzene ring fused to a $C_5$-$C_{10}$ carbocyclic ring" includes, but is not limited to, naphthyl, dihydronaphthyl, tetrahydronaphthyl, indanyl, indenyl, benzocycloheptene, tetrahydrobenzocycloheptene, and the like. In one embodiment, a benzene ring is fused to a $C_5$-$C_6$ carbocyclic ring. Such fused ring may be attached to the rest of the molecule via a carbon atom on either ring.

Within the definition for Z, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" includes, but is not limited to, naphthyridinyl, dihydronaphthyridinyl, tetrahydronaphthyridinyl, imidazopyridinyl, pteridinyl, purinyl, quinolizinyl, indolizinyl, tetrahydroquinolizinyl, and tetrahydroindolizinyl. In one embodiment, Z is selected from the group consisting of:

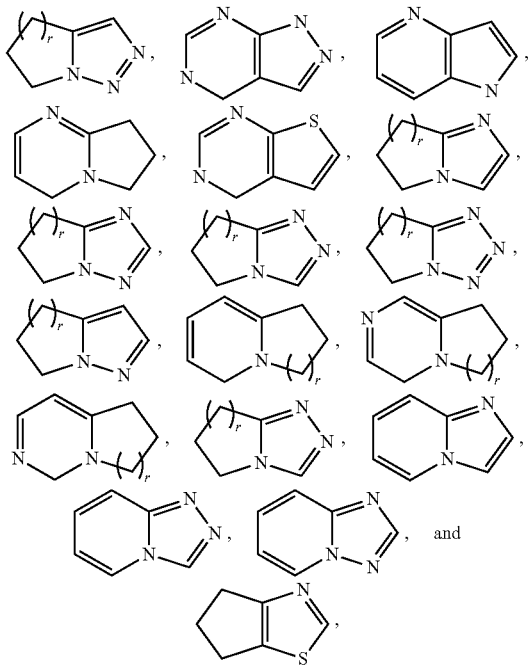

wherein r is 1 or 2. Such fused ring may be attached to the rest of the molecule via a carbon atom or a nitrogen atom on either ring.

To avoid any doubt, the term "a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen" as used herein includes compounds having only one nitrogen as the sole heteroatom when the nitrogen is located at the bridgehead.

Within the definition for Z, the term "a 5- or 6-membered heterocyclic ring with from 1 to 4 heteroatoms selected from oxygen, sulfur and nitrogen fused to a $C_5$-$C_{10}$ carbocyclic ring" includes, but is not limited to, indolyl, isoindolyl, benzofuranyl, benzothienyl, benzimidazolyl, benzotriazolyl, benzoxazolyl, benzisoxazolyl, benzthiazolyl, benzisothiazolyl, quinolinyl, isoquinolinyl, quinoxalinyl, quinazolinyl, cinnolinyl, indazolyl, tetrahydroquinolinyl, tetrahydroindazolyl, dihydroindazolyl, chromenyl, chromanyl benztriazolyl,

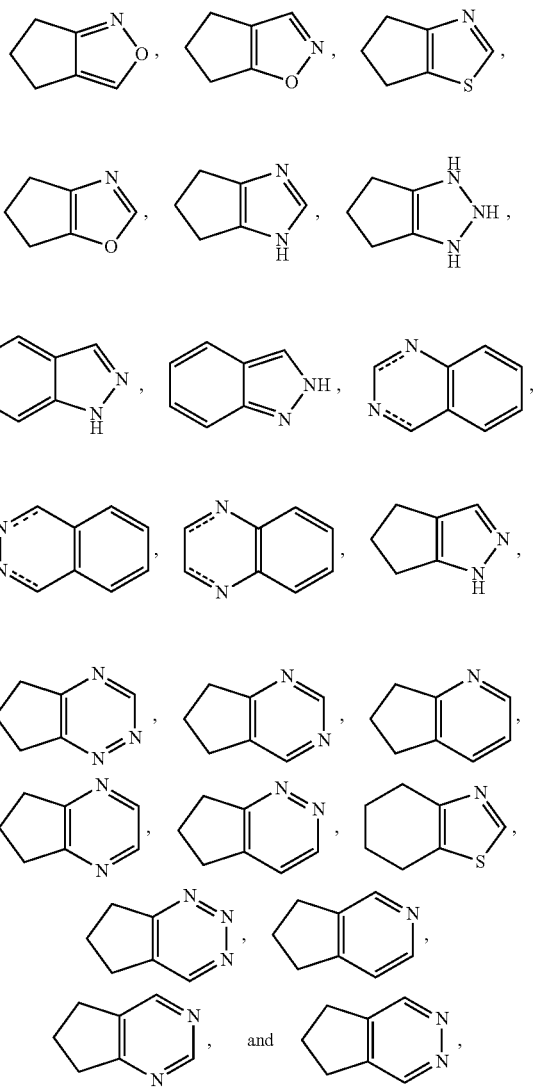

where the dash bond "----" means a single or double bond while conforming to the valency rule for the ring atoms. Such fused ring may be attached to the rest of the molecule via a carbon atom on either ring or a nitrogen atom on the heterocyclic ring.

For the terms $(R^1)_m$, $(R^2)_q$, $(R^3)_n$, as well as other similar notations, when m or q or n is 0, then $R^1$, $R^2$ or $R^3$ is hydrogen; when m, q or n is greater than 1, then each occurrence of $R^1$, $R^2$ or $R^3$ is independently selected from other occurrences of $R^1$, $R^2$ or $R^3$, respectively. For example, when n is 2, the two $R^3$ substituents can be the same or different.

In one embodiment, Y is

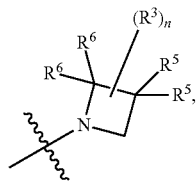

wherein n is 0, 1, 2, 3, 4, or 5; $R^3$ is as defined above; $R^5$ and $R^6$ are each a hydrogen; or two $R^5$ groups or two $R^6$ groups, together with the carbon atom to which they are attached, form a 4- to 5-membered ring containing 0 or 1 hetero atom selected from oxygen and nitrogen; and wherein the 4- to 5-membered ring is optionally substituted with 1 to 3 $R^3$ groups.

In another embodiment, Y is

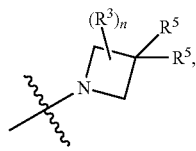

wherein n is 0, 1, 2, or 3; $R^3$ is as defined above; each $R^5$ is a hydrogen; or two $R^5$ groups, together with the carbon atom to which they are attached, form a 4-membered ring containing 0 or 1 nitrogen atom; and wherein the 4-membered ring is optionally substituted with 1 to 2 $R^3$ groups.

In one embodiment, Y is

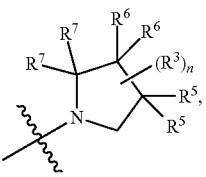

wherein n is 0, 1, 2, 3, or 4;

$R^3$ is as defined above;

$R^5$, $R^6$, and $R^7$ are each a hydrogen;

or two $R^5$ groups, two $R^6$ groups, or two $R^7$ groups, together with the carbon atom to which they are attached, form a 4- to 6-membered ring containing 0, 1, or 2 hetero atoms selected from oxygen and nitrogen; and wherein the 4- to 6-membered ring is optionally substituted with 1 to 3 $R^3$ groups;

or $R^5$ and $R^6$, or $R^6$ and $R^7$, together with the carbon atoms to which they are attached, form a 5- to 6-membered ring containing 0, 1, 2, or 3 hetero atoms independently selected from oxygen and nitrogen; and wherein the 5- to 6-membered ring or the fused ring is optionally substituted with 1 to 3 $R^3$ groups.

In another embodiment, Y is

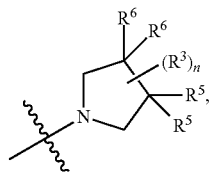

wherein n is 0, 1, 2, or 3;

R$^3$ is as defined above;

R$^5$ and R$^6$ are each a hydrogen;

or two R$^5$ groups, together with the carbon atom to which they are attached, form a 5-membered ring containing 0 or 1 hetero atom selected from oxygen and nitrogen; and wherein the 5-membered ring is optionally substituted with 1 to 2 R$^3$ groups;

or R$^5$ and R$^6$, together with the carbon atoms to which they are attached, form a 5- to 6-membered ring containing 0, 1, or 2 hetero atoms independently selected from oxygen and nitrogen; and wherein the 5- to 6-membered ring or the fused ring is optionally substituted with 1 to 2 R$^3$ groups.

In one embodiment, Y is

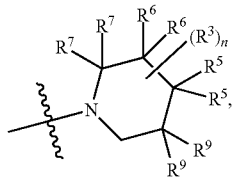

wherein n is 0, 1, 2, 3, 4, or 5;

R$^3$ is as defined above;

R$^5$, R$^6$, R$^7$, and R$^9$ are each a hydrogen;

or two R$^5$ groups, two R$^6$ groups, or two R$^7$ groups, together with the carbon atom to which they are attached, form a 4- to 6-membered ring containing 0, 1, 2, or 3 hetero atoms selected from oxygen, sulfur, and nitrogen; wherein the 4- to 6-membered ring is optionally fused to a phenyl or a 4- to 6-membered heterocyclic ring with from 1 to 4 heteroatoms selected from oxygen, sulfur and nitrogen to form a fused ring; and wherein the 4- to 6-membered ring or the fused ring is optionally substituted with 1 to 5 R$^3$ groups;

or R$^5$ and R$^6$, or R$^6$ and R$^7$, together with the carbon atoms to which they are attached, form a 5- to 6-membered ring containing 0, 1, 2, or 3 hetero atoms independently selected from oxygen, sulfur, and nitrogen; wherein the 5- to 6-membered ring is optionally fused to a phenyl or a 4- to 6-membered heterocyclic ring with from 1 to 4 heteroatoms selected from oxygen, sulfur and nitrogen to form a fused ring; and wherein the 5- to 6-membered ring or the fused ring is optionally substituted with 1 to 5 R$^3$ groups;

or R$^6$ and R$^9$ form a direct bond;

or R$^6$ and R$^9$ form a C$_1$-C$_4$ alkylene bridge; wherein the alkylene bridge is optionally substituted with 1 to 3 R$^3$ groups;

or R$^7$ and R$^9$ form a C$_1$-C$_4$ alkylene bridge; and wherein the alkylene bridge is optionally substituted with 1 to 3 R$^3$ groups.

In another embodiment, Y is

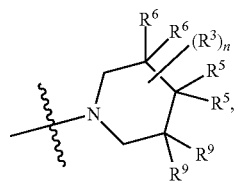

wherein n is 0, 1, 2, or 3;

R$^3$ is as defined above;

R$^5$, R$^6$, and R$^9$ are each a hydrogen;

or two R$^5$ groups, or two R$^6$ groups, together with the carbon atom to which they are attached, form a 4- to 6-membered ring containing 0, 1, or 2 hetero atoms selected from oxygen, sulfur, and nitrogen; wherein the 4- to 6-membered ring is optionally fused to a phenyl or a 4- to 6-membered heterocyclic ring with from 1 to 4 heteroatoms selected from oxygen, sulfur and nitrogen to form a fused ring; and wherein the 4- to 6-membered ring or the fused ring is optionally substituted with 1 to 3 R$^3$ groups;

or R$^5$ and R$^6$, or R$^6$ and R$^7$, together with the carbon atoms to which they are attached, form a 5- to 6-membered ring containing 0, 1, 2, or 3 hetero atoms independently selected from oxygen, sulfur, and nitrogen; wherein the 5- to 6-membered ring is optionally fused to a phenyl or a 4- to 6-membered heterocyclic ring with from 1 to 4 heteroatoms selected from oxygen, sulfur and nitrogen to form a fused ring; and wherein the 5- to 6-membered ring or the fused ring is optionally substituted with 1 to 3 R$^3$ groups;

or R$^6$ and R$^9$ form a direct bond;

or R$^6$ and R$^9$ form a C$_1$-C$_4$ alkylene bridge; wherein the alkylene bridge is optionally substituted with 1 to 2 R$^3$ groups;

or R$^7$ and R$^9$ form a C$_1$-C$_4$ alkylene bridge; and wherein the alkylene bridge is optionally substituted with 1 to 2 R$^3$ groups.

In another embodiment, Y is

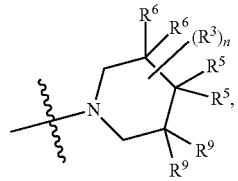

wherein n is 0, 1, 2, or 3;

R$^3$ is as defined above;

R$^5$, R$^6$, and R$^9$ are each a hydrogen;

or two R$^5$ groups, or two R$^6$ groups, together with the carbon atom to which they are attached, form a 5- to 6-membered ring containing 0, 1, or 2 hetero atoms selected from oxygen, sulfur, and nitrogen; wherein the 5- to 6-membered ring is optionally fused to a phenyl or a 4- to 6-membered heterocyclic ring with from 1 to 4 heteroatoms selected from oxygen, sulfur and nitrogen to form a fused ring; and wherein the 5- to 6-membered ring or the fused ring is optionally substituted with 1 to 3 R$^3$ groups;

or R$^5$ and R$^6$, together with the carbon atoms to which they are attached, form a 5- to 6-membered ring containing 0, 1, 2, or 3 hetero atoms independently selected from oxygen and nitrogen; wherein the 5- to 6-membered ring is optionally fused to a phenyl or a 4- to 6-membered heterocyclic ring with from 1 to 4 heteroatoms selected from oxygen, sulfur and nitrogen to form a fused ring; and wherein the 5- to 6-membered ring or the fused ring is optionally substituted with 1 to 3 $R^3$ groups;

or $R^6$ and $R^9$ form a direct bond;

or $R^6$ and $R^9$ form a $C_1$-$C_4$ alkylene bridge; and wherein the alkylene bridge is optionally substituted with 1 to 2 $R^3$ groups.

In one embodiment, Y is

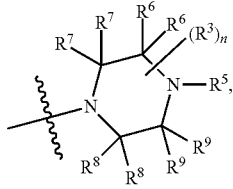

wherein n is 0, 1, 2, 3, or 4;

$R^3$ is as defined above;

$R^5$, $R^6$, $R^7$, $R^8$, and $R^9$ are each a hydrogen;

or two $R^6$ groups, or two $R^7$ groups, together with the carbon atom to which they are attached, form a 5- to 6-membered ring containing 0, 1, 2, or 3 hetero atoms selected from oxygen, sulfur, and nitrogen; wherein the 5- to 6-membered ring is optionally fused to a phenyl or a 4- to 6-membered heterocyclic ring with from 1 to 4 heteroatoms selected from oxygen, sulfur and nitrogen to form a fused ring; and wherein the 4- to 6-membered ring or the fused ring is optionally substituted with 1 to 5 $R^3$ groups;

or $R^5$ and $R^6$, or $R^6$ and $R^7$, together with the carbon or nitrogen atoms to which they are attached, form a 5- to 6-membered ring containing 0, 1, 2, or 3 hetero atoms independently selected from oxygen, sulfur, and nitrogen; wherein the 5- to 6-membered ring is optionally fused to a phenyl or a 4- to 6-membered heterocyclic ring with from 1 to 4 heteroatoms selected from oxygen, sulfur and nitrogen to form a fused ring; and wherein the 5- to 6-membered ring or the fused ring is optionally substituted with 1 to 5 $R^3$ groups;

or $R^6$ and $R^8$ form a $C_1$-$C_4$ alkylene bridge; wherein the alkylene bridge is optionally substituted with 1 to 3 $R^3$ groups;

or $R^6$ and $R^9$ form a $C_1$-$C_4$ alkylene bridge; wherein the alkylene bridge is optionally substituted with 1 to 3 $R^3$ groups;

or $R^7$ and $R^8$ form a $C_1$-$C_4$ alkylene bridge; wherein the alkylene bridge is optionally substituted with 1 to 3 $R^3$ groups.

In another embodiment, Y is

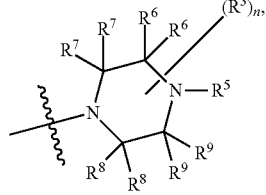

wherein n is 0, 1, 2, or 3;

$R^3$ is as defined above;

$R^5$, $R^6$, $R^7$, $R^8$, and $R^9$ are each a hydrogen;

or $R^5$ and $R^6$, or $R^6$ and $R^7$, together with the carbon or nitrogen atoms to which they are attached, form a 5- to 6-membered ring containing 0, 1, 2, or 3 hetero atoms independently selected from oxygen, sulfur, and nitrogen; wherein the 5- to 6-membered ring is optionally fused to a phenyl or a 4- to 6-membered heterocyclic ring with from 1 to 4 heteroatoms selected from oxygen, sulfur and nitrogen to form a fused ring; and wherein the 5- to 6-membered ring or the fused ring is optionally substituted with 1 to 3 $R^3$ groups;

or $R^6$ and $R^8$ form a $C_1$-$C_4$ alkylene bridge; wherein the alkylene bridge is optionally substituted with 1 to 3 $R^3$ groups;

or $R^6$ and $R^9$ form a $C_1$-$C_4$ alkylene bridge; wherein the alkylene bridge is optionally substituted with 1 to 3 $R^3$ groups;

or $R^7$ and $R^8$ form a $C_1$-$C_4$ alkylene bridge; wherein the alkylene bridge is optionally substituted with 1 to 3 $R^3$ groups.

In yet another embodiment, Y is

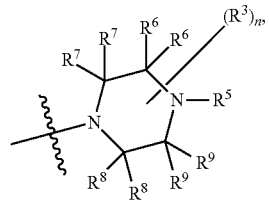

wherein n is 0, 1, 2, or 3;

$R^3$ is as defined above;

$R^5$, $R^6$, $R^7$, $R^8$, and $R^9$ are each a hydrogen;

or $R^5$ and $R^6$, together with the carbon and nitrogen atoms to which they are attached, form a 5- to 6-membered ring containing 0, 1, 2, or 3 hetero atoms independently selected from oxygen, sulfur, and nitrogen; wherein the 5- to 6-membered ring or the fused ring is optionally substituted with 1 to 2 $R^3$ groups;

or $R^6$ and $R^8$ form a $C_1$-$C_4$ alkylene bridge; wherein the alkylene bridge is optionally substituted with 1 to 2 $R^3$ groups;

or $R^6$ and $R^9$ form a $C_1$-$C_4$ alkylene bridge; wherein the alkylene bridge is optionally substituted with 1 to 2 $R^3$ groups;

or $R^7$ and $R^8$ form a $C_1$-$C_4$ alkylene bridge; wherein the alkylene bridge is optionally substituted with 1 to 2 $R^3$ groups.

In one embodiment, Y is

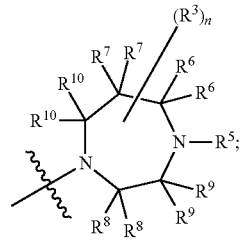

wherein $R^5$, $R^6$, $R^7$, $R^8$, $R^9$, and $R^{10}$ are each a hydrogen;

or two $R^6$ groups, two $R^7$ groups, or two $R^8$ groups, together with the carbon atom to which they are attached, form a 5- to 6-membered ring containing 0, 1, 2, or 3 hetero atoms independently selected from oxygen, sulfur, and nitrogen; wherein the 5- to 6-membered ring is optionally fused to a phenyl or a 4- to 6-membered heterocyclic ring with from 1 to 4 heteroatoms selected from oxygen, sulfur and nitrogen to form a fused ring; and wherein the 5- to 6-membered ring or the fused ring is optionally substituted with 1 to 5 $R^3$ groups;

or $R^5$ and $R^6$, $R^6$ and $R^7$, or $R^5$ and $R^9$, together with the nitrogen or carbon atoms to which they are attached, form a 5- to 6-membered ring containing 0, 1, 2, or 3 hetero atoms independently selected from oxygen and nitrogen; wherein the 5- to 6-membered ring is optionally fused to a phenyl or a 4- to 6-membered heterocyclic ring with from 1 to 4 heteroatoms selected from oxygen, sulfur and nitrogen to form a fused ring; and wherein the 5- to 6-membered ring or the fused ring is optionally substituted with 1 to 5 $R^3$ groups;

or $R^6$ and $R^9$ form a direct bond;

or $R^6$ and $R^8$ form a $C_1$-$C_4$ alkylene bridge; and wherein the alkylene bridge is optionally substituted with 1 to 3 $R^3$ groups;

or $R^6$ and $R^9$ form a $C_1$-$C_4$ alkylene bridge; and wherein the alkylene bridge is optionally substituted with 1 to 3 $R^3$ groups;

or $R^7$ and $R^8$ form a $C_1$-$C_4$ alkylene bridge; and wherein the alkylene bridge is optionally substituted with 1 to 3 $R^3$ groups.

In another embodiment, Y is

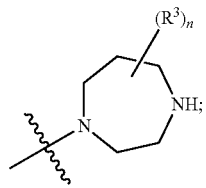

wherein n is 0, 1, 2, or 3; and $R^3$ is as defined above.

In one embodiment, each occurrence of $R^1$ is independently selected from the group consisting of:
(1) $C_1$-$C_6$ alkyl optionally substituted with 1 to 5 halogen atoms,
(2) $C_3$-$C_6$ cycloalkyl,
(3) halogen,
(4) —$OR^a$,
(5) oxo,
(6) cyano,
(7) —$C(O)R^a$,
(8) —$C(O)NR^aR^b$,
(9) —$NR^aR^b$,
(10) —$S(O)p$-$C_1$-$C_6$ alkyl, and
(11) Z optionally substituted with 1 to 5 halogen atoms.

In another embodiment, each occurrence of $R^1$ is independently selected from the group consisting of:
(1) $C_1$-$C_6$ alkyl optionally substituted with 1 to 5 halogen atoms,
(2) $C_3$-$C_6$ cycloalkyl,
(3) halogen,
(4) —$OR^a$,
(5) —$C(O)R^a$,
(6) —$NR^aR^b$, and
(7) phenyl optionally substituted with 1 to 5 halogen atoms.

In another embodiment, each occurrence of $R^1$ is independently selected from the group consisting of:
(1) $C_1$-$C_4$ alkyl optionally substituted with 1 to 3 halogen atoms,
(2) $C_3$-$C_6$ cycloalkyl,
(3) —$OR^a$,
(4) —$NR^aR^b$, and
(5) halogen.

In yet another embodiment, each occurrence of $R^1$ is independently a $C_1$-$C_4$ alkyl.

In one embodiment, each occurrence of $R^2$ is independently selected from the group consisting of:
(1) halogen,
(2) —$OR^a$, and
(3) $C_1$-$C_6$ alkyl optionally substituted with 1 to 5 halogen atoms.

In another embodiment, each occurrence of $R^2$ is independently a $C_1$-$C_4$ alkyl.

In one embodiment, each occurrence of $R^3$ is independently selected from the group consisting of:
(1) $C_1$-$C_6$ alkyl optionally substituted with 1 to 5 groups independently selected from:
 (a) halogen,
 (b) oxo,
 (c) cyano,
 (d) —$OR^a$,
 (e) —$C(O)R^a$,
 (f) —$CO_2R^a$,
 (g) —$C(O)R^c$,
 (h) —$C(O)NR^aR^b$,
 (i) —$NR^aR^b$,
 (j) —$N(R^a)C(O)R^a$,
 (k) —$S(O)p$—$C_1$-$C_6$ alkyl,
 (l) $C_3$-$C_6$ cycloalkyl optionally substituted with 1 to 5 groups independently selected from halogen, $C_1$-$C_6$ alkyl optionally substituted with 1 to 5 halogen atoms, —$OR^a$, and oxo, and
 (m) Z optionally substituted with 1 to 5 groups independently selected from halogen, $C_1$-$C_6$ alkyl optionally substituted with 1 to 5 halogen atoms, oxo, cyano, —$OR^a$, —$CO_2R^a$, $C_3$-$C_6$ cycloalkyl, and Z,
(2) $C_3$-$C_6$ cycloalkyl, optionally substituted with 1 to 5 groups independently selected from halogen, $C_1$-$C_6$ alkyl optionally substituted with 1 to 5 halogen atoms, oxo, —$OR^a$, and Z optionally substituted with 1 to 5 halogen atoms,
(3) halogen,
(4) oxo,
(5) cyano,
(6) —$OR^a$,
(7) —$C(O)R^a$,
(8) —$CO_2R^a$,
(9) —$C(O)NR^aR^b$,
(10) —$NR^aR^b$,
(11) —$N(R^a)C(O)R^a$,
(12) —$N(R^a)CO_2R^a$,
(13) —$N(R^a)C(O)NR^aR^b$,
(14) =$N$—$OR^a$,
(15) —$S(O)p$-$R^a$, and
(16) Z optionally substituted with 1 to 5 groups independently selected from
 (a) $C_1$-$C_6$ alkyl optionally substituted with 1 to 5 groups independently selected from halogen, oxo, cyano, —$OR^a$, —$CO_2R^a$, $C_3$-$C_6$ cycloalkyl, and Z,
 (b) $C_3$-$C_6$ cycloalkyl optionally substituted with 1 to 5 groups independently selected from halogen, $C_1$-$C_6$ alkyl optionally substituted with 1 to 5 halogen atoms, oxo, —$OR^a$, —$CO_2R^a$, and Z,
 (c) halogen,
 (d) nitro,
 (e) oxo,
 (f) cyano,
 (g) —$OR^a$,
 (h) —$C(O)R^a$, (i) —CO$_2$R$^a$,
(j) —C(O)NR$^a$R$^b$,
(k) —NR$^a$R$^b$,
(l) —S(O)p-C$_1$-C$_6$ alkyl, and
(m) Z optionally substituted with 1 to 5 groups independently selected from halogen, C$_1$-C$_6$ alkyl optionally substituted with 1 to 5 halogen atoms, oxo, cyano, —OR$^a$, —CO$_2$R$^a$, and C$_3$-C$_6$ cycloalkyl.

In another embodiment, each occurrence of R$^3$ is independently selected from the group consisting of:
(1) C$_1$-C$_6$ alkyl optionally substituted with 1 to 3 groups independently selected from:
  (a) halogen,
  (b) oxo,
  (c) —OR$^a$,
  (d) —C(O)R$^a$,
  (e) —CO$_2$R$^a$,
  (f) —C(O)NR$^a$R$^b$,
  (g) —NR$^a$R$^b$,
  (h) —N(R$^a$)C(O)R$^a$,
  (i) —S(O)p-C$_1$-C$_6$ alkyl,
  (j) C$_3$-C$_6$ cycloalkyl optionally substituted with 1 to 3 groups independently selected from halogen, C$_1$-C$_6$ alkyl optionally substituted with 1 to 3 halogen atoms, and —OR$^a$,
  (k) Z optionally substituted with 1 to 3 groups independently selected from halogen, C$_1$-C$_6$ alkyl optionally substituted with 1 to 3 halogen atoms, oxo, cyano, —OR$^a$, C$_3$-C$_6$ cycloalkyl, and Z,
(2) C$_3$-C$_6$ cycloalkyl, optionally substituted with 1 to 3 groups independently selected from halogen, C$_1$-C$_6$ alkyl optionally substituted with 1 to 3 halogen atoms, —OR$^a$, and Z optionally substituted with 1 to 3 halogen atoms,
(3) halogen,
(4) oxo,
(5) —OR$^a$,
(6) —C(O)R$^a$,
(7) —CO$_2$R$^a$,
(8) —C(O)NR$^a$R$^b$,
(9) —NR$^a$R$^b$,
(10) —N(R$^a$)C(O)R$^a$,
(11) —S(O)p-R$^a$, and
(12) Z optionally substituted with 1 to 3 groups independently selected from
  (a) C$_1$-C$_6$ alkyl optionally substituted with 1 to 3 groups independently selected from halogen, oxo, —OR$^a$, C$_3$-C$_6$ cycloalkyl, and Z,
  (b) C$_3$-C$_6$ cycloalkyl optionally substituted with 1 to 3 groups independently selected from halogen, C$_1$-C$_6$ alkyl optionally substituted with 1 to 3 halogen atoms, —OR$^a$, and Z,
  (c) halogen,
  (d) oxo,
  (e) —OR$^a$,
  (f) —C(O)R$^a$,
  (g) —CO$_2$R$^a$,
  (h) —C(O)NR$^a$R$^b$,
  (i) —NR$^a$R$^b$,
  (j) —S(O)p-C$_1$-C$_6$ alkyl, and
  (k) Z optionally substituted with 1 to 3 groups independently selected from halogen, C$_1$-C$_6$ alkyl optionally substituted with 1 to 3 halogen atoms, oxo, —OR$^a$, —CO$_2$R$^a$, and C$_3$-C$_6$ cycloalkyl.

In yet another embodiment, each occurrence of R$^3$ is independently selected from the group consisting of:
(1) C$_1$-C$_4$ alkyl optionally substituted with 1 to 3 groups independently selected from:
  (a) halogen,
  (b) oxo,
  (c) —OR$^a$,
  (d) —C(O)R$^a$,
  (e) —CO$_2$R$^a$,
  (f) —C(O)NR$^a$R$^b$,
  (g) —NR$^a$R$^b$,
  (h) C3-C6 cycloalkyl optionally substituted with 1 to 3 groups independently selected from halogen, C$_1$-C$_6$ alkyl optionally substituted with 1 to 3 halogen atoms, and —OR$^a$,
  (i) Z optionally substituted with 1 to 3 groups independently selected from halogen, C$_1$-C$_4$ alkyl optionally substituted with 1 to 3 halogen atoms, oxo, —OR$^a$, C$_3$-C$_6$ cycloalkyl, and Z,
(2) C$_3$-C$_6$ cycloalkyl, optionally substituted with 1 to 3 groups independently selected from halogen, C$_1$-C$_6$ alkyl optionally substituted with 1 to 3 halogen atoms, —OR$^a$, and Z optionally substituted with 1 to 3 halogen atoms,
(3) halogen,
(4) oxo,
(5) —OR$^a$,
(6) —C(O)R$^a$,
(7) —CO$_2$R$^a$,
(8) —C(O)NR$^a$R$^b$,
(9) —NR$^a$R$^b$,
(10) —N(R$^a$)C(O)R$^a$,
(11) —S(O)p-R$^a$, and
(12) Z optionally substituted with 1 to 3 groups independently selected from
  (a) C$_1$-C$_4$ alkyl optionally substituted with 1 to 3 groups independently selected from halogen, oxo, —OR$^a$, C$_3$-C$_6$ cycloalkyl, and Z,
  (b) C$_3$-C$_6$ cycloalkyl optionally substituted with 1 to 3 groups independently selected from halogen, C$_1$-C$_6$ alkyl optionally substituted with 1 to 3 halogen atoms, —OR$^a$, and Z,
  (c) halogen,
  (d) oxo,
  (e) —OR$^a$,
  (f) —C(O)R$^a$,
  (g) —CO$_2$R$^a$,
  (h) —C(O)NR$^a$R$^b$,
  (i) —NR$^a$R$^b$,
  (j) —S(O)p-C$_1$-C$_6$ alkyl, and
  (k) Z optionally substituted with 1 to 3 groups independently selected from halogen, C$_1$-C$_4$ alkyl optionally substituted with 1 to 3 halogen atoms, oxo, —OR$^a$, —CO$_2$R$^a$, and C$_3$-C$_6$ cycloalkyl.

In one embodiment, each occurrence of R$^a$ is independently selected from the group consisting of:
(1) hydrogen,
(2) C$_1$-C$_6$ alkyl optionally substituted with 1 to 3 groups independently selected from:
  (a) halogen,
  (b) —OR$^b$,
  (c) —C(O)R$^b$,
  (d) —C(O)NR$^b$R$^b$,
  (e) —S(O)$_p$—C$_1$-C$_6$ alkyl;
  (f) C$_3$-C$_6$ cycloalkyl optionally substituted with 1 to 3 groups independently selected from C$_1$-C$_6$ alkyl and —OR$^b$, and (g) Z optionally substituted with 1 to 3 groups independently selected from halogen, $C_1$-$C_6$ alkyl optionally substituted with 1 to 3 halogen atoms, oxo, —$OR^b$, $C_3$-$C_6$ cycloalkyl, and Z, (3) $C_3$-$C_6$ cycloalkyl optionally substituted with 1 to 3 groups independently selected from halogen, $C_1$-$C_6$ alkyl optionally substituted with 1 to 3 groups independently selected from halogen, —$OR^b$, and Z, and (4) Z optionally substituted with 1 to 3 groups independently selected from:
(a) halogen,
(b) oxo,
(c) —$OR^b$,
(d) —$C(O)R^b$,
(e) —$NR^bR^b$,
(f) —$S(O)_p$—$C_1$-$C_6$ alkyl,
(g) $C_1$-$C_6$ alkyl optionally substituted with 1 to 3 groups independently selected from halogen, oxo, —$OR^b$, $C_3$-$C_6$ cycloalkyl, and Z,
(h) $C_3$-$C_6$ cycloalkyl, and
(i) Z optionally substituted with 1 to 3 groups independently selected from halogen, $C_1$-$C_6$ alkyl optionally substituted with 1 to 3 halogen atoms, oxo, —$OR^b$, and $C_3$-$C_6$ cycloalkyl.

In another embodiment, each occurrence of $R^a$ is independently selected from the group consisting of:
(1) hydrogen,
(2) $C_1$-$C_4$ alkyl optionally substituted with 1 to 3 groups independently selected from:
(a) halogen,
(b) —$OR^b$,
(c) —$C(O)R^b$,
(d) —$C(O)NR^bR^b$,
(e) $C_3$-$C_6$ cycloalkyl optionally substituted with 1 to 3 groups independently selected from $C_1$-$C_6$ alkyl and —$OR^b$, and
(f) Z optionally substituted with 1 to 3 groups independently selected from halogen, $C_1$-$C_4$ alkyl optionally substituted with 1 to 3 halogen atoms, oxo, —$OR^b$, $C_3$-$C_6$ cycloalkyl, and Z, (3) $C_3$-$C_6$ cycloalkyl optionally substituted with 1 to 3 groups independently selected from halogen, $C_1$-$C_6$ alkyl optionally substituted with 1 to 3 groups independently selected from halogen, —$OR^b$, and Z, and (4) Z optionally substituted with 1 to 3 groups independently selected from:
(a) halogen,
(b) oxo,
(c) —$OR^b$,
(d) —$C(O)R^b$,
(e) —$NR^bR^b$,
(f) $C_1$-$C_4$ alkyl optionally substituted with 1 to 3 groups independently selected from halogen, oxo, —$OR^b$, $C_3$-$C_6$ cycloalkyl, and Z,
(g) $C_3$-$C_6$ cycloalkyl, and
(h) Z optionally substituted with 1 to 3 groups independently selected from halogen, $C_1$-$C_4$ alkyl optionally substituted with 1 to 3 halogen atoms, oxo, —$OR^b$, and $C_3$-$C_6$ cycloalkyl.

In one embodiment, each occurrence of $R^b$ is independently selected from the group consisting of:
(1) hydrogen,
(2) $C_1$-$C_6$ alkyl optionally substituted with 1 to 5 groups independently selected from halogen, $C_1$-$C_6$ alkyl optionally substituted with 1 to 5 groups independently selected from halogen, oxo, cyano, hydroxy, $C_1$-$C_6$ alkoxy, —$C(O)NH_2$, —$CO_2H$, $C_3$-$C_6$ cycloalkyl optionally substituted with 1 to 5 groups independently selected from hydroxy and $C_1$-$C_6$ alkyl, and Z optionally substituted with 1 to 5 groups independently selected from halogen, hydroxy, oxo, and $C_1$-$C_6$ alkyl, (3) $C_3$-$C_6$ cycloalkyl optionally substituted with 1 to 5 groups independently selected from halogen, $C_1$-$C_6$ alkyl optionally substituted with 1 to 5 halogen atoms, hydroxy, $C_1$-$C_6$ alkoxy, and oxo, and (4) Z optionally substituted with 1 to 5 groups independently selected from halogen, trifluoromethyl, $C_1$-$C_6$ alkyl, oxo, hydroxy, and $C_1$-$C_6$ alkoxy.

In one embodiment, each occurrence of $R^c$ is independently selected from the group consisting of:

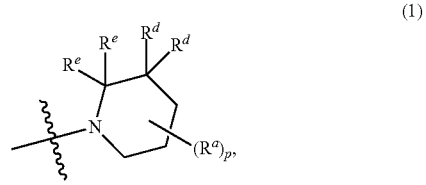

(1)

wherein $R^d$ and $R^e$ are each hydrogen or $C_1$-$C_6$ alkyl; or two $R^d$ groups or two $R^e$ groups together with the carbon atom to which they are attached form a 3- to 6-membered ring containing 0 or 1 hetero atom selected from oxygen and nitrogen; and wherein the 3- to 6-membered ring is optionally substituted with 1 to 5 $R^3$ groups;

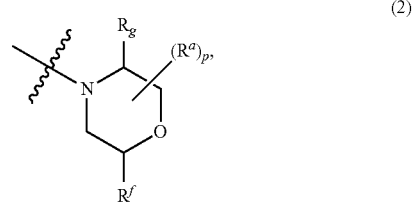

(2)

wherein $R^f$ and $R^g$ are each hydrogen or $C_1$-$C_6$ alkyl; or $R^f$ and $R^g$ form a $C_1$-$C_4$ alkylene bridge;

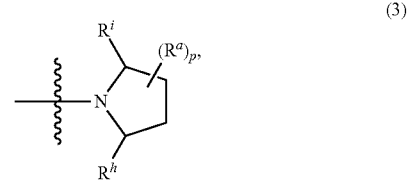

(3)

wherein $R^h$ and $R^i$ are each hydrogen or $C_1$-$C_6$ alkyl; or $R^h$ and $R^i$ form a $C_1$-$C_4$ alkylene bridge; and

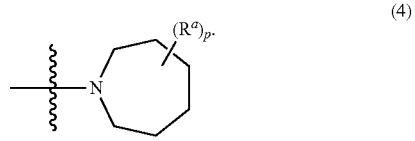

(4)

In one embodiment of Formula I are compounds having formula Ia:

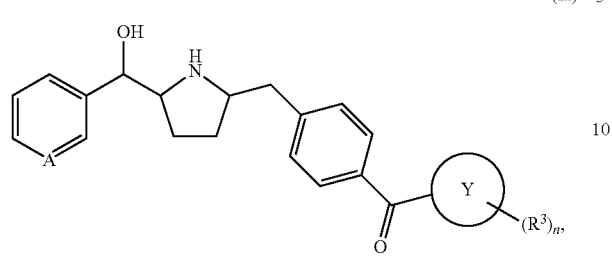

(Ia)

wherein A is N or CH.

In one embodiment, Z is selected from the group consisting of:

(1) phenyl, (2) a 5-membered heterocyclic ring having one nitrogen atom and 0 to 3 additional heteroatoms independently selected from nitrogen, oxygen and sulfur, (3) a 6-membered heterocyclic ring having 1, 2 or 3 nitrogen atoms, or 1 nitrogen atom and one oxygen or sulfur atom, and (4) a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen, and (5) a 5- or 6-membered heterocyclic ring with from 1 to 4 heteroatoms selected from oxygen, sulfur and nitrogen fused to a $C_5$-$C_{10}$ carbocyclic ring.

In another embodiment, Z is a 5- or 6-membered heterocyclic ring with from 1 to 4 heteroatoms selected from oxygen, sulfur and nitrogen. In one subset Z is a 5-membered heterocycle having one nitrogen atom and 0 to 3 additional heteroatoms independently selected from N, O and S. In another subset Z is a 6-membered heterocycle having 1, 2 or 3 nitrogen atoms, or 1 nitrogen atom and an oxygen or sulfur atom. In yet another subset, Z is selected from the group consisting of thiazolyl, oxazolyl, pyridyl, dihydropyridyl, triazolyl (including 1,2,4-triazolyl and 1,2,3-triazolyl), tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, and oxadiazolyl (including 1,2,4-oxadiazolyl and 1,2,5-oxadiazolyl). In one subset of this embodiment, Y is methylene. In another subset of this embodiment Y is a bond.

In another embodiment, Z is a 5- or 6-membered heterocyclic ring with from 1 to 4 heteroatoms selected from oxygen, sulfur and nitrogen fused to a $C_5$-$C_{10}$ carbocyclic ring. In one subset the carbocyclic ring has 5 or 6 carbon atoms. In another subset the heterocycle is either a 5-membered heterocycle having one nitrogen atom and 0 to 3 additional heteroatoms independently selected from N, O and S, or a 6-membered heterocycle having 1, 2 or 3 nitrogen atoms, or 1 nitrogen atom and an oxygen or sulfur atom, and the carbocycle has 5 or 6 carbon atoms. In yet another subset Z is selected from the group consisting of: indolyl, benzimidazolyl, benzthiazolyl, quinolinyl, isoquinolinyl, tetrahydroquinolinyl, tetrahydroisoquinolinyl, chromenyl, benztriazolyl,

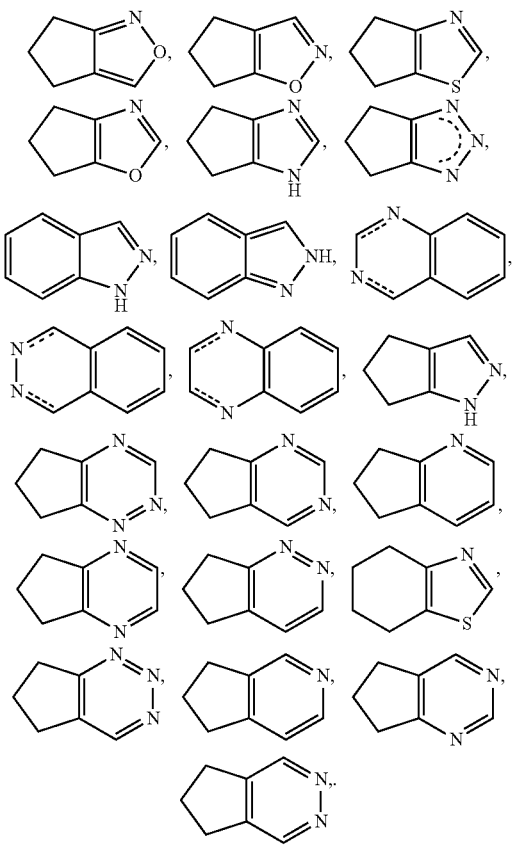

In another embodiment, Z is a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen. In one subset the fused ring has 2 to 5 heteroatoms, at least one of which is nitrogen. In another subset the fused ring has 2 to 4 nitrogen atoms and no other heteroatoms. In yet another subset the fused ring has one oxygen or sulfur atom, and 1 to 3 nitrogen atoms. In yet another subset, Z is selected from the group consisting of

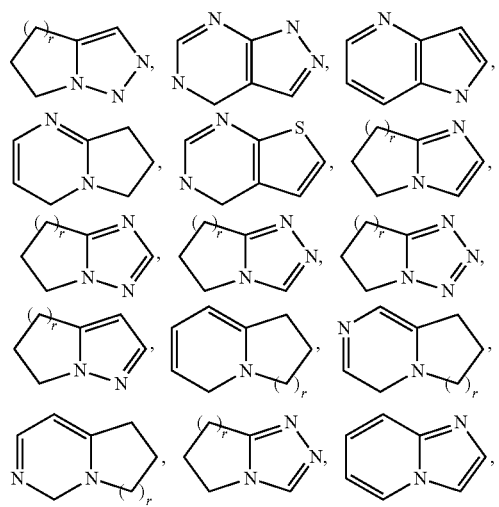

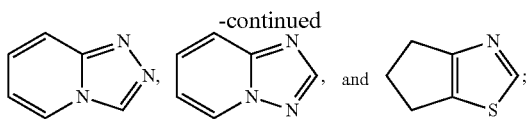, and 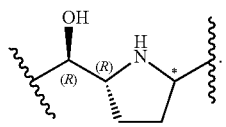;

and wherein r is 1 or 2. In one subset of this embodiment Y is methylene. In another subset of this embodiment Y is a bond.

In compounds described herein, examples of $R^3$ (when n is not 0) include, but are not limited to, —$NR^aR^a$, $C_1$-$C_6$alkyl optionally substituted with halogen or —$OR^a$, —$OR^a$, $C_3$-$C_6$cycloalkyl, phenyl optionally substituted with halogen, benzyl, pyridyl, pyrrolyl, thiazolyl, oxo, halogen, cyano, optionally halo-substituted $C_1$-$C_6$alkanoyl, ($C_1$-$C_6$alkyl)NHC(O)NH—, and —C(O)$NR^aR^a$. More particular examples of $R^3$ include methyl, ethyl, propyl, isopropyl, trifluoromethyl, oxo, fluoro, chloro, pyridyl and pyrrolyl.

In another embodiment, $R^3$ is selected from the group consisting of:
(1) $C_1$-$C_6$ alkyl optionally substituted with 1 to 5 groups independently selected from halogen, —$OR^a$, —$CO_2R^a$, and —$CONR^aR^b$,
(2) oxo,
(3) halogen,
(4) —$OR^a$,
(5) —$C(O)R^a$,
(6) —$C(O)NR^aR^b$, and
(7) —$NR^aR^b$;
wherein $R^a$ and $R^b$ are as defined above.

In one subset of this embodiment, $R^3$ is selected from the group consisting of:
(1) $C_1$-$C_6$ alkyl optionally substituted with 1 to 5 groups independently selected from halogen, —$OR^a$, —$CO_2R^a$, and —$CONR^aR^b$,
(2) oxo,
(3) halogen, and
(4) —$NR^aR^b$;
wherein each of $R^a$ and $R^b$ is selected from the group consisting of hydrogen and $C_1$-$C_6$ alkyl optionally substituted with 1 to 5 halogen atoms.

In another subset of this embodiment, $R^3$ is selected from the group consisting of:
(1) $C_1$-$C_6$ alkyl,
(2) oxo, and
(3) —$NH_2$.

In another subset of this embodiment, $R^3$ is methyl or ethyl. In another subset, $R^3$ is oxo. In yet another subset, $R^3$ is —$NH_2$.

In another embodiment, compounds described herein have the specified stereo configuration at the indicated chiral center:

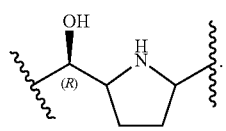

In another embodiment, compounds described herein have the specified stereoconfiguration at the indicated chiral centers, with the chiral center marked with an asterisk being R or S:

[Structure with OH, (R), N-H, and asterisk]

In one subset, the configuration at the chiral center marked with an asterisk is S.

In one embodiment, compounds described herein are as described in the Examples below.

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. The above Formulas I and Ia are shown without a definitive stereochemistry at certain positions. The present invention includes all stereoisomers of Formulas I and Ia and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound described herein may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH═C(OH)— groups (enol forms). Both keto and enol forms, individually as well as mixtures thereof, are included within the scope of the present invention.

Isotopes

In the compounds disclosed herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds disclosed herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds disclosed herein can be prepared without undue experimentation by conventional techniques well known to those skilled in the art or by processes analogous to those described in the Schemes and Examples herein using appropriate isotopically-enriched reagents and/or intermediates.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formulas I and Ia. As used herein, the term "solvate" refers to a complex of variable stoichiometry formed by a solute (i.e., a compound of Formula I or Ia) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrates include, but are not limited to, hemi-, mono, sesqui-, di- and trihydrates.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound described herein or with a compound which may not be a compound described herein, but which converts to a compound described herein in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are potent agonists of the β3-adrenoceptor, and as such are useful in treating or preventing diseases, disorders or conditions mediated by the activation of β3-adrenoceptor. Thus one aspect of the present invention provides a method for the treatment, control or prevention of such diseases, disorders, or conditions in a mammal which comprises administering to such mammal a therapeutically effective amount of a compound described herein. The term "mammal" includes human and non-human animals such as dogs and cats and the like. The diseases, disorders or conditions for which compounds of the present invention are useful in treating or preventing include, but are not limited to, (1) overactive bladder, (2) urinary incontinence, (3) urge urinary incontinence, (4) urinary urgency, (5) diabetes mellitus, (6) hyperglycemia, (7) obesity, (8) hyperlipidemia, (9) hypertriglyceridemia, (10) hypercholesterolemia, (11) atherosclerosis of coronary, cerebrovascular and peripheral arteries, (12) gastrointestinal disorders including peptid ulcer, esophagitis, gastritis and duodenitis, (including that induced by *H. pylori*), intestinal ulcerations (including inflammatory bowel disease, ulcerative colitis, Crohn's disease and proctitis) and gastrointestinal ulcerations, (13) neurogenic inflammation of airways, including cough, asthma, (14) depression, (15) prostate diseases such as benign prostate hyperplasia, (16) irritable bowel syndrome and other disorders needing decreased gut motility, (17) diabetic retinopathy, (18) preterm labor, and (19)-elevated intraocular pressure and glaucoma.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds described herein are administered orally.

The effective dosage of active ingredient employed may vary depending on the particular compound employed, the mode of administration, the condition being treated and the severity of the condition being treated. Such dosage may be ascertained readily by a person skilled in the art.

When treating overactive bladder (OAB) in conjunction with other anti-OAB agents, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release form. In the case of a 70 kg adult human, the total daily dose will generally be from about 0.7 mg to about 3500 mg, or more specifically, from about 0.7 mg to about 2000 mg. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 mg to about 100 mg per kg of animal body weight, preferably given in a single dose or in divided doses two to six times a day, or in sustained release faun. In the case of a 70 kg adult human, the total daily dose will generally be from about 0.7 mg to about 3500 mg. This dosage regimen may be adjusted to provide the optimal therapeutic response.

When treating diabetes mellitus and/or hyperglycemia, as well as other diseases or disorders for which compounds described herein are useful, generally satisfactory results are obtained when the compounds of the present invention are administered at a daily dosage of from about 0.001 mg to about 100 mg per kg of animal body weight, preferably given in a single dose or in divided doses two to six times a day, or in sustained release form. In the case of a 70 kg adult human, the total daily dose will generally be from about 0.07 mg to about 350 mg. This dosage regimen may be adjusted to provide the optimal therapeutic response.

In one embodiment, a compound of the present invention is used in the manufacture of a medicament for the treatment or prevention of a disease or disorder mediated by the activation of β3-adrenoceptor.

Another aspect of the present invention provides pharmaceutical compositions which comprises a compound described herein and a pharmaceutically acceptable carrier. The pharmaceutical compositions of the present invention comprise a compound described herein as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, intravesical, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds described herein can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds described herein may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Compounds described herein may be used in combination with other drugs that are used in the treatment/prevention/suppression or amelioration of the diseases or conditions for which compounds described herein are useful. Such other drugs may be administered, by a route and in an amount commonly used therefor, contemporaneously or sequentially with a compound described herein. When a compound described herein is used contemporaneously with one or more other drugs, a pharmaceutical unit dosage form containing such other drugs in addition to the compound described herein is preferred. Accordingly, the pharmaceutical compositions of the present invention include those that also contain one or more other active ingredients, in addition to a compound described herein. Examples of other active ingredients that may be combined with a compound described herein, either administered separately or in the same pharmaceutical compositions, include, but are not limited to:

(a) overactive bladder medicines including (i) muscarinic receptor antagonists (e.g. tolterodine, oxybutynin including S-oxybutynin, hyoscyamine, propantheline, propiverine, trospium including trospium chloride, solifenacin, darifenacin, imidafenacin, fesoterodine, temiverine, SVT-40776, 202405 by GlaxoSmithKline, TD6301, RBX9841, DDP200, PLD179, and other anticholinergics. See, for example, U.S. Pat. No. 5,382,600; U.S. Pat. No. 3,176,019; U.S. Pat. No. 3,480,626; U.S. Pat. No. 4,564,621; U.S. Pat. No. 5,096,890; U.S. Pat. No. 6,017,927; U.S. Pat. No. 6,174,896; U.S. Pat. No. 5,036,098; U.S. Pat. No. 5,932,607; U.S. Pat. No. 6,713,464; U.S. Pat. No. 6,858,650; and DD 106643. See also, U.S. Pat. No. 6,103,747; U.S. Pat. No. 6,630,162; U.S. Pat. No. 6,770,295; U.S. Pat. No. 6,911,217; U.S. Pat. No. 5,164,190; U.S. Pat. No. 5,601,839; U.S. Pat. No. 5,834,010; U.S. Pat. No. 6,743,441; WO2002000652; WO200400414853. As will be appreciated by those of skill in the art, these drugs may be administered orally or topically in standard or extended release forms, such as extended release tolterodine, extended release oxybutynin and transdermal oxybutynin), (ii) NK-1 or NK-2 antagonists (e.g. aprepitant, cizolirtine, compounds disclosed in WO2005/073191, WO2005/032464, and other reported NK-1 antagonists), (iii) alpha adrenergic receptor antagonists (e.g. alfuzosin, doxazocin, prazosin, tamsulosin, terazosin, and others), (iv) potassium channel openers (e.g. cromakalim, pinacidil, and others), (v) vanilloids and other afferent-nerve modulators—agonists and antagonists (e.g. capsaicin, resiniferatoxin, and others), (vi) dopamine D1 receptor agonists (e.g. pergolinde), (vii) serotonergic and/or norepinephrine reuptake inhibitors (e.g. duloxetine), (viii) neuromuscular junction inhibition of acetylcholine release (e.g. botulinum toxin), (ix) calcium channel blockers (e.g. diltiazem, nifedipine, verapamil, and others), (x) inhibitors of prostaglandin synthesis (e.g. flurbiprofen), (xi) gamma aminobutyric acid receptor antagonists (e.g. baclofen), (xii) vaginal estrogen preparations (xiii) selective norepinephrine reuptake inhibitors, (xiv) 5-HT2C agonists, (xv) voltage gated sodium channel blocker, (xvi) P2X purinergic receptor antagonists (e.g. P2X1 or P2X3 antagonists), (xvii) PAR2 inhibitors, (xviii) phosphodiesterase inhibitors (e.g. PDE1, PDE4, and PDE5 inhibitors); and (xix) ATP sensitive potassium channel openers.

(b) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(c) insulin or insulin mimetics;

(d) sulfonylureas such as tolbutamide and glipizide;

(e) α-glucosidase inhibitors (such as acarbose), (f) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrat, fenofibrate and benzafibrate), (iv) inhibitors of cholesterol absorption for example beta-sitosterol and ezetimibe, and (acyl CoA:cholesterol acyltransferase) inhibitors for example melinamide, (v) probucol, (vi) vitamin E, and (vii) thyromimetics;

(g) PPARδ agonists such as those disclosed in WO97/28149;

(h) antiobesity compounds such as fenfluramine, dexfenfluramine, phentermine, sibutramine, orlistat, and other β$_3$ adrenergic receptor agonists;

(i) feeding behavior modifying agents such as neuropeptide Y antagonists (e.g. neuropeptide Y5) such as those disclosed in WO 97/19682, WO 97/20820, WO 97/20821, WO 97/20822 and WO 97/20823;

(j) PPARα agonists such as described in WO 97/36579 by Glaxo;

(k) PPARγ antagonists as described in WO97/10813; and (l) serotonin reuptake inhibitors such as fluoxetine and sertraline.

In one embodiment, a compound of the present invention and a second active agent as described above are used in the manufacture of a medicament for the treatment or prevention of a disease or disorder mediated by the activation of β3-adrenoceptor.

The compounds of disclosed herein can be prepared according to the procedures of the following Schemes and Examples using appropriate materials, and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

A variety of chromatographic techniques may be employed in the preparation of the compounds. These techniques include, but are not limited to: High Performance Liquid Chromatography (HPLC) including normal phase, reversed phase, and chiral phase HPLC; Medium Pressure Liquid Chromatography (MPLC), Super Critical Fluid Chromatography; preparative Thin Layer Chromatography (prep TLC); flash chromatography with silica gel or reversed-phase silica gel; ion-exchange chromatography; and radial chromatography. All temperatures are degrees Celsius unless otherwise noted.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Throughout the application, the following terms have the indicated meanings unless noted otherwise:

| Term | Meaning |
|---|---|
| Ac | Acyl ($CH_3C(O)$-) |
| Aq. | Aqueous |
| Bn | Benzyl |
| BOC (Boc) | t-Butyloxycarbonyl |
| BOP | Benzotriazol-1-yloxytris(dimethylamino)-phosphonium hexafluorophosphate |
| ° C. | Degree Celsius |
| Calc. or calc'd | Calculated |
| Celite | Celite ™ diatomaceous earth |
| DCC | Dicyclohexylcarbodiimide |
| DCM | Dichloromethane |
| DIEA | N,N-diisopropyl-ethylamine |
| DMAP | 4-Dimethylaminopyridine |
| DMF | N,N-dimethylformamide |
| EDC | 1-Ethyl-3-(3-dimethylaminopropyl)carbodiimide |
| Eq. or equiv. | Equivalent(s) |
| ES-MS and ESI-MS | Electron spray ion-mass spectroscopy |
| Et | Ethyl |
| EtOAc | Ethyl acetate |
| g | Gram(s) |
| h or hr | Hour(s) |
| HATU | O-(7-azabenzotriazol-1-yl)-N,N,N',N'-tetramethyluronium hexafluorophosphate |
| HCl | Hydrogen chloride |
| HOAc | Acetic acid |
| HOAT | 1-Hydroxy-7-azabenzotriazole |
| HOBT | 1-Hydroxybenzotriazole |
| HPLC | High performance liquid chromatography |
| IPA | Isopropyl alcohol |
| kg | Kilogram(s) |
| LC/MS or LC-MASS | Liquid chromatography mass spectrum |
| L | Liter(s) |
| LDA | Lithium diisopropylamide |
| LiOH | Lithium hydroxide |
| LiHMDS | Lithium bis(trimethylsilyl)amide |
| M | Molar(s) |
| Me | Methyl |
| MeOH | Methanol |
| MF | Molecular formula |
| min | Minute(s) |
| mg | Milligram(s) |
| mL | Milliliter(s) |
| mmol | Millimole(s) |
| MOZ (Moz) | p-Methoxybenzyloxycarbonyl |
| MP | Melting point |
| MS | Mass spectrum |
| NaH | Sodium hydride |
| nM | Nanomolar |
| OTf | Trifluoromethanesulfonyl |
| 10% Pd/C | Palladium, 10 weight percent on activated carbon |
| Ph | Phenyl |
| Prep. | Preparative |
| Ref. | Reference |
| r.t. or rt or RT | RT |
| Sat. | Saturated |
| SCF $CO_2$ S | Super critical fluid carbon dioxide |
| TBAF | Tetrabutylammonium fluoride |
| TBAI | Tetrabutylammonium iodide |
| TBDPS | Tert-butyl diphenylsilyl |
| TBS, TBDMS | Tert-butyl dimethylsilyl |
| TEA or $Et_3N$ | Triethylamine |
| Tf | Triflate or trifluoromethanesulfonate |
| TFA | Trifluoroacetic acid |
| THF | Tetrahydrofuran |
| TLC | Thin-layer chromatography |
| TMS | Trimethylsilyl |
| TMSOK | Potassium trimethylsilanolate |

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT and HOAT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. MOZ and BOC are commonly used protecting groups in organic synthesis, and their removal conditions are known to those skilled in the art. For example, MOZ may be removed, by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of MOZ groups can also be achieved by treatment with a solution of trifluoroacetic acid, hydrochloric acid or hydrogen chloride gas, in a solvent such as dichloromethane, methanol, or ethyl acetate. Removal of BOC protecting groups is carried out with a strong acid, such as trifluoroacetic acid, hydrochloric acid, or hydrogen chloride gas, in a solvent such as dichloromethane, methanol, or ethyl acetate.

Reaction Schemes below illustrate the methods employed in the synthesis of the compounds described herein. All substituents are as defined above unless indicated otherwise. The synthesis of the novel compounds described herein may be accomplished by one or more of several similar routes. The Examples further illustrate details for the preparation of the compounds described herein. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless noted otherwise. Mass spectra (MS) were measured by electron-spray ion-mass spectroscopy.

In Scheme I, amino diol (I-1) is treated with acetone in toluene and the reaction mixture is refluxed under a Dean-Stark trap to remove water. After removal of the solvent, the unpurified acetonide compound is treated with di-tert-butyl dicarbonate ($Boc_2O$) at ambient temperature to afford Boc protected compound I-2. Conversion of alcohol I-2 to aldehyde I-3 can be achieved by oxidation such as a Swern oxidation (Jayaraman, M.; Deshmukh, A. R.; Bhawal. B. M. Tetrahedron, 1996, 52, 8989-9004). Treatment of I-3 with (triphenylphosphoranylidene)acetaldehyde for a period of 24-40 h in an inert organic solvent, such as dichloromethane, affords unsaturated aldehyde I-4. The carbon-carbon double bond in I-4 is then reduced via catalytic hydrogenation with 10% palladium on carbon under hydrogen atmosphere in a solvent such as acetone to afford the saturated aldehyde 1-5. Treatment of aldehyde I-5 with a Wittig reagent derived from a phosphonium salt such as (4-methoxycarbonylbenzyl) triphenylphosphonium chloride in the presence of a base such as N,N-diisopropylethylamine or sodium tert-butoxide affords I-6. The product is a mixture of cis and trans alkene. The reaction is usually performed in an inert organic solvent such as tetrahydrofuran or dimethyl sulfoxide and under an inert atmosphere such as nitrogen.

After both the acetonide and Boc groups are removed under acid conditions such as via treatment with a hydrochloride methanol solution, amino alcohol I-7 is converted to I-8 via treatment with tert-butyldimethylsilyl chloride (TBSCl) and benzyl chloroformate (CbzCl) in the presence of an anhydrous organic base, such as N,N-diisopropylethylamine. Oxidation of the olefin with 3-chloroperbenzoic acid (mCPBA) at ambient temperature affords expoide I-9 which contains a mixture of diastereomers.

Scheme I

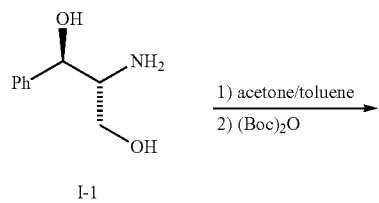

I-1

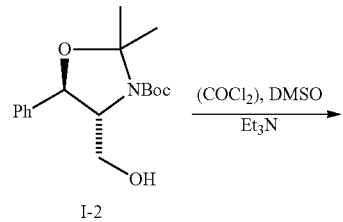

I-2

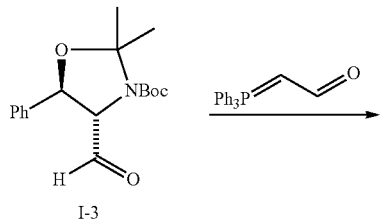

I-3

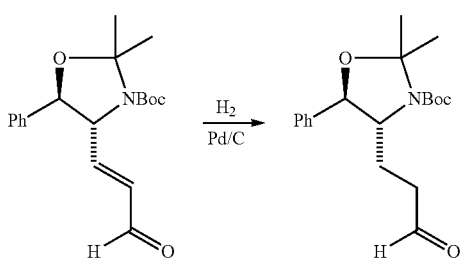

I-4     I-5

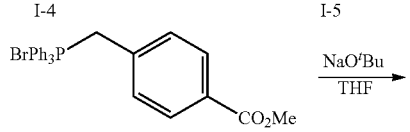

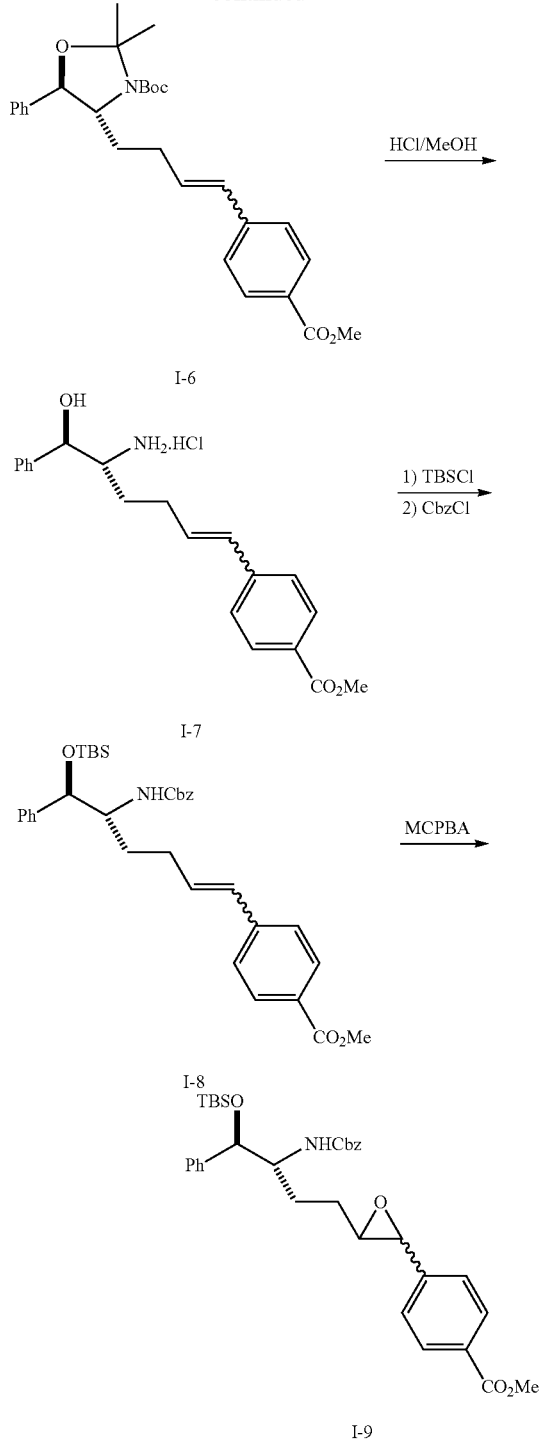

In Scheme II, conversion of epoxide I-9 to ketone compound I-10 can be achieved by Pd catalyzed rearrangement in the presence of a ligand such as triphenylphosphine under an inert atmosphere such as nitrogen. The reaction is usually performed in refluxed ethanol for a period of 5-16 h. This ketone material I-10 forms the basis in which the pyrrolidine core can be synthesized. Hydrogenation of intermediate I-10 by treatment with 10% palladium on carbon catalyst under hydrogen atmosphere in a solvent such as ethanol achieves hydrogenation of the olefin along with removal of the Cbz protecting group in addition to a ring closure via an intramolecular imine formation between the free amine and ketone and reduction of the imine to form the pyrrolidine compound I-11. Protection of the pyrrolidine is accomplished by the addition of tert-butyl Bicarbonate (Boc₂O) to I-11. The reaction is usually performed in an inert organic solvent, such as THF, and under an inert atmosphere, such as nitrogen, affording the product I-12. Removal of the tert-butyldimethylsilyl (TBS) group via treatment with a tetrabutylammonium fluoride solution in an inert organic solvent, such as THF, containing 5% water, followed by ester hydrolysis via treatment with sodium hydroxide or lithium hydroxide solution, produces carboxylic acid compound I-13 which can be used for standard amide coupling.

Scheme III outlines the process of synthesizing the acetylene intermediate via aldol chemistry to set the chirality of both the hydroxyl group and left hand portion of the pyrrolidine. From there, this acetylene intermediate can be used to synthesize both the cis and trans pyrrolidines. Commercially available I-14 is first treated with trimethylacetyl chloride in the presence of a weak organic base such as triethylamine at −25° C. for 2 h. The sequential addition of anhydrous lithium chloride and (S)-(−)-4-benzyl-2-oxazolidinone to the mixture followed by gradual warming to RT over a period of time between 12 and 16 h affords imide I-15. The reaction is usually performed in an inert organic solvent, such as THF, under an inert atmosphere, such as nitrogen. The alcohol I-17 is prepared according to published procedures (See Evans et al., *J. Am. Chem. Soc.* 2002, 124, 392-394). For example, treatment of I-15 with anhydrous magnesium chloride, triethylamine, the appropriate aldehyde I-16, such as 6-chloropyridine-3-carboxaldehyde, and chlorotrimethylsilane at RT over a period of 72 h yields the trimethylsilyl ether of the aldol product I-17. The reaction is usually performed in an organic solvent such as ethyl acetate under an inert atmosphere such as nitrogen. Treatment of the trimethylsilyl ether intermediate with a trifluoroacetic acid and methanol mixture affords the alcohol I-17.

Conversion of I-17 to I-18 can be achieved by selecting an appropriate silyl protecting agent, such as tert-butyl dimethylsilyl trifluoromethanesulfonate, and reacting it in the presence of a weak organic base, such as 2,6-lutidine, at 0° C. for a period of between 12 to 16 h. The hydrolysis of imide 1-18 is achieved by treatment with lithium peroxide at 0° C. for a period of 15-18 h. The peroxy acid is subsequently reduced with an aqueous solution of sodium sulfite to afford the carboxylic acid 1-19. The reaction is usually performed in a mixture of an inert organic solvent, such as THF, and water under an inert atmosphere, such as nitrogen.

Finally, I-19 is treated with diphenylphosphoryl azide in the presence of a weak organic base such as triethylamine for a period of 6 h at RT. Addition of the appropriate alcohol, such as 4-methoxybenzyl alcohol, with heating to 100° C. for a period between 12 and 16 h yields the corresponding carbamate I-20. The reaction is usually performed in an inert organic solvent, such as toluene, under an inert atmosphere, such as nitrogen. This material forms the basis in which the pyrrolidine core can be synthesized.

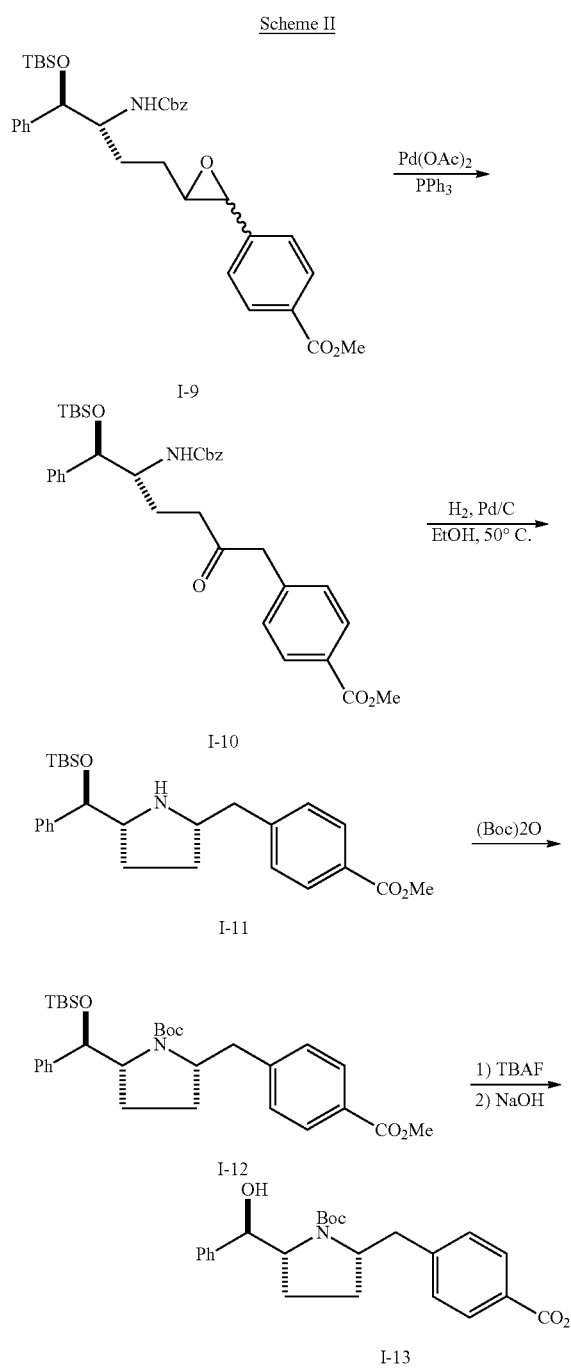

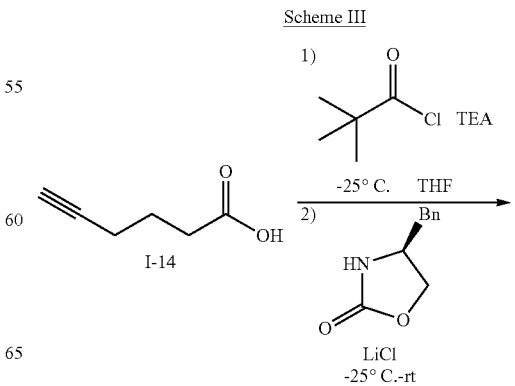

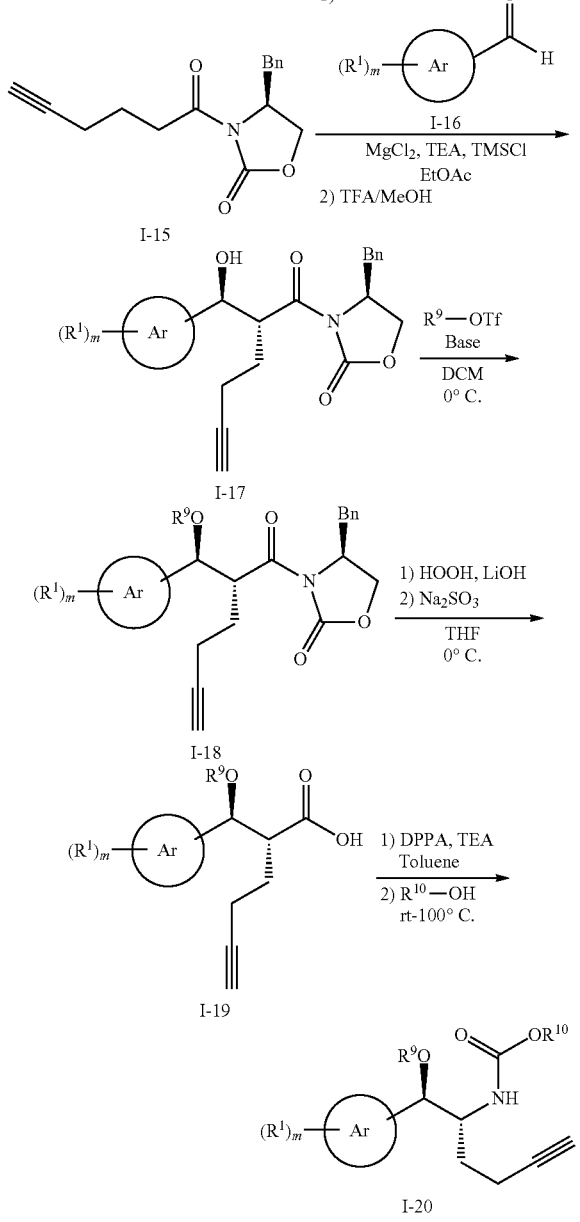

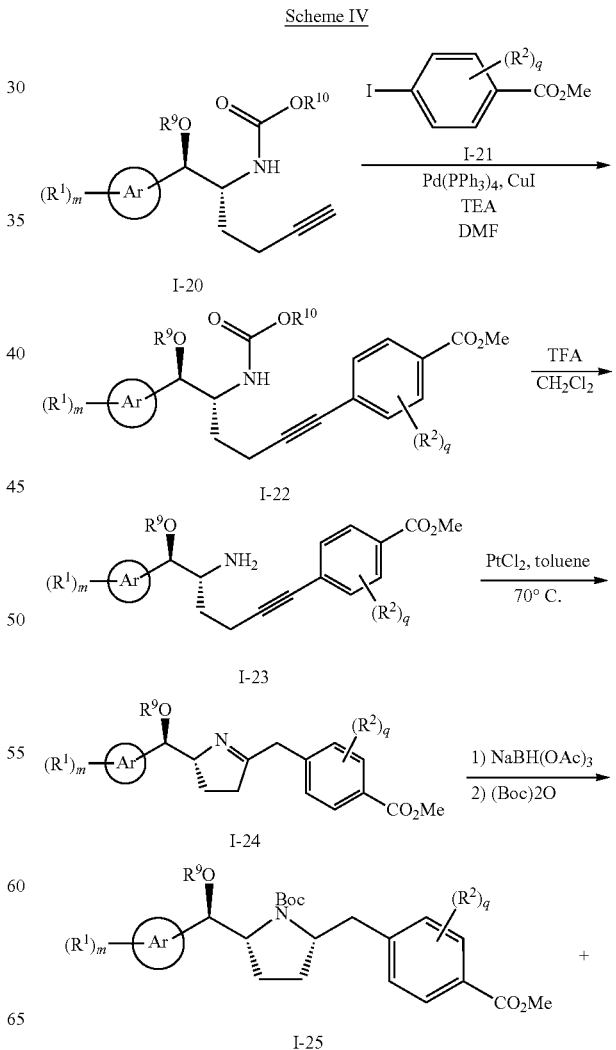

include trifluoroacetic acid in an organic solvent, such as dichloromethane and hydrochloric acid in an organic solvent such as ether. Amine I-23 subsequently undergoes an intramolecular ring closure with the alkyne to afford the imine I-24 under the influence of catalytic amount $PtCl_2$, in an inert organic solvent such as toluene, at a temperature of 70° C. under an inert atmosphere, such as argon. Reduction of the imine I-24 can be achieved by treatment with sodium triacetoxyborohydride $NaBH(OAc)_3$ in an organic solvent, such as dichloromethane, at a temperature of 0° C. under an inert atmosphere, such as nitrogen. This affords mixture of cis- and trans-pyrrolidine which can be used in the next step. Protection of the cis and trans pyrrolidine is accomplished by the addition of tert-butyl dicarbonate ($Boc_2O$) in the presence of a weak organic base, such as triethylamine or N,N-diisopropylethylamine. The reaction is usually performed in an inert organic solvent, such as dichloromethane, and under an inert atmosphere, such as nitrogen. This affords Boc protected cis-pyrrolidine (I-25) and trans-pyrrolidine (I-26) intermediates which can be separated by silica gel chromatography. I-25 is the major diastereomer produced in the reaction and is the first diastereomer to elute off the column.

Scheme IV describes the synthesis of the cis-pyrrolidine (I-25) and trans-pyrrolidine (I-26) intermediates from the appropriately protected amine 1-20 described in Scheme III. The alkyne I-20 may be reacted in a Sonagashira type cross-coupling reaction with the corresponding aryl halide I-21 to afford I-22 using the appropriate reaction conditions known to those skilled in the art. The reaction conditions can include the use of catalysts, such as tetrakis(triphenylphosphine)-palladium(0), with copper(I) iodide in the presence of an organic base, such as triethylamine, or palladium(II) acetate with an organic base, such as tetrabutylammonium acetate, in an organic solvent, such as acetonitrile or DMF, under an inert atmosphere, such as nitrogen. The carbamate protecting group of I-22 can be removed using the appropriate reaction conditions known to those skilled in the art to afford the corresponding amine I-23. The reaction conditions can

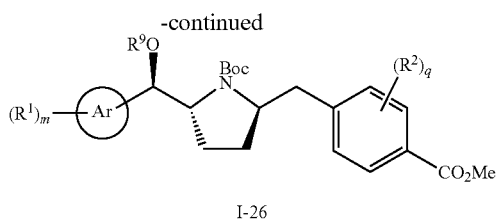

I-26

Scheme V describes the synthesis of cis and trans-pyrrolidine carboxylic acid from their corresponding intermediates I-25 and I-26 described in Scheme IV. In some cases hydrogenation is required in order to remove halogen substituents $R^1$ and $R^2$. The reaction is usually performed by treatment of I-25 or I-26 with 10% palladium on carbon in the presence of potassium acetate under an atmosphere of hydrogen between 15 and 50 psi in a solvent, such as ethanol, over an 8-14 h period of time. Ester hydrolysis via treatment with sodium hydroxide or lithium hydroxide aqueous solution produces carboxylic acid compound I-27. Removal of the silyl protecting group of I-27 via treatment with a tetrabutylammonium fluoride solution in an inert organic solvent, such as THF, containing 5% water affords alcohol acids of general structural formula I-28. The reaction is usually performed in an inert organic solvent such as THF, between RT and 50° C., for a period of 12-24 h.

Scheme V

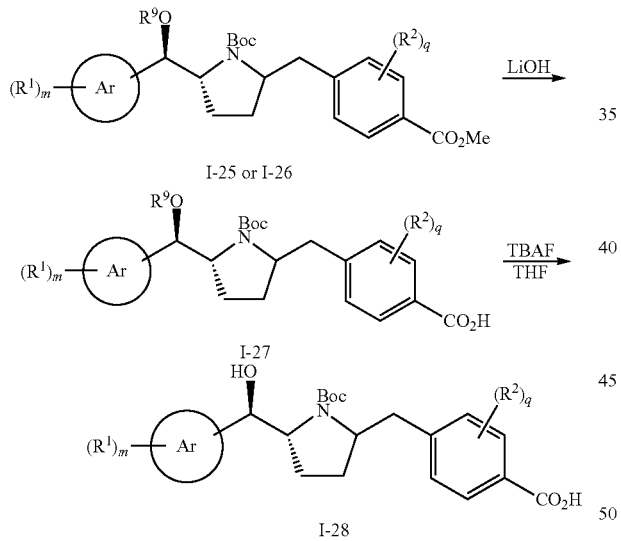

Scheme VI describes an alternative synthesis of pyrrolidine carboxylic acid ester I-25 from the appropriately protected amine I-20 described in Scheme III and appropriate 1-bromo-4 iodobenzene. The alkyne I-20 reacts in a Sonagashira type cross-coupling reaction with the corresponding 1-bromo-4 iodobenzene I-29 to afford I-30 using the appropriate reaction conditions known to those skilled in the art. The carbamate protecting group of I-30 can be removed using the appropriate reaction conditions such as trifluoroacetic acid in dichloromethane. Subsequent intramolecular ring closure affords the imine I-31 under the influence of catalytic amount of $PtCl_2$, in an inert organic solvent such as toluene, at a temperature of 85° C. under an inert atmosphere, such as nitrogen. Reduction of the imine I-31 can be achieved by treatment with sodium triacetoxyborohydride $NaBH(OAc)_3$ in an organic solvent, such as dichloromethane, at a temperature of 0° C. under an inert atmosphere, such as nitrogen. This affords mixture of cis- and trans-pyrrolidine which can be used in the next step. Protection of the cis and trans pyrrolidine is accomplished by the addition of tert-butyl dicarbonate ($Boc_2O$) in the presence of a weak organic base, such as triethylamine or N,N-diisopropylethylamine. The reaction is usually performed in an inert organic solvent, such as dichloromethane, and under an inert atmosphere, such as nitrogen. This affords Boc protected cis-pyrrolidine (I-32) and trans-pyrrolidine intermediates which can be separated by silica gel chromatography. I-32 is the major diastereomer produced in the reaction and is the first diastereomer to elute off the column. Carbonylation of bromide I-32 can be achieved by the use of catalysts, such as $Pd(dppf)Cl_2$, in the presence of an organic base, such as triethylamine in an organic solvent, such as methanol, under carbon monoxide atmosphere.

Scheme VI

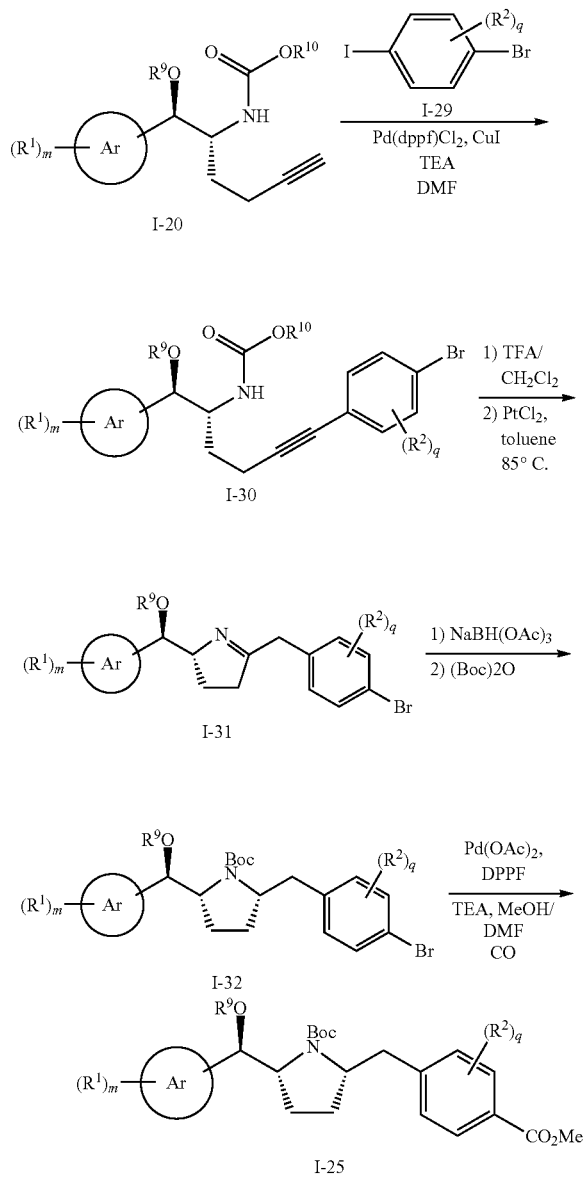

Scheme VII describes the synthesis of amides of structural formula I-35 via appropriate amide bond formation conditions known to those skilled in the arts such as EDC, DCC, HATU or BOP in the presence of the appropriate additive such as HOAT or HOST, and either with or without a suitable organic base, such as N,N-diisopropylethylamine or triethylamine. For example, a desired amine I-33 and pyrrolidine carboxylic acid I-28 can be treated with N-(3-dimethylaminopropyl)-N-ethylcarbodiimide (EDC) hydrochloride and 1-hydroxybenzotriazole (HOBt) in the presence of a suitable organic base, such as N,N-diisopropylethylamine. The reaction is usually performed in an inert organic solvent such as N,N-dimethylformamide, at RT for a period of 2-24 h. Removal of the Boc protecting groups of I-34 via treatment with a solution of TFA in an inert organic solvent, such as dichloromethane, at ambient temperature for a period of time between 1 and 6 h affords the final desired products of various amides shown in the general structural formula I-35. Alternatively, treatment of I-34 with a solution of hydrogen chloride in an organic solvent, such as 1,4-dioxane or ethyl acetate, also yields the desired product of structural formula I-35. Additional de-protection steps may be included if there are useful protecting groups known to those skilled in the art necessary to allow the chemistry to proceed in a facile fashion. These protecting groups may include trityl groups, benzylcarbamate groups, ester groups, silyl groups or other groups suitable for the protection of heterocyclic compounds or the functional groups such as amines, hydroxyls, carboxylic acids or other groups known to those skilled in the art.

Scheme VII

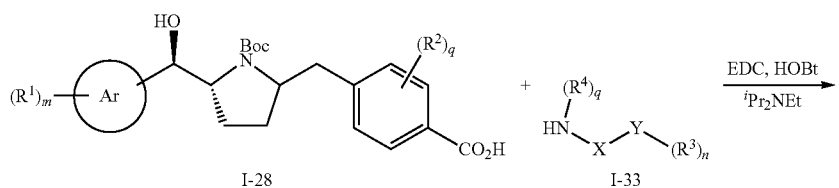

I-28 + I-33

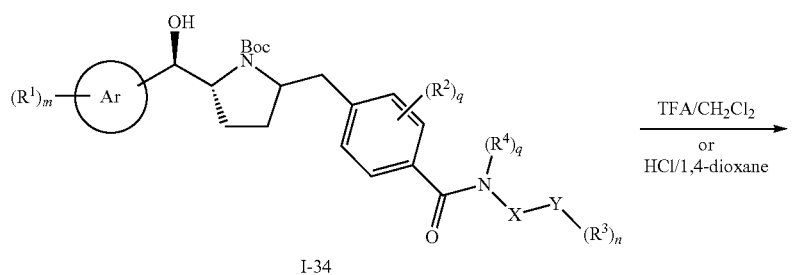

I-34

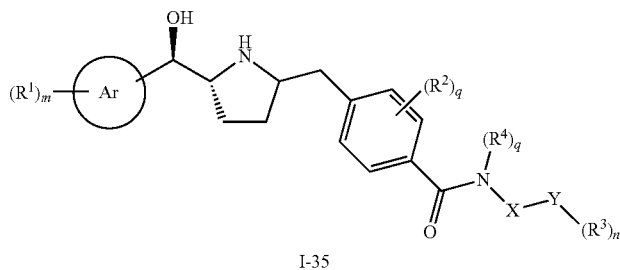

I-35

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Intermediate 1

4-({(2S,5R)-1-(tert-butoxycarbonyl)-5-[(R)-hydroxy(phenyl)methyl]pyrrolidin-2-yl}methyl)benzoic acid (i-1)

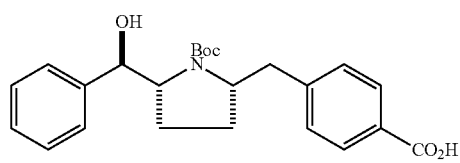

Step A: tert-butyl (4R,5R)-2,2-dimethyl-4-[(1E)-3-oxoprop-1-en-1-yl]-5-phenyl-1,3-oxazolidine-3-carboxylate

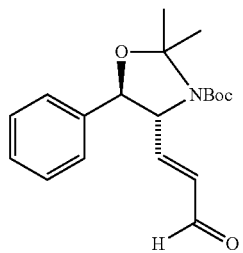 [SMILES: CC(C)(C)OC(=O)N1[C@H](/C=C/C=O)[C@@H](c2ccccc2)OC1(C)C]

Compound tert-butyl (4S,5R)-4-formyl-2,2-dimethyl-5-phenyl-1,3-oxazolidine-3-carboxylate (1.30 g, 4.26 mmol) in dichloromethane (10 ml) at ambient temperature was added to (triphenylphosphoranylidene)acetaldehyde (1.69 g, 5.54 mmol). The reaction mixture was stirred at ambient temperature for 40 h. After removal of the solvent, the residue was purified by using a Biotage Horizon® system (0-20% ethyl acetate/hexanes mixture) to afford the title compound (0.96 g, 68%) as a viscous oil. $^1$H NMR (CDCl$_3$, 500 MHz): δ9.61 (d, J=7.6 Hz, 1H), 7.42-7.37 (m, 5H), 6.73 (m, 1H), 5.96 (dd, J=15.8, 7.7 Hz, 1H), 4.78 (m, 1H), 4.29 (br, 1H), 1.80-1.41 (m, 15H). LC-MS 354.3 (M+23).

Step B: 3-oxazolidinecarboxylic acid, 2,2-dimethyl-4-(3-oxopropyl)-5-phenyl-, 1,1-dimethylethyl ester, (4R,5R)

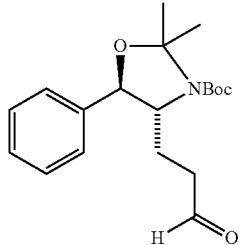 [SMILES: CC(C)(C)OC(=O)N1[C@H](CCC=O)[C@@H](c2ccccc2)OC1(C)C]

To a solution of the title compound from Step A above (19.6 g, 59.1 mmol) in acetone (150 ml) was added 10% palladium on activated carbon (1.9 g). The reaction mixture was flushed with N$_2$ then it was stirred at ambient temperature under a hydrogen balloon for 24 h. The palladium was filtered off on celite. After removal of the solvent, the residue was purified by using a Biotage Horizon® system (0-20% then 20% ethyl acetate/hexanes mixture) to afford the title compound (11.5 g, 58%) as colorless oil. $^1$H NMR (CDCl$_3$, 500 MHz): δ9.77 (s, 1H), 7.46-7.35 (m, 5H), 4.73 (d, J=7.3 Hz, 1H), 3.92 (m, 1H), 2.50-2.44 (m, 2H), 2.25-2.07 (m, 2H), 1.67 (s, 3H), 1.60 (s, 3H), 1.52 (s, 9H). LC-MS 356.4 (M+23).

Step C: tert-butyl (4R,5R)-4-{(3E)-4-[4-(methoxycarbonyl)phenyl]but-3-en-1-yl}-2,2-dimethyl-5-phenyl-1,3-oxazolidine-3-carboxylate and tert-butyl (4R,5R)-4-{(3Z)-4-[4-(methoxycarbonyl)phenyl]but-3-en-1-yl}-2,2-dimethyl-5-phenyl-1,3-oxazolidine-3-carboxylate

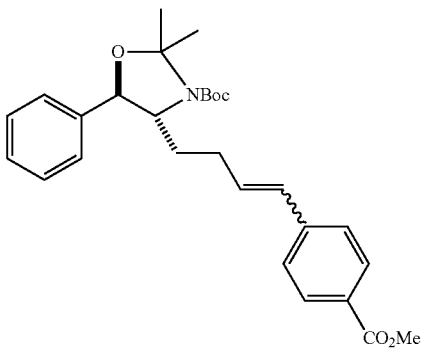 [SMILES: COC(=O)c1ccc(C=CCC[C@@H]2[C@@H](c3ccccc3)OC(C)(C)N2C(=O)OC(C)(C)C)cc1]

To a solution of 4-carbomethoxybenzyl triphenylphosphonium chloride (7.68 g, 17.2 mmol) in dimethyl sulfoxide (40 ml) in ambient temperature water bath was added sodium tert-butoxide (1.58 g, 16.4 mmol) in portions. The reaction mixture was stirred at ambient temperature for 45 minutes then was added a solution of the title compound from Step B above (5.21 g, 15.6 mmol) in DMSO (10 ml). The reaction mixture was stirred at ambient temperature for 1.5 h. 200 ml of ether was added and the solid was filtered off. The filtrate was washed with water and the solvent was removed under reduced pressure. The residue was purified by using a Biotage Horizon® system (0-10% then 10% ethyl acetate/hexanes mixture) to afford the title compound as a cis/trans mixture (5.64 g, 77%). LC-MS 488.4 (M+23).

Step D: methyl 4-[(1E,5R,6R)-5-amino-6-hydroxy-6-phenylhex-1-en-1-yl]benzoate and methyl 4-[(1Z,5R,6R)-5-amino-6-hydroxy-6-phenylhex-1-en-1-yl]benzoate

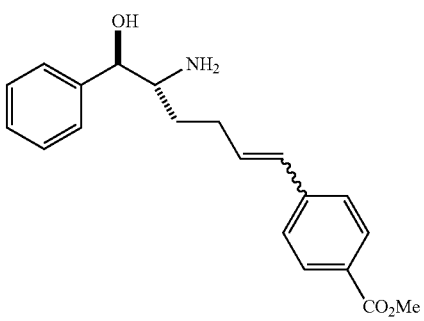 [SMILES: COC(=O)c1ccc(C=CCC[C@@H](N)[C@H](O)c2ccccc2)cc1]

Acetyl chloride (3.55 ml, 50.0 mmol) was added to methanol (50 ml) at 0° C. After being stirred at that temperature for 1 h, the resulting hydrogen chloride methanol solution was added to the title compound from Step C above (5.64 g, 12.1 mmol). The reaction mixture was stirred at ambient temperature for 5 h. About 100 ml ether was added to the reaction mixture and the solid was collected. After removal most of the solvent of the filtrate under reduced pressure, more ether was added and the solid was collected again by filtration. Combined white solid (2.96 g, 61%) was obtained as hydrogen chloride salt of the title compounds which contains both cis and trans olefin. LC-MS 326.2 (M+1).

Step E: methyl 4-((1E,5R,6R)-5-{[(benzyloxy)carbonyl]amino}-6-{[tert-butyl(dimethyl)silyl]oxy}-6-phenylhex-1-en-1-yl)benzoate and methyl 4-((1Z,5R,6R)-5-{[(benzyloxy)carbonyl]amino}-6-{[tert-butyl(dimethyl)silyl]oxy}-6-phenylhex-1-en-1-yl)benzoate

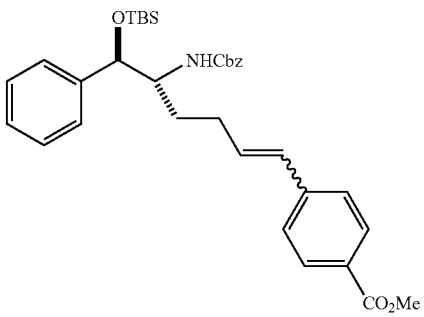 [SMILES: COC(=O)c1ccc(C=CCC[C@@H](NC(=O)OCc2ccccc2)[C@H](O[Si](C)(C)C(C)(C)C)c2ccccc2)cc1]

To a solution of the title compound from Step D above (2.96 g, 8.18 mmol) in dichloromethane (40 ml) and N,N-dimethylformamide (5 ml) was added N,N-diisopropylethylamine (5.84 ml, 32.7 mmol), followed by tert-butyldimethylsilyl chloride (1.60 g, 10.6 mmol). The reaction mixture was stirred at ambient temperature for 2 h. Saturated NaHCO$_3$ (50 ml) was added to quench the reaction and the organic layer was separated, dried over Na$_2$SO$_4$. After removal of the volatiles, the residue was purified by using a Biotage Horizon® system (0-5% then 5% methanol with 10% ammonia/dichloromethane mixture) to afford the TBS intermediate as a cis/trans mixture (3.65 g, 100%). LC-MS 440.3 (M+1).

The TBS intermediate (4.37 g, 9.95 mmol) in dichloromethane (80 ml) at −78° C. was added N,N-diisopropylethylamine (3.46 ml, 19.9 mmol) followed by benzyl chloroformate (1.83 ml, 13.0 mmol). The reaction mixture was stirred at −78° C. for 30 minutes, then at ambient temperature for 4 h. Saturated NaHCO$_3$ (50 ml) was added to quench the reaction and the organic layer was separated. After removal of the volatiles, the residue was purified by column chromatography eluting with 0-10% then 10% ethyl acetate in hexanes to afford the title compound as a cis/trans mixture (3.3 g, 58%). MS: m/z (ESI) 574 (M+1).

Step F: methyl 4-[3-((3R,4R)-3-{[(benzyloxy)carbonyl]amino}-4-{[tert-butyl(dimethyl)silyl]oxy}-4-phenylbutyl)oxiran-2-yl]benzoate

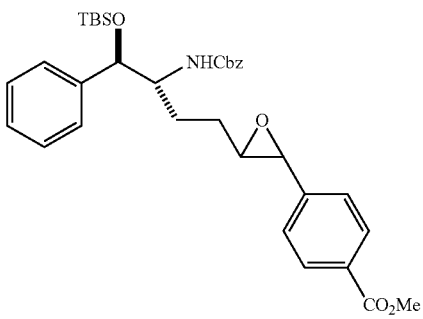 [SMILES: COC(=O)c1ccc(C2OC2CC[C@@H](NC(=O)OCc2ccccc2)[C@H](O[Si](C)(C)C(C)(C)C)c2ccccc2)cc1]

To a solution of the title compound from Step E above (0.880 g, 1.85 mmol) in dichloromethane (20 ml) was added 3-chloroperbenzoic acid (0.60 g, 2.0 mmol) in portions. The reaction mixture was stirred at ambient temperature overnight and it was then washed with sodium carbonate and dried over magnesium sulfate. After concentration, the residue was purified by flash column chromatography (0-70% ethyl acetate in hexanes) and 0.90 g (100%) of the title compound was obtained as mixture of diastereomers. MS: m/z (ESI) 590 (M+1).

Step G: methyl 4-((5R,6R)-5-{[(benzyloxy)carbonyl]amino}-6-{[tert-butyl(dimethyl)silyl]oxy}-2-oxo-6-phenylhexyl)benzoate

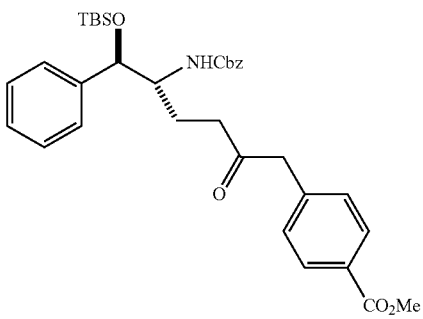 [SMILES: COC(=O)c1ccc(CC(=O)CC[C@@H](NC(=O)OCc2ccccc2)[C@H](O[Si](C)(C)C(C)(C)C)c2ccccc2)cc1]

A mixture of the title compound from Step F above (1.00 g, 1.69 mmol) and palladium acetate Pd(OAc)$_2$ (0.064 g, 0.28 mmol) in ethanol (15 ml) was degassed and flushed with N$_2$, and then triphenylphosphine (0.298 g, 1.137 mmol) was added. The reaction mixture was refluxed overnight. After removal of the solvent, the residue was purified by column chromatography (0-20% then 20% ethyl acetate in hexanes). 0.50 g (50%) of the title compound was obtained. $^1$H NMR (CDCl$_3$, 400 MHz): δ8.14 (d, J=8.6 Hz, 2H), 7.53-7.28 (m, 12H), 5.13 (s, 2H), 4.97 (d, J=9.4 Hz, 1H), 4.86 (s, 1H), 4.06 (s, 3H), 3.85 (s, 2H), 2.77-2.64 (m, 2H), 2.07 (m, 1H), 1.85-1.79 (m, 2H), 1.05 (s, 9H), 0.19 (s, 3H), 0.00 (s, 3H). MS: m/z (ESI) 590 (M+1).

Step H: methyl 4-({(5S,5R)-5-[(R)-{[tert-butyl(dimethyl)silyl]oxy}(phenyl)methyl]pyrrolidin-2-yl}methyl)benzoate

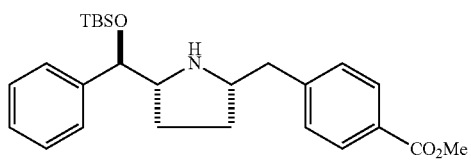

To a solution of the title compound from Step G above (9.00 g, 0.625 mmol) in ethanol (200 ml) was added 3.0 g of 10% Pd/C under argon. The reaction mixture was stirred at 50° C. under a H$_2$ balloon overnight. After filtration and removal of the solvent, 6.0 g (90%) of the title compound was obtained which was directly used for the next step without further purification. $^1$H NMR (CDCl$_3$, 400 MHz): δ7.89 (d, J=7.9 Hz, 2H), 7.24-7.19 (m, 7H), 4.40 (d, J=7.0 Hz, 1H), 3.82 (s, 3H), 3.26-3.09 (m, 2H), 2.75 (d, J=7.0 Hz, 2H), 1.71-1.63 (m, 2H), 1.33-1.25 (m, 2H), 0.75 (s, 9H), 0.00 (s, 6H). MS: m/z (ESI) 440 (M+1).

Step I: tert-butyl (2R,5S)-2-[(R)-{[tert-butyl(dimethyl)silyl]oxy}(phenyl)methyl]-5-[4-(methoxycarbonyl)benzyl]pyrrolidine-1-carboxylate

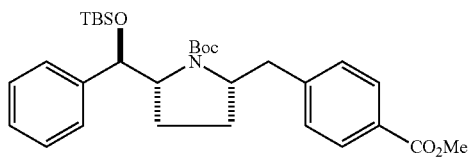

To a solution of the title compound from Step H (1.01 g 2.29 mmol) in tetrahydrofuran (10 ml) was added di-tert-butyl dicarbonate (0.749 g 3.43 mmol) and the reaction mixture was allowed to stir at ambient temperature overnight. After concentration, the residue was purified by using a Biotage Horizon® system (0-10% ethyl acetate/hexanes mixture) to afford the title compound (0.81 g, 66%) as a colorless viscous oil. LC-MS 562.3 (M+23).

Step J: 4-({(2S,5R)-1-(tert-butoxycarbonyl)-5-[(R)-hydroxy(phenyl)methyl]pyrrolidin-2-yl}methyl)benzoic acid (i-1)

To the title compound from Step I above (1.30 g, 2.41 mmol) was added 10 ml of 2N tetrabutylammonium fluoride tetrahydrofuran solution and the reaction mixture was allowed to stir at ambient temperature overnight. The reaction mixture was poured into water (50 ml), extracted with tert-butyl methyl ether (20 ml×3). The combined organic layers were washed with water, dried over anhydrous sodium sulfate, and concentrated. 1.00 g (100%) of the hydroxyl ester compound was obtained which was directly used for the next step without further purification. $^1$H NMR (CDCl$_3$, 400 MHz): δ7.93 (d, J=8.2 Hz, 2H), 7.31-7.19 (m, 7H), 4.39 (d, J=8.6 Hz, 1H), 4.09-4.01 (m, 2H), 3.84 (s, 3H), 3.08 (br, 1H), 2.54 (br, 2H), 1.67-1.41 (m, 13H). MS: m/z (ESI) 426 (M+1).

To a solution of the hydroxyl eater compound (4.50 g, 10.6 mmol) in methanol (100 ml) was added lithium hydroxide (1.30 g, 54.2 mmol) and water (50 ml), and the reaction mixture was stirred at ambient temperature overnight. Water (20 ml) was added, and the reaction mixture was extracted with ether (50 ml). The aqueous layer was adjusted to pH=4.5 using 1N hydrochloric acid solution, then extracted with ethyl acetate (50 mL×3). The combined organic layers were washed with brine, dried over anhydrous sodium sulfate, concentrated to afford the title compound (i-1) (2.6 g, 60%) as a white solid. $^1$H NMR (CDCl$_3$, 400 MHz): δ7.98 (d, J=7.82 Hz, 2H), 7.30~7.19 (m, 7H), 4.46 (d, J=8.6 Hz, 1H), 4.09-4.03 (m, 2H), 3.40 (s, 1H), 3.09 (br, 1H), 2.53 (br, 1H), 1.65-1.43 (m, 13H). MS: m/z (ESI) 412 (M+1).

Intermediate 2

4-Methoxybenzyl {(1R)-1-[(R)-{[tert-butyl(dimethyl)silyl]oxy}(6-chloropyridin-3-yl)methyl]pent-4-yn-1-yl}carbamate (i-2)

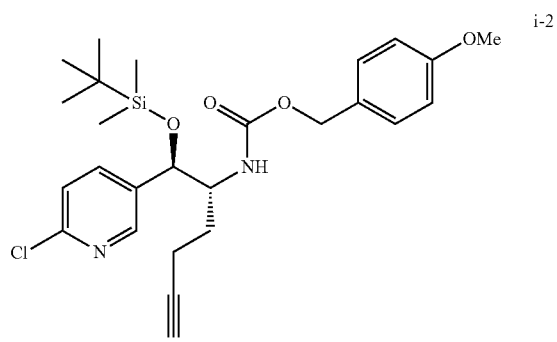 [SMILES: C#CCC[C@@H](NC(=O)OCc1ccc(OC)cc1)[C@H](O[Si](C)(C)C(C)(C)C)c1ccc(Cl)nc1]

Step A: (4S)-4-Benzyl-3-hex-5-ynoyl-1,3-oxazolidin-2-one

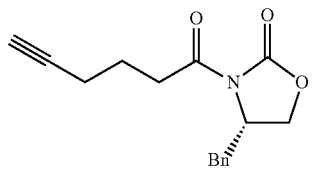 [SMILES: C#CCCCC(=O)N1C(=O)OC[C@@H]1Cc1ccccc1]

To a solution of 10 g (89 mmol) of 5-hexynoic acid and 31.0 mL (223 mmol) of triethylamine in 450 mL of anhydrous tetrahydrofuran at −25° C. under an atmosphere of nitrogen was added 12 mL (98 mmol) of trimethylacetyl chloride over 20 min. Upon addition a white precipitate formed and the resulting suspension was stirred for 2 h. Next, 4.2 g (98 mmol) of anhydrous lithium chloride and 17 g (94 mmol) of (S)-(−)-4-benzyl-2-oxazolidinone were added sequentially and the mixture was allowed to gradually warm to ambient temperature over 12 h. All volatiles were removed in vacuo and the residue was diluted with water (500 mL) and extracted with ether (3×200 mL). The combined organic layers were washed with brine (100 mL), dried over magnesium sulfate, filtered and concentrated in vacuo. The crude residue was purified by silica gel chromatography eluting with a 10-25% ethyl acetate in hexanes gradient to afford the title compound as a colorless solid (22 g, 93%). $^1$H NMR (500 MHz, CDCl$_3$): δ 7.35-7.31 (m, 2H), 7.28-7.25 (m, 1H), 7.19-7.21 (m, 2H), 4.69-4.64 (m, 1H), 4.22-4.15 (m, 2H), 3.28 (dd, J=13.4, 3.3 Hz, 1H), 3.13-3.01 (m, 2H), 2.78 (dd, J=13.4, 9.6 Hz, 1H), 2.34-2.30 (m, 2H), 1.99 (t, J=2.7 Hz, 1H), 1.96-1.88 (m, 2H). LC-MS: m/z (ES) 272.2 (MH)$^+$, 294.3 (MNa)$^+$.

Step B: (4S)-4-Benzyl-3-{(2R)-2-[(S)-(6-chloropyridin-3-yl)(hydroxy)methyl]hex-5-ynoyl}-1,3-oxazinan-2-one

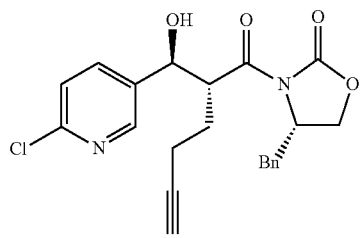 [SMILES: C#CCC[C@@H](C(=O)N1C(=O)OC[C@@H]1Cc1ccccc1)[C@H](O)c1ccc(Cl)nc1]

To a stirred solution of 23.0 g (837 mmol) of the title compound from step A above in 200 mL of anhydrous ethyl acetate at ambient temperature under an atmosphere of nitrogen was added 1.6 g (17 mmol) of anhydrous magnesium chloride, 23.0 mL (166 mmol) of triethylamine, 14.0 g (100 mmol) of 6-chloropyridine-3-carboxaldehyde and 16.0 mL (124 mmol) of chlorotrimethylsilane and the resulting mixture was stirred for 72 h. The heterogeneous reaction mixture was filtered through a 300 mL plug of silica gel eluting with an additional 1 L of ethyl acetate. The filtrate was evaporated to dryness in vacuo and the residue suspended in 200 mL of methanol and 5.0 mL of trifluoroacetic acid. The resulting mixture was stirred at ambient temperature under nitrogen for 5 h during which time the reaction became homogeneous. All volatiles were then removed in vacuo and the residue was purified by silica gel chromatography eluting with a 10-15% ethyl acetate in hexanes gradient to afford the title compound as a white solid (30 g, 88%). LC-MS: m/z (ES) 413.2 (MH)$^+$.

Step C: (4S)-4-Benzyl-3-{(2R)-2-[(S)-{[tert-butyl(dimethyl)silyl]oxy}(6-chloropyridin-3-yl)methyl]hex-5-ynoyl}-1,3-oxazinan-2-one

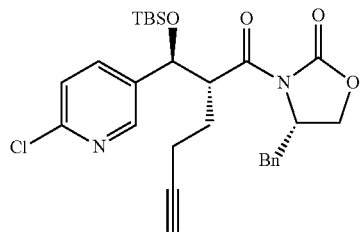 [SMILES: C#CCC[C@@H](C(=O)N1C(=O)OC[C@@H]1Cc1ccccc1)[C@H](O[Si](C)(C)C(C)(C)C)c1ccc(Cl)nc1]

To a stirred solution of 29.7 g (71.9 mmol) of the title compound from Step B above and 15.0 mL (126 mmol) of 2,6-lutidine in 300 mL of anhydrous dichloromethane at 0° C. under an atmosphere of nitrogen was added 22 mL (94 mmol) of tert-butyldimethylsilyl trifluoromethanesulfonate at a rate slow enough to keep the internal temperature below 3° C. The reaction mixture was stirred for 16 h at 0° C. then evaporated in vacuo to remove all volatiles. The residue was diluted with 400 mL of water and extracted with diethyl ether (3×300 mL). The combined organics were washed sequentially with a 0.5 M aqueous hydrochloric acid solution (100 mL), water (100 mL), brine (100 mL) then dried over magnesium sulfate. After filtration and evaporation in vacuo the residue was purified by silica gel chromatography eluting with a 5-8% ethyl acetate in hexanes gradient to afford the title compound as a colorless foam (37 g, 97%). LC-MS: m/z (ES) 527.3 (MH)$^+$.

Step D: (2R)-2-[(S)-{[Tert-butyl(dimethyl)silyl]oxy}(6-chloropyridin-3-yl)methyl]hex-5-ynoic acid

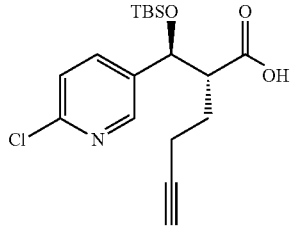 [SMILES: C#CCC[C@@H](C(=O)O)[C@H](O[Si](C)(C)C(C)(C)C)c1ccc(Cl)nc1]

To a stirred solution of 37 g (70 mmol) of the title compound from Step C above in 520 mL of a 3 to 1 mixture of anhydrous tetrahydrofuran to water at 0° C. under an atmosphere of nitrogen was added 30 ml, (350 mmol) of a 35% aqueous hydrogen peroxide solution at a rate slow enough to keep the internal temperature below 3° C. Next, 140 mL (140 mmol) of a 1.0 M aqueous sodium hydroxide solution was added at a rate slow enough to keep the internal temperature of the reaction below 5° C. After complete addition the resulting mixture was stirred for 18 h at 0° C. then quenched with a solution of 350 mL (420 mmol) of a 12 M aqueous sodium sulfite solution at a rate slow enough to keep the internal temperature of the mixture below 15° C. All volatiles were removed in vacuo and the remaining aqueous phase was cooled to 0° C. and acidified with a 2.5 M aqueous hydrogen chloride solution until a pH of 3 was achieved. The aqueous phase was then extracted with ethyl acetate (3×200 mL) and the combined organics were washed with brine (10 ml), dried over magnesium sulfate, filtered and evaporated in vacuo. The residue was purified by silica gel chromatography eluting with 15% ethyl acetate and 3% acetic acid in hexanes to afford the title compound as a white solid (16 g, 62%). LC-MS: m/z (ES) 368.2 (MH)+.

Step E: 4-Methoxybenzyl{(1R)-1-[(R)-{[tert-butyl (dimethyl)silyl]oxy}(6-chloropyridin-3-yl)methyl] pent-4-yn-1-yl}carbamate (i-2)

To a solution of 16 g (44 mmol) of the title compound from Step D above and 12 mL (87 mmol) of triethylamine in 150 mL of anhydrous toluene at ambient temperature under an atmosphere of nitrogen was added 10 mL (46 mmol) of diphenylphosphoryl azide. The mixture was stirred for 6 h and then 14.0 mL (109 mmol) of 4-methoxybenzyl alcohol was added. The resulting mixture was heated to 100° C. for 16 h, cooled to ambient temperature and then evaporated in vacuo to remove all volatiles. The crude residue was purified by silica gel chromatography eluting with 15% ethyl acetate in hexanes to afford the title compound (i-2) as a yellow foam (17 g, 78%). 1H NMR (500 MHz, CDCl3): δ 8.28 (d, J=2.0 Hz, 1H), 7.53 (dd, J=8.2, 2.3 Hz, 1H), 7.22 (d, J=8.4 Hz, 2H), 7.18 (d, J=8.2 Hz, 1H), 6.90 (d, J=8.4 Hz, 2H), 4.96-4.89 (m, 2H), 4.82 (d, J=2.5 Hz, 1H), 4.74 (d, J=9.6 Hz, 1H), 3.90-3.84 (m, 1H), 3.82 (s, 3H), 2.30-2.26 (m, 2H), 1.97 (t, J=2.5 Hz, 1H), 1.89-1.83 (m, 1H), 1.58-1.52 (m, 1H), 0.89 (s, 9H), 0.08 (s, 3H), −0.12 (s, 3H). LC-MS: m/z (ES) 503.3 (MH)+.

Intermediate 3

4-({(2S,5R)-1-(tert-butoxycarbonyl)-5-[(R)-{[tert-butyl(dimethyl)silyl]oxy}(pyridin-3-yl)methyl]pyrrolidin-2-yl}methyl)benzoic acid (i-3)

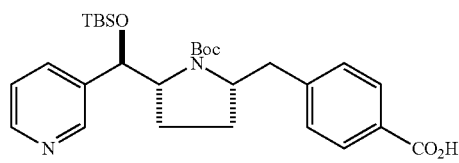

i-3

Step A: Methyl 4-[(5R,6R)-6-{[tert-butyl(dimethyl) silyl]oxy}-6-(6-chloropyridin-3-yl)-5-({[(4-methoxybenzyl)oxy]carbonyl}amino)hex-1-yn-1-yl]benzoate

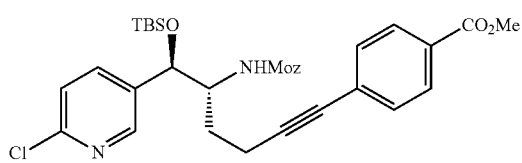

Methyl 4-iodobenzoate (54.4 g, 0.21 mol), 4-methoxybenzyl{(1R)-1-[(R)-{[tert-butyl(dimethyl)silyl]oxy}(6-chloropyridin-3-yl)methyl]pent-4-yn-1-yl}carbamate (i-2) (95.0 g, 0.19 mol) and triethylamine (79.0 mL, 0.57 mol) were suspended in N,N-dimethylformamide (500 mL) and nitrogen was bubbled through the reaction mixture for 15 min. Then tetrakis(triphenylphosphine)palladium (11.0 g, 9.5 mmol) and copper(I) iodide (3.61 g, 1.9 mmol) were added and the resulting reaction mixture was stirred at ambient temperature overnight. The reaction was slowly quenched with water and extracted with ethyl acetate. The combined extracts were washed with water, brine, dried over Na2SO4, filtered and evaporated. The residue was purified by column chromatography (petroleum ether/ethyl acetate=10:1) to give 92.1 g (77%) of the title compound as a yellow foam. 1H NMR (400 MHz, CDCl3): δ 8.46 (s, 1H), 8.10 (d, J=7.8 Hz, 2H), 7.71 (d, J=7.8 Hz, 1H), 7.59 (d, J=8.6 Hz, 2H), 7.51 (d, J=8.6 Hz, 1H), 7.47-7.42 (m, 3H), 7.37-7.35 (m, 2H), 5.11 (d, J=7.0 Hz, 1H), 5.06-4.92 (m, 3H), 4.13-4.06 (m, 1H), 3.93 (s, 6H), 2.69 (t, J=7.0 Hz, 2H), 2.61-2.54 (m, 1H), 2.15-2.11 (m, 1H), 0.80 (s, 9H), 0.20 (s, 3H), 0.00 (s, 3H). MS: m/z (ESI) 637 (M+23).

Step B: Methyl 4-[(5R,6R)-5-amino-6-{[tert-butyl (dimethyl)silyl]oxy}-6-(6-chloropyridin-3-yl)hex-1-yn-1-yl]benzoate

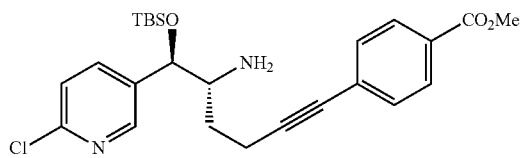 [SMILES: COC(=O)c1ccc(C#CCC[C@@H](N)[C@H](O[Si](C)(C)C(C)(C)C)c2ccc(Cl)nc2)cc1]

To a stirred solution of the title compound from Step A (83.0 g, 0.13 mol) in dichloromethane (400 mL) was added triethylamine (20 mL) and the resulting mixture was stirred for 3 h. The reaction mixture turned to dark red color. All volatiles were evaporated and the residue was diluted with water and based by NaHCO3. It was then extracted with dichloromethane (3×250 mL). The combined organic layers were washed with water and brine, dried over Na2SO4 and concentrated. The residue was purified by column chromatography with dichloromethane/methanol=20:1 to afford 47.0 g (77%) of the title compound as yellow gum. 1H NMR (400 MHz, CDCl3): δ 8.35 (s, 1H), 7.95 (d, J=8.6 Hz, 2H), 7.63 (d, J=7.8 Hz, 1H), 7.41 (d, J=8.6 Hz, 2H), 7.31 (d, J=8.6 Hz, 1H), 4.55 (d, J=4.7 Hz, 1H), 3.93 (s, 3H), 2.96-2.93 (m, 1H), 2.64-2.53 (m, 2H), 1.71-1.68 (m, 1H), 1.52-1.41 (m, 3H), 0.90 (s, 9H), 0.20 (s, 3H), 0.00 (s, 3H). MS: m/z (ESI) 473 (M+1).

Step C: Tert-butyl (2R,5S)-2-[(R)-{[tert-butyl(dimethyl)silyl]oxy}(6-chloropyridin-3-yl)methyl]-5-[4-(methoxycarbonyl)benzyl]pyrrolidine-1-carboxylate and Tert-butyl (2R,5R)-2-[(R)-{[tert-butyl(dimethyl) silyl]oxy}(6-chloropyridin-3-yl)methyl]-5-[4-(methoxycarbonyl)benzyl]pyrrolidine-1-carboxylate

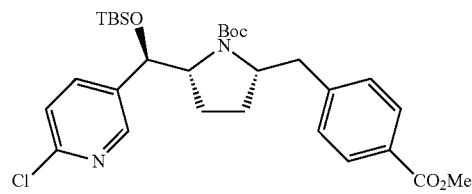

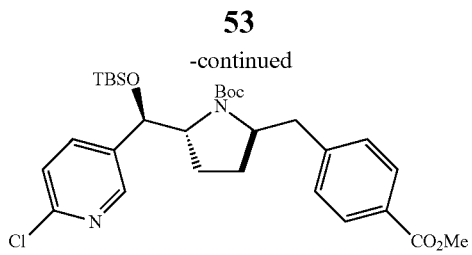

A stirred solution of the title compound from Step B (47.0 g, 99.3 mmol) in toluene (800 mL) was degassed by argon gas, then platinumdichloride (2.64 g, 9.93 mmol) was added. The resulting mixture was heated to 80° C. overnight under argon. The reaction mixture was concentrated to afford 47 g of product which was used in the next step without purification. MS: m/z (ESI) 473 (M+1).

To a cooled (0° C.), stirred solution of unpurified product (47 g, 99 mmol) from the above step in dichloromethane (500 mL) was added 4 A molecular sieve followed by sodium triacetoxyborohydride (42.2 g, 199 mmol). The reaction mixture was allowed to warm to RT and stirred overnight. Methanol (50 mL) was added. The reaction mixture was filtered and concentrated. Dichloromethane (100 mL) and saturated sodium bicarbonate (100 mL) were added and the organic layer was separated. The aqueous layer was extracted with dichloromethane. The combined organic layers were washed with water and brine, dried over $Na_2SO_4$ and concentrated to afford 47 g of product which was used in the next step without further purification. MS: m/z (ESI) 473 (M+1).

To a stirred solution of unpurified product (47 g, 99 mmol) from the above step in dichloromethane (400 mL) was added N,N-diisopropylethylamine (25.9 mL, 148 mmol), followed by slow addition of di-tert-butyl dicarbonate (24.9 g, 114 mmol). The resulting solution was stirred at ambient temperature for 5 h, and then the solvent was evaporated. The residue was purified by column chromatography (petroleum ether/ethyl acetate=80:1 then 50:1).

First spot to elute (cis isomer): tert-butyl (2R,5S)-2-[(R)-{[tert-butyl(dimethyl)silyl]oxy}(6-chloropyridin-3-yl)methyl]-5-[4-(methoxycarbonyl)benzyl]pyrrolidine-1-carboxylate as a colorless foam (15.2 g, 26%). $^1$H NMR (400 MHz, $CDCl_3$): δ 8.38 (s, 1H), 7.91 (d, J=8.1 Hz, 2H), 7.70 (d, J=7.5 Hz, 1H), 7.37 (d, J=8.2 Hz, 1H), 7.03 (s, 2H), 5.65-5.55 (m, 1H), 4.12-3.09 (m, 1H), 3.91 (s, 3H), 3.86-3.73 (m, 1H), 3.11-2.93 (m, 1H), 2.71-2.68 (m, 1H), 1.98-1.82 (m, 2H), 1.59 (s, 9H), 1.32-1.28 (m, 2H), 0.95 (s, 9H), 0.16 (s, 3H), 0.00 (s, 3H). MS: m/z (ESI) 575 (M+1).

Second spot to elute (trans isomer): tert-butyl (2R,5R)-2-[(R)-{[tert-butyl(dimethyl)silyl]oxy}(6-chloropyridin-3-yl)methyl]-5-[4-(methoxycarbonyl)benzyl]pyrrolidine-1-carboxylate as a colorless gum (5.1 g, 9%): $^1$H NMR (400 MHz, $CDCl_3$): δ 8.59 (s, 1H), 8.30 (d, J=7.9 Hz, 2H), 7.84 (d, J=7.6 Hz, 1H), 7.45-7.34 (m, 3H), 5.71 (s, 1H), 4.28-4.14 (m, 1H), 3.95 (s, 3H), 3.93-3.91 (m, 1H), 3.36-3.33 (m, 1H), 2.84-2.75 (m, 1H), 2.43-2.33 (m, 1H), 1.77-1.59 (m, 13H), 0.95 (s, 9H), 0.16 (s, 3H), 0.00 (s, 3H). MS: m/z (ESI) 575 (M+1).

Step D: Tert-butyl (2R,5S)-2-[(R)-{[tert-butyl(dimethyl)silyl]oxy}(pyridin-3-yl)methyl]-5-[4-(methoxycarbonyl)benzyl]pyrrolidine-1-carboxylate

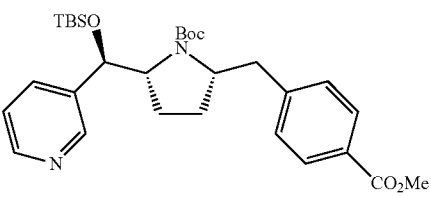

To a solution of tert-butyl (2R,5S)-2-[(R)-{[tert-butyl(dimethyl)silyl]oxy}(6-chloropyridin-3-yl)methyl]-5-[4-(methoxycarbonyl)benzyl]pyrrolidine-1-carboxylate from Step C (14.0 g, 24.3 mmol) in ethanol (200 mL) was added potassium acetate (3.58, 36.5 mmol) and 10% palladium on carbon (4.0 g) under argon. The reaction mixture was heated to 50° C. and agitated under an atmosphere of hydrogen at 50 psi for 14 h. The mixture was cooled to RT and filtered. The filtrate was concentrated to afford 12.1 g (92%) of the title compound as yellow foam. $^1$H NMR (400 MHz, $CDCl_3$): δ 8.62 (s, 1H), 8.58 (s, 1H), 7.89 (d, J=7.9 Hz, 2H), 7.36-7.32 (m, 1H), 7.02-6.99 (m, 2H), 5.62 (s, 1H), 4.20-4.11 (m, 2H), 3.94 (s, 3H), 2.99-2.96 (m, 1H), 2.64-2.60 (m, 1H), 2.02-1.88 (m, 2H), 1.61 (s, 9H), 1.56-1.43 (m, 2H), 0.96 (s, 9H), 0.17 (s, 3H), 0.00 (s, 3H). MS: m/z (ESI) 541 (M+1).

Step E: 4-({(2S,5R)-1-(tert-butoxycarbonyl)-5-[(R)-{[tert-butyl(dimethyl)silyl]oxy}(pyridin-3-1 methyl]pyrrolidin-2-yl}methyl)benzoic acid (i-3)

To a stirred solution of the title compound from Step D (2.5 g, 4.6 mmol) in methanol/water=4:1 (30 mL) was added lithium hydroxide (533 mg, 23.1 mmol). The resulting mixture was stirred at RT overnight. The mixture was diluted with water and extracted with ether. The aqueous layer was acidified with 1N citric acid to PH 4.5, and then extracted with ethyl acetate. The organic layer was separated and washed with water, brine, dried over $Na_2SO_4$, and concentrated. The residue was purified by reverse phase HPLC (Lunal Ou, 250× 50 mm I.D.; 45-65% 0.1% trifluoroacetic acid in acetonitrile/0.1% trifluoroacetic acid in water gradient) to afford 1.31 g (74%) of the title compound (i-3) as a white solid. $^1$H NMR (400 MHz, $CDCl_3$): δ 8.64 (s, 2H), 7.93 (d, J=7.8 Hz, 2H), 7.80 (s, 1H), 7.44-7.38 (m, 1H), 7.03 (s, 2H), 5.66-5.33 (m, 1H), 4.16 (s, 1H), 4.00-3.88 (m, 1H), 3.01-2.95 (m, 1H), 2.68-1.58 (m, 1H), 2.04-1.83 (m, 2H), 1.60 (s, 9H), 1.31-1.20 (m, 2H), 0.96 (s, 9H), 0.17 (s, 3H), 0.00 (s, 3H). MS: m/z (ESI) 527 (M+1).

Intermediate 4

4-({(2S,5R)-1-(tert-butoxycarbonyl)-5-[(R)-hydroxy (pyridin-3-yl)methyl]pyrrolidin-2-yl}methyl)benzoic acid (i-4)

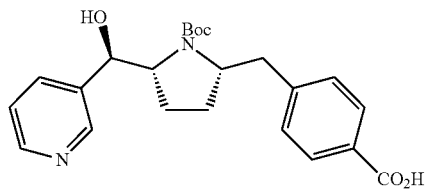

Step A: Tert-butyl (2R,5S)-2-[(R)-hydroxy(pyridin-3-yl)methyl]-5-[4-(methoxycarbonyl)benzyl]pyrrolidine-1-carboxylate

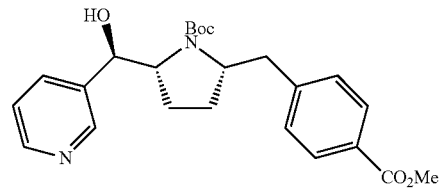 [SMILES: COC(=O)c1ccc(C[C@@H]2CC[C@H]([C@H](O)c3cccnc3)N2C(=O)OC(C)(C)C)cc1]

A solution of tert-butyl (2R,5S)-2-[(R)-{[tert-butyl(dimethyl)silyl]oxy}(pyridin-3-yl)methyl]-5-[4-(methoxycarbonyl)benzyl]pyrrolidine-1-carboxylate (11.0 g, 20.3 mmol) in 100 mL of 2 M tetrabutylammonium fluoride tetrahydrofuran solution was stirred at RT overnight. The mixture was then diluted with water and extracted with ethyl acetate (50 mL×3). The combined organic layers were washed with water, brine, dried over Na$_2$SO$_4$, and concentrated to afford 8.51 g (98%) of the title compound. $^1$H NMR (400 MHz, CDCl$_3$): δ 8.55 (s, 2H), 7.93 (d, J=8.0 Hz, 2H), 7.76 (d, J=8.0 Hz, 1H), 7.34-7.28 (m, 3H), 6.36 (s, 1H), 4.54 (d, J=8.5 Hz, 1H), 4.18-4.09 (m, 2H), 3.92 (s, 3H), 3.23 (s, 1H), 3.13-3.10 (m, 1H), 2.61-2.52 (m, 1H), 1.78-1.60 (m, 2H), 1.49 (s, 9H). MS: m/z (ESI) 427 (M+1).

Step B: 4-({(2S,5R)-1-(tert-butoxycarbonyl)-5-[(R)-hydroxy(pyridin-3-yl)methyl]pyrrolidin-2-yl}methyl)benzoic acid (i-4)

To a stirred solution of the title compound from Step A (8.51 g, 20.0 mmol) in methanol/water=4:1 (50 mL) was added lithium hydroxide (2.39 g, 100 mmol). The resulting mixture was stirred at RT overnight. The mixture was diluted with water and extracted with ether. The aqueous layer was acidified with 1N citric acid to PH 4.5, and then extracted with ethyl acetate. The organic layer was separated and washed with water, brine, dried over Na$_2$SO$_4$, and concentrated. The residue was purified by SFC (using an AD column 35% MeOH/65% CO$_2$, 150 ml/min 100 bar) to afford 6.90 g (84%) of the title compound (i-4) as a white solid. $^1$H NMR (400 MHz, CDCl$_3$): δ 8.53 (s, 2H), 8.00 (d, J=7.7 Hz, 2H), 7.77 (d, J=6.4 Hz, 1H), 7.32-7.29 (m, 1H), 7.21 (d, J=8.0 Hz, 2H), 5.22 (s, 1H), 4.51 (d, J=8.4 Hz, 1H), 4.13-4.11 (m, 1H), 4.09-4.01 (m, 1H), 3.07-3.04 (m, 1H), 2.58-2.56 (m, 1H), 1.68-1.51 (m, 2H), 1.42 (s, 9H). MS: m/z (ESI) 413 (M+1).

Intermediate 5

4-({(2S,5R)-1-(tert-butoxycarbonyl)-5-[(R)-{[tert-butyl(dimethyl)silyl]oxy}(phenyl)methyl]pyrrolidin-2-yl}methyl)benzoic acid

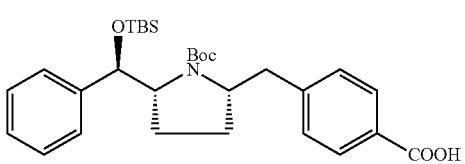

Step A: 4-methoxybenzyl{(1R)-5-(4-bromophenyl)-1-[(R)-{[tert-butyl(dimethyl)silyl]oxy}-1-phenyl]hex-5-yn-2-amine

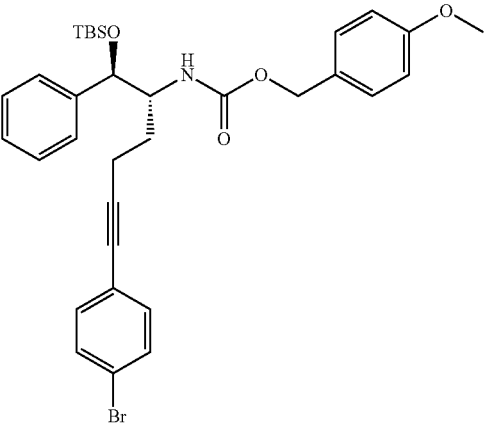 [SMILES: COc1ccc(COC(=O)N[C@H](CCC#Cc2ccc(Br)cc2)[C@H](O[Si](C)(C)C(C)(C)C)c2ccccc2)cc1]

To a solution of 4-methoxybenzyl{(1R)-1-[(R)-{[tert-butyl(dimethyl)silyl]oxy}(phenyl)methyl]pent-4-yn-1-yl}carbamate (25.0 g, 53.5 mmol), triethylamine (74.5 ml, 535 mmol), copper(I) iodide (0.611 g, 3.21 mmol) and 1-bromo-4-iodobenzene (16.6 g, 58.8 mmol) in DMF (250 ml) was added PdCl$_2$(dppf)-CH$_2$Cl$_2$ (1.31 g, 1.60 mmol) and the mixture was degassed three times and stirred at RT for 6 h. LC-MS showed no more starting material left. Poured into water 750 ml, the mixture was extracted with ethyl acetate (3×500 mL). The combined organic fractions were washed with water and brine (500 mL), dried with sodium sulfate and filtered and the solvent was evaporated under reduced pressure. The residue was purified by column chromatography on silica gel Biotage 65i, eluting with EtOAc to afford the title compound as an orange oil. Yield is 86%. LC-MS: m/z (E/S) 624.1 (MH)⁺.

Step B: (1R,2R)-6-(4-bromophenyl)-1-{[tert-butyl(dimethyl)silyl]oxy}-1-phenylhex-5-yn-2-amine

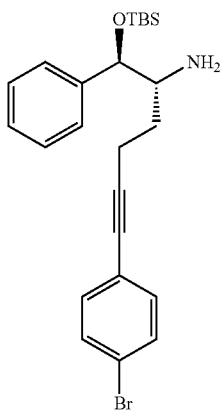 [SMILES: CC(C)(C)[Si](C)(C)O[C@H](c1ccccc1)[C@H](N)CCC#Cc1ccc(Br)cc1]

To a solution of the title compound from Step A (29.0 g, 46.6 mmol) in $CH_2Cl_2$ (200 ml) was added TFA (20 ml) and the reaction was stirred at RT for 3 h. LC-MS showed no more starting left. The residue was evaporated to dryness. The residue was purified by column chromatography on silica gel Biotage 40M, eluting with EtOAc/isohexane to afford the title compound as an orange oil. Yield is 89%. LC-MS: ink (E/S) 460.1 (MH)⁺.

Step C: (2S,5R)-2-(4-bromophenyl)-5-[(R)-{[tert-butyl(dimethyl)silyl]oxy}(phenyl)methyl]pyrrolidine

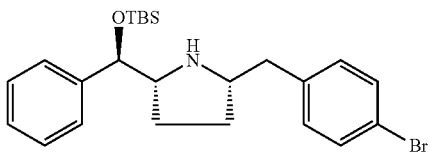 [SMILES: CC(C)(C)[Si](C)(C)O[C@H](c1ccccc1)[C@H]1CC[C@@H](Cc2ccc(Br)cc2)N1]

To a solution of the title compound from Step B (5.00 g, 10.9 mmol) in toluene (50 ml) was added platinum (II) chloride (0.290 g, 1.09 mmol). The mixture of degassed by bubble nitrogen for 25 min and the mixture was stirred at 80° C. for 6 h under nitrogen. The resulting product was filtered through celite and the solvent was removed and the resulting product was dissolved in $CH_2Cl_2$ (50.0 ml), sodium triacetoxyborohydride (5.78 g, 27.3 mmol) was added to it at 0° C. The mixture was stirred at RT overnight. The mixture was cooled, diluted with dichloromethane (250 mL), washed with aqueous sodium hydrogen carbonate (saturated, 3×100 mL), dried ($Na_2SO_4$), filtered and the solvent was evaporated under reduced pressure. The residue was purified by column chromatography on silica gel Biotage 40M, eluting with Acetone/hexane 10%-20% to afford the title compound as colorless solid. Yield is 24%. LC-MS: m/z (E/S) 460.3 (MH)⁺.

Step D: tert-butyl (2S,5R)-2-(4-bromophenyl)-5-[(R)-{[tert-butyl(dimethyl)silyl]oxy}(phenyl)methyl]pyrrolidine-1-carboxylate

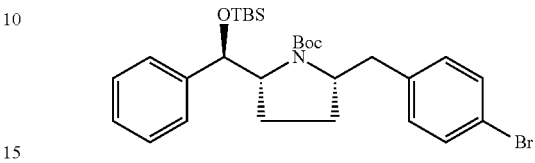

To a solution of the title compound from Step C (1.20 g, 2.61 mmol) and N,N-diisopropylethylamine (0.910 ml, 5.21 mmol) in $CH_2Cl_2$ (15 ml) was added $BOC_2O$ (1.21 ml, 5.21 mmol) and the mixture was stirred at RT for overnight. The mixture was diluted with ethyl acetate (200 mL), washed with aqueous sodium hydrogen carbonate (saturated, 2×100 mL), with brine (100 mL), dried ($Na_2SO_4$), filtered and the solvent was evaporated under reduced pressure. The residue was purified by column chromatography on silica gel Biotage 40M, eluting with EtOAc/isohexane 0%-10% to afford title compound as a colorless solid. Yield is 96%. LC-MS: m/z (E/S) 562.1 (MH)⁺.

Step E: tert-butyl (2R,5S)-2-[(R)-{[tert-butyl(dimethyl)silyl]oxy}(phenyl)methyl]-5-[4-(methoxycarbonyl)benzyl]pyrrolidine-1-carboxylate

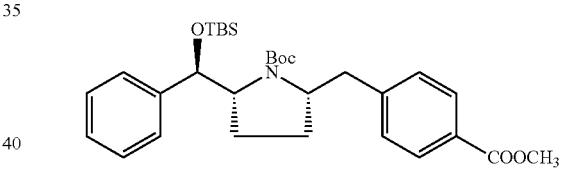

To a solution of the title compound from Step D and triethylamine (0.125 ml, 0.896 mmol) in MeOH (1 ml) was added Pd(OAc)₂ (5.03 mg, 0.0220 mmol) and the mixture was degassed three times filled with CO and stirred at 120° C. for overnight. LC-MS showed no more starting material left. The mixture was diluted with ethyl acetate, washed with aqueous sodium hydrogen carbonate (saturated, 3×10 mL), and brine, dried ($Na_2SO_4$), filtered and the solvent was evaporated under reduced pressure. The residue was purified by preparative TLC eluting with 10%/90% EtOAc/isohexane to afford title compound. Yield is 56%. LC-MS: m/z (E/S) 539.2 (MH)⁺.

Step F: 4-({(2S,5R)-1-(tert-butoxycarbonyl)-5-[(R)-{[tert-butyl(dimethyl)silyl]oxy}(phenyl)methyl]-pyrrolidin-2-yl}methyl)benzoic acid (I-5)

To a solution of the title compound from Step E (800 mg, 1.48 mmol) in MeOH (7.5 ml) was added 1 N LiOH (7.41 ml, 7.41 mmol) and the mixture was stirred at RT overnight. LC-MS showed no more starting material left. The mixture was evaporated to remove MeOH, extracted the aqueous layer with ether 3×50 ml, the aqueous layer was adjusted to PH=4.5 with 1N HCl, then extracted with ethyl acetate 3×50 ml. The combined organic layers was washed with brine (saturated, 1×50 mL), dried (Na$_2$SO$_4$), filtered and the solvent evaporated under reduced pressure to afford title compound (i-5). Yield is 99%. LC-MS: m/z (E/S) 526.2 (MH)$^+$.

Intermediate 6

4-Methyl-2-pyrimidinemethanamine (i-6)

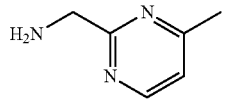
(i-6)

Step A: 2-Cyano-4-methylpyrimidine

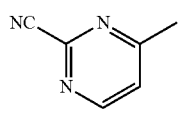

To a solution of 2-chloro-4-methylpyrimidine (1 g, 7.78 mmol) and zinc cyanide (475 mg, 4.04 mmol) in anhydrous DMF (10 ml) was added Pd(PPh$_3$)$_4$ (449 mg, 0.366 mmol) and nitrogen flushed through the mixture for 5 min. The mixture was heated at 180° C. for 30 min in a microwave reactor. The reaction was repeated on the same scale and the reaction mixtures were combined. The mixture was partitioned between EtOAc and water (filtered through celite to remove some insolubles), and the organic layer washed with sat. NaCl, dried over MgSO$_4$, filtered and evaporated. The residue was purified by MPLC (Biotage Horizon: FLASH 25+M) eluent: 100% Hexanes (90 ml), gradient rising from 100% Hexanes to 15% EtOAc in Hexanes (900 ml), then 15% EtOAc in Hexanes (500 ml) to give 1 g of the title compound (54%) as an off-white solid. $^1$H NMR (CDCl$_3$): 2.62 (s, 3H), 7.42 (d, J 5.1 Hz, 1H), 8.69 (d, J 5.1 Hz, 1H).

Step B: 4-Methyl-2-pyrimidinemethanamine (i-6)

To a nitrogen flushed solution of the title compound from Step A (1 g, 8.39 mmol) in methanol (40 ml) was added 10% palladium on carbon (100 mg) and the resulting mixture stirred under a balloon of hydrogen for 3 h. The mixture was filtered through celite and evaporated to give 950 mg (91%) of the title compound (i-6) as an orange oil. $^1$H NMR (CDCl$_3$): 2.54 (s, 3H), 4.16 (s, 2H), 7.03 (d, J 5.0 Hz, 1H), 8.56 (d, J 5.0 Hz, 1H).

Intermediate 7

4-(Trifluoromethyl)-2-pyrimidinemethanamine (i-7)

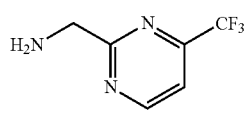
(i-7)

Step A: 2-Cyano-4-(trifluoromethyl)pyrimidine

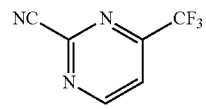 [SMILES: N#Cc1nccc(C(F)(F)F)n1]

Prepared according to the procedure described in Intermediate 6 step A, replacing 2-chloro-4-methylpyrimidine with 2-chloro-4-(trifluoromethyl)pyrimidine, (39%) as an off-white solid. $^1$H NMR (CDCl$_3$): 7.91 (d, J 5.1 Hz, 1H), 9.20 (d, J 5.1 Hz, 1H).

Step B: 4-(Trifluoromethyl)-2-pyrimidinemethanamine (i-7)

Prepared from the title compound from Step A according to the procedure described in Intermediate 6, step B. MS (m/z): 178 (M+1).

Intermediate 8

4-Cyclopropyl-2-pyrimidinemethanamine (i-8)

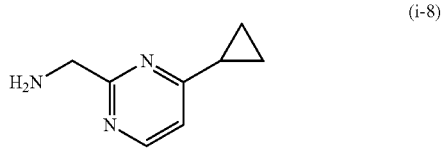 [SMILES: NCc1nccc(C2CC2)n1]
(i-8)

Step A: 2-Chloro-4-cyclopropylpyrimidine

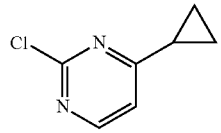

Nitrogen gas was bubbled through a mixture of 2,4-dichloropyrimidine (1.49 g, 10 mmol), cyclopropaneboronic acid (0.86 g, 10 mmol) and K$_3$PO$_4$ (5.31 g, 25 mmol) in THF (50 ml) for 10 min. Pd(dppf)Cl$_2$ (817 mg, 1 mmol) was added and the mixture heated at 90° C. in a sealed tube overnight. The mixture was cooled and partitioned between water and EtOAc, the organic layer washed with sat. NaCl, dried over MgSO$_4$, filtered and evaporated. The residue purified by MPLC (Biotage Horizon: FLASH 25+M) eluent: 100% Hexanes (90 ml), gradient rising from 100% Hexanes to 20% EtOAc in Hexanes (900 ml), then 20% EtOAc in Hexanes (500 ml) to give 750 mg (48%) as an off-white solid. ¹H NMR (CDCl₃): 1.18 (m, 4H), 1.99 (m, 1H), 7.09 (d, J 5.1 Hz, 1H), 8.36 (d, J 5.1 Hz, 1H).

Step B: 2-Cyano-4-cyclopropylpyrimidine

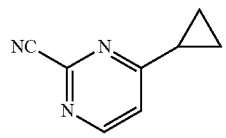 [SMILES: N#Cc1nccc(C2CC2)n1]

Prepared according to the procedure described in Intermediate 6, step A, replacing 2-chloro-4-methylpyrimidine with 2-chloro-4-cyclopropylpyrimidine, (82%) as an off-white solid. ¹H NMR (CDCl₃): 1.23 (m, 4H), 2.05 (m, 1H), 7.38 (d, J 5.2 Hz, 1H), 8.56 (d, J 5.2 Hz, 1H).

Step C: 4-Cyclopropyl-2-pyrimidinemethanamine (i-8)

Prepared from the title compound from Step B according to the procedure described in Intermediate 6, step B (96%). ¹H NMR (CDCl₃): 1.07 (m, 2H), 1.18 (m, 2H), 1.99 (m, 1H), 4.07 (s, 2H), 6.99 (d, J 5.2 Hz, 1H), 8.46 (d, J 5.2 Hz, 1H).

Intermediate 9

4-Cyclopropyl-6-methyl-2-pyrimidinemethanamine (i-9)

(i-9)

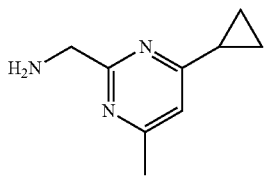

Step A: 2-Chloro-4-cyclopropyl-6-methylpyrimidine

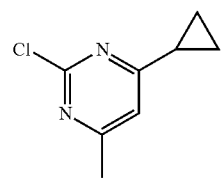

Prepared according to the procedure described in Intermediate 8, Step A, replacing 2,4-dichloropyrimidine with 2,4-dichloro-6-methylpyrimidine, (51%) as an off-white solid. ¹H NMR (CDCl₃): 1.12 (m, 2H), 1.19 (m, 2H), 1.94 (m, 1H), 2.47 (s, 3H), 6.95 (s, 1H).

Step B: 2-Cyano-4-cyclopropyl-6-methylpyrimidine

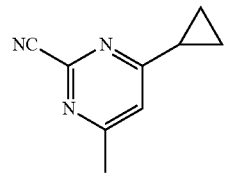

Prepared according to the procedure described in Intermediate 6, step A, replacing 2-chloro-4-methylpyrimidine with 2-chloro-4-cyclopropyl-6-methylpyrimidine, (82%) as a white solid. ¹H NMR (CDCl₃): 1.16 (m, 2H), 1.20 (m, 2H), 1.98 (m, 1H), 2.53 (s, 3H), 7.22 (s, 1H).

Step C:
4-Cyclopropyl-6-methyl-2-pyrimidinemethanamine (i-9)

Prepared from the title compound from Step B according to the procedure described in Intermediate 6, step B (87%) orange oil. ¹H NMR (CDCl₃): 1.03 (m, 2H), 1.15 (m, 2H), 1.92 (m, 1H), 2.44 (s, 3H), 4.01 (s, 2H), 6.85 (s, 1H).

Intermediate 10

4-Phenyl-2-pyrimidinemethanamine (i-10)

(i-10)

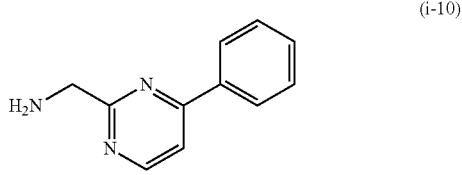 [SMILES: NCc1nccc(-c2ccccc2)n1]

Step A: 2-Chloro-4-phenylpyrimidine

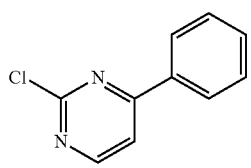 [SMILES: Clc1nccc(-c2ccccc2)n1]

To a mixture of 2,4-dichloropyrimidine (1.47 g, 9.8 mmol), benzene boronic acid (1 g, 8.2 mmol), Na₂CO₃ (2.61 g, 24.61=01) in a mixture of DME (15 ml), EtOH (2 ml) and water (3 ml) was added Pd(PPh₃)₄ (190 mg, 0.16 mmol) and the resulting mixture heated in a microwave at 125° C. for 30 min. The reaction was repeated on same scale. The reaction mixtures were combined and diluted with water and extracted with EtOAc (×2). The EtOAc layers were combined and washed with sat. NaCl, dried over MgSO₄, filtered and evaporated. The residue was purified by MPLC (Biotage Horizon: FLASH 40+M) eluent: 100% Hexanes (180 ml), gradient rising from 100% Hexanes to 10% EtOAc in Hexanes (900 ml), then 10% EtOAc in Hexanes (500 ml) to give 1.3 g of the title compound (41%) as a white solid. ¹H NMR (CDCl₃): 7.54 (m, 3H), 7.76 (s, 1H), 8.08 (m, 2H), 9.04 (s, 1H).

Step B: 2-Cyano-4-phenylpyrimidine

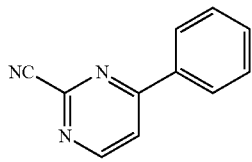 [SMILES: N#Cc1nccc(-c2ccccc2)n1]

Prepared according to the procedure described in Intermediate 6, step A, replacing 2-chloro-4-methylpyrimidine with 2-chloro-4-phenylpyrimidine, (70%) as an off-white solid. ¹H NMR (CDCl₃): 7.59 (m, 3H), 8.03 (s, 1H), 8.15 (m, 2H), 9.38 (s, 1H).

Step C: 4-Phenyl-2-pyrimidinemethanamine (i-10)

Prepared from the title compound from Step B according to the procedure described in Intermediate 6, step B. ¹H NMR (CDCl₃): 4.07 (s, 2H), 7.52 (m, 3H), 7.78 (s, 1H), 8.11 (m, 2H), 9.21 (s, 1H).

Intermediate 11

4-Methyl-6-phenyl-2-pyrimidinemethanamine (i-11)

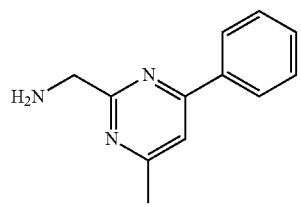

(i-11)

Step A: 2-Chloro-4-methyl-6-phenylpyrimidine

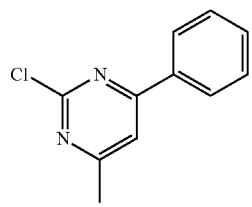

A mixture of 2,4-dichloro-6-methylpyrimidine (5 g, 30.7 mmol), benzeneboronic acid (3.74 g, 30.7 mmol), K₂CO₃ (12.72 g, 92 mmol) and Pd(PPh₃)₄ (1.06 g, 0.92 mmol) in toluene (150 ml) and methanol (35 ml) was degassed with nitrogen and heated at 90° C. overnight. The mixture was cooled and water (200 ml) added. The organic layer was separated and the aqueous extracted with EtOAc (×2). The organic layers were combined and dried over MgSO₄, filtered and evaporated. The residue was purified by MPLC (Biotage Horizon: FLASH 40+M) eluent: 100% Hexanes (180 ml), gradient rising from 100% Hexanes to 20% EtOAc in Hexanes (1800 ml), then 20% EtOAc in Hexanes (1000 ml) to give 3 g (48%). ¹H NMR (CDCl₃): 2.61 (s, 3H), 7.52 (m, 4H), 8.08 (m, 2H).

Step B: 2-Cyano-4-methyl-6-phenylpyrimidine

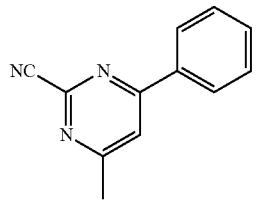

Prepared according to the procedure described in Intermediate 6, step A, replacing 2-chloro-4-methylpyrimidine with 2-chloro-4-methyl-6-phenylpyrimidine, (70%) as an off-white solid. ¹H NMR (CDCl₃): 2.66 (s, 3H), 7.54 (m, 3H), 7.75 (s, 1H), 8.11 (m, 2H).

Step C:
4-Methyl-6-phenyl-2-pyrimidinemethanamine (i-11)

Prepared from the title compound from Step B according to the procedure described in Intermediate 6, step B, as an orange oil. ¹H NMR (CDCl₃): 2.57 (s, 3H), 4.27 (s, 2H), 7.48 (m, 4H), 8.12 (m, 2H).

Intermediate 12

5-Phenyl-2-pyrimidinemethanamine (i-12)

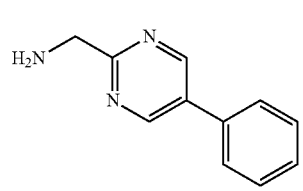

(i-12)

Step A: 2-Chloro-5-phenylpyrimidine

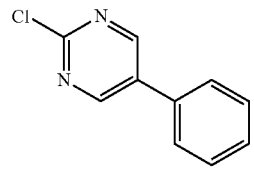 [SMILES: Clc1ncc(-c2ccccc2)cn1]

Prepared according to the procedure described in Intermediate 11, step A, replacing 2,4-dichloro-6-methylpyrimidine with 2-chloro-5-bromopyrimidine, (53%) as an off-white solid. ¹H NMR (CDCl₃): 7.57 (m, 5H), 8.86 (s, 2H).

Step B: 2-Cyano-5-phenylpyrimidine

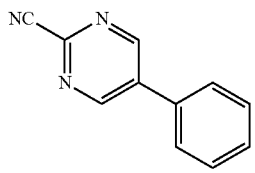 [SMILES: N#Cc1ncc(-c2ccccc2)cn1]

Prepared according to the procedure described in Intermediate 6, step A, replacing 2-chloro-4-methylpyrimidine with 2-chloro-5-phenylpyrimidine, (70%) as an off-white solid. ¹H NMR (CDCl₃): 7.64 (m, 5H), 9.08 (s, 2H).

Step C: 5-Phenyl-2-pyrimidinemethanamine (i-12)

Prepared from the title compound from Step B according to the procedure described in Intermediate 6, step B. ¹H NMR (CDCl₃): 4.30 (s, 2H), 7.58 (m, 5H), 8.95 (s, 2H).

Intermediate 13

6-Phenyl-4-pyrimidinemethanamine (i-13)

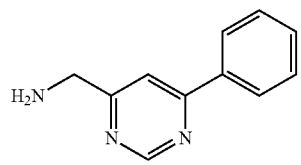

Step A: 4-Chloro-6-phenylpyrimidine

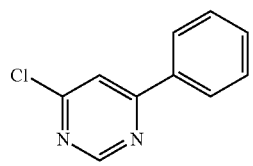 [SMILES: Clc1cc(-c2ccccc2)ncn1]

Prepared according to the procedure described in Intermediate 11, step A, replacing 2,4-dichloropyrimidine with 4,6-dichloropyrimidine, (83%) as a white solid. ¹H NMR (CDCl₃): 7.54 (m, 3H), 7.76 (s, 1H), 8.08 (m, 2H), 9.05 (s, 1H).

Step B: 4-Cyano-6-phenylpyrimidine

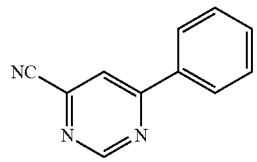 [SMILES: N#Cc1cc(-c2ccccc2)ncn1]

Prepared according to the procedure described in Intermediate 6, step A, replacing 2-chloro-4-methylpyrimidine with 4-chloro-6-phenylpyrimidine, (70%) as an off-white solid. ¹H NMR (CDCl₃): 7.59 (m, 3H), 8.03 (s, 1H), 8.15 (m, 2H), 9.38 (s, 1H).

Step C: 6-Phenyl-4-pyrimidinemethanamine (i-13)

Prepared from the title compound from Step B according to the procedure described in Intermediate 6, step B. ¹H NMR (CDCl₃): 2.00 (brs, 2H), 4.05 (s, 2H), 7.52 (m, 3H), 7.78 (s, 1H), 8.11 (m, 2H), 9.21 (s, 1H).

Intermediate 14

1-(6-Methylpyridin-2-yl)ethanamine (i-14)

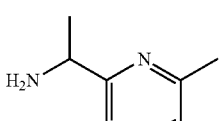

To a solution of 2-acetyl-6-methylpyridine (4.7 g, 34.8 mmol) in anhydrous methanol (100 ml) was added ammonium acetate (26.8 g, 348 mmol) and sodium cyanoborohydride (1.75 g, 27.8 mmol) and the resulting mixture stirred at RT overnight. The mixture was evaporated and the residue dissolved in water and basified by the addition of KOH and extracted with DCM (×3). The DCM layers were combined and washed with sat. NaCl, dried over MgSO₄, filtered and evaporated. The residue was purified by column chromatography on silica to afford the title compound (i-14) (eluent: 5% MeOH in DCM) to give 2.8 g (59%) as a clear oil. ¹H NMR (CDCl₃): 1.41 (d, J 6.7 Hz, 3H), 1.78 (brs, 2H), 2.54 (s, 3H), 4.21 (q, J 6.7 Hz, 1H), 6.99 (d, J 7.6 Hz, 1H), 7.09 (d, J 7.7 Hz, 1H), 7.52 (m, 1H).

Intermediate 15

1-(Pyrazin-2-yl)ethylamine (i-15)

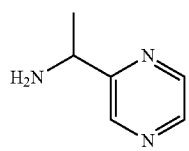

(i-15)

Prepared according to the procedure described in Intermediate 14, replacing 2-acetyl-6-methylpyridine with acetylpyrazine to yield the title compound (i-15) (60%) as a light yellow oil. ¹H NMR (CDCl₃): 1.42 (d, J 6.7 Hz, 3H), 1.86 (brs, 2H), 2.54 (s, 3H), 4.19 (q, J 6.7 Hz, 1H), 8.41 (d, J 2.5 Hz, 1H), 8.47 (t, J 2.2 Hz, 1H), 8.59 (d, J 2.2 Hz, 1H).

Intermediate 16 tert-butyl 4-(ethylsulfonyl)piperine-1-carboxylate (i-16)

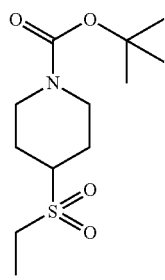

(i-16)

Step A: tert-butyl 4-[(methylsulfonyl)oxy]piperidine-1-carboxylate

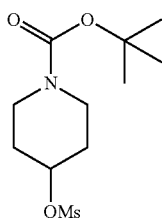 [SMILES: CC(C)(C)OC(=O)N1CCC(OS(C)(=O)=O)CC1]

To a solution of tert-butyl 4-hydroxypiperidine-1-carboxylate (5.0 g, 36 mmol) and triethyl amine (6.0 ml, 43 mmol) in 50 ml of THF at 0° C. under an atmosphere of nitrogen was added MsCl (3.4 ml, 43 mmol). The mixture was stirred at 0° C. for 3 h and quenched with aqueous sodium hydrogen carbonate (saturated, 100 mL). The mixture was extracted with ethyl acetate (3×100 mL). The combined organic fractions were washed with brine (1×100 mL), dried (Na₂SO₄), filtered and the solvent was evaporated under reduced pressure. The residue was purified by column chromatography on silica gel Biotage 40M, eluting with EtOAc/isohexane to hexanes to afford the title compound as a colorless solid (4.2 g, 42%). ¹H-NMR (500 MHz, CDCl₃) δ 4.90 (s, 1H), 3.70 (m, 2H), 3.30 (m, 2H), 3.05 (s, 3H), 1.95 (m, 2H), 1.82 (m, 2H), 1.45 (s, 9H).

Step B: tert-butyl 4-(ethylsulfanyl)piperidine-1-carboxylate

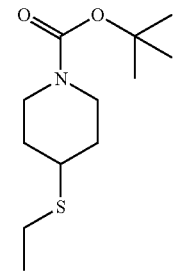 [SMILES: CCSC1CCN(C(=O)OC(C)(C)C)CC1]

To a cooled (0° C.) solution of 0.20 ml (2.6 mmol) of ethanethiol in 7 ml of DMF was added 0.11 g (2.7 mmol) of sodium hydride. The mixture was stirred at 0° C. for 30 min, then 0.50 g, (1.7 mmol) of the title compound from Step A was added. The solution was allowed to stir for 2 h and then quenched with 50 mL of a saturated aqueous sodium bicarbonate solution. The layers were separated and the aqueous phase extracted with ethyl acetate (3×50 mL). The combined organic extracts were washed with brine, dried over sodium sulfate, filtered and evaporated in vacuo to yield the title compound as a light brown solid that was used without further purification. ¹H-NMR (500 MHz, CDCl₃) δ 4.00 (s, 2H), 2.90 (m, 2H), 2.82 (m, 1H), 2.58 (q, J=7 Hz, 2H), 1.90 (m, 2H), 1.55 (m, 2H), 1.45 (s, 9H), 1.29 (t, J=5 Hz, 3H).

Step C: tert-butyl 4-(ethylsulfonyl)piperidine-1-carboxylate (i-16)

To a cooled (0° C.) solution of 0.31 g (1.3 mmol) of the title compound from Step B above in 6 mL of dichloromethane was added 0.78 g (3.2 mmol) of m-CPBA. The solution was allowed to stir for 1 h and then quenched with 50 mL of a saturated aqueous sodium bicarbonate solution. The layers were separated and the aqueous phase extracted with dichloromethane (3×50 mL). The combined organic extracts were washed with brine, dried over sodium sulfate, filtered and evaporated in vacuo. The residue was purified by column chromatography on silica gel Biotage 405, eluting with EtOAc/hexane to afford the title compound (i-16) as a solid (0.23 g, 52%). $^1$H-NMR (500 MHz, CDCl$_3$) δ 4.35 (s, 2H), 3.00 (m, 3H), 2.75 (s, 2H), 2.05 (m, 2H), 1.78 (m, 2H), 1.48 (s, 9H), 1.40 (t, J=4 Hz, 3H).

Intermediate 17

4-(1H-pyrazol-1-yl)piperidine (i-17)

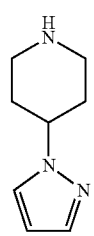
(i-17)

Step A: tert-butyl 4-[(methylsulfonyl)oxy]piperidine-1-carboxylate

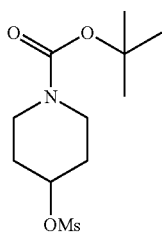 [SMILES: CC(C)(C)OC(=O)N1CCC(OS(C)(=O)=O)CC1]

To a solution of tert-butyl 4-hydroxypiperidine-1-carboxylate (550 mg, 2.5 mmol) and DMAP (296 mg, 2.5 mmol) in dichloromethane (15 mL) cooled to 0° C. by ice/water bath was added methanesulfonylchloride (189 μL, 2.5 mmol) and the resulting mixture stirred for 10 min at 0° C. and then for an additional hour at RT. The mixture was quenched with ice water and extracted with ethyl acetate (2×30 mL). The organic layer was washed with water and brine, dried over sodium sulfate, filtered and concentrated under vacuum. The residue oil was purified via silica gel preparative plates (3×1000 mM) eluting with 50% ethyl acetate in hexane to afford the title compound (555 mg, 89%). ESI-MS calculated for C$_{11}$H$_{21}$NO$_5$S: Exact Mass: 279.11. Found 302.13 (MNa)$^+$.

Step B: tert-butyl 4-(1H-pyrazol-1-yl)piperidine-1-carboxylate

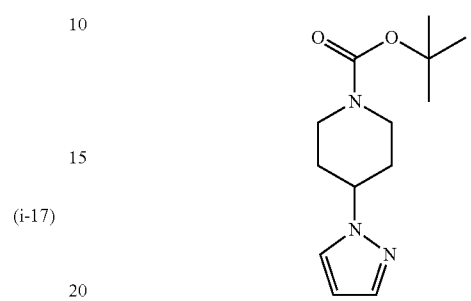

To a solution of pyrazole (100 mg, 1.50 mmol) in DMF (10.0 ml) under nitrogen atmosphere was added sodium hydride (60 mg, 1.65 mmol) and the solution stirred for 5 min. After bubbling ceased, the title compound from Step A (204 mg, 1.50 mmol) in 2.5 mL of DMF was added to the solution. The mixture was placed in a microwave reaction vessel and nitrogen was blown into it before closing.

Microwave: The reaction was set at 150° C. for 15 minutes on high absorption. After the reaction cooled, it was quenched with ammonium chloride solution and extracted with ethyl acetate. The organic layer was dried over sodium sulfate, filtered and concentrated to dryness. Purification of the residue was done on silica gel preparative plate (500 μM) eluting with 70% ethyl acetate in hexane to afford the product (52.2 mg, 55%). ESI-MS calculated for C$_{13}$H$_{21}$N$_3$O: Exact Mass: 251.16. Found: 252.16 (MH)$^+$ and 274.15 (MNa)$^+$.

Step C: 4-(1H-pyrazol-1-yl)piperidine (i-17)

The title compound from Step B above (50 mg, 0.2 mmol) was dissolved in 4 M HCl in dioxane (2.0 mL) and stirred at RT for 1 h. The product was concentrated under reduced pressure and dried under high vacuum to give the title compound (i-17) (30 mg, 96%). ESI-MS calculated for C$_{81}$H$_{13}$N$_3$: Exact Mass: 151.11. Found 152.10.

Intermediates 18-27 (i-18-i-27)

The following N-heterocyclic substituted piperidine intermediates were prepared from the appropriate starting materials using the procedures described above and procedures known in the art.

TABLE 1

| INTERMEDIATE | STRUCTURE | Calc. Mass | MS (e/z) (MH)$^+$ |
|---|---|---|---|
| i-18 | 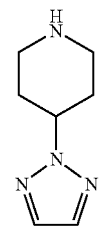 [SMILES: c1cnn(C2CCNCC2)n1] | 152.11 | 153.10 |

TABLE 1-continued

| INTERMEDIATE | STRUCTURE | Calc. Mass | MS (e/z) (MH)+ |
|---|---|---|---|
| i-19 | 4-(1H-1,2,3-triazol-1-yl)piperidine | 152.11 | 153.10 |
| i-20 | 4-(1H-1,2,4-triazol-1-yl)piperidine | 152.11 | 153.10 |
| i-21 | 4-(4H-1,2,4-triazol-4-yl)piperidine | 152.11 | 153.10 |
| i-22 | 4-(2H-tetrazol-2-yl)piperidine | 153.12 | 154.12 |
| i-23 | 4-(1H-tetrazol-1-yl)piperidine | 153.12 | 154.12 |
| i-24 | 4-(5-methyl-1H-tetrazol-1-yl)piperidine | 167.12 | 168.11 |
| i-25 | 4-(5-methyl-2H-tetrazol-2-yl)piperidine | 167.12 | 168.11 |
| i-26 | 4-(4-methyl-1H-imidazol-1-yl)piperidine | 165.13 | 166.11 |
| i-27 | 4-(5-methyl-1H-imidazol-1-yl)piperidine | 165.13 | 166.12 |

Intermediate 28

4-(1H-pyrazol-1-ylmethyl)piperidine (i-28)

(i-28)

Step A: tert-butyl 4-[(methylsulfonyl)oxymethyl]piperidine-1-carboxylate

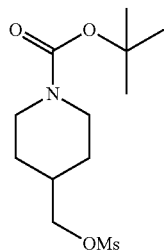 [SMILES: CC(C)(C)OC(=O)N1CCC(COS(C)(=O)=O)CC1]

To a solution of tort-butyl 4-(hydroxymethyl)piperidine-1-carboxylate (1.0 g, 5.0 mmol) and DMAP (600 mg, 5.0 mmol) in dichloromethane (30 mL) cooled to 0° C. by ice/water bath was added methanesulfonylchloride (380 µL, 5.0 mmol) and the resulting mixture stirred for 10 min at 0° C. and then for an additional hour at RT. The mixture was quenched with ice water and extracted with ethyl acetate (2×50 mL). The organic layer was washed with water and brine, dried over sodium sulfate, filtered and concentrated under vacuum. The residue oil was purified via silica gel preparative plates (4×1000 mM) eluting with 50% ethyl acetate in hexane to afford the title compound (989 mg, 79%). ESI-MS calculated for $C_{12}H_{23}NO_5S$: Exact Mass: 293.13. Found 316.15 $(MNa)^+$.

Step B: tert-butyl 4-(1H-pyrazol-1-ylmethyl)piperidine-1-carboxylate

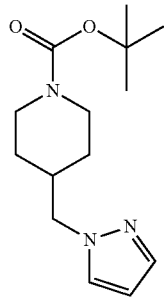 [SMILES: CC(C)(C)OC(=O)N1CCC(Cn2cccn2)CC1]

To a solution of the pyrazole (200 mg, 3.0 mmol) in DMF (20.0 ml) under nitrogen atmosphere was added sodium hydride (120 mg, 3.3 mmol) and the solution stirred for 5 min. After bubbling ceased, the title compound from Step A (400 mg, 3.0 mmol) in 5.0 mL of DMF was added to the solution. The mixture was placed in a microwave reaction vessel and nitrogen was blown into it before closing.

Microwave: The reaction was set at 150° C. for 15 min on high absorption. After the reaction cooled, it was quenched with ammonium chloride solution and extracted with ethyl acetate. The organic layer was dried over sodium sulfate, filtered and concentrated to dryness. Purification of the residue was done on silica gel preparative plate (1000 µM) eluting with 70% ethyl acetate in hexane to afford the product (436.6 mg, 55%). ESI-MS calculated for $C_{14}H_{23}N_3O$: Exact Mass: 265.16. Found: 266.16 $(MH)^+$ and 288.15 $(MNa)^+$.

Step C: 4-(1H-pyrazol-1-ylmethyl)piperidine (i-28)

The title compound from Step B above (100 mg, 0.4 mmol) was dissolved in 4 M HCl in dioxane (4.0 mL) and stirred at RT for 1 h. The product was concentrated under reduced pressure and dried under high vacuum to give the title compound (i-28) (59 mg, 95%). ESI-MS calculated for $C_9H_{15}N_3$: Exact Mass: 165.13. Found 166.12.

Intermediate 29

4-(1H-imidazol-1-ylmethyl)piperidine (i-29)

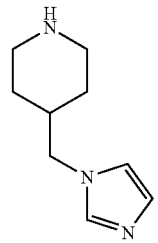

Prepared according to the procedures described in Intermediate 28 replacing pyrazole with imidazole. ESI-MS calculated for $C_9H_{15}N_3$: Exact Mass: 165.13. Found 166.12.

Intermediate 30

4-(1,3-thiazol-4-yl)piperidine (i-30)

Step A: tert-butyl 4-{1-[(trimethylsilyl)oxy]vinyl}piperidine-1-carboxylate

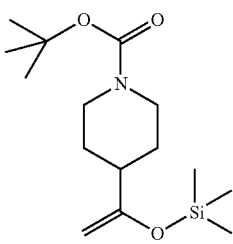 [SMILES: C=C(O[Si](C)(C)C)C1CCN(C(=O)OC(C)(C)C)CC1]

To a solution of LDA in THF (70 mL) under nitrogen atmosphere, cooled to −78° C. via dry ice/acetone bath, was added tert-butyl 4-acetylpiperidine-1-carboxylate (5 g, 22 mmol) in THF (30 mL) dropwise over 30 min. The resulting mixture was stirred for an additional 30 min and then TMSCl (2.81 mL) was added via syringe dropwise over 10 min and the resulting solution stirred for 1 h at −78° C. Quench with saturated sodium bicarbonate (300 mL) and extracted with ether (2×200 mL). Combined the organics, wash with brine, dry over sodium sulfate, filter, and concentrate under vacuum. The compound obtained (6.0 g, 92%) was used for the next reaction without further purification.

Step B: tert-butyl 4-(bromoacetyl)piperidine-1-carboxylate

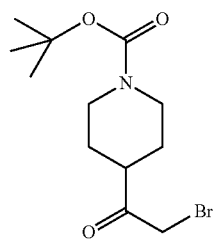 [SMILES: CC(C)(C)OC(=O)N1CCC(C(=O)CBr)CC1]

Dissolve the title compound from Step A above (6.0 g, 20 mmol) in THF (120 mL), cool to 0° C. and add sodium bicarbonate. To the resulting suspension was added NBS and the mixture stirred for 1.5 h. TLC showed no starting material left. Poured reaction into sat'd aqueous sodium buicarbonate solution (200 mL) and extracted with ether (2×200 mL). The organics were combined, washed with water and brine, dried over magnesium sulfate, filtered and concentrated under vacuum. The resulting product (6.4 g, 99%) was used without further purification for the next reaction. ESI-MS calculated for $C_{12}H_{20}BrNO_3$: Exact Mass: 305.06. Found: 305.15 (M)$^+$ and 307.09 (M+2)$^+$.

Step C: tert-butyl 4-(1,3-thiazol-4-yl)piperidine-1-carboxylate

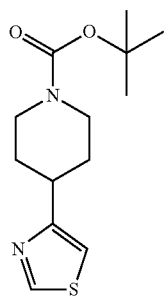 [SMILES: CC(C)(C)OC(=O)N1CCC(c2cscn2)CC1]

The title compound from Step B above (500 mg, 1.63 mmol) was combined with thioformamide (100 mg, 1.63 mmol) in 5 mL of THF, warmed to 60° C., and stirred overnight. The mixture was cooled to RT and diluted with ethyl acetate. The solution was then washed with water followed by brine. The organics were dried over magnesium sulfate, filtered and concentrated under vacuum. Purification via preparative TLC plates (3×1000 µM) eluting with 60% ethyl acetate/hexane afforded the title compound (282 mg, 63%) as a clear oil. ESI-MS calculated for $C_{13}H_{20}N_2O_2S$: Exact Mass: 268.12. Found: 169.12 (M-Boc)$^+$ and 291.14 (MNa)$^+$.

Step D: 4-(1,3-thiazol-4-yl)piperidine (i-30)

The title compound from Step C above (280 mg, 1.04 mmol) was dissolved in 4 M HCl in dioxane (4.0 mL) and stirred at RT for 1 h. The product was concentrated under reduced pressure and dried under high vacuum to give the title compound (i-30) (237 mg, 94%). ESI-MS calculated for $C_8H_{12}N_2S$: Exact Mass: 168.07. Found 169.07.

Intermediate 31

4-(1H-imidazol-4-yl)piperidine (i-31)

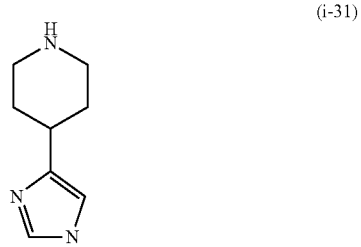 [SMILES: c1nc(C2CCNCC2)c[nH]1]

Prepared according to the procedures described in Intermediate 30 replacing thioformamide with imidoformamide acetate at Step. ESI-MS calculated for $C_9H_{15}N_3$: Exact Mass: 165.13. Found 166.12.

Intermediate 32

4-(1H-tetrazol-5-yl)piperidine (i-32)

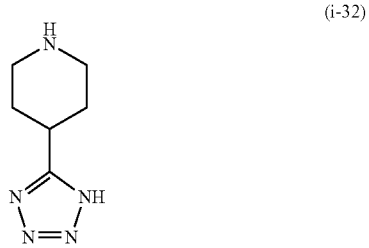 [SMILES: C1CC(c2nnn[nH]2)CCN1]

Step A: tert-butyl 4-(1H-tetrazol-5-yl)piperidine-1-carboxylate

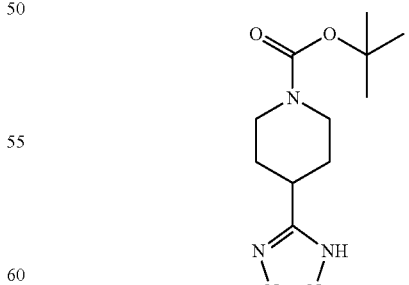

Sodium azide (228 mg, 3.50 mmol) was added to a stirred, cooled RT mixture of tert-butyl 4-cyanopiperidine-1-carboxylate (243 mg, 1.167 mmol) in DMF (5 ml) and the mixture was stirred at 100° C. for 48 h. The mixture was cooled, diluted with ethyl acetate (100 mL), washed with brine (3×50 mL), dried over sodium sulfate, filtered, and the solvent was evaporated under reduced pressure. The residue was purified by column chromatography on silica gel Biotage 40S, eluting with 10% methanol in dichloromethane to afford the title compound (197 mg, 75%) as a colorless liquid. ESI-MS calculated for $C_{11}H_{19}N_5O_2$: Exact Mass: 253.13. Found 254.12.

Step B: 4-(1H-tetrazol-5-yl)piperidine (i-32)

The title compound from Step A above (197 mg, 0.77 mmol) was dissolved in 4 M HCl in dioxane (3.0 mL) and stirred at RT for 1 h. The product was concentrated under reduced pressure and dried under high vacuum to give the title compound (i-32) (116 mg, 98%). ESI-MS calculated for $C_6H_{11}N_5$: Exact Mass: 153.13. Found 154.12.

Intermediate 33 and 34

4-(1-methyl-1H-tetrazol-5-yl)piperidine (i-33) and 4-(2-methyl-2H-tetrazol-5-yl)piperidine (i-34)

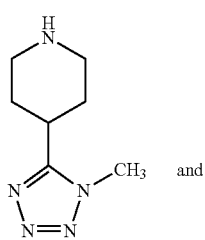

(i-33)

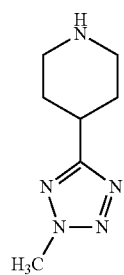

(i-34)

Step A: tert-butyl 4-(1-methyl-1H-tetrazol-5-yl)piperidine-1-carboxylate and tert-butyl 4-(2-methyl-2H-tetrazol-5-yl)piperidine-1-carboxylate

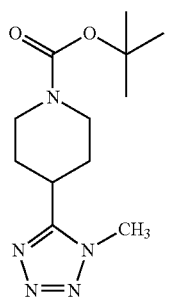 [SMILES: CC(C)(C)OC(=O)N1CCC(c2nnn[nH]2)CC1] and 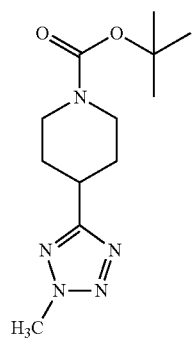

To a solution of tert-butyl 4-(1H-tetrazol-5-yl)piperidine-1-carboxylate (100 mg, 0.4 mmol) and iodomethane (174 μL, 1.2 mmol) in anhydrous DMF (3 ml) was added cesium carbonate (800 mg, 2.4 mmol) and the resulting mixture heated to 80° C. for 2 h. After allowing to cool to RT, the mixture was poured into water and extracted with ethyl acetate (3×10 mL). The organics were combined, dried over magnesium sulfate, filtered and concentrated under reduced pressure. The residue was purified via preparative TLC plate (1000 μM) eluting with 80% ethyl acetate in hexane which also separate the two isomers. The isomers were labeled as isomer 1 and isomer 2 in the order that they eluted off the plate. Isomer 1 (45 mg, 25%) was identified as the Boc-4-(1-methyl-1H-tetrazol-5-yl)piperidine and the other (isomer 2, 30 mg, 16%) to be the 2-methyl substituted tetrazole.

Isomer 1: ESI-MS calculated for $C_{12}H_{23}N_5O_2$: Exact Mass: 267.13. Found 268.12.

Isomer 2: ESI-MS calculated for $C_{12}H_{23}N_5O_2$: Exact Mass: 267.13. Found 268.12.

Step B: 4-(1-methyl-1H-tetrazol-5-yl)piperidine (i-33)

The isomer 1 from Step A above (45 mg, 0.16 mmol) was dissolved in 4 M HCl in dioxane (1.0 mL) and stirred at RT for 1 h. The product was concentrated under reduced pressure and dried under high vacuum to give the title compound (i-33) (25 mg, 95%). ESI-MS calculated for $C_7H_{15}N_5$: Exact Mass: 167.13. Found 168.12.

Step C: 4-(2-methyl-2H-tetrazol-5-yl)piperidine (i-34)

The title compound (i-34) was prepared according to the procedure outlined above in Step B replacing the isomer 1 with the isomer 2 from Step A above. ESI-MS calculated for both is $C_9H_{17}N_5$: Exact Mass: 167.13. Found 168.12.

Intermediate 35 and 36

4-(1-isopropyl-1H-tetrazol-5-yl)piperidine (i-35) and 4-(2-isopropyl-2H-tetrazol-5-yl)piperidine (i-36)

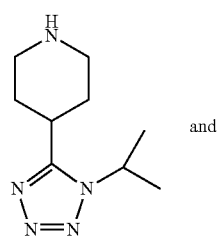 and (i-35)

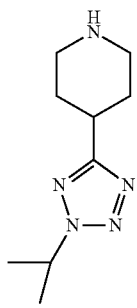
(i-36)

Prepared according to the procedures outlined in Intermediates (33 and 34) replacing iodomethane with isopropyl iodide at Step A. ESI-MS calculated for both is $C_9H_{17}N_5$: Exact Mass: 195.13. Found 196.12 for both.

Intermediate 37

4-(1-cyclopropyl-1H-tetrazol-5-yl)piperidine (i-37)

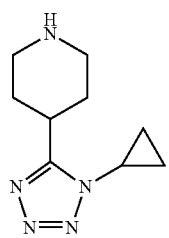
(i-37)

Step A: tert-butyl 4-[(cyclopropylamino)carbonyl]piperidine-1-carboxylate

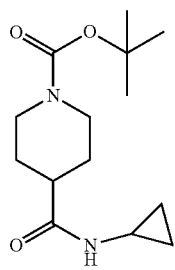 [SMILES: CC(C)(C)OC(=O)N1CCC(C(=O)NC2CC2)CC1]

To a solution of 1-(tert-butoxycarbonyl)piperidine-4-carboxylic acid (670 mg, 2.92 mmol) and cyclopropylamine (167 mg, 2.92 mmol) in 15 mL anhydrous DMF was added HATU (1.11 g, 2.92 mmol) and the resulting mixture stirred at RT under nitrogen atmosphere for 3 h. The mixture was washed with water and extracted with ethyl acetate (2×50 mL). The organics were washed with brine, separated, dried over sodium sulfate, filtered and concentrated under vacuum. The residue was purified by Biotage MPLC (silica gel 40+ column) eluting with 50% ethyl acetate in hexane to afford the product (704 mg, 89%). ESI-MS calculated for $C_{14}H_{24}N_2O_3$: Exact Mass: 268.18. Found 169.17 (M-Boc)$^+$ and 291.15 (MNa)$^+$.

Step B: Tert-butyl 4-(1-cyclopropyl-1H-tetrazol-5-yl)piperidine-1-carboxylate

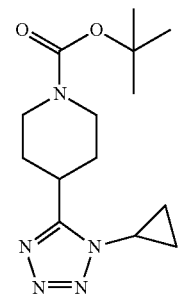 [SMILES: CC(C)(C)OC(=O)N1CCC(c2nnnn2C2CC2)CC1]

The title compound from Step A above (200 mg, 0.745 mmol) and triphenylphosphine (391 mg, 1.49 mmol) were placed in a 50 ml round bottom flask and then THF (20 ml) was added followed by DIAD (0.29 mL, 1.49 mol) at RT. After 5 min of stirring, trimethylsilylazide (0.2 mL, 1.50 mmol) was added and the resulting mixture was stirred overnight at RT. The volatiles were removed under reduced pressure and the resulting residue was partitioned between ethyl acetate and brine, combined, dried over sodium sulfate, filtered and concentrated. The material was purified by Mass Directed HPLC to give the title compound (52 mg, 24%) as a clear oil/film. ESI-MS calculated for $C_{14}H_{23}N_5O_2$: Exact Mass: 293.38. Found 194.35 (M-Boc)$^+$ and 316.36 (MNa)$^+$.

Step C: 4-(1-cyclopropyl-1H-tetrazol-5-yl)piperidine (i-37)

The title compound from Step B above (200 mg, 0.68 mmol) was dissolved in 4 M HCl in dioxane (4.0 mL) and stirred at RT for 1 h. The product was concentrated under reduced pressure and dried under high vacuum to the title compound (i-37) (127 mg, 96%). ESI-MS calculated for $C_9H_{15}N_5$: Exact Mass: 193.13. Found 194.14.

Intermediate 38

5-(1H-tetrazol-1-yl)-octahydrocyclopenta[c]pyrrole (i-38)

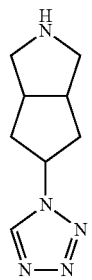
(i-38)

Step A: tert-butyl 5-(1H-tetrazol-1-yl)hexahydrocyclopenta[c]pyrrole-2(1H)-carboxylate

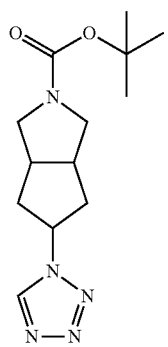 [SMILES: CC(C)(C)OC(=O)N1CC2CC(n3cnnn3)CC2C1]

To a solution of tert-butyl 5-aminohexahydrocyclopenta[c]pyrrole-2(1H)-carboxylate (1.0 g, 4.4 mmol) and triethylorthoformate (4.4 mL, 26.4 mmol) in acetic acid (20 mL) was added sodium azide (1.7 g, 26.4 mmol) and the resulting mixture was set under inert atmosphere. The mixture was heated at 100° C. for 4 h and then cooled to RT at which time the volatiles were removed in vacuo. The residue was taken up in ethyl acetate (100 mL) and washed with aqueous sodium bicarbonate solution, followed by brine. The organics were dried over sodium sulfate, filtered, and concentrate to dryness under vacuum. The residue was placed in the refrigerator overnight and the next day a solid white precipitate was observed. The precipitate was triturated with hexane and the solvent was carefully decanted to give the pure product (675 mg, 55%) as a white solid. ESI-MS calculated for $C_{13}H_{21}N_5O_2$: Exact Mass: 279.28. Found 280.28 (MH) and 302.27 (MNa)$^+$.

Step B: 5-(1H-tetrazol-1-yl)-octahydrocyclopenta[c]pyrrole (i-38)

The title compound from Step A above (670 mg, 2.4 mmol) was dissolved in 4 M HCl in dioxane (5 mL) and stirred at RT overnight. The product was concentrated under reduced pressure and dried under high vacuum to afford the title compound (i-38) (395 mg, 92%). ESI-MS calculated for $C_8H_{13}N_5$: Exact Mass: 179.09. Found 180.05.

Intermediate 39 tert-butyl 5-[(methylsulfonyl)oxy]hexahydrocyclopenta[c]pyrrole-2(1H)-carboxylate (i-39)

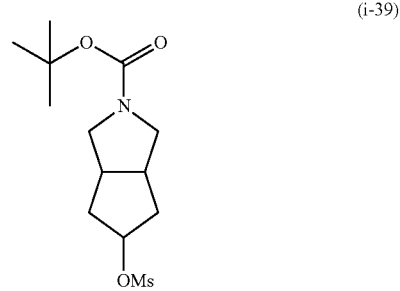 [SMILES: CC(C)(C)OC(=O)N1CC2CC(OS(C)(=O)=O)CC2C1]

Step A: tert-butyl 5-hydroxyhexahydrocyclopenta[c]pyrrole-2(1H)-carboxylate

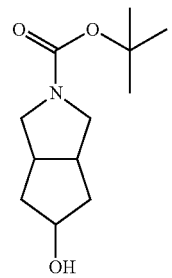 [SMILES: CC(C)(C)OC(=O)N1CC2CC(O)CC2C1]

To a solution of tert-butyl 5-hydroxyhexahydrocyclopenta[c]pyrrole-2(1H)-carboxylate (4.4 g, 19.4 mmol) in water (100 mL) was added a solution of sodium nitrite (1.38 g, 20.0 mmol) in 0.01M HCl (20 mL) and the resulting solution stirred at RT overnight. The solution was azeotroped with toluene down to ⅕ its starting concentration at which point ethyl acetate (100 mL) was added. The ethyl acetate was separated, dried over sodium sulfate, filtered, and concentrated. The residue was purified by preparative TLC plates (10×1000 mM) eluting with 5% methanol in DCM to afford the title compound (720 mg, 17%) ESI-MS calculated for $C_{12}H_{21}NO_3$: Exact Mass: 227.15. Found 250.14 (MNa)$^+$.

Step B: tert-butyl 5-[(methylsulfonyl)oxy]hexahydrocyclopenta[c]pyrrole-2(1H)-carboxylate (i-39)

To a solution of the title compound from Step A above (550 mg, 2.4 mmol) and DMAP (296 mg) in DCM (15 mL) was added MsCl (189 μL) at 0° C. The mixture was stirred for 10 min at the same temperature and for an additional hour at RT. The mixture was quenched with ice water and extracted with ethyl acetate (2×50 mL). The organic layer was washed with water and brine, dried over sodium sulfate, filtered, and concentrated under vacuum. The residue oil was purified via prep-plate purification eluting with 50% ethyl acetate in hexane to afford the title compound (i-39) (555 mg, 75%). ESI-MS calculated for $C_{13}H_{23}NO_5S$: Exact Mass: 305.13. Found 328.14 (MNa)+.

Intermediate 40

6-(1H-tetrazol-1-yl)-3-azabicyclo[3.1.0]hexane (i-40)

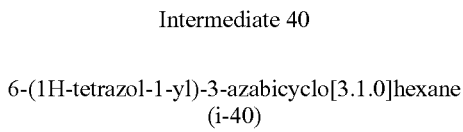

Step A: tert-butyl 6-(1H-tetrazol-1-yl)-3-azabicyclo[3.1.0]hexane-3-carboxylate

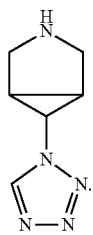

To a solution of tert-butyl 6-amino-3-azabicyclo[3.1.0]hexane-3-carboxylate (7.3 g, 25.3 mmol) and triethylorothoformate (24 mL, 152 mmol) in acetic acid (200 mL) was added sodium azide (9.9 g, 152 mmol) and the resulting mixture was set under inert atmosphere. The mixture was heated at 100° C. for 4 h and then cooled to RT at which time the volatiles were removed in vacuo. The residue was taken up in ethyl acetate (200 mL) and washed with aqueous sodium bicarbonate solution, followed by brine. The organics were dried over sodium sulfate, filtered, and concentrate to dryness under vacuum. The residue was placed in the refrigerator overnight and the next day a solid white precipitate was observed. The precipitate was triturated with hexane and the solvent was carefully decanted to give the title compound 3.2 g (50.3%) as a white solid. ESI-MS calculated for $C_{11}H_{17}N_5O_2$: Exact Mass: 251.28. Found 252.28.

Step B: 6-(1H-tetrazol-1-yl)-3-azabicyclo[3.1.0]hexane (i-40)

The title compound from Step A above (2.6 g, 12.2 mmol) was dissolved in 4 M HCl in dioxane (200 mL) and stirred at RT overnight. The product was concentrated under reduced pressure and dried under high vacuum to give 6-(1H-tetrazol-1-yl)-3-azabicyclo[3.1.0]hexane. ESI-MS calculated for $C_6H_9N_5$: Exact Mass: 151.09. Found 152.05.

Intermediate 41

(1R,5S,6r)-6-(1H-pyrazol-1-ylmethyl)-3-azabicyclo[3.1.0]hexane (i-41)

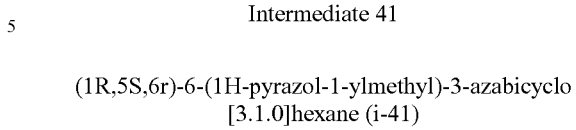

Step A: tert-butyl (1R,5S,6r)-6-{[(methylsulfonyl)oxy]methyl}-3-azabicyclo[3.1.0]hexane-3-carboxylate

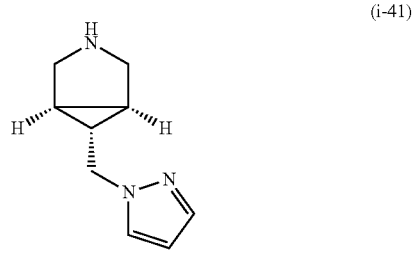 [SMILES: c1cnn(C[C@H]2[C@@H]3CNC[C@@H]32)c1]

To a solution of tert-butyl (1R,5S,6r)-6-(hydroxymethyl)-3-azabicyclo[3.1.0]hexane-3-carboxylate (1.0 g, 5.0 mmol) and DMAP (600 mg, 5.0 mmol) in dichloromethane (30 mL) cooled to 0° C. by ice/water bath was added methanesulfonylchloride (380 μL, 5.0 mmol) and the resulting mixture stirred for 10 mM at 0° C. and then for an additional hour at RT. The mixture was quenched with ice water and extracted with ethyl acetate (2×50 mL). The organic layer was washed with water and brine, dried over sodium sulfate, filtered and concentrated under vacuum. The residue oil was purified via silica gel preparative plates (4×1000 mM) eluting with 50% ethyl acetate in hexane to afford the title compound (1.01 g, 81%). ESI-MS calculated for $C_{12}H_{21}NO_5S$: Exact Mass: 291.11. Found 314.14 (MNa)+.

Step B: tert-butyl (1R,5S,6r)-6-(1H-pyrazol-1-ylmethyl)-3-azabicyclo[3.1.0]hexane-3-carboxylate

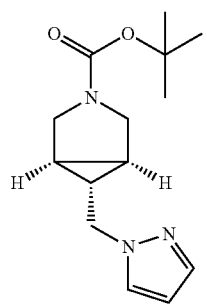 [SMILES: CC(C)(C)OC(=O)N1C[C@@H]2[C@H](C1)[C@H]2Cn1cccn1]

To a solution of the pyrazole (200 mg, 3.0 mmol) in DMF (20.0 ml) under nitrogen atmosphere was added sodium hydride (120 mg, 3.3 mmol) and the solution stirred for 5 min. After bubbling ceased, the title compound from Step A above (400 mg, 3.0 mmol) in 5.0 mL of DMF was added to the solution. The mixture was placed in a microwave reaction vessel and nitrogen was blown into it before closing.

Microwave: The reaction was set at 150° C. for 15 min on high absorption. After the reaction cooled, it was quenched with ammonium chloride solution and extracted with ethyl acetate. The organic layer was dried over sodium sulfate, filtered and concentrated to dryness. Purification of the residue was done on silica gel preparative plate (1000 μM) eluting with 70% ethyl acetate in hexane to afford the title compound (388.8 mg, 49%). EST-MS calculated for $C_{14}H_{21}N_3O$: Exact Mass: 263.16. Found: 264.16 (MH)+ and 286.15 (MNa)+.

Step C: (1R,5S,6r)-6-(1H-pyrazol-1-ylmethyl)-3-azabicyclo[3.1.0]hexane (i-41)

The title compound from Step B above (100 mg, 0.4 mmol) was dissolved in 4 M HCl in dioxane (4.0 mL) and stirred at RT for 1 h. The product was concentrated under reduced pressure and dried under high vacuum to give the title compound (i-41) (61.9 mg, 97%). EST-MS calculated for $C_9H_{13}N_3$: Exact Mass: 163.13. Found 164.12.

Intermediates 42-49 (i-42-i-49)

The following N-heterocyclic substituted piperidine intermediates were prepared from the appropriate starting materials using the procedures described above and procedures known in the art.

TABLE 2

| INTERMEDIATE | STRUCTURE | Calc. Mass | MS (e/z) (MH)+ |
|---|---|---|---|
| i-42 | 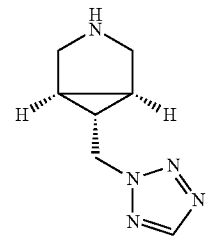 [SMILES: c1nnn(C[C@H]2[C@@H]3CNC[C@@H]32)n1] | 165.11 | 166.10 |
| i-43 | 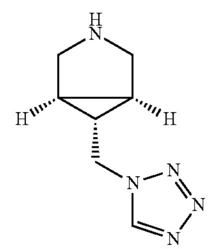 [SMILES: c1nnnn1C[C@H]1[C@@H]2CNC[C@@H]21] | 165.11 | 166.12 |
| 44 | 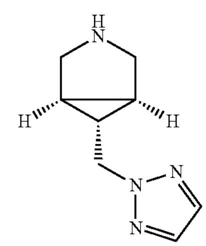 [SMILES: c1cnn(C[C@H]2[C@@H]3CNC[C@@H]32)n1] | 164.10 | 165.10 |
| 45 | 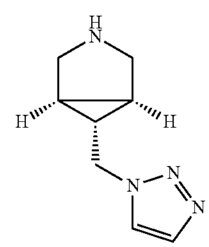 [SMILES: c1cn(C[C@H]2[C@@H]3CNC[C@@H]32)nn1] | 164.10 | 165.10 |
| 46 | 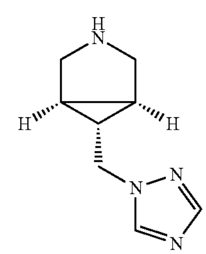 [SMILES: c1ncn(C[C@H]2[C@@H]3CNC[C@@H]32)n1] | 164.10 | 165.09 |
| 47 | 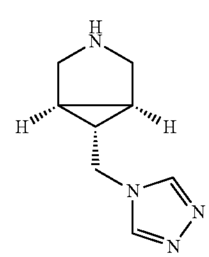 [SMILES: c1nncn1C[C@H]1[C@@H]2CNC[C@@H]21] | 164.10 | 165.10 |

TABLE 2-continued

| INTERMEDIATE | STRUCTURE | Calc. Mass | MS (e/z) (MH)+ |
|---|---|---|---|
| 48 | 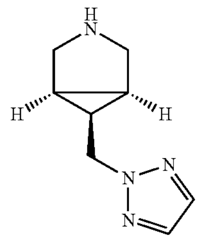 [SMILES: c1cnn(C[C@@H]2[C@@H]3CNC[C@@H]32)n1] | 164.10 | 165.11 |
| 49 | 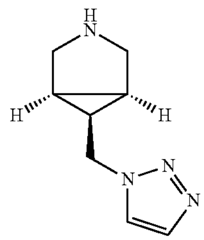 [SMILES: c1cn(C[C@@H]2[C@@H]3CNC[C@@H]32)nn1] | 164.10 | 165.10 |

Intermediate 50

6-(1H-tetrazol-1-yl)-3-azabicyclo[3.1.0]hexane
(i-50)

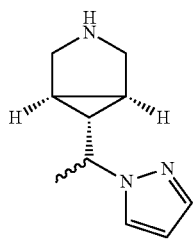

(i-50)

Step A: benzyl (1R,5S,6r)-6-formyl-3-azabicyclo
[3.1.0]hexane-3-carboxylate

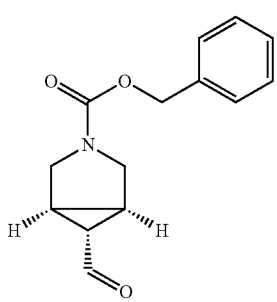 [SMILES: O=C[C@@H]1[C@H]2CN(C(=O)OCc3ccccc3)C[C@@H]12]

To a solution of benzyl (1R,5S,6r)-6-(hydroxymethyl)-3-azabicyclo[3.1.0]hexane-3-carboxylate (1.0 g, 4.1 mmol) in DCM (20.0 ml) under nitrogen atmosphere was added Dess Martin reagent (643 mg, 6.0 mmol) and the resulting solution stirred for 5 h. To the mixture was added solid calcium hydroxide (1.16 g, 60 mmol) and the suspension stirred vigorously to remove all benzoic and acetic acid by-products of the Dess Martin reagent. The solid was filtered off through celite and washed with DCM (50 mL). The solution was then washed with saturated sodium bicarbonate (10 mL) and the organics dried over sodium sulfate, filtered and concentrated under vacuum. The residue was purified via Biotage Flash 40+ silica gel MPLC eluting with 50% ethyl acetate in hexane to afford the title compound (860 mg, 87%). ESI-MS calculated for $C_{14}H_{15}NO_3$: Exact Mass: 245.45. Found 268.42 (MNa)+.

Step B: benzyl (1R,5S,6r)-6-[1-hydroxyethyl]-3-azabicyclo[3.1.0]hexane-3-carboxylate

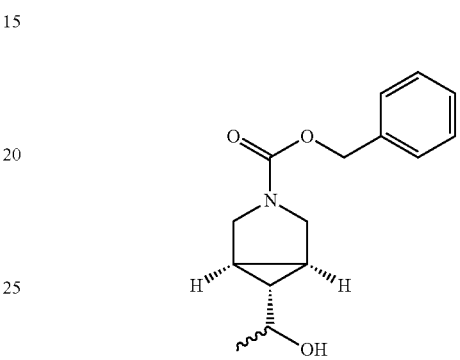

To a solution of the title compound from Step A above (215 mg, 0.88 mmol) in anhydrous THF (5 mL) under nitrogen atmosphere cooled to −60° C. via dry ice/isopropanol bath was added 3.0 M methyl magnesium chloride in THF (0.29 mL, 0.88 mmol). The resulting solution was stirred for 30 min at −60° C. and then allowed to warm to RT. 1N HCl was added slowly to the solution and the mixture was extracted with ethyl acetate (2×20 mL). The organics were combined, washed with water and then brine, dried over sodium sulfate, filtered, and concentrated to dryness under vacuum. The residue was purified via Biotage Flash MPLC (25 M silica gel cartridge) using a gradient eluting system of 40-100% ethyl acetate hexane to afford the title compound (107 mg, 46%).

Step C: benzyl (1R,5S,6r)-6-{1-[(methylsulfonyl)oxy]ethyl}-3-azabicyclo[3.1.0]hexane-3-carboxylate

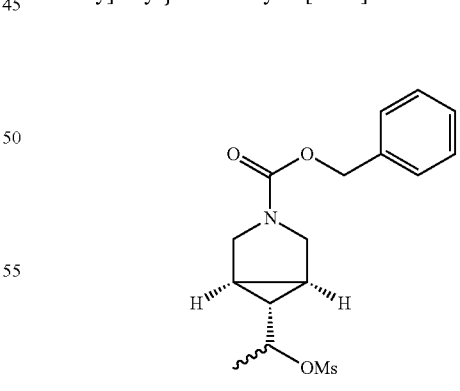

To a solution of the title compound from Step B above (175 mg, 0.65 mmol) and TEA (0.18 mL, 1.30) in dichloromethane (50 mL) cooled to 0° C. via ice/water bath was added methanesulfonylchloride (0.8 mL, 0.98 mmol) and the resulting solution stirred for 15 min at 0° C. The ice bath was removed and the solution allowed to stir for an additional 2 h at RT. The mixture was poured into water and extracted with ethyl acetate. The organic layer was then washed with brine, dried over sodium sulfate, filtered and concentrated under vacuum. The residue was purified via preparative plate (2×1000 mM silica) eluting with 40% ethyl acetate in hexane to afford the title compound (122 mg, 55.2%).

Step D: (1R,5S,6r)-6-[1-(1H-pyrazol-1-yl)ethyl]-3-azabicyclo[3.1.0]hexane-3-carboxylate

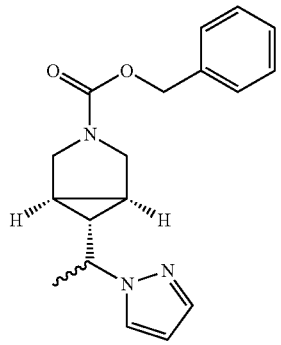 [SMILES: CC([C@H]1[C@@H]2CN(C(=O)OCc3ccccc3)C[C@@H]21)n1cccn1]

To a solution of the pyrazole (18 mg, 0.27 mmol) in DMF (20.0 ml) under nitrogen atmosphere was added sodium hydride (12 mg, 0.30 mmol) and the solution stirred for 5 min. After bubbling ceased, the title compound from Step C above (60 mg, 0.18 mmol) in 1.0 mL of DMF was added to the solution. The mixture was placed in a microwave reaction vessel and nitrogen was blown into it before closing.

Microwave: The reaction was set at 150° C. for 15 min on high absorption. After the reaction cooled, it was quenched with ammonium chloride solution and extracted with ethyl acetate. The organic layer was dried over sodium sulfate, filtered and concentrated to dryness. Purification of the residue was done on silica gel preparative plate (500 µM) eluting with 75% ethyl acetate in hexane to afford the title compound (27.7 mg, 51%). ESI-MS calculated for $C_{18}H_{21}N_3O_2$: Exact Mass: 311.16. Found: 312.16 (MH)$^+$ and 334.15 (MNa)$^+$.

Step E: 6-(1H-tetrazol-1-yl)-3-azabicyclo[3.1.0]hexane (i-50)

To a solution of the title compound from Step D above (27 mg, 0.10 mmol) in EtOH (1.0 ml) was added 10% palladium on carbon and the resulting suspension set under hydrogen atmosphere via a balloon of hydrogen. The mixture was stirred vigorously under hydrogen gas for 2 h at RT. The catalyst was filtered off using a Gilmen 0.45 PFTE syringe filter disc and then washed with methanol (2×5 mL). The filtrate was combined and concentrated to dryness under vacuum to afford the title compound (i-50). ESI-MS calculated for $C_{10}H_{15}N_3$: Exact Mass: 177.14. Found: 177.15 (MH)$^+$.

Intermediates 51-55

The following N-heterocyclic substituted piperidine intermediates were prepared from the appropriate starting materials using the procedures described above and procedures known in the art.

TABLE 3

| INTERMEDIATE | STRUCTURE | Calc. Mass | MS (e/z) (MH)$^+$ |
|---|---|---|---|
| i-51 | 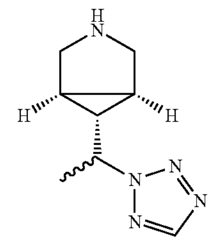 | 152.11 | 153.10 |
| i-52 | 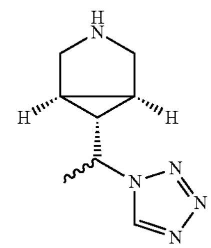 | 152.11 | 153.10 |
| i-53 | 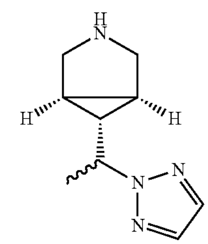 | 152.11 | 153.10 |
| i-54 | 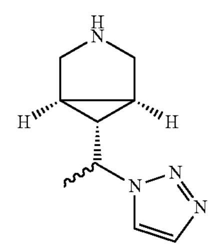 | 152.11 | 153.10 |
| i-55 | 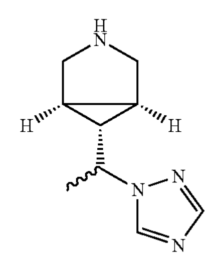 | 152.11 | 153.10 |

Intermediate 56 tert-butyl (1R,5S,6r)-6-(aminocarbonyl)-3-azabicyclo[3.1.0]hexane-3-carboxylate (i-56)

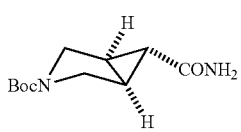

(i-56)

To a solution of 2.81 g (12.4 mmol) (1R,5S,6r)-3-(tert-butoxycarbonyl)-3-azabicyclo[3.1.0]hexane-6-carboxylic acid in anhydrous tetrahydrofuran (35 ml) at −10° C. was added triethylamine (1.90 ml, 13.6 mmol) followed by ethyl chloroformate (1.30 ml, 13.6 mmol). The reaction mixture was stirred between −20° C. and −10° C. for 20 min. The solid was filtered off and rinsed with tetrahydrofuran. The tetrahydrofuran filtrate was added into 7 M ammonia methanol solution (30 ml, 210 mmol) at 0° C. The reaction mixture was stirred at ambient temperature for 2 h. After concentration, it was purified by using a Biotage Horizon® system (0-5% methanol/dichloromethane) to give 2.7 g (96%) of the title compound as a white solid. LC-MS: m/z (ESI) 209.2 (M+1).

Intermediate 57 tert-butyl (1R,5S,6r)-6-cyano-3-azabicyclo[3.1.0]hexane-3-carboxylate (i-57)

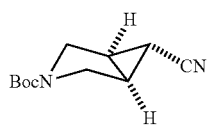

(i-57)

Tert-butyl (1R,5S,6r)-6-(aminocarbonyl)-3-azabicyclo[3.1.0]hexane-3-carboxylate (0.515 g, 2.28 mmol) in dichloromethane (10 ml) at 0° C. was added N,N-diisopropylethylamine (0.991 ml, 5.69 mmol) followed by trifluoroacetic anhydride (0.348 ml, 2.50 mmol) dropwise. The reaction mixture was stirred at 0° C. for 1 h then at ambient temperature for 1 h. After washed with brine, dried over Na$_2$SO$_4$ and concentrated, it was purified by using a Biotage Horizon® system (0-40% EtOAc in hexanes) to afford 0.383 g (84%) pale yellow solid. $^1$H NMR (500 MHz, CDCl$_3$): δ 3.77-3.67 (m, 2H), 3.42 (d, J=11.5 Hz, 2H), 2.20 (s, 2H), 1.46 (s, 9H), 1.28 (t, J=3.4 Hz, 1H).

Intermediate 58 tert-butyl (1R,5S,6r)-6-(5-methyl-1,3-oxazol-2-yl)-3-azabicyclo[3.1.0]hexane-3-carboxylate (i-58)

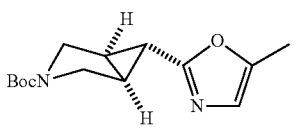

(i-58)

(1R,5S,6r)-3-(tert-butoxycarbonyl)-3-azabicyclo[3.1.0]hexane-6-carboxylic acid (0.250 g, 1.10 mmol), 1-hydroxybenzotriazole (0.178 mg, 1.32 mmol), propargylamine (0.121 g, 2.20 mmol) in DMF (1 ml) was added to N,N-diisopropylethylamine (0.961 ml, 5.50 mmol) followed by 0.300 g (1.56 mmol) of N-(3-dimethylaminopropyl)-N-ethylcarbodiimide (EDC) hydrochloride. The reaction mixture was stirred at ambient temperature for 3 h. After removal of the volatiles, it was purified by using a Biotage Horizon® system (0-100% EtOAc in hexanes).

Amide from above (0.065 g, 0.25 mmol) in dichloromethane (1 ml) was added to a solution of gold (III) chloride (0.0075 g, 0.025 mmol) in CH$_3$CN (0.1 ml). The reaction mixture was stirred at ambient temperature overnight. After removal of the volatiles, the mixture was filtered and purified by reverse phase HPLC (TMC Pro-Pac C18; 10-100% 0.1% trifluoroacetic acid in acetonitrile/0.1% trifluoroacetic acid in water gradient). The resulting pure fractions were lyophilized overnight to give the title compound (i-58). LC-MS: m/z (ESI) 265.3 (M+1).

Intermediate 59 tert-butyl (1R,5S,6r)-6-(4-methyl-1,3-oxazol-2-yl)-3-azabicyclo[3.1.0]hexane-3-carboxylate

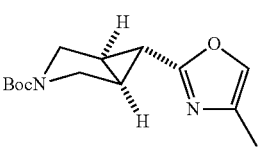

(i-59)

Tert-butyl (1R,5S,6r)-6-(aminocarbonyl)-3-azabicyclo[3.1.0]hexane-3-carboxylat (0.192 g, 0.849 mmol) in ethanol (2 ml) was added to chloroacetone (0.338 ml, 4.24 mmol). The reaction mixture was refluxed overnight. Chloroacetone (0.338 ml, 4.24 mmol) was added again and the mixture was refluxed for another 6 h. After removal of the volatiles, it was purified by using a Biotage Horizon® system (0-5% metha-

Intermediate 60 tert-butyl (1R,5S,6r)-6-(3-methyl-1,2,4-oxadiazol-5-yl)-3-azabicyclo[3.1.0]hexane-3-carboxylate (i-60)

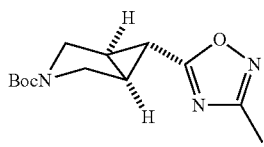

Tert-butyl (1R,5S,6r)-6-(aminocarbonyl)-3-azabicyclo[3.1.0]hexane-3-carboxylate (0.250 g, 1.10 mmol) in N,N-dimethylacetamide dimethyl acetal (3.00 ml, 20.5 mmol) was heated at 110° C. oil bath for 2 h. The volatiles were removed under vacuum. The residue in dioxane (1.5 ml) was added to hydroxylamine solution (50%, 0.081 ml, 1.3 mmol) followed by acetatic acid (0.158 ml, 2.76 mmol). The reaction mixture was heated at 90° C. for 6 h. After removal of the volatiles, it was purified by using a Biotage Horizon® system (0-40% then 40% EtOAc in hexanes) to afford 0.239 g (82%) of the title compound as colorless oil. $^1$H NMR (500 MHz, CDCl$_3$): δ 3.85-3.74 (m, 2H), 3.52 (d, H=10.5 Hz, 2H), 2.37 (s, 3H), 2.28 (s, 2H), 2.07 (t, J=3.2 Hz, 1H), 1.49 (s, 9H).

Intermediate 61 tert-butyl (1R,5S,6r)-6-(1,2,4-oxadiazol-5-yl)-3-azabicyclo[3.1.0]hexane-3-carboxylate (i-61)

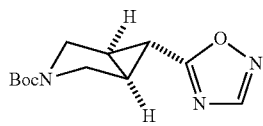

Prepared according to the procedure described above for tert-butyl (1R,5S,6r)-6-(3-methyl-1,2,4-oxadiazol-5-yl)-3-azabicyclo[3.1.0]hexane-3-carboxylate as described in Intermediate 60, replacing N,N-dimethylacetamide dimethyl acetal with N,N-dimethylformamide dimethyl acetal. $^1$H NMR (500 MHz, CDCl$_3$): δ 8.29 (s, 1H), 3.86-3.76 (m, 2H), 3.53 (m, 2H), 2.32 (s, 2H), 2.17 (t, J=3.2 Hz, 1H), 1.49 (s, 9H).

Intermediate 62 tert-butyl (1R,5S,6r)-6-(4H-1,2,4-triazol-3-yl)-3-azabicyclo[3.1.0]hexane-3-carboxylate (i-62)

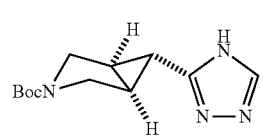

Tert-butyl (1R,5S,6r)-6-(aminocarbonyl)-3-azabicyclo[3.1.0]hexane-3-carboxylate (0.227 g, 1.00 mmol) in N,N-dimethylformamide dimethyl acetal (3.00 ml, 22.4 mmol) was heated at 110° C. oil bath for 2 h. The volatiles were removed under vacuum. The residue in dioxane (1.5 ml) was added to hydrazine (0.058 ml, 1.2 mmol) followed by acetatic acid (0.144 ml, 2.51 mmol). The reaction mixture was heated at 11° C. for 5 h. After removal of the volatiles, it was purified by using a Biotage Horizon® system (0-8% then 8% methanol with 10% ammonia in dichloromethane) to afford 0.240 g (96%) of the title compound as a white solid. LC-MS: m/z (ESI) 251.2 (M+1).

Intermediate 63 tert-butyl (1R,5S,6r)-6-(1,3,4-oxadiazol-2-yl)-3-azabicyclo[3.1.0]hexane-3-carboxylate (i-62)

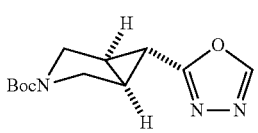

Step A: tert-butyl (1R,5S,6r)-6-(hydrazinocarbonyl)-3-azabicyclo[3.1.0]hexane-3-carboxylate To a solution of 4.50 g (19.8 mmol) (1R,5S,6r)-3-(tert-butoxycarbonyl)-3-azabicyclo[3.1.0]hexane-6-carboxylic acid in 50 ml anhydrous tetrahydrofuran at −10° C. was added 3.04 ml (21.8 mmol) triethylamine followed by 2.08 ml (21.8 mmol) ethyl chloroformate slowly. The reaction was stirred between −20° C. to −10° C. for 20 min. The solid was filtered off and rinsed with tetrahydrofuran. The tetrahydrofuran filtrate was added into 1.04 ml (33.4 mmol) hydrazine hydrate in 50 ml anhydrous methanol at 0° C. The reaction was stirred at ambient temperature for 2 h. The crude product was concentrated and purified by using a Biotage Horizon® system (0-10% ethyl acetate/methanol with 10% ammonia) to give 3.0 g (75%) of the title compound as white solid. $^1$H NMR (CDCl$_3$): δ 3.67 (d, J=11.2 Hz, 1H), δ 3.65 (d, J=10.8 Hz, 1H), S 3.42 (d, J=10.7 Hz, 2H), δ 2.09 (s, 2H), δ 1.43 (s, 9H), δ 1.31 (m, 1H).

Step B: tert-butyl (1R,5S,6r)-6-(1,3,4-oxadiazol-2-yl)-3-azabicyclo[3.1.0]hexane-3-carboxylate (i-63)

0.10 g (0.40 mmol) of the title compound from Step A above in 2.0 ml (12 mmol) triethyl orthoformate was added to 0.024 ml acetic acid. The solution was heated at 110° C. for 24 h. The crude product was concentrated and purified using a Biotage Horizon® system (0-60% ethyl acetate/hexanes mixture) to give 52 mg 50% of the title compound (i-63) as colorless oil. $^1$H NMR (CDCl$_3$): δ 8.26 (s, 1H), δ 3.72 (d, J=11.0 Hz, 1H), δ 3.65 (d, J=11.0 Hz, 1H), δ 3.40 (d, J=11.3 Hz, 2H), δ 2.15 (s, 2H), δ 1.97 (t, J=3.6 Hz, 1H), δ 1.37 (s, 9H)

Intermediate 64 tert-butyl (1R,5S,6r)-6-(5-methyl-1,3,4-oxadiazol-2-yl)-3-azabicyclo[3.1.0]hexane-3-carboxylate (i-64)

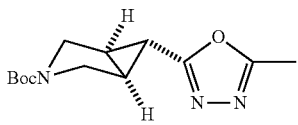

0.10 g (0.40 mmol) of tert-butyl (1R,5S,6r)-6-(hydrazinocarbonyl)-3-azabicyclo[3.1.0]hexane-3-carboxylate in 2.0 ml (12 mmol) trimethyl orthoacetate was added to 0.024 ml acetic acid. The solution was heated at 120° C. for 3 h. The crude product was concentrated and purified using a Biotage Horizon® system (50-100% ethyl acetate/hexanes mixture) to give 75 mg (69%) of the title compound (i-64) as white solid. ¹H NMR (CDCl₃): δ 3.78 (d, J=9.7 Hz, 2H), δ 3.70 (d, J=10.0 Hz, 1H), δ 3.46 (d, J=11.1 Hz, 1H), δ 2.47 (s, 3H), δ 2.17 (s, 2H), δ 1.95 (t, J=2.9 Hz, 1H), δ 1.45 (s, 9H)

Intermediate 65 tert-butyl (1R,5S,6r)-6-(5-cyclopropyl-1,3,4-oxadiazol-2-yl)-3-azabicyclo[3.1.0]hexane-3-carboxylate (i-65)

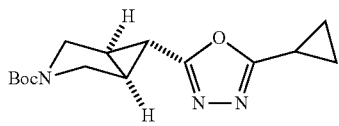

(i-65)

Step A: tert-butyl (1R,5S,6r)-6-{[2-(cyclopropylcarbonyl)hydrazino]carbonyl}-3-azabicyclo[3.1.0]hexane-3-carboxylate

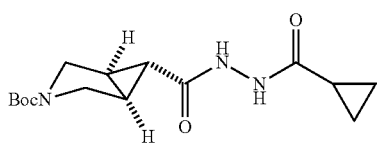

To a solution of 72 mg (0.30 mmol) tert-butyl (1R,5S,6r)-6-(hydrazinocarbonyl)-3-azabicyclo[3.1.0]hexane-3-carboxylate in 2 ml anhydrous acetonitrile at ambient temperature was added 50 mg (0.36 mmol) potassium carbonate, followed by 0.030 ml (0.30 mmol) cyclopropanecarbonyl chloride dropwise. The solution was stirred for 2 h. The crude product was concentrated and purified using a Biotage Horizon® system (0-100% ethyl acetate/hexanes mixture) to give 56 mg (61%) of the title compound as white solid. ¹H NMR (CDCl₃): δ 9.98 (d, J=4.6 Hz, 1H), δ 9.84 (d, J=4.1 Hz, 1H), δ 3.59 (d, J=10.9 Hz, 1H), δ 3.52 (d, J=10.8 Hz, 1H), δ 3.43 (s, 2H), δ 2.03 (s, 2H), δ 1.55-1.60 (m, 2H), δ 1.41 (s, 9H), δ 0.91 (m, 2H), δ 0.77 (m, 2H).

Step B: tert-butyl (1R,5S,6r)-6-(5-cyclopropyl-1,3,4-oxadiazol-2-yl)-3-azabicyclo[3.1.0]hexane-3-carboxylate

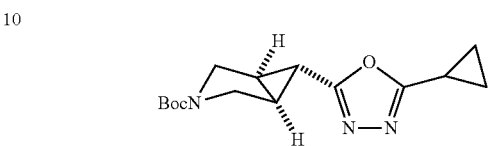

To a solution of 56 mg (0.18 mmol) of the title compound from Step A above in 1 ml anhydrous acetonitrile at ambient temperature was added 140 mg (0.54 mmol) triphenylphosphine, followed by 64 mg (0.27 mmol) hexachloroethane and 0.20 ml (1.1 mmol) diisopropylethylamine. The solution was stirred for 4 h. The solution was poured into water (10 ml) and extracted with ethyl acetate (2×10 ml). The combined organic layers were extracted with brine (10 ml). It was dried over magnesium sulfate and concentrated. The crude product was purified using a Biotage Horizon® system (0-100% ethyl acetate/hexanes mixture) to give 47 mg (90%) of the title compound (i-65) as white solid. ¹H NMR (CDCl₃): δ 3.71 (d, J=10.9 Hz, 1H), δ 3.63 (d, J=10.9 Hz, 1H), S 3.38 (d, J=11.2 Hz, 2H), δ 2.09 (s, 2H), δ 1.99-2.04 (m, 1H), δ 1.84 (t, J=3.2 Hz, 1H), δ 1.37 (s, 9H), δ 1.00-1.03 (m, 4H).

Intermediate 66 tert-butyl (1R,5S,6r)-6-[5-(2,2,2-trifluoroethyl)-1,3,4-oxadiazol-2-yl]-3-azabicyclo[3.1.0]hexane-3-carboxylate (i-66)

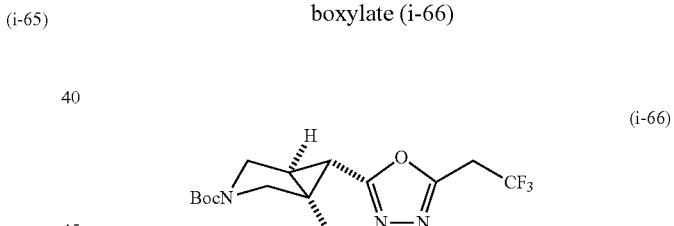

(i-66)

Step A: tert-butyl (1R,5S,6r)-6-{[2-(3,3,3-trifluoropropanoyl)hydrazino]carbonyl}-3-azabicyclo[3.1.0]hexane-3-carboxylate

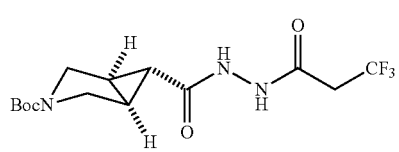

To a solution of 72 mg (0.30 mmol) tert-butyl (1R,5S,6r)-6-(hydrazinocarbonyl)-3-azabicyclo[3.1.0]hexane-3-carboxylate in 2 ml anhydrous acetonitrile at ambient temperature was added 50 mg (0.36 mmol) potassium carbonate, followed by 0.030 ml (0.30 mmol) cyclopropanecarbonyl chloride dropwise. The solution was stirred for 2 h. The crude product was concentrated and purified using a Biotage Horizon® system (0-100% ethyl acetate/hexanes mixture) to give 60 mg (57%) of the title compound as white solid. $^1$H NMR (DMSO): δ 10.20 (bs, 1H), δ 10.12 (bs, 1H), δ 3.48 (dd, J=10.6, 3.5 Hz, 2H), δ 3.31 (q, J=11.1 Hz, 4H), δ 1.89 (s, 2H), δ 1.41 (t, j=3.1 Hz, 1H), δ 1.38 (s, 9H)

Step B: tert-butyl (1R,5S,6r)-6-[5-(2,2,2-trifluoroethyl)-1,3,4-oxadiazol-2-yl]-3-azabicyclo[3.1.0]hexane-3-carboxylate (i-66)

To a solution of 56 mg (0.18 mmol) of the title compound from Step A above in 1 ml anhydrous acetonitrile at ambient temperature was added 140 mg (0.54 mmol) triphenylphosphine, followed by 64 mg (0.27 mmol) hexachloroethane and 0.20 ml (1.1 mmol) diisopropylethylamine. The solution was stirred for 4 h. The solution was poured into water (10 ml) and extracted with ethyl acetate (2×10 ml). The combined organic layers were extracted with brine (10 ml). It was dried over magnesium sulfate and concentrated. The crude product was purified using a Biotage Horizon® system (0-100% ethyl acetate/hexanes mixture) to give 36 mg (64%) of the title compound (i-66) as white solid. $^1$H NMR (CDCl$_3$): δ 3.77 (d, J=11 Hz, 1H), δ 3.68 (q, J=9.6 Hz, 3H), δ 3.44 (d, J=13.3 Hz, 2H), δ 2.20 (s, 2H), δ 1.98 (t, J=3.3 Hz, 1H), δ 1.42 (s, 9H).

Intermediate 67 tert-butyl (1R,5S,6r)-6-(5-(trifluoromethyl)-1,3,4-oxadiazol-2-yl)-3-azabicyclo[3.1.0]hexane-3-carboxylate (i-67)

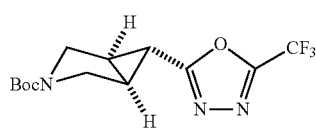

Prepared according to the procedure described above for tert-butyl (1R,5S,6r)-6-[5-(2,2,2-trifluoroethyl)-1,3,4-oxadiazol-2-yl]-3-azabicyclo[3.1.0]hexane-3-carboxylate in Intermediate 66, as a yellow solid (50%). LC-MS: m/z (ESI) 320.2 (M+1).

Intermediate 68 tert-butyl (1R,5S,6r)-6-(5-amino-1,3,4-oxadiazol-2-yl)-3-azabicyclo[3.1.0]hexane-3-carboxylate (i-68)

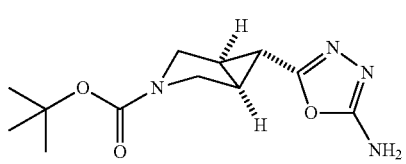

To a solution of 0.65 g (2.7 mmol) of tert-butyl (1R,5S,6r)-6-(hydrazinylcarbonyl)-3-azabicyclo[3.1.0]hexane-3-carboxylate and 0.27 g (3.2 mmol) of sodium bicarbonate in 10 mL of dioxane and 2 ml of water was added 1.1 ml cyanogen bromide, 3 M solution in dichloromethane. The reaction mixture turned cloudy. Then the mixture was stirred at RT for 1 h. LC-MS showed the desired product formed. The mixture was diluted with ethyl acetate (50 mL), washed with aqueous sodium hydrogen carbonate (saturated, 3×25 mL) and brine, dried with sodium sulfate, filtered and the solvent was evaporated under reduced pressure. The residue was purified by column chromatography on silica gel Biotage 40S, eluting with EtOAc to afford the title compound as a colorless solid (0.485 g, 68%). LC-MS: m/z (ES) 267.0 (MH)$^+$. $^1$H-NMR (500 MHz, CDCl$_3$) δ 5.48 (s, 2H), 3.75 (m, 2H), 3.45 (m, 2H), 2.10 (s, 2H), 1.80 (s, 1H), 1.45 (s, 9H).

Intermediate 69 tert-butyl (1R,5S,6r)-6-(2H-tetrazol-5-yl)-3-azabicyclo[3.1.0]hexane-3-carboxylate (i-69)

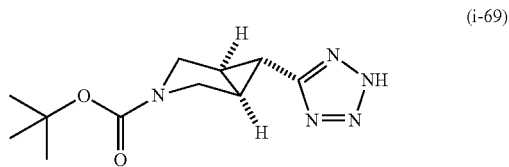

To a solution of 0.15 g (0.70 mmol) of tert-butyl (1R,5S,6r)-6-cyano-3-azabicyclo[3.1.0]hexane-3-carboxylate 3 mL of DMF was added 0.14 g (2.1 mmol) of sodium azide and 0.11 g (2.1 mmol) of ammonia chloride. Then the mixture was stirred at 100° C. overnight. LC-MS showed the desired product formed. The mixture was diluted with ethyl acetate (50 mL), washed with aqueous sodium hydrogen carbonate (saturated, 3×25 mL) and brine, dried with sodium sulfate, filtered and the solvent was evaporated under reduced pressure. The residue was purified by column chromatography on silica gel Biotage 40S, eluting with dichloromethane/methanol to afford the title compound as a colorless solid (0.12 g, 70%). LC-MS: m/z (ES) 252.1 (MH)$^+$.

Intermediates 70 and 71 tert-butyl (1R. 5S,6r)-6-(1-methyl-1H-tetrazol-5-yl)-3-azabicyclo[3.1.0]hexane-3-carboxylate (i-70) and tert-butyl (1R,5S,6r)-6-(2-methyl-2H-tetrazol-5-yl)-3-azabicyclo[3.1.0]hexane-3-carboxylate (i-71)

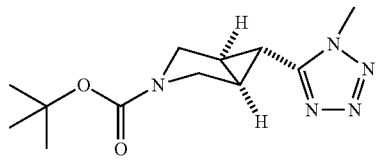

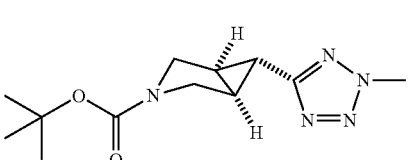

To a solution of 0.12 g (0.15 mmol) of tert-butyl (1R,5S,6r)-6-(2H-tetrazol-5-yl)-3-azabicyclo[3.1.0]hexane-3-carboxylate and 0.10 g (0.75 mmol) of potassium carbonate in 3 mL of DMF was added 0.019 ml (0.30 mmol) of MeI. Then the mixture was stirred at RT for overnight. LC-MS showed the desired product formed. The mixture was diluted with ethyl acetate (50 mL), washed with aqueous sodium hydrogen carbonate (saturated, 3×25 mL) and brine, dried with sodium sulfate, filtered and the solvent was evaporated under reduced pressure. The residue was purified by column chromatography on silica gel Biotage 12S, eluting with EtOAc/hexane to afford the title compounds higher Rf: tert-butyl (1R,5S,6r)-6-(2-methyl-2H-tetrazol-5-yl)-3-azabicyclo [3.1.0]hexane-3-carboxylate (i-71) as a colorless solid (0.021 g, 53%). LC-MS: m/z (ES) 266.1 (MH)+. 1H-NMR (500 MHz, CDCl3) δ 4.25 (s, 3H), 3.80 (d, 11 Hz, 1H), 3.70 (d, J=11 Hz, 1H), 3.46 (m, 2H), 2.12 (d, J=11 Hz, 2H), 2.01 (s, 1H), 1.43 (s, 9H). Lower Rf: tert-butyl (1R,5S,6r)-6-(1-methyl-1H-tetrazol-5-yl)-3-azabicyclo[3.1.0]hexane-3-carboxylate (i-70) as a colorless solid (0.01 g, 25%). LC-MS: m/z (ES) 266.1 (MH)+. 1H-NMR (500 MHz, CDCl3) δ 4.05 (s, 3H), 3.82 (d, J=11 Hz, 1H), 3.75 (d, J=11 Hz, 1H), 3.55 (m, 2H), 2.35 (s, 1H), 2.25 (s, 1H), 1.75 (s, 1H), 1.45 (s, 9H).

Intermediate 72 tert-butyl (1R,5S,6r)-6-(5-methyl-1,2,4-oxadiazole-3-yl)-3-azabicyclo[3.1.0]hexane-3-carboxylate

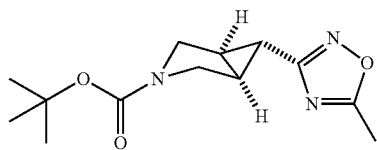

(i-72)

Step A: tert-butyl (1R,5S,6r)-6-[amino(hydroxyimino)methyl]-3-azabicyclo[3.1.0]hexane-3-carboxylate

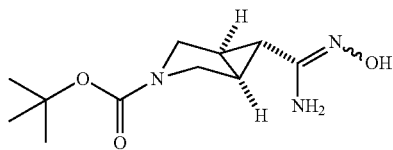

To a solution of 0.20 g (0.96 mmol) of tert-butyl (1R,5S,6r)-6-cyano-3-azabicyclo[3.1.0]hexane-3-carboxylate in 3 mL of ethanol was added 1.3 g (9.6 mmol) of hydroxylamine hydrochloride. The mixture was stirred at 100° C. for 3 h. The residue was evaporated in vacuo to yield the title compound as a white solid that was used without purification. LC-MS: m/z (E/S) 242.1 (MH)+.

Step B: tert-butyl (1R,5S,6r)-6-(5-methyl-1,2,4-oxadiazole-3-yl)-3-azabicyclo[3.1.0]hexane-3-carboxylate (i-72)

To a solution of 0.12 g (0.48 mmol) of the title compound from Step A and 0.17 ml (0.96 mmol) of DIEA in 2 ml of dichloromethane was added 0.068 ml (0.72 mmol) of acetic anhydride. The mixture was stirred at RT for 3 h. LC-MS showed no more starting material left. The solvent was evaporated under reduced pressure. The residue was purified by column chromatography on silica gel Biotage 25S, eluting with EtOAc/hexanes to afford the intermediate, 123 mg, LC-MS: m/z (E/S) 284, as a colorless solid. This intermediate in Toluene (2.0 ml) was heated to 110° C. for 28 h, LC-MS showed no more starting material. The solvent was evaporated under reduced pressure. The residue was purified by column chromatography on silica gel Biotage 12S, eluting with EtOAc/hexane to afford the title compound (i-72). LC-MS: m/z (E/S) 266.1 (MH)+.

Intermediate 73 tert-butyl (1R,5S,6r)-6-(5-cyclopropyl-1,2,4-oxadiazol-3-yl)-3-azabicyclo[3.1.0]hexane-3-carboxylate (i-73)

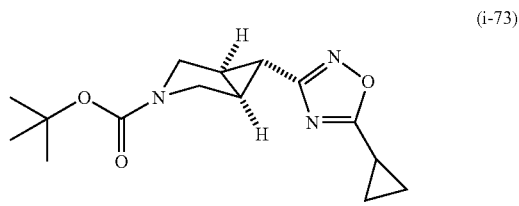

(i-73)

To a solution of 0.021 g (0.25 mmol) of cyclopropanecarboxylic acid in 2 ml of dichloromethane was added 0.044 g (0.27 mmol) of CDI. The mixture was stirred at RT for 1 h. Then 0.06 mg (0.25 mmol) of tert-butyl (1R,5S,6r)-6-[amino (hydroxyimino)methyl]-3-azabicyclo[3.1.0]hexane-3-carboxylate was added to the reaction mixture. The reaction was stirred at RT for 3 h. LC-MS showed no more starting material left. The mixture was cooled and the solvent was evaporated under reduced pressure. The residue was purified by column chromatography on silica gel Biotage 25S, eluting with EtOAc/isohexane 0%-40% to afford the title compound (i-73). LC-MS: m/z (E/S) 292.1 (MH)+.

Intermediate 74 tert-butyl (1R,5S,6r)-6-[5-(1-hydroxy-1-methylethyl)-1,2,4-oxadiazol-3-yl)-3-azabicyclo[3.1.0]hexane-3-carboxylate (i-74)

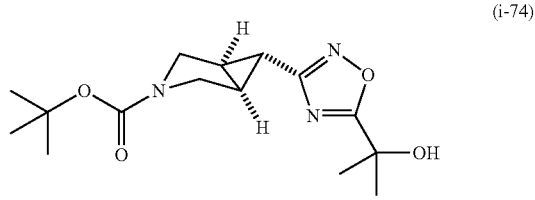

(i-74)

Step A: tert-butyl (1R,5S,6r)-6-[5-(1-acetyloxy-1-methylethyl)-1,2,4-oxadiazol-3-yl]-3-azabicyclo[3.1.0]hexane-3-carboxylate

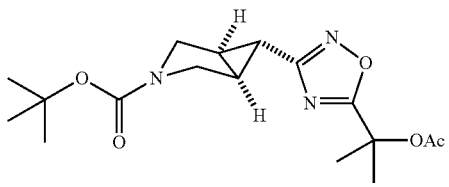

To a solution of 0.060 g (0.25 mmol) of tert-butyl (1R,5S,6r)-6-[amino(hydroxyimino)methyl]-3-azabicyclo[3.1.0]hexane-3-carboxylate in 3 ml of pyridine was added 0.21 g (1.2 mmol) of 1-chloro-2-methyl-1-oxopropan-2-yl acetate. The mixture was stirred at 100° C. for overnight. LC-MS showed no more starting material left. The mixture was cooled, diluted with ethyl acetate (50 mL), washed with aqueous sodium hydrogen carbonate (saturated, 2×25 mL) and brine, dried with sodium sulfate, filtered and the solvent was evaporated under reduced pressure. The residue was purified by column chromatography on silica gel Biotage 25S, eluting with EtOAc/hexanes 0%-60% to afford the title compounds. Yield is 69%. LC-MS: m/z (E/S) 352.98 (MH)+.

Step B: tert-butyl (1R,5S,6r)-6-[5-(1-hydroxy-1-methylethyl)-1,2,4-oxadiazol-3-yl]-3-azabicyclo[3.1.0]hexane-3-carboxylate (i-74)

To a solution of 0.045 g (0.13 mmol) of the title compound from Step A above in 1 ml of methanol was added 0.18 g (1.3 mmol) of potassium carbonate. The mixture was stirred at 50° C. for overnight. LC-MS showed no more starting material left. The mixture was cooled, diluted with ethyl acetate (50 mL), washed with aqueous sodium hydrogen carbonate (saturated, 2×25 mL) and brine, dried with sodium sulfate, filtered and the solvent was evaporated under reduced pressure. The residue was purified by column chromatography on silica gel Biotage 25S, eluting with EtOAc/hexanes 0%-60% to afford the title compound (i-74) 40 mg. Yield is 81%. LC-MS: m/z (E/S) 310.1 (MH)+.

Intermediate 75 tert-butyl 3-methyl-1-oxo-2-oxa-8-azaspiro[4.5]decane-8-carboxylate

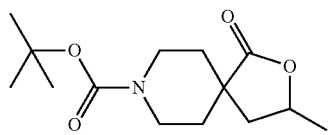 [SMILES: CC1CC2(CCN(C(=O)OC(C)(C)C)CC2)C(=O)O1]

Step A: 1-tert-butyl-4-ethyl 4-(2-oxoethyl)piperidine-1,4-dicarboxylate

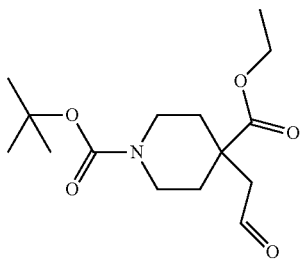 [SMILES: CCOC(=O)C1(CC=O)CCN(C(=O)OC(C)(C)C)CC1]

To a solution of 500 mg (1.68 mmol) 1-tert-butyl-4-ethyl 4-allylpiperidine-1,4-dicarboxylate in 6 ml of anhydrous methanol at −78° C. was bubbled ozone gas for 10 min followed by 440 mg (1.68 mmol) triphenylphosphine. The solution was stirred at −78° C. for 30 minutes and at ambient temperature for 2 h. The crude product was concentrated and purified using a Biotage Horizon® system (0-20% ethyl acetate/hexanes mixture) to give 125 mg (25%) of the title compound as colorless oil. NMR (CDCl$_3$): δ 9.72 (t, J=1.5 Hz, 1H), 4.20 (q, J=7.1 Hz, 2H), 3.68 (dt, J=13.8, 4.7 Hz, 2H), 3.20 (ddd, J=13.5, 9.9, 3.1 Hz, 2H), 2.67 (d, J=1.6 Hz, 2H), 2.12 (dt, J=13.8, 3.9 Hz, 2H), 1.52 (ddd, J=14, 10.1, 4.3 Hz, 2H), 1.45 (s, 9H), 1.26 (t, 7.1 Hz, 3H).

Step B: tert-butyl 3-methyl-1-oxo-2-oxa-8-azaspiro[4.5]decane-8-carboxylate (i-75)

To a solution of 125 mg (0.42 mmol) of the title compound from Step A above in 2 ml of anhydrous tetrahydrofuran at −78° C. was added 0.15 ml (0.46 mmol) 3 M methyl magnesium chloride. The solution was warmed to ambient temperature after half an hour, and was stirred another 1 h. The solution was poured into 1 M ammonium chloride (10 ml) and extracted with ethyl acetate (2×10 ml). The combined organic layers were extracted with brine (10 ml). It was dried over magnesium sulfate and concentrated. The crude product was purified using a Biotage Horizon® system (0-50% ethyl acetate/hexanes mixture) to give 56 mg (50%) of the title compound (i-75) as colorless oil. $^1$H NMR (CDCl$_3$): δ 4.56-4.63 (m, 1H), δ 3.97 (dt, J=13.4, 5.0 Hz, 1H), δ 3.82 (dt, J=13.9, 5.0 Hz, 1H), δ 3.17 (ddd, J=13.3, 9.6, 3.4 Hz, 1H), δ 3.06 (ddd, J=13.5, 9.8, 3.5 Hz, 1H), δ 2.37 (dd, J=12.9, 6.1 Hz, 1H), δ 1.96 (ddd, J=13.7, 9.7, 4.1 Hz, 1H), δ 1.81 (ddd, J=13.7, 9.7, 4.1 Hz, 1H), δ 1.67 (dd, J=12.9, 9.6 Hz, 1H), δ 1.46 (s, 9H), δ 1.44 (d, J=6.2 Hz, 3H).

Intermediate: 76 tert-butyl-3-cyclopropyl-1-oxo-2-oxa-8-azaspiro[4.5]decane-8-carboxylate (i-76)

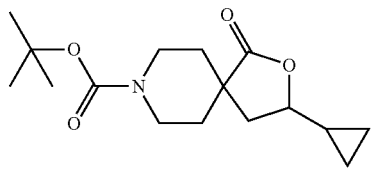

(i-76)

To a solution of 125 mg (0.42 mmol) 1-tert-butyl-4-ethyl 4-(2-oxoethyl)piperidine-1,4-dicarboxylate in 3 ml anhydrous tetrahydrofuran at −78° C. was added 0.84 ml (0.42 mmol) 0.5 M cyclopropyl magnesium bromide. The solution was warmed to ambient temperature after half an hour, and was stirred another 1 h. The solution was poured into 1 M ammonium chloride (10 ml) and extracted with ethyl acetate (2×10 ml). The combined organic layers were extracted with brine (10 ml). It was dried over magnesium sulfate and concentrated. The crude product was purified using a Biotage Horizon® system (0-50% ethyl acetate/hexanes mixture) to give 62 mg (50%) of the title compound (i-76) as colorless oil. ¹H NMR (CDCl₃): δ 3.94-3.97 (m, 1H), δ 3.79-3.86 (m, 2H), δ 3.14 (ddd, J=13.4, 9.8, 3.3 Hz, 1H), δ 3.06 (ddd, J=13.4, 9.9, 3.4 Hz, 1H), δ 2.36 (dd, J=13.1, 6.3 Hz, 1H), δ 1.95 (ddd, J=13.8, 9.9, 4.1 Hz, 1H), δ 1.87 (dd, J=13.0, 9.5 Hz, 1H), δ 1.77 (ddd, J=13.6, 9.7, 4.1 Hz, 1H), δ 1.44 (s, 9H), δ 0.98-1.01 (m, 1H), δ 0.59-0.66 (m, 2H), δ 0.43-0.47 (m, 1H), δ 0.29-0.32 (m, 1H).

Intermediate: 77 tert-butyl 4-methyl-1-oxo-2-oxa-8-azaspiro[4.5]decane-8-carboxylate (i-77)

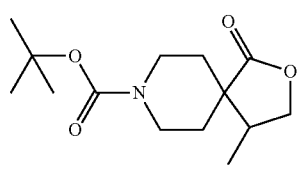

(i-77)

Step A: 3-[(2E)-but-2-en-1-yl]1-tert-butyl piperidine-1,4-dicarboxylate

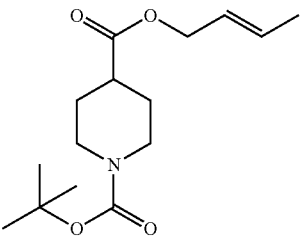 [SMILES: C/C=C/COC(=O)C1CCN(C(=O)OC(C)(C)C)CC1]

To a solution of 3.00 g (13.1 mmol) 1-(tert-butoxycarbonyl)piperidine-4-carboxylic acid in 60 ml dichloromethane was added 1.22 ml (14.4 mmol) (2E)-but-2-en-1-ol and 0.32 g (2.6 mmol) 4-dimethylaminopyridine (DMAP), and followed by 2.97 g (14.4 mmol) N,N'-dicyclohexylcarbodiimide (DCC) at 0° C. The reaction was stirred at ambient temperature overnight. The reaction was cooled, and extracted with ethyl acetate (100 ml) and saturated sodium hydrogen carbonate (3×50 ml) and brine (50 ml). It was dried (sodium sulfate) and concentrated under reduced pressure. The crude product was purified using a Biotage Horizon® system (0-50% ethyl acetate/hexanes mixture) to give 3.3 g (89%) of the title compound as colorless oil. ¹H NMR (CDCl₃): δ 5.69-5.75 (m, 1H), δ 5.50-5.55 (m, 1H), δ 4.64 (d, J=6.9 Hz, 2H), δ 4.00 (bs, 2H), δ 2.83 (t, J=11.6 Hz, 2H), δ 2.41-2.47 (m, 1H), δ 1.86 (d, J=12.2 Hz, 1H), δ 1.70 (d, 6.8 Hz, 31-1), δ 1.60-1.66 (m, 2H), δ 1.44 (s, 9H).

Step B: 1-tert-butyl 4-methyl-4-(1-methylprop-2-en-1-yl)piperidine-1,4-dicarboxylate

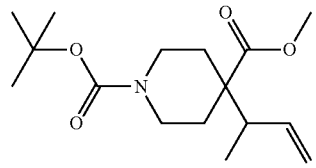 [SMILES: C=CC(C)C1(C(=O)OC)CCN(C(=O)OC(C)(C)C)CC1]

To a solution of 1.30 g (4.59 mmol) of the title compound from Step A above in 8 ml anhydrous tetrahydrofuran at −78° C. was added 3.44 ml (6.88 mmol) 2 M lithium diisopropylamide and stirred for 30 min, followed by 0.64 ml (4.6 mmol) triethylamine and 0.59 ml (4.6 mmol) chlorotrimethylsilane at −78° C. The reaction was stirred for 30 min, and warmed up to ambient temperature for 1 h. The reaction was heated to reflux for 3 h. It was monitored by TLC (20% ethyl acetate in hexane). The solution was diluted with ethyl acetate (100 ml), and washed with hydrochloric acid (1M, 2×50 ml) and brine. It was dried by sodium sulfate, filtered and evaporated. The product in 8 ml methanol was treated with 3.44 ml (6.88 mmol) 2 M trimethylsilyl diazomethane at 0° C. for 30 min, and it was stirred at ambient temperature for 1.5 h. Acetic acid was added into the mixture. The mixture was extracted with ethyl acetate and saturated sodium bicarbonate. The crude product was dried and purified using a Biotage Horizon® system (0-10% ethyl acetate/hexanes mixture) to give 600 mg (44%) of the title compound as colorless oil. ¹H NMR (CDCl₃): δ 5.65 (dt, J=19.2, 10.1 Hz, 1H), δ 5.03 (d, J=10.3 Hz, 1H), δ 5.01 (d, J=19.0 Hz, 1H), δ 3.99 (d, J=13.2 Hz, 2H), δ 3.70 (s, 3H), δ 2.71 (q, 2H), δ 2.27-2.29 (m, 1H), δ 2.03-2.08 (m, 2H), δ 1.44 (s, 9H), δ 1.32-1.40 (m, 2H), δ 0.95 (d, J=6.9 Hz, 3H).

Step C: 1-tert-butyl 4-methyl-4-(1-methyl-2-oxoethyl)piperidine-1,4-dicarboxylate

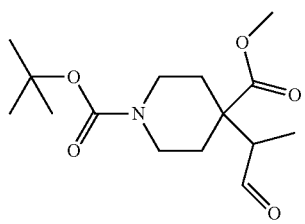 [SMILES: COC(=O)C1(C(C)C=O)CCN(C(=O)OC(C)(C)C)CC1]

To a solution of 70 mg (0.23 mmol) of the title compound from Step B above in 2 ml anhydrous methanol at −78° C. was bubbled ozone gas for 10 min, followed by 60 mg (0.23 mmol) triphenylphosphine. The solution was stirred at −78° C. for 30 min and at ambient temperature for 2 h. The crude product was concentrated and purified using a Biotage Horizon® system (0-50% ethyl acetate/hexanes mixture) to give 75 mg (25%) of the title compound as colorless oil. $^1$H NMR (CDCl$_3$): δ 9.65 (d, J=2.3 Hz, 1H), δ 3.88-3.92 (m, 2H), δ 3.68 (s, 3H), δ 2.74-2.86 (m, 2H), δ 2.38 (dd, J=7.1, 2.4 Hz, 1H), δ 2.08-2.13 (m, 2H), δ 1.52-1.60 (m, 2H), δ 1.42 (s, 9H), δ 1.01 (d, J=7.1 Hz, 3H).

Step D: tert-butyl 4-methyl-1-oxo-2-oxa-8-azaspiro [4.5]decane-8-carboxylate (i-77)

To a solution of 55 mg (0.18 mmol) of the title compound from Step C above in 1 ml anhydrous methanol was added 14 mg (0.37 mmol) sodium borohydride. The reaction mixture was stirred at ambient temperature for 1 h. It was neutralized by acetic acid. The solution was poured into 1M hydrochloric acid (10 ml) and extracted with ethyl acetate (2×10 ml). The combined organic layers were extracted with brine (10 ml). It was dried over magnesium sulfate and concentrated. The crude product was purified using a Biotage Horizon® system (0-20% ethyl acetate/hexanes mixture) to give 25 mg (80%) of the title compound (i-77) as colorless oil. $^1$H NMR (CDCl$_3$): δ 4.34 (dd, J=9.0, 7.1 Hz, 1H), δ 3.85 (dd, J=9.1, 6.9 Hz, 1H), δ 3.66 (dd, J=7.0, 4.5 Hz, 2H), δ 3.42 (t, J=10.5 Hz, 1H), δ 2.30-2.37 (m, 1H), δ 1.64-1.70 (m, 2H), δ 1.52-1.61 (m, 2H), δ 1.44 (s, 9H), δ 1.01 (d, J=7.1 Hz, 3H).

Intermediate 78 tert-Butyl 4-[1H-1,2,3-benzotriazol-1-yl(pyridin-2-yl)methyl]piperazine-1-carboxylate (i-78)

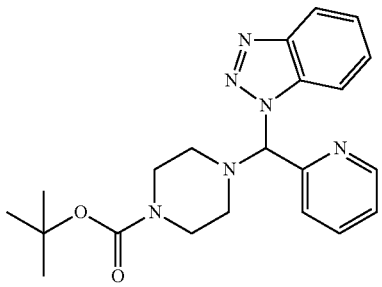

To a stirred solution of 1.50 mL (15.7 mmol) of pyridine-2-carbaldehyde in 70 mL of benzene under an atmosphere of nitrogen was added 2.92 g (15.7 mmol) of tert-butyl 1-piperazine-carboxylate followed by 1.87 g (15.7 mmol) of 1H-benzotriazole. The reaction mixture was heated to reflux for 3 h employing a Dean-Stark® Trap. The resulting mixture was cooled to ambient temperature and all volatiles were removed in vacuo to afford the title compound (i-78).

Intermediates 79 and 80

1-[(1S)-1-Pyridin-2-ylpropyl]piperazine, bis(trifluoroacetic acid) salt (i-79) and 1-[(1R)-1-Pyridin-2-ylpropyl]piperazine, (bis-trifluoroacetic acid) salt (i-80)

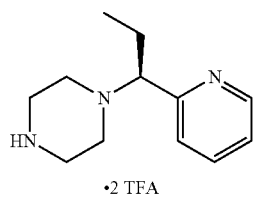

·2 TFA

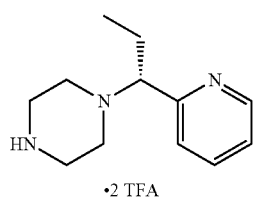

·2 TFA

Step A: Tert-butyl 4-[(1S)-1-pyridin-2-ylpropyl]piperazine-1-carboxylate and Tert-butyl 4-[(1R)-1-pyridin-2-ylpropyl]piperazine-1-carboxylate

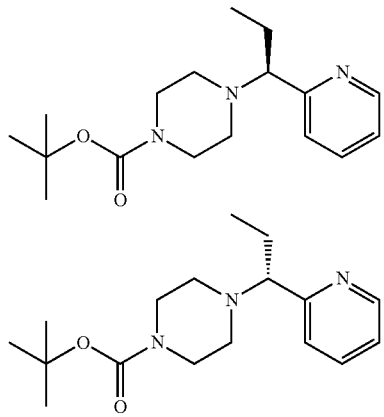

To a stirred solution of 2.0 g (5.0 mmol) of i-78 in 25 mL of anhydrous tetrahydrofuran cooled to −78° C. under an atmosphere of nitrogen was added 6.6 mL (6.6 mmol) of a 1.0 M solution of ethyl magnesium bromide in anhydrous tetrahydrofuran. The resulting dark red solution was allowed to gradually warm to 0° C. over 3 h then quenched with 5 mL of a saturated aqueous ammonium chloride solution. The layers were then separated and the aqueous phase extracted with ethyl acetate (3×25 mL). The combined organic layers were washed with brine, dried over magnesium sulfate, filtered and evaporated in vacuo. The residue was purified by silica gel chromatography eluting with a 0-100% ethyl acetate in hexanes gradient to afford the title compounds as a racemic mixture. The two enantiomers were separated by chiral HPLC employing a Daicel PREP CHIRALCEL® OD® column (eluent: 3% isopropanol in heptane). The first eluting enantiomer was designated as Isomer 1 and is a colorless foam (0.50 g, 32%): $^1$H-NMR (500 MHz, CDCl$_3$) δ 8.60 (d, J=5.0 Hz, 1H), 7.64 (td, J=7.6, 1.8 Hz, 1H), 7.24 (d, J=7.6 Hz, 1H), 7.17 (dd, J=7.5, 5.0 Hz, 1H), 3.43-3.40 (m, 4H), 2.50-2.46 (m, 2H), 2.50-2.46 (m, 2H) 2.40-2.35 (m, 2H), 1.98-1.84 (m, 2H), 1.43 (s, 9H), 0.76 (t, J=7.5 Hz, 3H). LC-MS: m/z (ES) 306.3 (MH)$^+$.

The second eluting enantiomer was designated as Isomer 2 and is a colorless foam (0.50 g, 32%): $^1$H-NMR (500 MHz, CDCl$_3$) δ 8.60 (d, J=5.0 Hz, 1H), 7.64 (td, J=7.6, 1.8 Hz, 1H), 7.24 (d, J=7.6 Hz, 1H), 7.17 (dd, J=7.5, 5.0 Hz, 1H), 3.43-3.40 (m, 4H), 2.50-2.46 (m, 2H), 2.50-2.46 (m, 2H) 2.40-2.35 (m, 2H), 1.98-1.84 (m, 2H), 1.43 (s, 9H), 0.76 (t, J=7.5 Hz, 3H). LC-MS: m/z (ES) 306.3 (MH)$^+$.

Step B: 1-[(1S)-1-Pyridin-2-ylpropyl]piperazine, bis(trifluoroacetic acid) salt (i-79) and 1-[(1R)-1-Pyridin-2-ylpropyl]piperazine, bis(trifluoroacetic acid) salt (i-80)

To a stirred solution of 0.50 g (1.6 mmol) of isomer 1 from Step A above in 10 mL of dichloromethane was added 3 mL of trifluoroacetic acid and the resulting mixture was stirred for 1 h. All volatiles were removed in vacuo and the pale orange residue was suspended in toluene. All volatiles were then removed in vacuo and this process was repeated two additional times. The pale orange solid residue that was obtained was dried under high vacuum overnight to afford either 1-[(1S)-1-pyridin-2-ylpropyl]piperazine, bis(trifluoroacetic acid) salt or 1-[(1R)-1-pyridin-2-ylpropyl]piperazine, bis(trifluoroacetic acid) salt as a clear gum (0.70 g, 98%). LC-MS: m/z (ES) 206.3 (MH)$^+$.

The same process was also repeated for isomer 2 from step A above to afford either 1-[(1S)-1-pyridin-2-ylpropyl]piperazine, bis(trifluoroacetic acid) salt or 1-[(1R)-1-pyridin-2-ylpropyl]piperazine, bis(trifluoroacetic acid) salt as a clear gum (0.70 g, 98% yield). LC-MS: m/z (ES) 206.3 (MH)$^+$.

Intermediates 81 and 82

1-[(1S)-2-Methyl-1-pyridin-2-ylpropyl]piperazine, bis(trifluoroacetic acid) salt (i-81) and 1-[(1R)-2-Methyl-1-pyridin-2-ylpropyl]piperazine, bis(trifluoroacetic acids salt

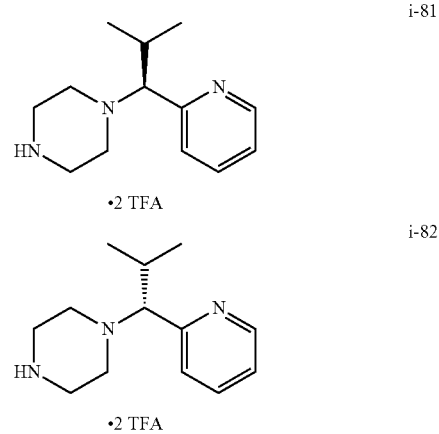

Intermediates 81 and 82 were prepared from Intermediate 78 and isopropyl magnesium bromide according to the same procedure used for the synthesis of Intermediates 79 and 80. The two enantiomers were separated by chiral HPLC employing a Daicel PREP CHIRALCEL® OD® column (eluent: 3% isopropyl alcohol in heptane). The first enantiomer to elute was designated as Isomer 1: LC-MS: m/z (ES) 220.2 (MH)$^+$. The second enantiomer to elute was designated as Isomer 2: LC-MS: m/z (ES) 220.2 (MH)$^+$.

Intermediate 83 and 84

1-[(S)-Cyclopropyl(pyridin-2-yl)methyl]piperazine, bis(trifluoroacetic acid) salt and 1-[(R)-Cyclopropyl(pyridin-2-yl)methyl]piperazine, bis(trifluoroacetic acid) salt

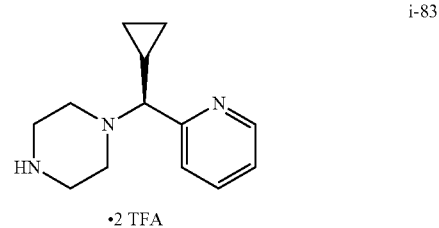

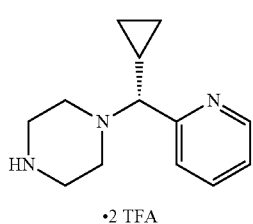

Intermediates 83 and 84 were prepared from Intermediate 78 and cyclopropyl magnesium bromide according to the same procedure used for the synthesis of Intermediates 79 and 80. The two enantiomers were separated by chiral HPLC employing a Daicel PREP CHIRALCEL® OD® column (eluent: 3% isopropyl alcohol in heptane). The first enantiomer to elute was designated as Isomer 1: LC-MS: m/z (ES) 218.3 (MH)⁺. The second enantiomer to elute was designated as Isomer 2: LC-MS: m/z (ES) 218.3 (MH)⁺.

Intermediate 85

1-[(1S)-1-Pyridin-2-ylethyl]piperazine, bis(trifluoroacetic acid) salt (i-85)

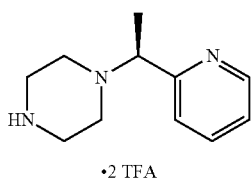

Step A: (1R)-1-Pyridin-2-ylethyl methanesulfonate

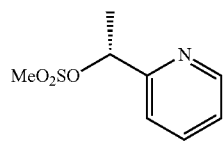

To a stirred solution of 0.27 g (2.2 mmol) of commercially available (1R)-1-pyridin-2-ylethanol in 5 mL of anhydrous dichloromethane was added 0.53 g (4.3 mmol) of 4-(dimethylamino)pyridine followed by 0.20 mL (2.6 mmol) of methanesulfonyl chloride. The resulting mixture was stirred with gradual warming to ambient temperature over 1 h. The resulting mixture was quenched with water and extracted with dichloromethane. The combined organics were washed with brine, dried over magnesium sulfate, filtered and evaporated to dryness to afford the title compound as a yellow oil (0.35 g, 81% yield).

Step B: Tert-butyl 4-[(1S)-1-pyridin-2-ylethyl]piperazine-1-carboxylate

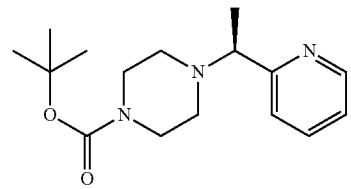 [SMILES: C[C@@H](c1ccccn1)N1CCN(C(=O)OC(C)(C)C)CC1]

To a stirred solution of 0.35 g (1.7 mmol) of the title compound from Step A above in 3.5 mL of anhydrous dimethyl sulfoxide was added 0.60 mL (3.5 mmol) of N,N-diisopropylethylamine followed by 0.49 g (2.6 mmol) of tert-butyl piperazine-1-carboxylate. The resulting mixture was heated to 80° C. for 3 h then cooled to ambient temperature. The reaction was diluted with water and the aqueous phase was extracted with ethyl acetate. The combined organic layers were washed with brine, dried over magnesium sulfate, filtered and evaporated to dryness in vacuo. The residue was purified by silica gel chromatography eluting with a 0-100% ethyl acetate in hexanes gradient to afford the title compound as a yellow gum (0.38 g, 75% yield. LC-MS: m/z (ES) 292.4 (MH)⁺.

Step C: 1-[(1S)-1-Pyridin-2-ylethyl]piperazine, bis(trifluoroacetic acid) salt (i-85)

To a stirred solution of 0.38 g (1.3 mmol) of the title compound from Step B above in 4 mL of dichloromethane was added 2 mL of trifluoroacetic acid and the resulting mixture was stirred for 1 h. All volatiles were removed in vacuo and the pale yellow residue was suspended in toluene. All volatiles were then removed in vacuo and this process was repeated two additional times. The yellow solid residue that was obtained was dried under high vacuum overnight to afford the title compound (i-85) as an orange solid (0.54 g, 99%). LC-MS: m/z (ES) 191.5 (MH)⁺.

Intermediate 86

1-[(1R)-1-Pyridin-2-ylethyl]piperazine, bis(trifluoroacetic acid) salt (i-86)

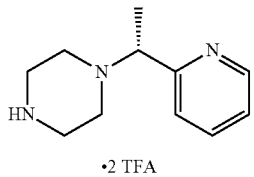

Intermediate 86 was prepared according to the same procedure used for the synthesis of Intermediates 85 using (1S)-

1-pyridin-2-ylethanol in place of (1R)-1-pyridin-2-ylethanol. LC-MS: m/z (ES) 191.5 (MH)+.

Intermediates 87 and 88

(7S)-7-piperazin-1-yl-6,7-dihydro-5H-cyclopenta[b]pyridine, bis(hydrochloride) salt (i-87) and (7R)-7-piperazin-1-yl-6,7-dihydro-5H-cyclopenta[b]pyridine, bis(hydrochloride) salt (i-88)

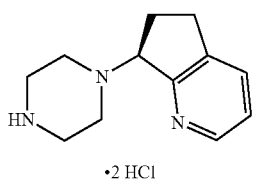

·2 HCl

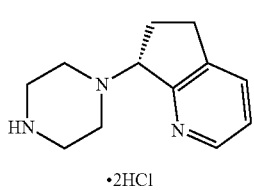

·2HCl

Step A: Tert-Butyl 4-[(7S)-6,7-dihydro-5H-cyclopenta[b]pyridin-7-yl]piperazine-1-carboxylate and Tert-butyl 4-[(7R)-6,7-dihydro-5H-cyclopenta[b]pyridin-7-yl]piperazine-1-carboxylate

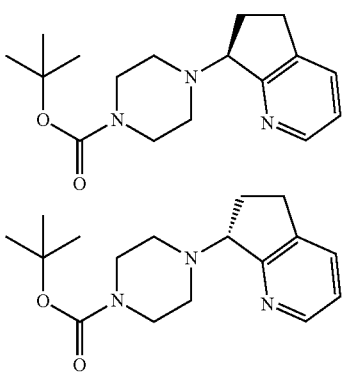

To a stirred solution of 0.144 g (1.08 mmol) of 5,6-dihydro-7H-cyclopenta[b]pyridin-7-one and 0.200 g (1.08 mmol) of tert-butyl piperazine-1-carboxylate in 1.5 mL of anhydrous tetrahydrofuran under an atmosphere of nitrogen was added 1.00 mL (3.46 mmol) of titanium(IV) isopropoxide. The resulting mixture was heated to 80° C. for 12 h then cooled to 0° C. Next, 0.73 g (3.5 mmol) of solid sodium triacetoxyborohydride was added in one portion and the resulting solution was then stirred with gradual warming to ambient temperature over 4 h. The reaction was quenched with 0.44 mL (11 mmol) of methanol and then diluted with dichloromethane and a saturated aqueous sodium hydrogen carbonate solution. The mixture was filtered through a pad of Celite® and the layers separated. The aqueous phase was extracted with dichloromethane and the combined organic layers were washed with brine, dried over magnesium sulfate, filtered and evaporated to dryness in vacuo. The crude residue was purified by reverse phase HPLC (TMC Pro-Paz C18; 0-75% 0.1% trifluoroacetic acid in acetonitrile/0.1% trifluoroacetic acid in water gradient) to yield a racemic mixture of the title compounds as a white solid. The two enantiomers were separated by chiral HPLC employing a Daicel PREP CHIRALPAK® AD® column eluting with a 5% isopropanol in heptane mixture to afford the title compounds. The first enantiomer to elute was designated as Isomer 1 (0.090 g, 28%). $^1$H-NMR (500 MHz, CDCl$_3$) δ 8.41 (d, J=4.6 Hz, 1H), 7.46 (d, J=7.6, 1H), 7.17 (dd, J=7.6, 4.5 Hz, 1H), 4.25 (t, J=7.0, 1H), 3.47-3.38 (m, 4H), 2.92-2.86 (m, 1H), 2.81-2.75 (m, 1H), 2.66 (br s, 2H), 2.41-2.37 (m, 2H), 2.16-2.10 (m, 2H), 1.40 (s, 9H). LC-MS: m/z (ES) 304.0 (MH)+. The second enantiomer to elute was designated as Isomer 2 (0.090 g, 28%). $^1$H-NMR (500 MHz, CDCl$_3$) δ 8.41 (d, J=4.6 Hz, 1H), 7.46 (d, J=7.6, 1H), 7.17 (dd, J=7.6, 4.5 Hz, 1H), 4.25 (t, J=7.0, 1H), 3.47-3.38 (m, 4H), 2.92-2.86 (m, 1H), 2.81-2.75 (m, 1H), 2.66 (br s, 2H), 2.41-2.37 (m, 2H), 2.16-2.10 (m, 2H), 1.40 (s, 9H). LC-MS: m/z (ES) 304.0 (MH)+

Step B: (7S)-7-piperazin-1-yl-6,7-dihydro-5H-cyclopenta[b]pyridine, bis(hydrochloride) salt (i-87) and (7R)-7-piperazin-1-yl-6,7-dihydro-5H-cyclopenta[b]pyridine, bis(hydrochloride) salt (i-88)

To a stirred solution of 0.063 g (0.21 mmol) of Isomer 1 from Step A above in 1 mL of methanol was added 4.0 mL (4.0 mmol) of a 4.0 M hydrogen chloride solution in 1,4-dioxane and the resulting mixture was stirred for 1 h. All volatiles were then removed in vacuo and the residue dried under high vacuum overnight to afford either (7S)-7-piperazin-1-yl-6,7-dihydro-5H-cyclopenta[b]pyridine, bis(hydrochloride) salt or (7R)-7-piperazin-1-yl-6,7-dihydro-5H-cyclopenta[b]pyridine, bis(hydrochloride) salt (0.055 g, 96% yield). LC-MS: m/z (ES) 203.0 (MH)+.

The same procedure was also repeated for Isomer 2 from step A above to afford either (7S)-7-piperazin-1-yl-6,7-dihydro-5H-cyclopenta[b]pyridine, bis(hydrochloride) salt or (7R)-7-piperazin-1-yl-6,7-dihydro-5H-cyclopenta[b]pyridine, bis(hydrochloride) salt. LC-MS: m/z (ES) 203.0 (MH)+.

Intermediate 89

1-[1-(2-Fluorophenyl)ethyl]piperazine, bis(hydrochloride) salt (i-89)

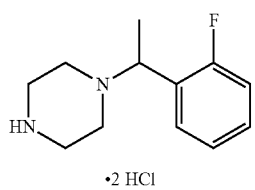

·2 HCl

Step A: Tert-Butyl 4-[1-(2-fluorophenyl)ethyl]piperazine-1-carboxylate

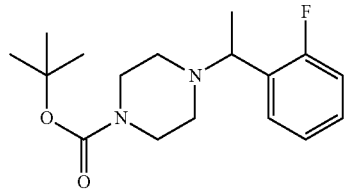 [SMILES: CC(c1ccccc1F)N1CCN(C(=O)OC(C)(C)C)CC1]

To a stirred solution of 0.500 mL (4.03 mmol) of 2-fluoroacetophenone and 0.50 g (2.68 mmol) of tert-butyl piperazine-1-carboxylate in 1.5 mL of anhydrous tetrahydrofuran under an atmosphere of nitrogen was added 2.50 mL (8.60 mmol) of titanium(IV) isopropoxide. The resulting mixture was heated to 80° C. for 12 h then cooled to 0° C. Next, 1.8 g (8.6 mmol) of solid sodium triacetoxyborohydride was added in one portion and the resulting solution was stirred with gradual warming to ambient temperature over 4 h. The reaction mixture was quenched with 1.0 mL (25 mmol) of methanol and then diluted with dichloromethane and a saturated aqueous sodium hydrogen carbonate solution. The mixture was filtered through a pad of Celite® and the layers separated. The aqueous phase was extracted with dichloromethane and the combined organic layers were washed with brine, dried over magnesium sulfate filtered and evaporated to dryness in vacuo. The crude residue was purified by silica gel chromatography eluting with a 0-100% ethyl acetate in hexanes gradient to afford the title compound as colorless oil (0.048 g, 58%). LC-MS: m/z (ES) 309.2 (MH)+

Step B: 1-[1-(2-Fluorophenyl)ethyl]piperazine, bis(hydrochloride) salt (i-89)

To a stirred solution of 0.048 g (0.16 mmol) of the title compound from step A above in 1 mL of methanol was added 4.0 mL (4.0 mmol) of a 4.0 M hydrogen chloride solution in 1,4-dioxane and the resulting mixture was stirred for 1 h. All volatiles were then removed in vacuo and the residue dried under high vacuum overnight to afford the title compound (i-89) as a pale yellow solid (0.043 g, 99% yield). LC-MS: m/z (ES) 209.0 (MH)+.

Intermediate 90

1-[1-(2-Fluorophenyl)-1-methylethyl]piperazine, bis(hydrochloride) salt (i-90)

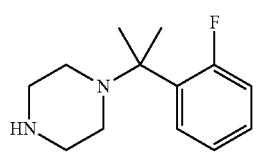

(i-90)

·2 HCl

Step A: Tert-butyl 4-[1-cyano-1-(2-fluorophenyl)ethyl]piperazine-1-carboxylate

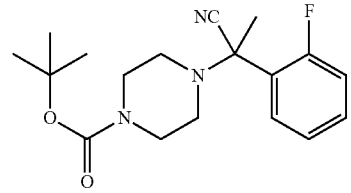 [SMILES: CC(C)(C)OC(=O)N1CCN(C(C)(C#N)c2ccccc2F)CC1]

To a stirred solution of 0.500 g (3.62 mmol) of 2-fluoroacetophenone and 0.67 g (3.62 mmol) of tert-butyl piperazine-1-carboxylate in 8.0 mL of anhydrous dichloromethane under an atmosphere of nitrogen was added 1.3 mL (4.3 mmol) of titanium(IV) isopropoxide. The resulting mixture was stirred at ambient temperature for 12 h then treated with 4.7 mL (4.7 mmol) of a 1.0 M solution of diethylaluminum cyanide. The mixture was then stirred for an additional 20 h at ambient temperature, and quenched with ethyl acetate and a saturated aqueous sodium bicarbonate solution. The resulting heterogeneous mixture was filtered through a pad of Celite®. The phases were separated, and the aqueous phase extracted with ethyl acetate. The combined organic layers were washed with brine, dried over magnesium sulfate, filtered and evaporated to dryness in vacuo to afford the crude title compound as yellow gum (1.0 g, 83%). This was used without further purification.

Step 13: Tert-butyl 4-[1-(2-fluorophenyl)-1-methylethyl]piperazine-1-carboxylate

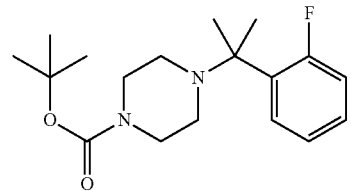 [SMILES: CC(C)(C)OC(=O)N1CCN(C(C)(C)c2ccccc2F)CC1]

To a stirred solution of 0.60 g (1.8 mmol) of the title compound from Step A above in 10 mL of anhydrous tetrahydrofuran cooled to 0° C. under a nitrogen atmosphere was added 3.0 mL (9.0 mmol) of a 3.0 M methyl magnesium bromide solution in tetrahydrofuran. The resulting mixture was allowed to warm to ambient temperature over 8 h then quenched with water. The layers were separated and the aqueous phase extracted with ethyl acetate. The combined organic layers were washed with brine, dried over magnesium sulfate, filtered and evaporated in vacuo. The residue was purified by silica gel chromatography eluting with a 0-100% ethyl acetate in hexanes gradient to afford the title compound as a yellow gum (0.40 g, 69% yield). (500 MHz, CDCl$_3$) δ 7.56 (td, J=8.1, 1.7 Hz, 1H), 7.21-7.16 (m, 1H), 7.06 (t, J=8.1, 1H), 6.97 (dd, J=12.7, 8.1 Hz, 1H), 3.40-3.38 (m, 4H), 2.45 (br s, 4H), 1.44 (s, 9H), 1.43 (s, 3H), 1.42 (s, 3H). LC-MS: m/z (ES) 323.0 (MH)+.

Step C: 1-[1-(2-Fluorophenyl)-1-methylethyl]piperazine, bis(hydrochloride) salt (i-90)

To a stirred solution of 0.40 g (1.2 mmol) of the title compound from Step B above in 1 mL of methanol was added 4.0 mL (4.0 mmol) of a 4.0 M hydrogen chloride solution in 1,4-dioxane and the resulting mixture was stirred for 1 h. All volatiles were then removed in vacuo and the residue dried under high vacuum overnight to afford the title compound (i-90) as a colorless solid (0.033 g, 89% yield). LC-MS: m/z (ES) 223.0 (MH)+.

Intermediate 91

1-[1-(1,3-Thiazol-2-yl)ethyl]piperazine, bis(hydrochloride) salt (i-91)

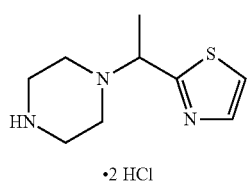

(i-91)

·2 HCl

Step A: Tert-butyl 4-[1-(1,3-thiazol-2-yl)ethyl]piperazine-1-carboxylate

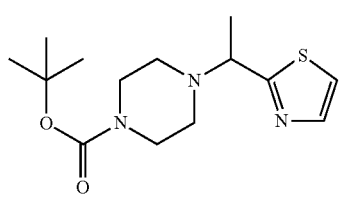 [SMILES: CC(c1nccs1)N1CCN(C(=O)OC(C)(C)C)CC1]

To a stirred solution of 1.0 g (8.8 mmol) of 1,3-thiazole-2-carbaldehyde in 25 mL of benzene under an atmosphere of nitrogen was added 1.6 g (8.8 mmol) of tert-butyl 1-piperazine-carboxylate followed by 1.0 g (8.8 mmol) of 1H-benzotriazole. The reaction mixture was heated to reflux for 3 h employing a Dean-Stark® Trap. The resulting mixture was cooled to ambient temperature and all volatiles were removed in vacuo. The residue was then dissolved in 25 mL of anhydrous tetrahydrofuran and cooled to −78° C. under an atmosphere of nitrogen.

Next, 4.0 mL (12 mmol) of a 3.0 M solution of methyl magnesium bromide in anhydrous tetrahydrofuran was added and the resulting dark red solution was allowed to gradually warm to 0° C. over 3 h. The mixture was then quenched with water, the layers were separated and the aqueous phase extracted with ethyl acetate. The combined organic layers were washed sequentially with a 0.5 M aqueous sodium hydroxide solution then brine, dried over magnesium sulfate, filtered and evaporated in vacuo. The residue was purified by silica gel chromatography eluting with a 0-100% ethyl acetate in hexanes gradient to afford the title compounds as a racemic mixture (1.4 g, 55%): $^1$H-NMR (500 MHz, CDCl$_3$) δ 7.70 (d, J=3.3 Hz, 1H), 7.27 (d, J=3.3 Hz, 1H), 4.03 (q, J=6.8 Hz, 1H), 3.46-3.44 (m, 4H), 2.57-2.50 (m, 4H), 1.48 (d, J=6.8 Hz, 3H), 1.45 (s, 9H). LC-MS: m/z (ES) 298.0 (MH)+.

Step B: 1-[1-(1,3-Thiazol-2-yl)ethyl]piperazine, bis(hydrochloride) salt

To a stirred solution of 0.25 g (0.84 mmol) of the title compound from Step A above in 1 mL of methanol was added 4.0 mL (4.0 mmol) of a 4.0 M hydrogen chloride solution in 1,4-dioxane and the resulting mixture was stirred for 1 h. All volatiles were then removed in vacuo and the residue dried under high vacuum overnight to afford the title compound as a yellow solid (0.022 g, 97% yield). LC-MS: m/z (ES) 198.0 (MH)+.

Intermediate 92

1-[1-(1,3-Thiazol-4-yl)ethyl]piperazine, bis(hydrochloride) salt (i-92)

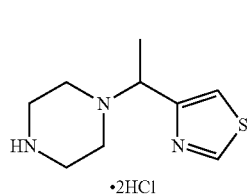

(i-92)

·2HCl

Intermediate 92 was prepared according to the same procedure used for the synthesis of Intermediates 91 using 1,3-thiazole-4-carbaldehyde in place of 1,3-thiazole-2-carbaldehyde. LC-MS: m/z (ES) 198.0 (MH)+.

Intermediate 93

1-[1-(1,3-Oxazol-2-yl)ethyl]piperazine, bis(hydrochloride) salt (i-93)

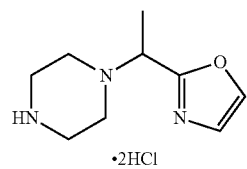

(i-93)

·2HCl

Intermediate 93 was prepared according to the same procedure used for the synthesis of Intermediates 91 using 1,3-oxazole-2-carbaldehyde in place of 1,3-thiazole-2-carbaldehyde. LC-MS: m/z (ES) 182.0 (MH)+.

Intermediate 94

1-[1-(1,3-Oxazol-4-yl)ethyl]piperazine, bis(hydrochloride) salt (i-94)

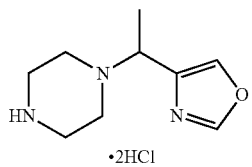

(i-94)

·2HCl

Intermediate 94 was prepared according to the same procedure used for the synthesis of Intermediates 91 using 1,3- oxazole-4-carbaldehyde in place of 1,3-thiazole-2-carbaldehyde. LC-MS: m/z (ES) 182.0 (MH)⁺.

Intermediate 95

3-(1-piperazin-1-ylethyl)pyridazine, bis(hydrochloride) salt (i-95)

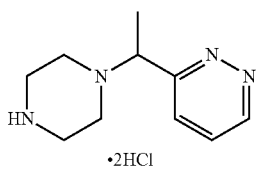

(i-95)

·2HCl

Step A: 1-Pyridazin-3-ylethanol

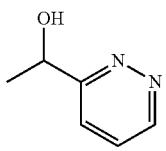

To a stirred solution of 13 ml (77 mmol) of 2,2,6,6-tetramethylpiperidine in 500 mL of anhydrous tetrahydrofuran cooled to 0° C. under an atmosphere of nitrogen was added 48 mL (77 mmol) of a 1.6 M solution of n-butyl lithium in hexanes slowly over 5 min. After complete addition the resulting mixture was stirred for an additional 30 min then cooled to −78° C. A solution of 1.4 mL (19 mmol) of pyridazine in 100 mL of anhydrous tetrahydrofuran was then added via cannula, and the resulting dark yellow solution was stirred for 1 h. Next, 11.0 mL (194 mmol) of neat acetaldehyde was added to the reaction mixture, which upon complete addition was allowed to gradually warm to 0° C. over 2 h. The reaction was then quenched with a saturated aqueous ammonium chloride solution and the layers were separated. The aqueous phase extracted with ethyl acetate and the combined organic layers were washed with brine, dried over magnesium sulfate, filtered and evaporated. The residue was purified by silica gel chromatography eluting with a 0-100% ethyl acetate in hexanes gradient to afford the title compounds as a dark yellow oil as a racemic mixture (0.85 g, 36%): ¹H-NMR (500 MHz, CDCl₃) δ 9.06 (dd, J=4.9, 1.5 Hz, 1H), 7.61 (dd, J=8.5, 1.5 Hz, 1H), 7.48 (dd, J=8.5, 4.9 Hz, 1H), 5.17-5.11 (m, 1H), 4.22 (d, J=3.8 Hz, 1H), 1.57 (d, J=6.7 Hz, 3H). LC-MS: m/z (ES) 125.0 (MH)⁺.

Step B: Tert-butyl 4-(1-pyridazin-3-ylethyl)piperazine-1-carboxylate

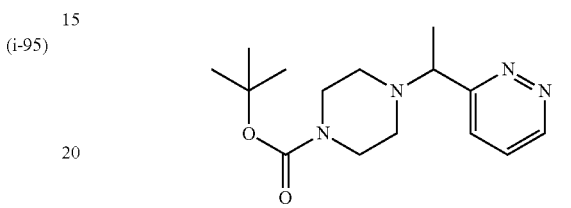

To a stirred solution of 0.20 g (1.6 mmol) of the title compound from Step A above in 5 mL of anhydrous dichloromethane was added 0.39 g (3.2 mmol) of 4-(dimethylamino)pyridine followed by 0.15 mL (1.9 mmol) of methanesulfonyl chloride. The resulting mixture was stirred with gradual warming to ambient temperature over 1 h then quenched with water. The aqueous phase was extracted with dichloromethane and the combined organics were washed with brine, dried over magnesium sulfate, filtered and evaporated to dryness. The residue was dissolved in 1.0 mL of anhydrous dimethyl sulfoxide and 0.74 mL (1.6 mmol) of N,N-diisopropylethylamine and 0.36 g (1.9 mmol) of tert-butyl piperazine-1-carboxylate were added to the solution sequentially. The resulting mixture was heated to 60° C. for 3 h then cooled to ambient temperature. The reaction was diluted with water and the aqueous phase was extracted with ethyl acetate. The combined organic layers were washed with brine, dried over magnesium sulfate, filtered and evaporated to dryness in vacuo. The residue was purified by silica gel chromatography eluting with a 0-100% ethyl acetate in hexanes gradient to afford the title compound as a yellow gum (0.27 g, 57% yield). ¹H-NMR (500 MHz, CDCl₃) δ 9.08 (dd, J=4.8, 1.6 Hz, 1H), 7.64 (dd, J=8.5, 1.5 Hz, 1H), 7.44 (dd, J=8.5, 4.9 Hz, 1H), 3.90 (q, J=6.7 Hz, 1H), 3.42-3.36 (m, 4H), 2.53-2.51 (m, 2H), 2.35-2.32 (m, 2H), 1.45 (d, J=6.7 Hz, 3H), 1.43 (s, 9H). LC-MS: m/z (ES) 293.0 (MH)⁺.

Step C: 3-(1-piperazin-1-ylethyl)pyridazine, bis(hydrochloride) salt (i-95)

To a stirred solution of 0.075 g (0.26 mmol) of the title compound from Step B above in 1 mL of methanol was added 4.0 mL (4.0 mmol) of a 4.0 M hydrogen chloride solution in 1,4-dioxane and the resulting mixture was stirred for 1 h. All volatiles were then removed in vacuo and the residue dried

Intermediate 96

2-(1-piperazin-1-ylethyl)pyrazine, bis(hydrochloride) salt (i-96)

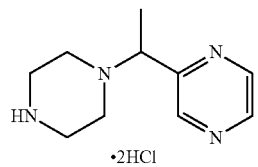

Intermediate 96 was prepared according to the same procedure used for the synthesis of Intermediates 95 using pyrazine in place of pyridazine. LC-MS: m/z (ES) 193.1 (MH)+.

Intermediates 97 and 98

1-[(1S)-1-(3-Chloropyridin-2-yl)ethyl]piperazine, bis(hydrochloride) salt (i-97) and 1-[(1R)-1-(3-Chloropyridin-2-yl)ethyl]piperazine, bis(hydrochloride) salt (i-98)

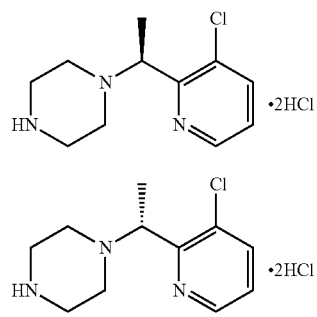

Step A: 1-(3-Chloropyridin-2-yl)ethanol

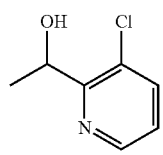

To a stirred solution of 0.20 g (1.2 mmol) of 1-(3-chloropyridin-2-yl)ethanone in 5 mL of methanol was added 0.072 g (1.9 mmol) of sodium borohydride and the resulting solution was stirred with gradual warming to ambient temperature over 1 h. The reaction mixture was carefully quenched with water and then all volatiles were removed in vacuo. The remaining aqueous phase was extracted with ethyl acetate and the combined organic layers were washed with brine, dried over magnesium sulfate, filtered and evaporated to dryness in vacuo. The residue was purified by silica gel chromatography eluting with a 0-100% ethyl acetate in hexanes gradient to afford the title compound as a colorless gum (0.15 g, 75% yield). LC-MS: m/z (ES) 158.2 (MH)+.

Step B: Tert-butyl 4-[(1S)-1-(3-chloropyridin-2-yl)ethyl]piperazine-1-carboxylate and Tert-butyl 4-[(1R)-1-(3-chloropyridin-2-yl)ethyl]piperazine-1-carboxylate

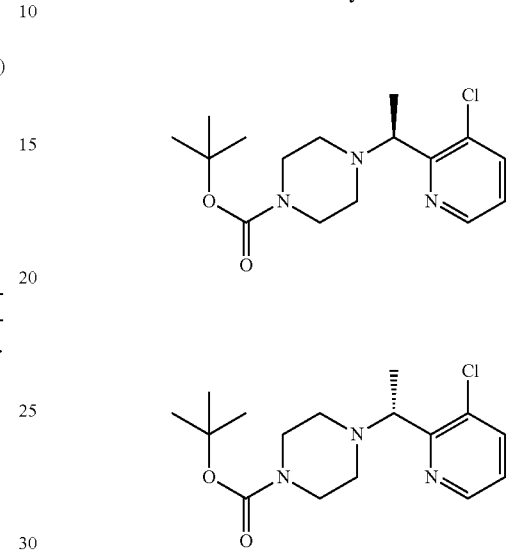

To a stirred solution of 0.16 g (1.0 mmol) of the title compound from Step A above in 5 mL of anhydrous dichloromethane was added 0.25 g (2.0 mmol) of 4-(dimethylamino)pyridine followed by 0.090 mL (1.1 mmol) of methanesulfonyl chloride. The resulting mixture was stirred with gradual warming to ambient temperature over 1 h then quenched with water. The aqueous phase was extracted with dichloromethane and the combined organics were washed with brine, dried over magnesium sulfate, filtered and evaporated to dryness. The residue was dissolved in 2.0 mL of anhydrous N,N-dimethylformamide and 0.36 mL (2.0 mmol) of N,N-diisopropylethylamine and 0.23 g (1.2 mmol) of tert-butyl piperazine-1-carboxylate were added to the solution sequentially. The resulting mixture was heated to 50° C. for 3 h then cooled to ambient temperature. The reaction was diluted with water and the aqueous phase was extracted with ethyl acetate. The combined organic layers were washed with brine, dried over magnesium sulfate, filtered and evaporated to dryness in vacuo. The residue was purified by silica gel chromatography eluting with a 0-100% ethyl acetate in hexanes gradient to afford the title compounds as a racemic mixture. The two enantiomers were separated by chiral HPLC employing a Daicel PREP CHIRALCEL® OD® column (eluent: 3% isopropanol in heptane). The first eluting enantiomer was designated as Isomer 1 and is a colorless foam (0.70 g, 21%): $^1$H-NMR (500 MHz, CDCl$_3$) δ 8.53 (d, J=4.6 Hz, 1H), 7.65 (d, J=8.0 Hz, 1H), 7.12 (dd, J=8.0, 4.6 Hz, 1H), 4.23 (q, J=6.7 Hz, 1H), 3.42-3.40 (m, 4H), 2.60-2.58 (m, 2H), 2.40-2.38 (m, 2H), 1.43 (s, 9H), 1.41 (d, J=6.7 Hz, 3H). LC-MS: m/z (ES) 326.2 (MH)+. The second eluting enantiomer was designated as Isomer 2 and is a colorless foam (0.70 g, 21%): $^1$H-NMR (500 MHz, CDCl$_3$) δ 8.53 (d, J=4.6 Hz, 1H), 7.65 (d, J=8.0 Hz, 1H), 7.12 (dd, J=8.0, 4.6 Hz, 1H), 4.23 (q, J=6.7 Hz, 1H), 3.42-3.40 (m, 4H), 2.60-2.58 (m, 2H), 2.40-2.38 (m, 2H), 1.43 (s, 9H), 1.41 (d, J=6.7 Hz, 3H). LC-MS: m/z (ES) 326.2 (MH)$^+$.

Step C: 1-[(1S)-1-(3-Chloropyridin-2-yl)ethyl]piperazine, bis(hydrochloride) salt and 1-[(1R)-1-(3-Chloropyridin-2-yl)ethyl]piperazine, bis(hydrochloride) salt

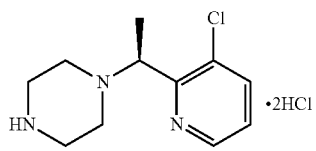

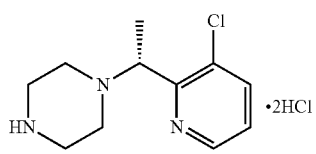

To a stirred solution of 0.13 g (0.38 mmol) of Isomer 1 from Step B above in 1 mL of methanol was added 4.0 mL (4.0 mmol) of a 4.0 M hydrogen chloride solution in 1,4-dioxane and the resulting mixture was stirred for 1 h. All volatiles were then removed in vacuo and the residue dried under high vacuum overnight to afford either 1-[(1S)-1-(3-chloropyridin-2-yl)ethyl]piperazine, bis(hydrochloride) salt or 1-[(1R)-1-(3-chloropyridin-2-yl)ethyl]piperazine, bis(hydrochloride) salt as a yellow solid (0.11 g, 96% yield). LC-MS: m/z (ES) 226.2 (MH)$^+$.

The same procedure was also repeated for Isomer 2 from step B above to afford either 1-[(1S)-1-(3-chloropyridin-2-yl)ethyl]piperazine, bis(hydrochloride) salt or 1-[(1R)-1-(3-chloropyridin-2-yl)ethyl]piperazine, bis(hydrochloride) salt as a yellow solid (0.060 g, 87% yield). LC-MS: m/z (ES) 226.2 (MH)$^+$.

Intermediates 99

1-[(3-Bromopyridin-2-yl)methyl]piperazine, bis(hydrochloride) salt (i-99)

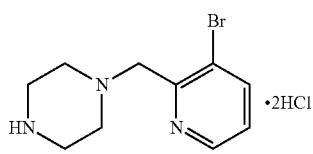
(i-99)

Step A: Tert-butyl 4-[(3-bromopyridin-2-yl)methyl]piperazine-1-carboxylate

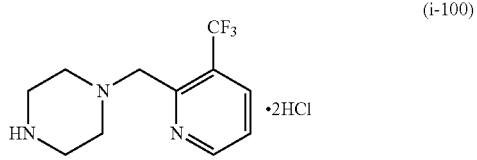 [SMILES: FC(F)(F)c1cccnc1CN1CCNCC1]

To a stirred suspension of 0.10 g (0.54 mmol) of 3-bromopyridine-2-carbaldehyde in 10 mL of dichloromethane was added activated powdered 4 Å molecular sieves, 0.20 mL (1.1 mmol) of N,N-diisopropylethylamine and 0.10 g (0.54 mmol) of tert-butyl piperazine-1-carboxylate. The resulting solution was stirred at ambient temperature for 1 h, then 0.34 g (1.6 mmol) of solid sodium triacetoxyborohydride was added in one portion. The heterogeneous reaction was allowed to stir at ambient temperature overnight and was then filtered through a pad of Celite®. The pad was washed with dichloromethane and the combined filtrates were washed with brine, dried over magnesium sulfate, filtered, and evaporated to dryness in vacuo. The residue was purified by silica gel chromatography eluting with a 0-100% ethyl acetate in hexanes gradient to afford the title compound as a colorless gum (0.055 g, 29%). LC-MS: m/z (ES) 356.2, 358.2 (MH)$^+$.

Step B: 1-[(3-Bromopyridin-2-yl)methyl]piperazine, bis(hydrochloride) salt (i-99)

To a stirred solution of 0.055 g (0.15 mmol) of the title compound from Step A above in 1 mL of methanol was added 4.0 mL (4.0 mmol) of a 4.0 M hydrogen chloride solution in 1,4-dioxane and the resulting mixture was stirred for 1 h. All volatiles were then removed in vacuo and the residue dried under high vacuum overnight to afford the title compound (i-99) as a yellow solid (0.047 g, 96% yield). LC-MS: m/z (ES) 256.2, 258.2 (MH)$^+$.

Intermediate 100

1-{[3-(Trifluoromethyl)pyridin-2-yl]methyl}piperazine, bis(hydrochloride) salt (i-100)

(i-100)

Intermediate 100 was prepared according to the same procedure used for the synthesis of Intermediates 99 using 3-(trifluoromethyl)pyridine-2-carbaldehyde in place of 3-bromopyridine-2-carbaldehyde. LC-MS: m/z (ES) 246.0 (MH)+.

Intermediate 101

1-[(3-fluoropyridin-2-yl)methyl]piperazine, bis(hydrochloride) salt (i-101)

(i-101)

Intermediate 101 was prepared according to the same procedure used for the synthesis of Intermediates 99 using 3-fluoropyridine-2-carbaldehyde in place of 3-bromopyridine-2-carbaldehyde. LC-MS: m/z (ES) 196.0 (MH)+.

Intermediate 102

1-(1-Pyridin-2-ylcyclopropyl)piperazine, bis(trifluoroacetic acid) salt (i-102)

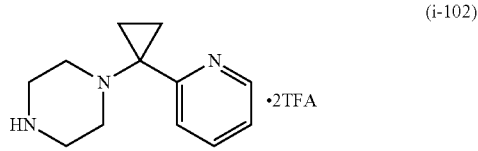 [SMILES: c1ccc(C2(N3CCNCC3)CC2)nc1]

(i-102)

Step A: Teri-butyl 4-(1-pyridin-2-ylcyclopropyl)piperazine-1-carboxylate

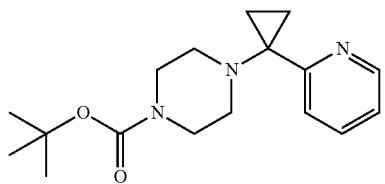 [SMILES: CC(C)(C)OC(=O)N1CCN(C2(c3ccccn3)CC2)CC1]

To a stirred suspension of 0.32 g (1.3 mmol) of tert-butyl bis(2-chloroethyl)carbamate in 5 ml of N,N-diisopropylethylamine and 0.5 mL of anhydrous N,N-dimethylformamide was added 0.23 g (1.1 mmol) of 1-pyridin-2-ylcyclopropanamine, bis(hydrochloride) salt and the resulting mixture was heated to 100° C. for 15 h. The mixture was cooled to ambient temperature, quenched with water, and the aqueous phase extracted with ethyl acetate. The combined organics were washed with brine, dried over magnesium sulfate, filtered and evaporated to dryness. The residue was purified by silica gel chromatography eluting with 50% acetone/hexanes mixture to afford the title compound as yellow gum (0.055 g, 17% yield). $^1$H-NMR (500 MHz, CDCl$_3$) δ 8.55 (d, J=4.7 Hz, 1H), 7.61 (td, J=7.7, 1.7 Hz, 1H), 7.33 (d, J=7.9, 4.6 Hz, 1H), 7.12 (dd, J=7.4, 4.9 Hz, 1H), 3.37-3.35 (m, 4H), 2.60-2.58 (m, 4H), 1.41 (s, 9H), 1.05-1.03 (m, 4H). LC-MS: m/z (ES) 304.5 (MH)+.

Step B: 1-(1-Pyridin-2-ylcyclopropyl)piperazine, bis(trifluoroacetic acid) salt (i-102)

To a stirred solution of 0.045 g (0.15 mmol) of the title compound from Step A above in 2 mL of dichloromethane was added 0.20 mL of trifluoroacetic acid and the resulting mixture was stirred for 1 h. All volatiles were removed in vacuo and the pale yellow residue was suspended in toluene. All volatiles were then removed in vacuo and this process was repeated two additional times. The pale yellow residue that was obtained was dried under high vacuum overnight to afford the title compound (i-102) as a yellow gum (0.060 g, 94%). LC-MS: m/z (ES) 204.5 (MH)+.

Intermediate 103

3-piperazin-1-yldihydrofuran-2(3H)-one, bis(trifluoroacetic acid) salt (i-103)

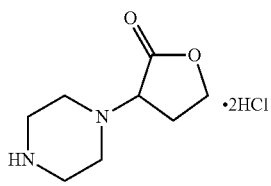

(i-103)

Step A: Tert-butyl 4-(2-oxotetrahydrofuran-3-yl)piperazine-1-carboxylate

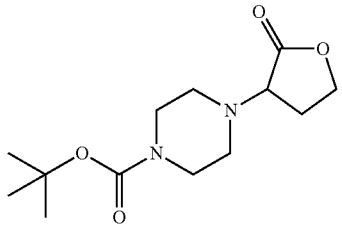 [SMILES: CC(C)(C)OC(=O)N1CCN(C2CCOC2=O)CC1]

To a stirred solution of 2.0 g (11 mmol) of tert-butyl piperazine-1-carboxylate in 30 mL of anhydrous N,N-dimethylformamide was added 1.9 g (14 mmol) of potassium carbonate followed by 0.09 mL (11 mmol) of 3-bromodihydrofuran-2(3H)-one. The resulting heterogeneous mixture was stirred at ambient temperature of 12 h, quenched with water, then extracted with ethyl acetate. The combined organic layers were washed with water then brine, dried over magnesium sulfate and evaporated to dryness in vacuo. The residue was purified by silica gel chromatography eluting with a 0-75% acetone in hexanes gradient to afford the title compound as clear gum (2.2 g, 75%). LC-MS: m/z (ES) 271.2 (MH)+.

Step B: 3-piperazin-1-yldihydrofuran-2(3H)-one, bis(trifluoroacetic acid) salt (i-103)

To a stirred solution of 1.6 g (5.9 mmol) of the title compound from Step A above in 10 mL of dichloromethane was added 5 mL of trifluoroacetic acid and the resulting mixture was stirred for 1 h. All volatiles were removed in vacuo and the pale yellow residue was suspended in toluene. All volatiles were then removed in vacuo and this process was repeated two additional times. The pale yellow residue that was obtained was dried under high vacuum overnight to afford the title compound (i-103) as a yellow gum (2.3 g, 98%). LC-MS: m/z (ES) 170.2 (MH)+.

Intermediate 104

3-piperazin-1-ylpyridin-2(1H)-one (i-104)

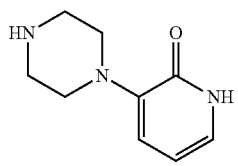
(i-104)

Step A: Benzyl 4-[2-(benzyloxy)pyridin-3-yl]piperazine-1-carboxylate

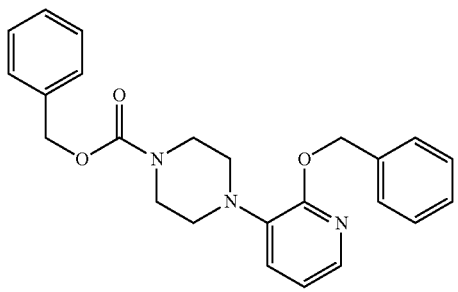 [SMILES: O=C(OCc1ccccc1)N1CCN(c2cccnc2OCc2ccccc2)CC1]

To a stirred suspension of 0.011 g (0.012 mmol) of (1E,4E)-1,5-diphenylpenta-1,4-dien-3-one-palladium (3:2) in 3 mL of anhydrous toluene under an atmosphere of nitrogen was added 0.015 g (0.037 mmol) of 2'-(dicyclohexylphosphino)-N,N-dimethylbiphenyl-2-amine and the resulting mixture was allowed to stir for 20 min. Next, 0.11 g (0.41 mmol) of 2-(benzyloxy)-3-bromopyridine was added followed by 0.11 g (0.49 mmol) of benzyl piperazine-1-carboxylate and 0.059 g (0.61 mmol) of sodium tert-butoxide. The resulting mixture was then heated to 80° C. overnight. After cooling to ambient temperature, the reaction mixture was diluted with water and extracted with ethyl acetate. The combined organic layers were washed with water then brine, dried over magnesium sulfate and evaporated to dryness in vacuo. The residue was purified by silica gel chromatography eluting with a 0-100% acetone in hexanes gradient to afford the title compound as clear gum (0.090 g, 55%). $^1$H-NMR (500 MHz, CDCl$_3$) δ 7.84 (dd, J=4.9, 1.6 Hz, 1H), 7.47-7.29 (m, 10H), 7.09 (dd, J=7.5, 1.6 Hz, 1H), 6.87 (dd, J=7.5, 4.9 Hz, 1H), 5.46 (s, 2H), 5.16 (s, 2H), 3.67-3.65 (m, 4H), 3.07 (br s, 4H). LC-MS: m/z (ES) 404.0 (MH)+.

Step B: 3-piperazin-1-ylpyridin-2(1H)-one (i-104)

To a 10 mL round bottomed flask was added 10 mg (0.009 mmol) of 10% palladium on activated carbon which was then flushed with nitrogen. Next, a solution of 0.090 (0.22 mmol) of benzyl 4-[2-(benzyloxy)pyridin-3-yl]piperazine-1-carboxylate from Step A above in 4 mL of methanol was added and the resulting mixture was placed under an atmosphere of hydrogen gas at atmospheric pressure for 3 h. The reaction was then flushed with nitrogen and filtered through a pad of Celite®. The pad was washed with methanol and the combined organics were evaporated to dryness to afford the title compound as a clear gum (0.035 g, 88%). LC-MS: m/z (ES) 180.1 (MH)+.

Intermediate 105

Tert-butyl 4-(1H-tetrazol-5-ylmethyl)piperazine-1-carboxylate (i-105)

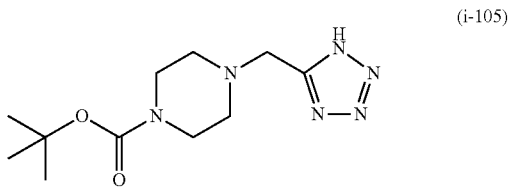 [SMILES: CC(C)(C)OC(=O)N1CCN(Cc2nnn[nH]2)CC1]
(i-105)

Step A: Tert-butyl 4-(cyanomethyl)piperazine-1-carboxylate

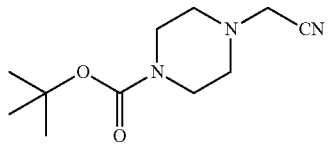 [SMILES: CC(C)(C)OC(=O)N1CCN(CC#N)CC1]

To a stirred solution of 2.7 g (15 mmol) of tert-butyl piperazine-1-carboxylate in 30 mL of anhydrous N,N-dimethylformamide was added 2.4 g (17 mmol) of potassium carbonate followed by 2.1 g (17 mmol) of bromoacetonitrile. The resulting heterogeneous mixture was stirred at ambient temperature of 12 h, quenched with water then extracted with ethyl acetate. The combined organic layers were washed with water then brine, dried over magnesium sulfate and evaporated to dryness in vacuo. The residue was purified by silica gel chromatography eluting with a 0-75% acetone in hexanes gradient to afford the title compound as clear gum (1.0 g, 30%). $^1$H-NMR (500 MHz, CDCl$_3$) δ 3.53 (s, 2H), 3.48 (t, J=5.0 Hz, 4H), 2.53 (t, J=5.0 Hz, 4H), 1.45 (s, 9H). LC-MS: m/z (ES) 226.2 (MH)+.

Step B: Tert-butyl 4-(1H-tetrazol-5-ylmethyl)piperazine-1-carboxylate (i-105)

To a stirred suspension of 1.50 g (6.66 mmol) of the title compound from Step A above in 25 mL of anhydrous toluene was added 1.38 g (10.0 mol) of triethylamine hydrochloride followed by 0.65 g (10 mmol) of sodium azide. The resoling mixture was heated to 80° C. for 12 h then cooled to ambient temperature. All volatiles were removed in vacuo, and the residue suspended in 5 mL of brine and 1.0 N aqueous hydrogen chloride solution was added until pH of ~4 was achieved. The aqueous phase was extracted with chloroform and the combined organics were dried over magnesium sulfate and evaporated to dryness in vacuo. The residue was purified by silica gel chromatography eluting with a 0-100% acetone in hexanes gradient to afford the title compound (i-105) as white solid (1.1 g, 63%). $^1$H-NMR (500 MHz, DMSO-$d_6$) δ 3.82 (s, 2H), 3.29 (br s, 4H), 2.38-2.34 (m, 4H), 1.36 (s, 9H). LC-MS: m/z (ES) 269.0 (MH)$^+$.

Intermediate 106

1-(1H-Tetrazol-5-ylmethyl)piperazine, bis(trifluoroacetic acid) salt (i-106)

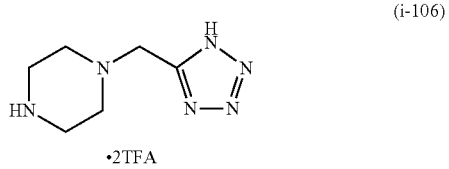 [SMILES: C1CN(Cc2nnn[nH]2)CCN1]

To a stirred solution of 0.050 g (0.19 mmol) of Intermediate i-105 in 3 mL of dichloromethane was added 1 mL of trifluoroacetic acid and the resulting mixture was stirred for 1 h. All volatiles were removed in vacuo and the pale yellow residue was suspended in toluene. All volatiles were then removed in vacuo and this process was repeated two additional times. The pale yellow residue that was obtained was dried under high vacuum overnight to afford the title compound as a yellow gum (0.072 g, 98%). LC-MS: m/z (ES) 169.0 (MH)$^+$.

Intermediate 107 And 108

1-[(2-Methyl-2H-tetrazol-5-yl)methyl]piperazine, bis(trifluoroacetic acid) salt (i-107) and 1-[(1-Methyl-1H-tetrazol-5-yl)methyl]piperazine, bis(trifluoroacetic acid) salt (i-108)

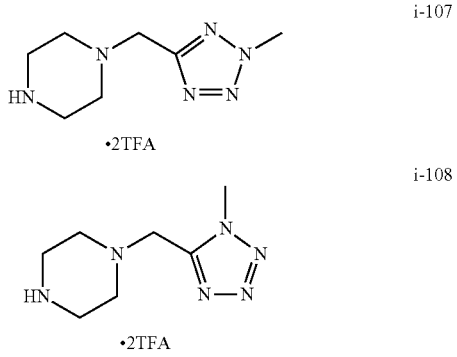

Step A: Tert-butyl 4-[(2-methyl-2H-tetrazol-5-yl)methyl]piperazine-1-carboxylate and Tert-butyl 4-[(1-methyl-1H-tetrazol-5-yl)methyl]piperazine-1-carboxylate To a stirred solution of 0.10 g (0.37 mmol) of Intermediate i-106 in 1 mL of anhydrous N,N-dimethylformamide was added 0.077 g (0.56 mmol) of potassium carbonate followed by 0.025 mL (0.37 mmol) of iodomethane. The resulting mixture was stirred at ambient temperature of 12 h, quenched with water then extracted with ethyl acetate. The combined organic layers were washed with water then brine, dried over magnesium sulfate and evaporated to dryness in vacuo. The residue was purified by silica gel chromatography eluting with a 5-25% acetone in hexanes gradient. The first eluted isomer (Isomer 1) is tert-butyl 4-[(2-methyl-2H-tetrazol-5-yl)methyl]piperazine-1-carboxylate as clear gum (0.007 g, 6.7%) (less polar—faster eluting isomer). $^1$H-NMR (500 MHz, CDCl$_3$) δ 4.34 (s, 3H), 3.87 (s, 2H), 3.47 (br s, 4H), 2.52 (br s, 4H) 1.45 (s, 9H). LC-MS: m/z (ES) 283.0 (MH)$^+$. And the second eluted isomer (Isomer 2) is tert-butyl 4-[(1-methyl-1H-tetrazol-5-yl)methyl]piperazine-1-carboxylate as clear gum (0.024 g, 23%) (more polar—slower eluting isomer). $^1$H-NMR (500 MHz, CDCl$_3$) δ 4.15 (s, 3H), 3.89 (s, 2H), 3.45 (br s, 4H), 2.48 (br s, 4H) 1.48 (s, 9H). LC-MS: m/z (ES) 283.0 (MH)$^+$.

Step B: 1-[(2-Methyl-2H-tetrazol-5-yl)methyl]piperazine, bis(trifluoroacetic acid) salt (i-107)

To a stirred solution of 0.007 g (0.025 mmol) of the Isomer 1 from Step A above in 3 mL of dichloromethane was added 1 mL of trifluoroacetic acid and the resulting mixture was stirred for 1 h. All volatiles were removed in vacuo and the pale yellow residue was suspended in toluene. All volatiles were then removed in vacuo and this process was repeated two additional times. The pale yellow residue that was obtained was dried under high vacuum overnight to afford the title compound as a yellow gum (0.010 g, 98%). LC-MS: m/z (ES) 183.0 (MH)$^+$.

Step C: 1-[(1-Methyl-1H-tetrazol-5-yl)methyl]piperazine, bis(trifluoroacetic acid) salt (i-108)

To a stirred solution of 0.024 g (0.085 mmol) of the Isomer 2 from Step A above in 3 mL of dichloromethane was added 1 mL of trifluoroacetic acid and the resulting mixture was stirred for 1 h. All volatiles were removed in vacuo and the pale yellow residue was suspended in toluene. All volatiles were then removed in vacuo and this process was repeated two additional times. The pale yellow residue that was obtained was dried under high vacuum overnight to afford the title compound as a yellow gum (0.033 g, 95%). LC-MS: m/z (ES) 183.0 (MH)$^+$.

Intermediate 109 and 110

1-[(2-Isopropyl-2H-tetrazol-5-yl)methyl]piperazine bis(trifluoroacetic acid) salt (i-109) and 1-[(1-Isopropyl-1H-tetrazol-5-yl)methyl]piperazine bis(trifluoroacetic acid) salt (i-110)

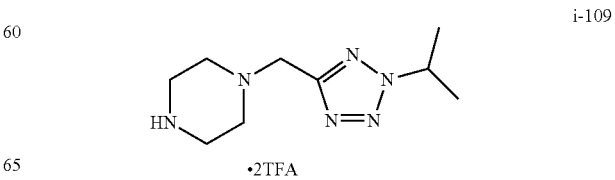

-continued

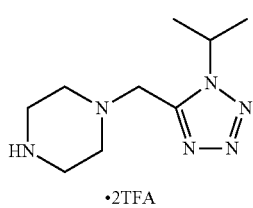

(i-110)

•2TFA

Intermediates 109 and 110 were prepared from Intermediate 105 and 2-iodopropane according to the same procedure used for the synthesis of Intermediates 107 and 108.

1-[(2-isopropyl-2H-tetrazol-5-yl)methyl]piperazine bis (trifluoroacetic acid) salt: LC-MS: m/z (ES) 211.2 (MH)$^+$.

1-[(1-isopropyl-1/1-tetrazol-5-yl)methyl]piperazine bis (trifluoroacetic acid) salt: LC-MS: m/z (ES) 211.2 (MH)$^+$.

Intermediate 111

1-(Isoxazol-3-ylmethyl)piperazine (i-111)

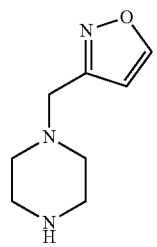

(i-111)

Step A: 3-(Bromomethyl)isoxazole

To a stirred solution of 0.50 g (5.1 mmol) of isoxazol-3-ylmethanol in 5 mL anhydrous dichloromethane under an atmosphere of nitrogen was added dropwise 1.5 mL (1.5 mmol) of a 1.0 M solution of phosphorus tribromide in dichloromethane. The reaction mixture was stirred for 1 h and then quenched with 10 mL water. The aqueous phase was then extracted with dichloromethane (3×10 mL) and the combined organics were dried over magnesium sulfate, filtered and evaporated in vacuo to afford the title compound as a brown residue that was used without further purification. LC/MS: m/z (ES) 163.9 (MH)$^+$.

Step B: Tert-butyl 4-(isoxazol-3-ylmethyl)piperazine-1-carboxylate

To a stirred solution of 0.74 g (4.6 mmol) of the title compound from Step A and 1.1 g (5.9 mmol) tart-butyl 1-piperazine-carboxylate in 8 mL anhydrous N,N-dimethylformamide under an atmosphere of nitrogen was added 2.40 mL (13.7 mmol) of N,N-diisopropylethylamine. The resulting reaction mixture was heated to 100° C. for 6 h. After cooling to ambient temperature, 25 mL water was added and the resulting solution was extracted with 35 mL ethyl acetate. The organic layer was washed with water (2×25 mL), dried over magnesium sulfate, filtered and evaporated in vacuo to afford the title compound which was purified by reverse-phase HPLC (TMC Pro-Pac C18; 10-100% 0.1% trifluoroacetic acid in acetonitrile/0.1% trifluoroacetic acid in water gradient). LC/MS: m/z (ES) 268.1 (MH)$^+$.

Step C: 1-(Isoxazol-3-ylmethyl)piperazine (i-111)

A solution of 0.84 g (3.2 mmol) of the title compound from Step B above in 5 mL dichloromethane and 5 mL trifluoroacetic acid was stirred at ambient temperature for 1 h. All volatiles were removed in vacuo and the crude light brown residue was carried forward without purification. LC/MS: m/z (ES) 168.1 (MH)$^+$.

Intermediate 112

4-(Piperazin-1-ylmethyl)pyrimidine (i-112)

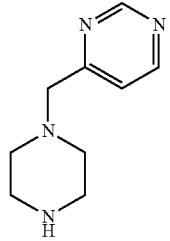

(i-112)

Step A: Benzyl 4-(pyrimidin-4-yl-methyl)piperazine-1-carboxylate

To a stirred solution of 0.20 g (1.8 mmol) of 1-(pyrimidin-4-yl)methanamine and 0.61 g (2.2 mmol) benzyl bis(2-chloroethyl)carbamate in 4 mL anhydrous diethylene glycol dimethyl ether was added 3.20 mL (18.3 mmol) of N,N-diisopropylethylamine and 0.05 g (0.40 mmol) of sodium iodide. The resulting solution was heated to 150° C. for 6 h. After cooling to ambient temperature, 12 mL of methanol was added to the mixture followed by 250 mL of diethyl ether. The resulting white precipitate was isolated by vacuum filtration while washing with diethyl ether. Diluted the solid with 100 mL of saturated sodium bicarbonate and extracted the aqueous solution with ethyl acetate (3×100 mL). The combined organic layers were dried with magnesium sulfate, filtered, and concentrated in vacuo to afford the title compound as a white solid which was used without further purification. LC/MS: m/z (ES) 313.1 (MH)$^+$ Step B: 4-(piperazin-1-ylmethyl)pyrimidine (i-112)

To 0.01 g (0.09 mmol) of 10% palladium on carbon was added a solution of 0.14 g (0.45 mmol) of the title compound from Step A in 5 mL anhydrous methanol. The resulting suspension was subjected to hydrogen at atmospheric pressure while stirring. After 4 h the mixture was filtered through a pad of Celite. The pad was washed with methanol (25 mL) and the combined filtrates were concentrated in vacuo to afford the title compound as a pale yellow residue without further purification. LC/MS: m/z (ES) 179.1 (MH)$^+$.

Intermediate 113

1-[(2-Phenyl-2H-1,2,3-triazol-4-yl)methyl]piperazine (i-113)

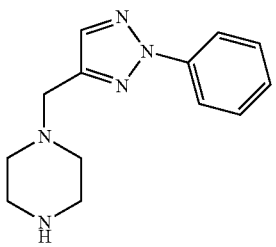

(i-113)

Step A: Teat-butyl 4-[2-phenyl-2H-1,2,3-triazol-4-yl)methyl]piperazine-1-carboxylate To a stirred suspension of 0.28 g (0.71 mmol) of sodium hydride (60% mineral oil dispersion) in 5 mL anhydrous N,N-dimethylformamide at 0° C. was added 0.12 g (0.65 mmol) tert-butyl 1-piperazine-carboxylate. The resulting mixture was stirred under an atmosphere of nitrogen for 15 min and then allowed to warm to ambient temperature at which point 0.14 g (0.59 mmol) of 4-(bromomethyl)-2-phenyl-2H-1,2,3-triazole was added. After 4 h, quench the reaction with 25 mL cold water and extract the resulting solution with 25 mL ethyl acetate. The organic layer was washed with water (2×25 mL), dried over magnesium sulfate, filtered and evaporated in vacuo to afford the title compound which was purified by reverse-phase HPLC (TMC Pro-Pac C18; 10-100% 0.1% trifluoroacetic acid in acetonitrile/0.1% trifluoroacetic acid in water gradient). LC/MS: m/z (ES) 344.0 (MH)$^+$.

Step B: 1-[(2-Phenyl-2H-1,2,3-triazol-4-yl)methyl]piperazine (i-113)

Prepared from the title compound from Step A using the procedure described in Step C of Intermediate 111. LC/MS: m/z (ES) 244.2 (MH)$^+$.

Intermediate 114

(8S)-8-(piperazin-1-yl)-5,6,7,8-tetrahydroquinoline (i-114) and (8R)-8-(piperazin-1-yl)-5,6,7,8-tetrahydroquinoline (i-115)

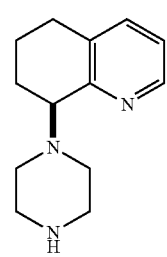

(i-114)

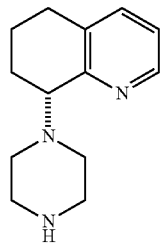

(i-115)

Step A: 5,6,7,8-Tetrahydroquinolin-8-yl methanesulfonate

To a stirred solution of 2.0 g (13 mmol) of 5,6,7,8-tetrahydroquinolin-8-ol and 3.3 g (27 mmol) of 4-(dimethylamino)pyridine in 30 mL of dichloromethane was added 1.3 mL (16 mmol) of methanesulfonyl chloride under an atmosphere of nitrogen. The reaction mixture was stirred for 8 h and then diluted with 30 mL water. The aqueous phase was then extracted with dichloromethane (3×30 mL) and the combined organics were dried over magnesium sulfate, filtered and evaporated in vacuo to afford the title compound as a light orange gum that was used without further purification. LC/MS: m/z (ES) 172.0 (MH)$^+$.

Step B: Text-butyl 4-[(8S)-5,6,7,8-tetrahydroquinolin-8-yl]piperazine-1-carboxylate and Tert-butyl 4-[(8R)-5,6,7,8-tetrahydroquinolin-8-yl]piperazine-1-carboxylate Prepared from the title compound from Step A using the procedure described in Step B of Intermediate 111. The crude residue was purified by silica gel chromatography eluting with 100% ethyl acetate to afford the title compound as a mixture of enantiomers. The mixture was separated by chiral HPLC employing a PREP CHIRALPAK® AD® column eluting with an 8% IPA in heptane mixture to afford the title compounds. The first enantiomer to elute was designated as Isomer 1 and the second as Isomer 2. Isomer 1 LC/MS: m/z (ES) 318.2 (MH)$^+$. Isomer 2 LC/MS: m/z (ES) 318.2 (MH)$^+$.

Step C: (8S)-8-(piperazin-1-yl)-5,6,7,8-tetrahydroquinoline (i-114) and (8R)-8-(piperazin-1-yl)-5,6,7,8-tetrahydroquinoline (i-115)

Prepared from Isomer 1 and Isomer 2 from Step B using the procedure described in Step C of Intermediate 111. Isomer 1 LC/MS: m/z (ES) 218.2 (MH)$^+$, Isomer 2 LC/MS: m/z (ES) 218.2 (MH)$^+$.

Intermediate 116

1-(2-Fluorobenzyl)piperazine (i-116)

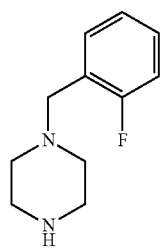

(i-116)

Step A: Tert-butyl 4-(2-fluorobenzyl)piperazine-1-carboxylate

Prepared from 1-(bromomethyl)-2-fluorobenzene and tert-butyl 1-piperazine-carboxylate using the procedure described in Step A of Intermediate 113. LC/MS: m/z (ES) 295.0 (MH)$^+$.

Step B: 1-(2-Fluorobenzyl)piperazine (i-116)

Prepared from the title compound from Step A above using the procedure described in Step C of Intermediate 109. LC/MS: m/z (ES) 195.1 (MH)$^+$.

Intermediate 117

1-(pyridine-2-ylmethyl)piperazine (i-117)

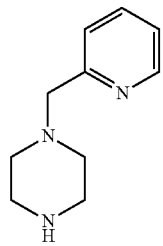

(i-117)

Step A: Tert-butyl 4-(pyridine-2-ylmethyl)piperazine-1-carboxylate

Prepared from 2-(bromomethyl)pyridine and tert-butyl 1-piperazine-carboxylate using the procedure described in Step A of Intermediate 113. LC/MS: m/z (ES) 278.1 (MH)$^+$.

Step B: 1-(pyridine-2-ylmethyl)piperazine

Prepared from the title compound from Step A using the procedure described in Step C of Intermediate 111. LC/MS: m/z (ES) 178.2 (MH)$^+$.

Intermediate 118

1-(2,3-Dihydro-1-benzofuran-3-y)piperazine, TFA salt (i-118)

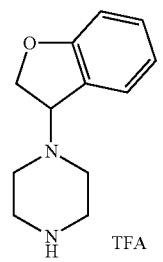

(i-118)

Step A: Ethyl 3-Hydroxypicolinate

To a stirred solution of 5.0 g (36 mmol) of 3-hydroxylpicolinic acid in 120 mL ethanol and 40 ml benzene was added 2.0 ml of 98% sulfuric acid. The reaction was refluxed for 40 h. After the solvents were evaporated, the residue was dissolved in 100 ml of water, neutralized with saturated sodium bicarbonate solution and extracted with dichloromethane 3 times. The combined organics were dried over magnesium sulfate, filtered and evaporated in vacuo to afford 3.5 g (58% yield) of the title compound as a brown residue that was used without further purification.

Step B: Ethyl 2-(2-Ethoxycarbonyl-3-pyridyloxy)acetate

To a stirred solution of 2.0 g (12 mmol) of the title compound from Step A in 50 mL of acetone under an atmosphere of nitrogen was added 2.5 g (18 mmol) of potassium carbonate and 2.4 g (14 mmol) of ethyl bromoacetate. The reaction mixture was refluxed overnight. After cooling, the inorganic materials were filtered off and washed with acetone. The filtration was concentrated and purified by MPLC (Biotage Horizone: Flash 65i) eluent: 100% dichloromethane to 12% methanol in dichloromethane to give 2.5 g of the title compound as an oil. LC/MS: (M+1) 240.9

Step C: 1-Benzofuran-3(2H)-one

To a stirred solution of 1.0 g (4.2 mmol) of the title compound from Step B in 30 ml toluene was added 2.9 g (9.2 mmol) of 21% sodium ethoxide. The reaction was refluxed overnight. After cooling down to RT, the reaction was filtered and the solid was collected. The solid was then dissolved in 20 ml water, and acidified by acetic acid. The solid was filtered and washed with dichloromethane and dried. The solid was added to 30 ml of 10% HCl aqueous solution and refluxed for 3 hr. Then HCl was evaporated to give 350 mg (62% yield) of the title compound. LC/MS: (M+1) 136.1

Step D: tert-Butyl 4-(2,3-dihydro-1-benzofuran-3-y)piperazine-1-carboxylate

To a stirred solution of 80 mg (0.47 mmol) of the title compound from Step C and 87 mg (0.47 mmol) tert-butyl 1-piperazine-carboxylate in 20 ml THF was added 39 mg (0.47 mmol) sodium bicarbonate and 0.27 ml (0.93 mmol) of titanium(IV) isopropoxide. The reaction was stirred at RT for 30 min, and was heated at 70° C. for 4 h. The reaction was cooled down to ambient temperature and 200 mg (0.93 mmol) of sodium triacetoxyborohydride was added into the mixture. The reaction was continued by stirring at ambient temperature overnight. The reaction was quenched with methanol and concentrated. The reaction was partitioned between ethyl acetate and water, the organic layer was washed with brine, dried over magnesium sulfate, filtered and evaporated in vacuo. The residue was purified by reverse-phase HPLC (TMC Pro-Pac C18; 10-100% 0.1% trifluoroacetic acid in acetonitrile/0.1% trifluoroacetic acid in water gradient) to give the intermediate with double bond. To the above intermediate was added 20 ml methanol and 5 mg of 10% Palladium on carbon. Hydrogenation was carried out under the hydrogen gas balloon for 4 hr. The reaction mixture was filtered and the filtrate was concentrated to afford the title compound. LC/MS: (M-56): 249.6

Step E: 1-(2,3-Dihydro-1-benzofuran-3-y)piperazine, TFA salt (i-118)

A solution of 30 mg (0.1 mmol) of the title compound from Step D above in 1 mL dichloromethane and 1 mL trifluoroacetic acid was stirred at ambient temperature for 1 h. All volatiles were removed in vacuo and the title compound was obtained as a crude light brown residue.

Intermediate 119

(2S)-2-methyl-1-(pyridin-2-ylmethyl)piperazine (i-119)

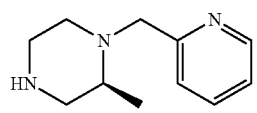

Step A: tert-butyl (3S)-3-methyl-4-(pyridin-2-ylmethyl)piperazine-1-carboxylate

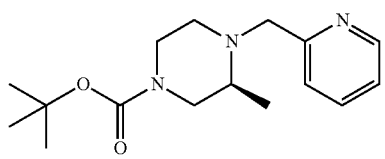 [SMILES: C[C@H]1CN(C(=O)OC(C)(C)C)CCN1Cc1ccccn1]

To a mixture of (S)-2-methyl-4-N—BOC-piperazine (400 mg, 1.997 mmol) and 2-(bromomethyl)pyridine hydrobromide (505 mg, 1.997 mmol) in anhydrous THF (5 ml) was added triethylamine (0.7 ml, 4.99 mmol) and the resulting mixture stirred at RT for 3 days. The mixture partitioned between water and EtOAc; organic layer washed with sat. NaCl, dried over MgSO4, filtered and evaporated. The residue purified by column chromatography (eluent: 5% MeOH in DCM) to give 320 mg (55%) to afford the title compound as a yellow oil. $^1$H NMR (CDCl$_3$): 1.14 (d, J 6.2 Hz, 3H), 1.47 (s, 9H), 2.25 (t, J 9.5 Hz, 1H), 2.51 (m, 1H), 2.70 (d, J 11.6 Hz, 1H), 2.84 (brs, 1H), 3.15 (t, J 10.1, 1H), 3.47 (d, J 14.2 Hz, 1H), 3.69 (d, J 13.0 Hz, 1H), 3.75 (brs, 1H), 4.08 (d, J 14.0, 1H), 7.17 (dd, J 7.1 and 5.3, 1H), 7.45 (d, J 7.8, 1H), 7.66 (m, 1H), 8.56 (d, J=4.7 Hz, 1H).

Step B: (2S)-2-methyl-1-(pyridin-2-ylmethyl)piperazine (i-119)

To a solution of the title compound from step A (320 mg, 1.1 mmol) in DCM (5 ml) was added TFA (2.1 ml, 27.5 mmol) and the resulting mixture stirred at RT for 4 h. Mixture evaporated and residue dissolved in MeOH and passed through an SCX cartridge (eluting with 2M ammonia in methanol) to form free base. Evaporated and residue lypholized from CH3CN/water to afford the title compound 44 mg (21%) as an orange oil. $^1$H NMR (CDCl$_3$): 1.14 (d, J 6.2 Hz, 3H), 2.24 (m, 1H), 2.47 (m, 1H), 2.64 (dd, J 12.3 and 9.3 Hz, 1H), 2.73 (m, 1H), 2.87-2.97 (m, 3H), 3.44 (d, J 14.2 Hz, 1H), 4.14 (d, J 14.3 Hz, 1H), 7.17 (dd, J 7.0 and 5.4, 1H), 7.47 (d, J 7.8, 1H), 7.66 (m, 1H), 8.56 (d, J 4.7 Hz, 1H).

Intermediate 120

(2R)-2-methyl-1-(pyridin-2-ylmethyl)piperazine (i-120)

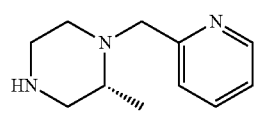

Step A: tert-butyl (3R)-3-methyl-4-(pyridin-2-ylmethyl)piperazine-1-carboxylate

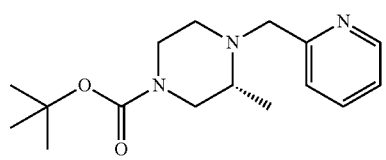 [SMILES: C[C@@H]1CN(C(=O)OC(C)(C)C)CCN1Cc1ccccn1]

Prepared according to the procedure described in Intermediate 119, Step A, replacing (S)-2-methyl-4-N—BOC-piperazine with (R)-2-methyl-4-N—BOC-piperazine. The title compound was obtained (57%) as a light yellow oil. $^1$H NMR (CDCl$_3$): 1.14 (d, J 6.2 Hz, 3H), 1.47 (s, 9H), 2.25 (t, J 9.5 Hz, 1H), 2.51 (m, 1H), 2.70 (d, J 11.6 Hz, 1H), 2.84 (brs, 1H), 3.15 (t, J 10.1, 1H), 3.47 (d, J 14.2 Hz, 1H), 3.69 (d, J 13.0 Hz, 1H), 3.75 (brs, 1H), 4.08 (d, J 14.0, 1H), 7.17 (dd, J 7.1 and 5.3, 1H), 7.45 (d, J 7.8, 1H), 7.66 (m, 1H), 8.56 (d, J 4.7 Hz, 1H).

Step B: (2R)-2-methyl-1-(pyridin-2-ylmethyl)piperazine (i-120)

Prepared from the title compound from Step A according to the procedure described in Intermediate 119, Step B, (40%). The title compound was obtained as an orange oil. $^1$H NMR (CDCl$_3$): 1.14 (d, J 6.2 Hz, 3H), 2.24 (m, 1H), 2.47 (m, 1H), 2.64 (dd, J 12.3 and 9.3 Hz, 1H), 2.73 (m, 1H), 2.87-2.97 (m, 3H), 3.44 (d, J 14.2 Hz, 1H), 4.14 (d, J 14.3 Hz, 1H), 7.17 (dd, J 7.0 and 5.4, 1H), 7.47 (d, J 7.8, 1H), 7.66 (m, 1H), 8.56 (d, J 4.7 Hz, 1H).

Intermediate 121

2-(1-piperazinylmethyl)-benzoxazole (i-121)

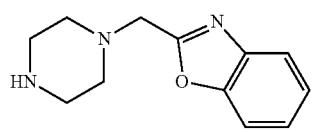

Step A: tert-butyl 4-(1,3-benzoxazol-2-ylmethyl)-3-methylpiperazine-1-carboxylate

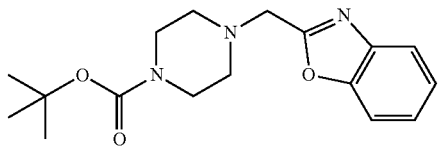 [SMILES: CC(C)(C)OC(=O)N1CCN(Cc2nc3ccccc3o2)CC1]

To a mixture of N—BOC-piperazine (2.22 g, 11.93 mmol) and 2-chloromethylbenzoxazole (2 g, 11.93 mmol) in anhydrous THF (20 ml) was added Et$_3$N (2.5 ml, 17.9 mmol) and the resulting mixture stirred at RT overnight. Partitioned between water and EtOAc, organic layer washed with sat. NaCl, dried over MgSO$_4$, filtered and evaporated. The residue purified by MPLC (Biotage Horizon: FLASH 40+M) eluent: 100% Hexanes (190 ml), gradient rising from 100% Hexanes to 50% EtOAc in Hexanes (900 ml), then 50% EtOAc in Hexanes (500 ml) to give 2.63 g (69%) of the title compound as a light pink solid. $^1$H NMR (CDCl$_3$): 1.45 (s, 9H), 2.58 (m, 4H), 3.49 (m, 4H), 3.89 (s, 2H), 7.33 (m, 2H), 7.53 (m, 1H), 7.71 (m, 1H).

Step B: 2-(1-piperazinylmethyl)-benzoxazole (i-121)

Prepared from the title compound from Step A according to the procedure described in Intermediate 116, Step B. The title compound was obtained (68%) as orange oil. $^1$H NMR (CDCl$_3$): 2.68 (m, 4H), 3.02 (m, 4H), 3.89 (s, 2H), 7.35 (m, 2H), 7.55 (m, 1H), 7.72 (m, 1H).

Intermediate 122

2-(1-piperazinylmethyl)-benzthiazole (i-122)

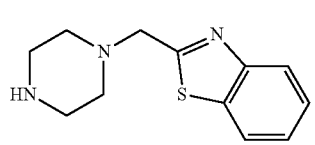

Step A: tert-butyl 4-(1,3-benzthiazol-2-ylmethyl)-3-methylpiperazine-1-carboxylate

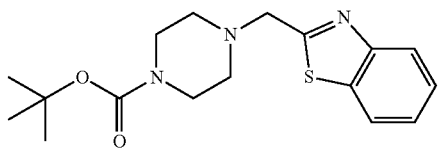

Prepared according to the procedure described in Intermediate 121, Step A, replacing 2-chloromethylbenzoxazole with 2-bromomethylthiazole. The title compound was obtained (88%) as light yellow oil. $^1$H NMR (CDCl$_3$): 1.47 (s, 9H), 2.60 (m, 4H), 3.50 (m, 4H), 3.98 (s, 2H), 7.38 (m, 1H), 7.46 (m, 1H), 7.88 (d, J 8.0 Hz, 1H), 7.98 (d, J 8.1 Hz, 1H).

Step B: 2-(1-piperazinylmethyl)-benzthiazole (i-122)

Prepared from the title compound from Step A according to the procedure described in Intermediate 116, Step B. The title compound was obtained (86%) as brown solid. $^1$H NMR (CDCl$_3$): 2.64 (m, 4H), 2.97 (m, 4H), 3.96 (s, 2H), 7.39 (m, 1H), 7.47 (m, 1H), 7.89 (d, J 7.9 Hz, 1H), 7.99 (d, J 8.1 Hz, 1H).

Intermediate 123

3-(1-piperazinylmethyl)-indazole (i-123)

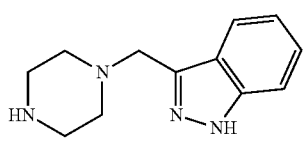

Step A: tert-Butyl 3-methyl-1H-indazole-1-carboxylate

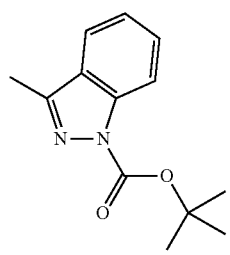 [SMILES: Cc1nn(C(=O)OC(C)(C)C)c2ccccc12]

To a solution of 3-methylindazole (5 g, 37.8 mmol), Et3N (7.9 ml, 56.7 mmol), and DMAP (4.62 g, 37.8 mmol) in acetonitrile (100 ml) was added BOC-anhydride (9.1 g, 41.6 mmol) and the resulting mixture stirred at RT overnight. The mixture partitioned between water and EtOAc, organic layer washed with 1N HCl, sat. NaCl, dried over MgSO4, filtered and evaporated. The residue was purified by MPLC (Biotage Horizon: FLASH 40+M) eluent: 100% Hexanes (190 ml), gradient rising from 100% Hexanes to 25% EtOAc in Hexanes (900 ml), then 25% EtOAc in Hexanes (500 ml) to afford the title compound 7.5 g (85%) as a white solid. $^1$H NMR (CDCl$_3$): 1.75 (s, 9H), 2.62 (s, 3H), 7.32 (m, 1H), 7.53 (m, 1H), 7.66 (d, J 7.9 Hz, 1H), 8.12 (d, J 8.3 Hz, 1H).

Step B: tert-Butyl 3-(bromomethyl)-1H-indazole-1-carboxylate

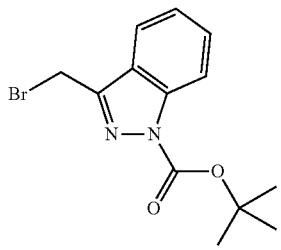 [SMILES: CC(C)(C)OC(=O)n1nc(CBr)c2ccccc21]

To a mixture of compound from step A (2 g, 8.61 mmol) and N-bromosuccinamide (1.84 g, 10.33 mmol) in carbon tetrachloride (50 ml) was added benzoyl peroxide (209 mg, 0.86 mmol) and the resulting mixture heated at reflux for 4 h. The reaction mixture cooled and filtered through celite, and filtrate evaporated. The residue purified by MPLC (Biotage Horizon: FLASH 40+s) eluent: 100% Hexanes (190 ml), gradient rising from 100% hexanes to 10% EtOAc in Hexanes (1000 ml), then 10% EtOAc in Hexanes (250 ml) to afford the title compound 2.04 g (76%). $^1$H NMR (CDCl$_3$): 1.75 (s, 9H), 4.82 (s, 2H), 7.39 (m, 1H), 7.58 (m, 1H), 7.87 (d, J 8.0 Hz, 1H), 8.15 (d, J 8.5 Hz, 1H).

Step C: tert-Butyl 3-{4-(-butoxycarbonyl)piperazin-1-yl]methyl}-1H-indazole-1-carboxylate

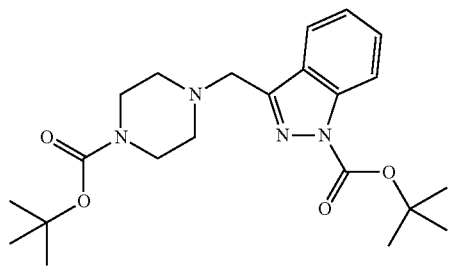 [SMILES: CC(C)(C)OC(=O)N1CCN(Cc2nn(C(=O)OC(C)(C)C)c3ccccc23)CC1]

Prepared according to the procedure described in Intermediate 121, Step A; replacing 2-chloromethylbenzoxazole with the title compound from step B above. The title compound was obtained (84%). $^1$H NMR (CDCl$_3$): 1.45 (s, 9H), 1.73 (s, 9H), 2.50 (m, 4H), 3.44 (m, 4H), 3.95 (s, 2H), 7.30 (m, 1H), 7.52 (m, 1H), 8.01 (d, J 8.0 Hz, 1H), 8.09 (d, J 8.5 Hz, 1H).

Step D: 3-(1-piperazinylmethyl)-indazole (i-123)

Prepared from the product from Step C according to the procedure described in Intermediate 116, Step B, (85%)

white solid. $^1$H NMR (CDCl$_3$): 2.56 (m, 4H), 2.94 (m, 4H), 3.95 (s, 2H), 7.15 (m, 1H), 7.36 (m, 1H), 7.43 (d, J 8.3 Hz, 1H), 7.90 (d, J 8.2 Hz, 1H).

Intermediate 124

(1-Quinazolin-2-ylethyl)piperazine (i-124)

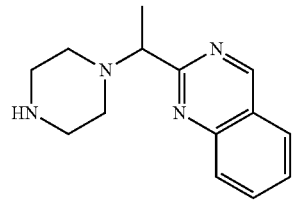

Step A: N-(2-Formylphenyl)-propionamide

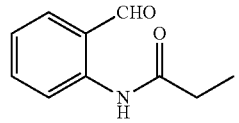

To a solution of 2-aminobenzaldehyde (1 g, 8.26 mmol) and Et3N (1.15 ml, 8.26 mmol) in DCM (50 ml) was added propionyl chloride (0.72 ml, 8.26 mmol) and the resulting mixture stirred at RT for 3 days. The mixture washed with water, sat. NaCl, dried over MgSO4, filtered and evaporated to afford the title compound 1.4 g (96%). $^1$H NMR (CDCl$_3$): 1.30 (t, J 7.6 Hz, 3H), 2.51 (q, J 7.6 Hz, 2H), 7.23 (m, 1H), 7.62 (m, 1H), 7.69 (m, 1H), 8.78 (m, 1H), 9.94 (s, 1H), 11.19 (brs, 1H).

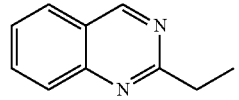

Step B: 2-Ethylquinazoline

A mixture of the title compound from Step A (1.4 g, 7.9 mmol) and 2M ammonia in methanol (40 ml, 80 mmol) was heated at 80° C. in a flask stoppered with a septa and vented with a 21 gauge needle, overnight. The mixture was cooled and evaporated to afford the title compound 1.39 g (100%).

¹H NMR (CDCl₃): 1.50 (t, J 7.6 Hz, 3H), 3.19 (q, J 7.6 Hz, 2H), 7.60 (d, J 7.4 Hz, 1H), 7.90 (m, 2H), 7.99 (d, J 8.5 Hz, 1H), 9.37 (d, J 8.5 Hz, 1H).

Step C: 2-(1-Bromomethyl)quinazoline

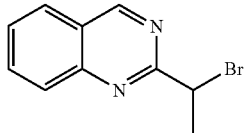

To a solution of the title compound from Step B (1.39 g 8.79 mmol) in chloroform (50 ml) was added NBS (1.56 g, 8.79 mmol) and benzoyl peroxide (213 mg, 0.88 mmol) and the resulting mixture heated at reflux for 5 h. The mixture cooled and evaporated, the residue purified by MPLC (Biotage Horizon: FLASH 25+M) eluent: 100% Hexanes (90 ml), gradient rising from 100% Hexanes to 10% EtOAc in Hexanes (1200 ml) to afford the title compound 240 mg (11.5%) as a red oil. ¹H NMR (CDCl₃): 2.25 (d, J 6.9 Hz, 3H), 5.51 (q, J 6.9 Hz, 1H), 7.64 (m, 1H), 7.71 (m, 1H), 7.97 (m, 1H), 8.08 (d, J 8.6 Hz, 1H), 9.49 (s, 1H).

Step D: tert-Butyl 4-(1-quinazolin-2-ylethyl)piperazine-1-carboxylate

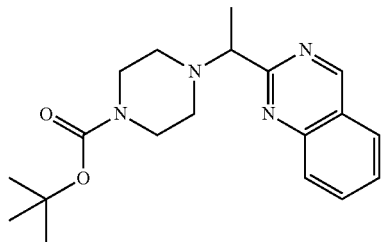 [SMILES: CC(c1ncc2ccccc2n1)N1CCN(C(=O)OC(C)(C)C)CC1]

To a mixture of the title compound from Step C (240 mg, 1.01 mmol) and N—BOC-piperazine (189 mg, 1.01 mmol), in acetonitrile (5 ml) was added K2CO3 (210 mg, 1.52 mmol) and sodium iodide (152 mg, 1.01 mmol) and the resulting mixture heated at reflux overnight. The mixture cooled and partitioned between water and EtOAc; organic layer washed with sat. NaCl, dried over MgSO4, filtered and evaporated. The residue purified by column chromatography (eluent: 5% MeOH in DCM) to afford the title compound 145 mg (42%) as an orange oil, which solidified on standing. ¹H NMR (CDCl₃): 1.45 (s, 9H), 1.60 (d, J 6.8 Hz, 3H), 2.46 (m, 2H), 2.69 (m, 2H), 3.49 (m, 4H), 3.97 (q, J 6.8 Hz, 1H), 7.66 (m, 1H), 7.93 (m, 2H), 8.06 (d, J 8.3 Hz, 1H), 9.44 (s, 1H).

Step E: (1-Quinazolin-2-ylethyl)piperazine (i-124)

Prepared from the title compound from Step D according to the procedure described in Intermediate 119, Step B. The title compound was obtained (99%) as brown oil. ¹H NMR (CDCl₃): 1.54 (d, J 6.6 Hz, 3H), 2.47 (m, 2H), 2.69 (m, 2H), 2.93 (m, 4H), 3.91 (q, J 6.6 Hz, 1H), 7.62 (m, 1H), 7.89 (m, 2H), 8.02 (d, J 7.8 Hz, 1H), 9.41 (d, J 6.9 Hz, 1H).

Intermediate 125

3-{[(2S)-2-methylpiperazin-1-yl]methyl}-1H-indazole (i-125)

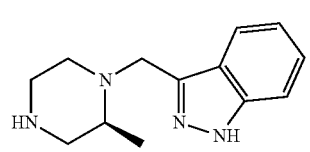

Step A: tert-Butyl 3{[(2S)-4-(-butoxycarbonyl)-2-methylpiperazin-1-yl]methyl}-1H-indazole-1-carboxylate

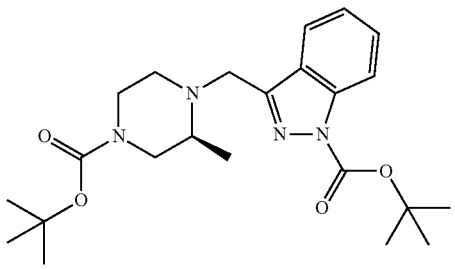 [SMILES: C[C@H]1CN(C(=O)OC(C)(C)C)CCN1Cc1nn(C(=O)OC(C)(C)C)c2ccccc12]

Prepared according to the procedure described in Intermediate 119, Step A, replacing 2-(bromomethyl)pyridine hydrobromide with the title compound of Step B in Intermediate 123. The title compound was obtained (58%) as light brown oil. ¹H NMR (CDCl₃): 1.24 (d, J 6.0 Hz, 3H), 1.47 (s, 9H), 1.75 (s, 9H), 2.26 (m, 1H), 2.55 (m, 1H), 2.71 (m, 1H), 2.92 (br m, 1H), 3.08 (m, 1H), 3.65 (d, J 13.0 Hz, 1H), 3.75 (d, J 13.3 Hz, 1H), 3.81 (br m, 1H), 4.33 (d, J 13.8 Hz, 1H), 7.32 (m, 1H), 7.54 (m, 1H), 8.04 (d, J 8.0 Hz, 1H), 8.10 (d, J 8.4 Hz, 1H).

Step B: 3-{[(2S)-2-methylpiperazin-1-yl]methyl}-1H-indazole (i-125)

Prepared from the title compound from Step A according to the procedure described in Intermediate 119, Step B. The title compound was obtained (80%). ¹H NMR (CDCl₃): 1.27 (d, J 6.2 Hz, 3H), 2.29 (m, 1H), 2.48 (m, 1H), 2.64 (dd, J 12.2 and 9.7 Hz, 1H), 2.79-2.92 (m, 2H), 2.96 (dd, J 12.3 and 2.8 Hz, 1H), 3.79 (d, J 13.8 Hz, 1H), 4.35 (d, J 13.8 Hz, 1H), 7.15 (m, 1H), 7.37 (m, 1H), 7.45 (d, J 8.5 Hz, 1H), 7.88 (d, J 8.1 Hz, 1H).

Intermediate 126

(2S)-1-(1,3-benzoxazol-2-ylmethyl)-2-methylpiperazine (i-126)

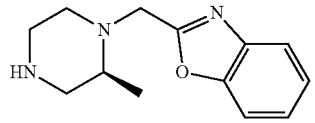

Step A: tert Butyl-(3S)-4-(1,3-benzoxazol-2-ylmethyl)-3-methylpiperazine-1-carboxylate

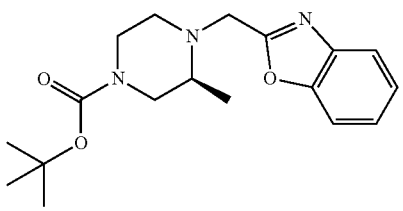 [SMILES: C[C@H]1CN(C(=O)OC(C)(C)C)CCN1Cc1nc2ccccc2o1]

Prepared according to the procedure described in Intermediate 119, Step A, replacing 2-(bromomethyl)pyridine hydrobromide with 2-chloromethylbenzoxazole. The title compound was obtained (31%) as light brown solid. ¹H NMR (CDCl₃): 1.24 (d, J 6.2 Hz, 3H), 1.46 (s, 9H), 2.55 (m, 2H), 2.79 (br m, 1H), 2.95 (m, 1H), 3.11 (m, 1H), 3.96 (m, 2H), 4.03 (d, J 15.1 Hz, 1H), 4.10 (d, J 15.1 Hz, 1H), 7.35 (m, 2H), 7.55 (m, 1H), 7.73 (m, 1H).

Step B: (2S)-1-(1,3-benzoxazol-2-ylmethyl)-2-methylpiperazine (i-126)

Prepared from the title compound from Step A according to the procedure described in Intermediate 119, Step B. The title compound was obtained (83%). ¹H NMR (CDCl₃): 1.22 (d, J 6.2 Hz, 3H), 2.47-2.63 (m, 3H), 2.89-2.97 (m, 4H), 4.03 (d, J 15.0 Hz, 1H), 4.10 (d, J 15.0 Hz, 1H), 7.35 (m, 2H), 7.55 (m, 1H), 7.73 (m, 1H).

Intermediate 127

2-(piperazin-1-ylmethyl)pyridazin-3(2H)-one (i-127)

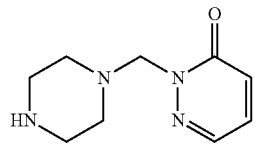

Step A: tert Butyl-4-[(6-oxopyridazin-1(6H)-yl)methyl]piperazine-1-carboxylate

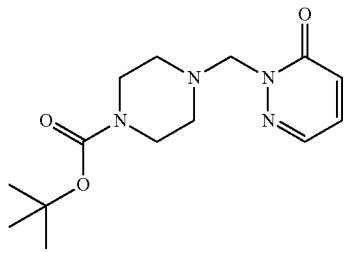 [SMILES: CC(C)(C)OC(=O)N1CCN(Cn2ncccc2=O)CC1]

To a solution of 1-N—BOC-4-bromomethylpiperidine (500 mg, 1.8 mmol) in anhydrous DMF (10 ml) was added 2(3H)pyridazinone (173 mg, 1.8 mmol) and K2CO3 (248 mg, 1.8 mmol) and the resulting mixture stirred at 45° C. for 3 days. The mixture was cooled and partitioned between EtOAc and water; aqueous extracted with further EtOAc (×2). Combined EtOAc layers were washed with sat. NaCl, dried over MgSO4, filtered and evaporated to give 555 mg (quant) of the title compound. ¹H NMR (CDCl₃): 1.22 (m, 2H), 1.42 (s, 9H), 1.58 (m, 2H), 2.10 (m, 1H), 2.65 (m, 2H), 4.05 (m, 4H), 6.90 (dd, J 9.4 and 1.6 Hz, 1H), 7.15 (dd, J 9.4 and 3.8 Hz, 1H), 7.72 (dd, J 3.8 and 1.6 Hz, 1H).

Step B: 2-(piperazin-1-ylmethyl)pyridazin-3(2H)-one (i-127)

Prepared from the title compound from Step A according to the procedure described in Intermediate 119, Step B. The title compound was obtained (90%) as white solid. ¹H NMR (CDCl₃): 1.26 (m, 2H), 1.60 (d, 12.6 Hz, 2H), 2.07 (m, 1H), 2.23 (br s, 1H), 2.56 (m, 2H), 3.06 (d, J 12.3 Hz, 2H), 4.03 (d, J 7.2 Hz, 2H), 6.90 (d, J 9.4 Hz, 1H), 7.15 (dd, J 9.4 and 3.8 Hz, 1H), 7.73 (d, J 3.8 Hz, 1H).

Intermediate 128

8-(1H-tetrazol-1-yl)-3-azabicyclo[3.2.1]octane (i-128)

Step A: 3-Benzyl-3-azabicyclo[3.2.1]octan-8-one

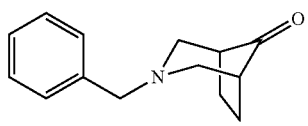 [SMILES: O=C1C2CCC1CN(Cc1ccccc1)C2]

To a solution of benzylamine (21.85 ml, 200 mmol) in tert-butanol (48 ml) was added paraformaldehyde (12 g, 400 mmol), conc. HCl (18 ml, 220 mmol) and cyclopentanone (46 ml, 520 mmol) and the resulting mixture heated at 800° C. for 3 h. The mixture was cooled and diluted with water (200 ml) and extracted with EtOAc (3×200 ml); combined organic layers discarded and remaining aqueous layer evaporated. The residue dissolved in acetic acid (200 ml) and added over 1 h to a mixture of paraformaldehyde (12 g, 400 mmol) and conc. HCl (16.4 ml, 200 mmol) in acetic acid (200 ml) heated at 95° C. After complete addition mixture continued heating at 95° C. for 1 h then cooled to RT and evaporated. The residue was partitioned between EtOAc and sat. NaHCO$_3$, the organic layer washed with sat. NaCl, dried over MgSO$_4$, filtered and evaporated. The residue was purified by MPLC (Biotage Horizon: FLASH 65i) eluent: 100% Hexanes (450 ml), gradient rising from 100% Hexanes to 25% EtOAc in Hexanes (1500 ml), then 25% EtOAc in Hexanes (1000 ml), to afford the title compound 19 g (44%) as a clear oil. $^1$H NMR (CDCl$_3$): 1.88 (m, 2H), 2.07 (m, 2H), 2.18 (s, 2H), 2.56 (d, J 10.0 Hz, 2H), 2.99 (m, 2H), 3.61 (d, J 2.0 Hz, 2H), 7.29 (m, 1H), 7.35 (m, 4H).

Step B: 3-Benzyl-3-azabicyclo[3.2.1]octan-8-one oxime

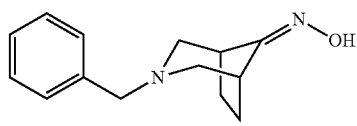 [SMILES: ON=C1C2CCC1CN(Cc1ccccc1)C2]

To a solution of the title compound of Step A (6.6 g, 30.7 mmol) in ethanol (80 ml) was added hydroxylamine (3.6 ml of a 50% Wt solution in water, 42.9 mmol) and the resulting mixture heated at reflux for 4 h. The cooled reaction mixture was evaporated and the residue triturated with hexanes, filtered and dried to afford the title compound 4.8 g (68%) as a white solid. $^1$H NMR (CDCl$_3$): 1.76 (m, 2H), 1.97 (m, 2H), 2.40 (d, J 10.1 Hz, 2H), 2.56 (s, 1H), 2.84 (dd, J 10.3 and 3.7 Hz, 1H), 2.91 (dd, J 10.1 and 3.0 Hz, 1H), 3.35 (s, 1H), 3.57 (s, 2H), 7.29 (m, 1H), 7.35 (m, 4H), 8.49 (s, 1H).

Step C: 3-Benzyl-3-azabicyclo[3.2.1]octan-8-exo-amine and 3-Benzyl-3-azabicyclo[3.2.1]octan-8-endo-amine

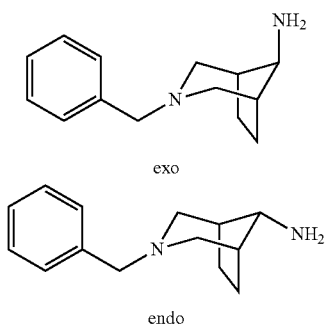

To a solution of the title compound from Step B (4.8 g, 20.8=01) in n-pentanol (150 ml) heated at reflux under a stream of nitrogen was added in multiple small portions sodium (5.27 g, 229 mmol). After all the sodium had dissolved the reaction was heated at reflux for a further 30 min then cooled to RT. The mixture was washed with water (2×100 ml) then extracted with 2N HCl (3×50 ml). The combined HCl extracts were treated under cooling with solid KOH until the mixture was alkaline. The mixture was extracted with DCM (3×100 ml) and combined DCM layers dried over MgSO$_4$, filtered and evaporated. The residue was purified by column chromatography on silica (eluent: gradient rising from 2% MeOH in DCM to 4% MeOH in DCM) to give first eluting exo isomer 2.7 g (60%) and second eluting endo isomer 650 mg (14%). $^1$H NMR (CDCl$_3$): 1.18 (br s, 2H), 1.73-1.86 (m, 4H), 1.93 (s, 2H), 2.12 (d, J 10.5 Hz, 2H), 2.68 (dd, J 10.8 and 3.7 Hz, 2H), 2.85 (s, 1H), 3.48 (s, 2H), 7.22 (m, 1H), 7.31 (m, 4H).

Step D: 3-Benzyl-8-(1H-tetrazol-1-yl)-3-azabicyclo[3.2.1]octane

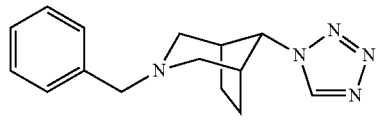 [SMILES: c1ccc(CN2CC3CCC(C2)C3n2cnnn2)cc1]

A mixture of the title compound from Step C (endo, 650 mg, 3.0 mmol), sodium azide (1.17 g, 18 mmol) and triethylorthoformate (3.0 ml, 18 mmol) in acetic acid (12 ml) was heated at 90° C. for 14 h. The cooled mixture was evaporated and the residue partitioned between EtOAc and sat. NaHCO$_3$. The organic layer was washed with sat. NaCl, dried over MgSO$_4$, filtered and evaporated. The residue was purified by reverse phase PREP-HPLC (C18 column—eluent: gradient rising from 10% CH$_3$CN in water to 90% CH$_3$CN in water) to give the title compound 790 mg (98%). $^1$H NMR (CDCl$_3$): 1.64 (m, 2H), 1.99 (d, J 8.0 Hz, 2H), 2.40 (d, J 11.0 Hz, 2H), 2.87 (m, 2H), 2.92 (dd, J 11.4 and 4.1 Hz, 2H), 3.60 (s, 2H), 4.42 (s, 1H), 7.30 (m, 5H), 8.59 (s, 1H).

Step E: 8-(1H-tetrazol-1-yl)-3-azabicyclo[3.2.1]octane (i-128)

To a nitrogen flushed solution of the title compound from Step D (790 mg, 2.93 mmol) in methanol (10 ml) was added 10% Palladium on carbon (75 mg) and the resulting mixture stirred under a balloon of hydrogen for 2 h. The mixture was filtered through Celite® and the filtrate evaporated to give the title compound 480 mg (91%) as a clear oil. $^1$H NMR (CDCl$_3$): 1.80 (m, 4H), 2.82 (m, 2H), 2.95 (dd, J 13.1 and 2.7 Hz, 2H), 3.03 (d, J 12.7 Hz, 2H), 4.55 (s, 1H), 8.62 (s, 1H).

Intermediate 129 tert-butyl 4-(2-methoxy-1-methyl-2-oxoethyl))piperazine-1-carboxylate

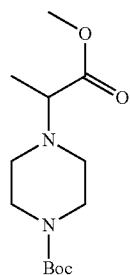
(i-129)

Step A: tert-butyl 4-(2-methoxy-1-methyl-2-oxoethyl))piperazine-1-carboxylate

To a stirred solution of 4.9 g (27 mmol) of methyl bromopropanoate and 5 g (27 mmol) tert-butyl 1-piperazinecarboxylate in 100 mL anhydrous acetonitrile under an atmosphere of nitrogen was added 19 g (134 mmol) of potassium carbonate. The resulting reaction mixture was refluxed overnight. After cooling to ambient temperature, the reaction mixture was concentrated. The residue was diluted with 100 mL of saturated aqueous sodium bicarbonate and the solution extracted with ethyl acetate (3×100 mL). The combined organic layers were dried with magnesium sulfate, filtered, and concentrated in vacuo. The mixture was purified by MPLC (Biotage Horizone: Flash 65i) eluent: (EtOAC/hexanes=1/5 to 100%) to give 5.8 g (21.5 mmol) of the title compound as an oil.

Intermediate 130

4-(2-(3,3-Difluoropyrrolidin-1-yl)-1-methyl-2-oxoethyl)piperazine, TFA salt (i-130)

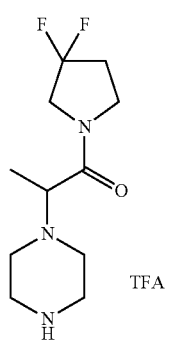
(i-130)

Step A:
2-[4-(tert-Butoxycarbonyl)piperazin-1-yl]propanoic acid

To a stirred solution of 5.0 g (18 mmol) of tert-butyl 4-(2-methoxy-1methyl-2-oxoethyl))piperazine-1-carboxylate from Intermediate 129, Step A, in 120 mL tetrahydrofuran, 40 ml water and 40 ml methanol was added 0.88 g (37 mmol) of lithium hydroxide. The resulting reaction mixture was stirred at ambient temperature overnight. The solvent was evaporated in vacuo and diluted with 50 ml water. The solution pH was adjusted to 4 using concentrated HCl solution. The reaction mixture was extracted with solvents (chloroform/isopropanol=3:1), dried over magnesium sulfate, filtered and evaporated in vacuo to afford 3.8 g of the title compound without further purification. LC/MS: (M+1): 259.2

Step B: tert-Butyl 4-{2-[(3,3-difluoropyrrolidin-1-yl)-1-methyl-2-oxoethyl}piperazine-1-carboxylate To a stirred solution of 100 mg (0.39 mmol) of the title compound from Step B and 56 mg (0.39 mmol) 3,3-difluoropyrrolidine in 1 mL anhydrous N,N-dimethylformamide under an atmosphere of nitrogen was added 250 mg (1.9 mmol) of N,N-diisopropylethylamine and 294 mg (0.77 mmol) of 2-(1H-7-azabezotriazole-1-yl)-1,1,3,3,-tetramethyl uranium hexafluoro phosphate methanium. The resulting reaction mixture was stirred at ambient temperature for 6 h. The reaction was purified by reverse-phase HPLC (TMC Pro-Pac C18; 10-100% 0.1% trifluoroacetic acid in acetonitrile/0.1% trifluoroacetic acid in water gradient) to give 78 mg (45% yield) of the title compound. LC/MS: (M+1)=348.1.

Step C: 4-(2-(3,3-Difluoropyrrolidin-1-yl)-1-methyl-2-oxoethyl)piperazine, TFA (i-130)

A solution of 78 mg (0.18 mmol) of the title compound from Step B above in 1 mL dichloromethane and 1 mL trifluoroacetic acid was stirred at ambient temperature for 1 h. All volatiles were removed in vacuo and the title compound was obtained as light brown residue.

Intermediates 131 and 132

(3R)-1-Phenyl-3-piperazin-1-ylpyrrolidin-2-one, bis(hydrochloride) salt (i-131) and (3S)-1-phenyl-3-piperazin-1-ylpyrrolidin-2-one, bis(hydrochloride) salt (i-132)

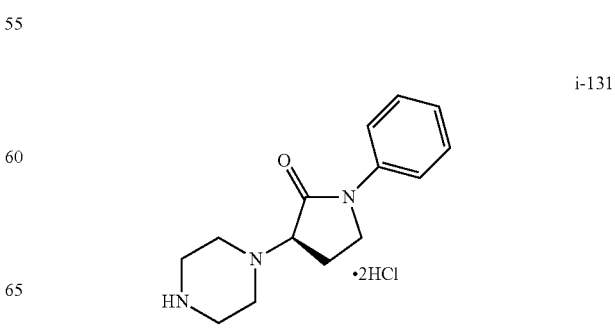
i-131

-continued

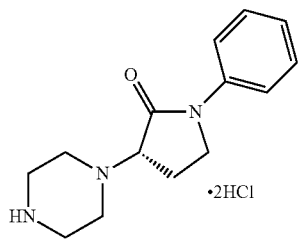

i-132

Step A; Tert-butyl 4-[(3R)-2-oxo-1-phenylpyrrolidin-3-yl]piperazine-1-carboxylate and tert-butyl 4-[(3S)-2-oxo-1-phenylpyrrolidin-3-yl]piperazine-1-carboxylate

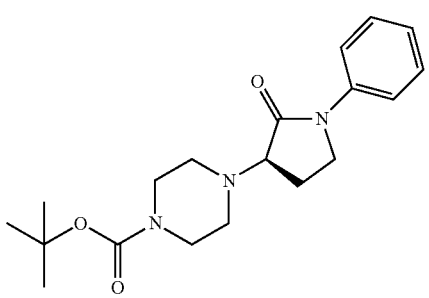

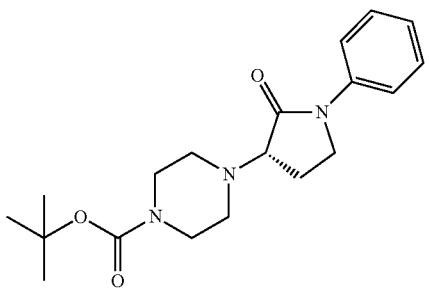

To a stirred solution of 0.15 g (0.81 mmol) of tert-butyl piperazine-1-carboxylate in 2 mL of anhydrous N,N-dimethylformamide was added 0.17 g (1.2 mmol) of potassium carbonate followed by 0.19 g (0.81 mmol) of 3-bromo-1-phenylpyrrolidin-2-one. The resulting heterogeneous mixture was stirred at ambient temperature of 3 h, quenched with water then extracted with ethyl acetate. The combined organic layers were washed with water then brine, dried over magnesium sulfate and evaporated to dryness in vacuo. The residue was purified by silica gel chromatography eluting with 50% acetone in hexanes to afford a racemic mixture of the title compounds as clear gum.

The two enantiomers were separated by chiral HPLC employing a Daicel PREP CHIRALCEL® OD® column (eluent: 40% isopropanol in heptane). The first eluting enantiomer was designated as Isomer 1 and is a colorless foam (0.042 g, 15%): LC-MS: m/z (ES) 346.0 (MH)⁺. The second eluting enantiomer was designated as Isomer 2 and is a colorless foam (0.042 g, 15%): LC-MS: m/z (ES) 346.0 (MH)⁺.

Step B: (3R)-1-Phenyl-3-piperazin-1-ylpyrrolidin-2-one, bis(hydro chloride) salt (i-131) and (3S)-1-phenyl-3-piperazin-1-ylpyrrolidin-2-one, bis(hydrochloride) salt (i-132)

To a stirred solution of 0.042 g (0.12 mmol) of Isomer 1 from Step A above in 1 mL of methanol was added 0.50 mL (2.0 mmol) of a 4.0 M hydrogen chloride solution in 1,4-dioxane and the resulting mixture was stirred for 1 h. All volatiles were then removed in vacuo and the residue dried under high vacuum overnight to afford either (3R)-1-phenyl-3-piperazin-1-ylpyrrolidin-2-one, bis(hydrochloride) salt or (3S)-1-phenyl-3-piperazin-1-ylpyrrolidin-2-one, bis(hydrochloride) salt as a yellow solid (0.036 g, 93% yield). LC-MS: m/z (ES) 246.1 (MH)⁺.

The same procedure was also repeated for Isomer 2 from Step A above to afford either (3R)-1-phenyl-3-piperazin-1-ylpyrrolidin-2-one, bis(hydrochloride) salt or (3S)-1-phenyl-3-piperazin-1-ylpyrrolidin-2-one, bis(hydrochloride) salt as a yellow solid (0.036 g, 93% yield). LC-MS: m/z (ES) 246.1 (MH)⁺.

Intermediates 133 and 134

(3R)-1-cyclopropyl-3-piperazin-1-ylpyrrolidin-2-one, bis(trifluoroacetic acid) salt (i-133) and (3S)-1-cyclopropyl-3-piperazin-1-ylpyrrolidin-2-one, bis(trifluoroacetic acid) salt (i-134)

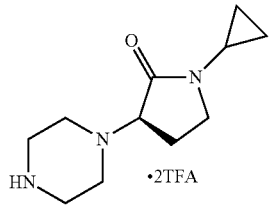

i-133

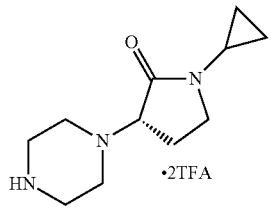

i-134

Step A: Tert-butyl 4-[(3R)-1-cyclopropyl-2-oxopyr-rolidin-3-yl]piperazine-1-carboxylate and tert-butyl 4[(3S)-1-cyclopropyl-2-oxopyrrolidin-3-yl]pipera-zine-1-carboxylate

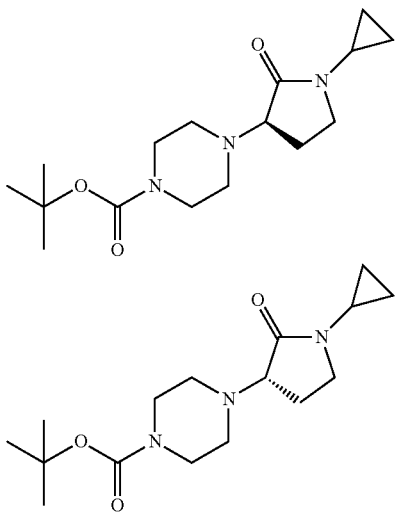

To a stirred solution of 0.42 mL (6.0 mmol) of cyclopropanamine in 15 mL of anhydrous dichloromethane cooled to 0° C. under an atmosphere of nitrogen was added 0.93 mL (6.7 mmol) of triethylamine followed by a solution of 0.80 mL (6.0 mmol) of 2,4-dibromobutanoyl chloride in 5 mL of anhydrous dichloromethane. The resulting mixture was stirred with gradual warming to ambient temperature over 1 h, then quenched with water. The layers were separated and the aqueous phase was extracted with dichloromethane. The combined organic layers were washed with water then brine, dried over magnesium sulfate and evaporated to dryness in vacuo. The residue was dissolved in 15 mL of anhydrous tetrahydrofuran and cooled to 0° C. under an atmosphere of nitrogen. Next, 0.49 g (12 mmol) of a 60% dispersion of sodium hydride in mineral oil was carefully added in 3 portions over 3 minutes. The resulting heterogeneous mixture was allowed to stir with gradual warming to ambient temperature over 2 h, then carefully quenched with water and extracted with ethyl acetate. The combined organic layers were washed with water then brine, dried over magnesium sulfate and evaporated to dryness in vacuo. The residue was then dissolved in 15 mL of anhydrous N,N-dimethylformamide and 1.1 g (6.0 mmol) of tert-butyl piperazine-1-carboxylate and 1.3 g (9.0 mmol) of potassium carbonate were added successively. The resulting heterogeneous mixture was stirred at ambient temperature for 12 h, quenched with water then extracted with ethyl acetate. The combined organic layers were washed with water then brine, dried over magnesium sulfate and evaporated to dryness in vacuo. The residue was purified by silica gel chromatography eluting with 50% acetone in hexanes to afford a racemic mixture of the title compounds as clear gum. The two enantiomers were separated by chiral HPLC employing a Daicel PREP CHIRAL-Pak® AD® column (eluent: 15% isopropanol in heptane). The first eluting enantiomer was designated as Isomer 1 and is a colorless foam (0.30 g, 17%): LC-MS: m/z (ES) 310.1 (MH)+.

The second eluting enantiomer was designated as Isomer 2 and is a colorless foam (0.30 g, 17%): LC-MS: m/z (ES) 310.1 (MH)+.

Step B: (3R)-1-cyclopropyl-3-piperazin-1-ylpyrroli-din-2-one, bis(trifluoroacetic acid) salt (i-133) and (3S)-1-cyclopropyl-3-piperazin-1-ylpyrrolidin-2-one, bis(trifluoroacetic acid) salt (i-134)

To a stirred solution of 0.30 g (0.97 mmol) of Isomer 1 from Step A above in 10 mL of dichloromethane was added 5 mL of trifluoroacetic acid and the resulting mixture was stirred for 1 h. All volatiles were removed in vacuo and the pale yellow residue was suspended in toluene. All volatiles were then removed in vacuo and this process was repeated two additional times. The pale yellow residue that was obtained was dried under high vacuum overnight to afford either (3R)-1-cyclopropyl-3-piperazin-1-ylpyrrolidin-2-one, bis(trifluoroacetic acid) salt or (3S)-1-cyclopropyl-3-piperazin-1-ylpyrrolidin-2-one, bis(trifluoroacetic acid) salt as a yellow gum (0.49 g, 95%). LC-MS: m/z (ES) 210.0 (MH)+.

The same procedure was also repeated for Isomer 2 from Step A above to afford either (3R)-1-cyclopropyl-3-piperazin-1-ylpyrrolidin-2-one, bis(trifluoroacetic acid) salt or (3S)-1-cyclopropyl-3-piperazin-1-ylpyrrolidin-2-one, bis(trifluoroacetic acid) salt as a yellow gum (0.49 g, 95%). LC-MS: m/z (ES) 210.0 (MH)+.

Biological Assays: The following in vitro assays are suitable for screening compounds that have selective β3 agonist activity:

Functional Assay: cAMP production in response to ligand is measured according to Barton, et al. (1991, Agonist-induced desensitization of D2 dopamine receptors in human Y-79 retinoblastoma cells. Mol. Pharmacol. v3229:650-658) modified as follows. cAMP production is measured using a homogenous time-resolved fluorescence resonance energy transfer immunoassay (LANCE™, Perkin Elmer) according to the manufacture's instructions. Chinese hamster ovary (CHO) cells, stably transfected with the cloned β-adrenergic receptor (β1, β2 or β3) are harvested after 3 days of subculturing. Harvesting of cells is done with Enzyme-free Dissociation Media (Specialty Media). Cells are then counted and resuspended in assay buffer (Hank's Balanced salt solution supplemented with 5 mM HEPES, 01% BSA) containing a phosphodiesterase inhibitor (IBMX, 0.6 mM). The reaction is initiated by mixing 6,000 cells in 6 μL with 6 μL Alexa Fluor labeled cAMP antibody (LANCE™ kit) which is then added to an assay well containing 12 μL of compound (diluted in assay buffer to 2× final concentration). The reaction proceeds for 30 minutes at RT and is terminated by the addition of 24 ul detection buffer (LANCE™ kit). The assay plate is then incubated for 1 h at RT and time-resolved fluorescence measured on a Perkin Elmer Envision reader or equivalent. The unknown cAMP level is determined by comparing fluorescence levels to a cAMP standard curve.

The non-selective, full agonist β-adrenergic ligand isoproterenol is used at all three receptors to determine maximal stimulation. The human β3 adrenergic receptor (AR) selective ligand (S)—N-[4-[2-[[2-hydroxy-3-(4-hydroxyphenoxy)propyl]amino]ethyl]-phenyl]-4-iodobenzenesulfonamide is used as a control in all assays. Isoproterenol is titrated at a final concentration in the assay of 10-10 M to 10-5 and the selective ligand (S)—N-[4-[2-[[2-hydroxy-3-(4-hydroxyphenoxy)propyl]amino]ethyl]phenyl]-4-iodobenzene-sulfonamide is titrated at the β3 receptor at concentration of 10-10 M to 10-5 M. Unknown ligands are titrated at all 3 β-adrenergic receptor subtypes at a final concentration in the assay of 10-10 M to 10-5 M to determine the $EC_{50}$. The $EC_{50}$ is defined as the concentration of compound that gives 50% activation of its own maximum. Data are analyzed using Microsoft Excel and Graphpad Prism or an internally developed data analysis software package.

Binding Assay Compounds are also assayed at the β1 and β2 receptors to determine selectivity. All binding assays are run using membranes prepared from CHO cells recombinantly expressing β1 or β2 receptors. Cells are grown for 3-4 days post splitting; the attached cells are washed with PBS and then lysed in 1 mM Tris, pH 7.2 for 10 minutes on ice. The flasks are scraped to remove the cells and the cells then homogenized using a Teflon/glass homogenizer. Membranes are collected by centrifuging at 38,000×g for 15 minutes at 4° C. The pelleted membranes are resuspended in TME buffer (50 mM Tris, pH 7.4, 5 mM $MgCl_2$, 2 mM EDTA) at a concentration of 1 mg protein/mL. Large batches of membranes can be prepared, aliquoted and stored at −70° C. for up to a year without loss of potency. The binding assay is performed by incubating together membranes (2-5 μg of protein), the radiolabelled tracer $^{125}$I-cyanopindolol ($^{125}$I-CYP, 45 pM), 200 ug of WGA-PVT SPA beads (GE Healthcare) and the test compounds at final concentrations ranging from 10-10 M to 10-5 M in a final volume of 200 μL of TME buffer containing 0.1% BSA. The assay plate is incubated for 1 h with shaking at RT and then placed in a Perkin Elmer Trilux scintillation counter. The plates are allowed to rest in the Trilux counter for approximately 10 h in the dark prior to counting. Data are analyzed using a standard 4-parameter non-linear regression analysis using either Graphpad Prism software or an internally developed data analysis package. The $IC_{50}$ is defined as the concentration of the title compound capable of inhibiting 50% of the binding of the radiolabelled tracer ($^{125}$I-CYP). A compound's selectivity for the β3 receptor may be determined by calculating the ratio ($IC_{50}$ β1 AR, β2 AR)/($EC_{50}$ β3 AR).

The following examples are provided to illustrate the invention and are not to be construed as limiting the scope of the invention in any manner.

Example 1

(R)-phenyl[(2R,5S)-5-(4-{[5-(1H-pyrazol-1-yl)hexahydrocyclopenta[c]pyrrol-2(1H)-yl]carbonyl}benzyl)pyrrolidin-2-yl]methanol (Ex. 1)

(Ex. 1)

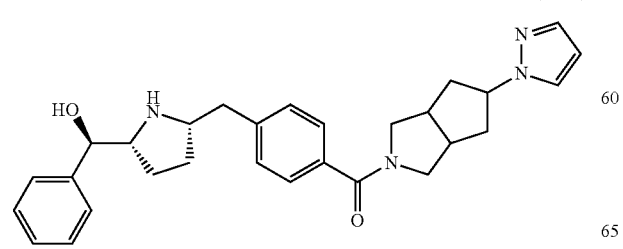

Step A: tert-butyl[pyrrol-5-(1H-pyrazol-1-yl)hexahydrocyclonenta]c-2(1H)-carboxylate

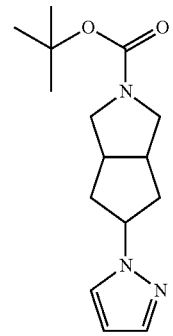

To a solution of the pyrazole (11 mg, 0.16 mmol) in DMF (0.5 ml) under nitrogen atmosphere was added sodium hydride (8 mg, 0.19 mmol) and the solution stirred for 5 minutes. After bubbling ceased, tert-butyl 5-[(methylsulfonyl)oxy]hexahydrocyclopenta[c]pyrrole-2(1H)-carboxylate (33 mg, 0.1 mmol) in 0.5 mL of DMF was added to the solution. The mixture was placed in a microwave reaction vessel and nitrogen was blown into it before closing.

Microwave: The reaction was set at 150° C. for 15 min on high absorption. After the reaction cooled, it was quenched with ammonium chloride solution and extracted with ethyl acetate. The organic layer was dried over sodium sulfate, filtered and concentrated to dryness. Purification of the residue was done on silica gel preparative plate (500 μM) eluting with 70% ethyl acetate in hexane to afford the product (15.2 mg, 49%). ESI-MS calculated for $C_{15}H_{23}N_3O_2$: Exact Mass: 277.16. Found: 278.17 $(MH)^+$ and 300.15 $(MNa)^+$.

Step B: 5-(1H-pyrazol-1-yl)octahydrocyclopenta[c]pyrrole

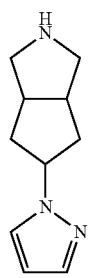 [SMILES: c1cnn(C2CC3CNCC3C2)c1]

The title compound from Step A above (15 mg, 0.08 mmol) was dissolved in 4 M HCl in dioxane plus 10% water (v/v) (1 mL) and stirred at RT for 2 h. The product was concentrated under reduced pressure and dried under high vacuum to give the title compound (12 mg, 92%). ESI-MS calculated for $C_{10}H_{15}N_3$: Exact Mass: 177.13. Found 178.13.

Step C: Tert-butyl (2R,5S)-2-[(R)-hydroxy(phenyl)methyl]-5-(4-{[5-(1H-pyrazol-1-yl)hexahydrocyclpenta[c]pyrrol-2(1H)-yl]carbonyl}benzyl)pyrrolidine-1-carboxylate

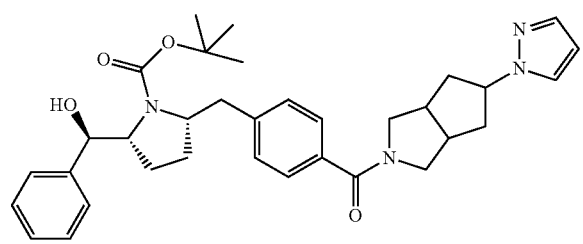 [SMILES: CC(C)(C)OC(=O)N1[C@H](Cc2ccc(C(=O)N3CC4CC(n5cccn5)CC4C3)cc2)CC[C@@H]1[C@H](O)c1ccccc1]

To a solution of 4-{((2S,5R)-1-(tert-butoxycarbonyl)-5-[(R)-hydroxy(phenyl)methyl]pyrrolidin-2-yl)methyl}benzoic acid (25 mg, 0.07 mmol) and the title compound from Step B above (12 mg, 0.07 mmol) in 1.0 mL anhydrous DMF was added a 0.5 M solution of HOAt in DMF (0.12 mL, 0.07 mmol) followed by EDC (23 mg, 0.14 mmol) and DIEA (9 µL, 0.07 mmol). The resulting mixture was stirred at RT under nitrogen atmosphere for 16 h. The mixture was washed with water and extracted with dichloromethane (2×5 mL). The organics were combined, dried over sodium sulfate, filtered and concentrated in vacuum. The residue was purified by preparative TLC plate (500 uM) eluting with 5% MeOH in dichloromethane to afford the title compound (16 mg, 42%). ESI-MS calculated for $C_{34}H_{42}N_4O_4$: Exact Mass: 570.35. Found 571.38 (MH)$^+$ and 594.33 (MNa)$^+$.

Step D: (R)-phenyl[(2R,5S)-5-(4-{[5-(1H-pyrazol-1-yl)hexahydrocyclopenta[c]pyrrol-2(1H)-yl]carbonyl}benzyl)pyrrolidin-2-yl]methanol (Ex. 1)

The title compound from Step C above (16 mg, 0.04 mmol) was dissolved in 4 M HCl in dioxane plus 10% water (v/v) (1 mL) and stirred at RT for 1 h. The product was concentrated under reduced pressure and dried under high vacuum to give the title compound. ESI-MS calculated for both is $C_{29}H_{34}N_4O_2$: Exact Mass: 470.27. Found 471.26 (MH)$^+$.

Using the Biological Assays as described above, the human β3 functional activity was determined to be between 10 to 99.9 nM.

Examples 2-63

Ex. 2-Ex. 63

Using procedures similar to those described above in Example 1, Examples 2-63 were prepared from the appropriate starting materials.

Using the Beta-3 agonist in vitro functional assay described above the human Beta-3 agonist functional activity of each compound was determined and shown in Table 4 as the following ranges:

TABLE 4

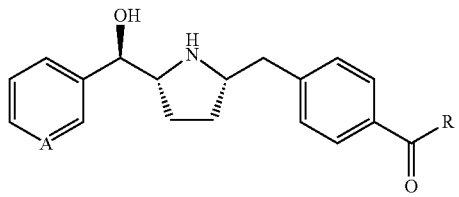

| Example (Ex.) # | A | R | MW | MS (MH)$^+$ | Human β3 agonist functional activity |
|---|---|---|---|---|---|
| 2 | CH | 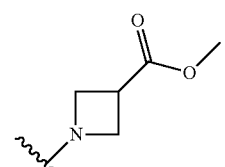 | 408.5 | 409.1 | ++++ |
| 3 | CH | 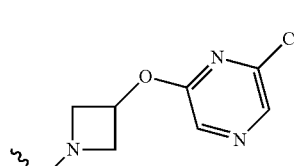 | 479.0 | 479.3 | ++++ |

TABLE 4-continued

| Example (Ex.) # | A | R | MW | MS (MH)+ | Human β3 agonist functional activity |
|---|---|---|---|---|---|
| 4 | CH | azetidine-3-carbonitrile, 3-fluoro | 411.5 | 412.3 | ++++ |
| 5 | CH | benzyl 2,6-diazaspiro[3.3]heptane-2-carboxylate | 525.6 | 526.4 | ++++ |
| 6 | CH | ethyl pyrrolidine-3-carboxylate | 436.6 | 437.3 | ++++ |
| 7 | CH | (3)-3-methoxypyrrolidine | 394.5 | 395.4 | ++++ |
| 8 | CH | (3)-3-methoxypyrrolidine | 394.5 | 395.4 | ++++ |
| 9 | CH | 3-(dimethylamino)pyrrolidine | 407.6 | 408.4 | ++++ |
| 10 | CH | 3-(1H-pyrazol-1-yl)pyrrolidine | 430.6 | 431.4 | ++++ |
| 11 | CH | 3-(3-methyl-1,2,4-oxadiazol-5-yl)pyrrolidine | 446.6 | 447.4 | ++++ |
| 12 | CH | 3-methyl-3-hydroxypyrrolidine | 394.5 | 395.4 | ++++ |

TABLE 4-continued
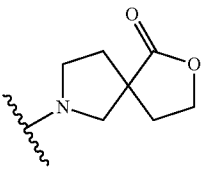 [SMILES: *N1CCC2(CCOC2=O)C1]
| Example (Ex.) # | A | R | MW | MS (MH)+ | Human β3 agonist functional activity |
|---|---|---|---|---|---|
| 13 | CH | 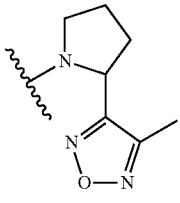 [SMILES: *N1CCCC1c1nonc1C] | 434.5 | 435.1 | +++ |
| 14 | CH | 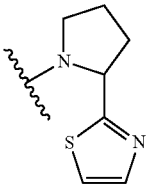 [SMILES: *N1CCCC1c1nccs1] | 446.5 | 447.3 | ++++ |
| 15 | CH | 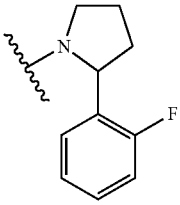 [SMILES: *N1CCCC1c1ccccc1F] | 447.6 | 448.3 | ++++ |
| 16 | N | 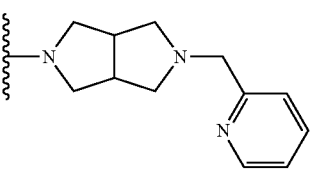 [SMILES: *N1CC2CN(Cc3ccccn3)CC2C1] | 459.6 | 460.3 | ++++ |
| 17 | CH | 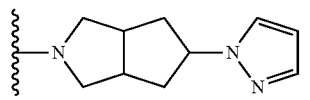 [SMILES: *N1CC2CC(n3cccn3)CC2C1] | 496.7 | 497.1 | ++++ |
| 18 | CH | 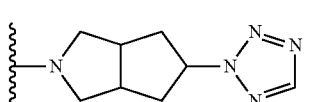 | 470.6 | 471.1 | ++ |
| 19 | CH | 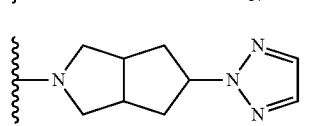 | 472.6 | 473.1 | +++ |
| 20 | CH | | 471.6 | 472.2 | +++ |

TABLE 4-continued

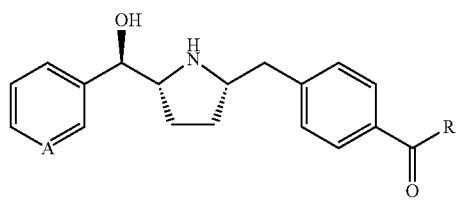

| Example (Ex.) # | A | R | MW | MS (MH)+ | Human β3 agonist functional activity |
|---|---|---|---|---|---|
| 21 | CH | (octahydropyrrolo[3,4-c]pyrrole-1,2,3-triazole) | 471.6 | 472.2 | +++ |
| 22 | CH | (octahydropyrrolo[3,4-c]pyrrole-1,2,4-triazole) | 471.6 | 472.2 | ++++ |
| 23 | CH | (octahydropyrrolo[3,4-c]pyrrole-tetrazole) | 472.6 | 473.2 | +++ |
| 24 | CH | (octahydropyrrolo[3,2-b]pyrrole) | 405.6 | 406.4 | ++++ |
| 25 | CH | (pyrrolo-pyrimidine) | 414.5 | 415.3 | ++++ |
| 26 | CH | (pyrrolo-furan) | 402.5 | 403.1 | +++ |
| 27 | CH | (pyrrolo-pyrazole) | 402.5 | 403 | +++ |
| 28 | CH | (N-methyl pyrrolo-pyrazole) | 416.5 | 417.1 | ++++ |
| 29 | CH | (N-ethylsulfonyl pyrrolo-pyrazole) | 494.6 | 495.1 | ++++ |

TABLE 4-continued
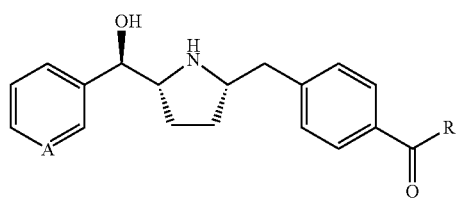
| Example (Ex.) # | A | R | MW | MS (MH)+ | Human β3 agonist functional activity |
|---|---|---|---|---|---|
| 30 | CH | *pyrrolo-pyrazole with N-CF3* | 470.5 | 471.2 | ++++ |
| 31 | CH | *piperidine-3-carboxylic acid ethyl ester* | 450.6 | 451.4 | +++ |
| 32 | CH | *piperidine-3-carboxylic acid benzyl ester* | 512.7 | 513.3 | +++ |
| 33 | CH | *3-(benzoxazol-2-yl)piperidine* | 495.6 | 496.4 | ++++ |
| 34 | CH | *3-(benzimidazol-2-yl)piperidine* | 494.6 | 495.2 | ++++ |
| 35 | CH | *3-(4-bromophenylsulfonyl)piperidine* | 597.6 | 596.9 598.8 | +++ |

TABLE 4-continued

| Example (Ex.) # | A | R | MW | MS (MH)+ | Human β3 agonist functional activity |
|---|---|---|---|---|---|
| 36 | CH | (piperidine with SO2Me and CO2Et) | 528.7 | 529.0 | +++ |
| 37 | CH | (piperidine with F and CO2Et) | 468.6 | 469.0 | ++++ |
| 38 | CH | (piperidine with SO2-thiazole-Br) | 604.6 | 603.9 605.8 | +++ |
| 39 | CH | (spiro piperidine lactam) | 461.6 | 462.4 | ++++ |
| 40 | CH | (spiro piperidine lactone) | 448.6 | 449.4 | +++ |
| 41 | CH | (spiro piperidine dimethyl lactone) | 476.6 | 477.4 | +++ |
| 42 | N | (spiro chromanone methoxy) | 541.7 | 542.2 | ++++ |

TABLE 4-continued
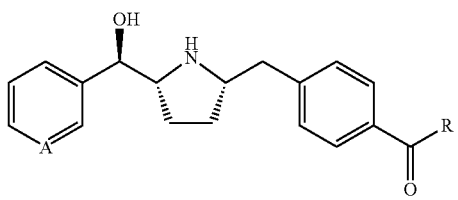
| Example (Ex.) # | A | R | MW | MS (MH)+ | Human β3 agonist functional activity |
|---|---|---|---|---|---|
| 43 | CH | (spiro piperidine chroman-4-one, 6-methoxy) | 540.7 | 541.1 | +++ |
| 44 | CH | (spiro piperidine chroman, 6-fluoro) | 514.6 | 515.1 | ++++ |
| 45 | CH | (spiro piperidine indolizinone) | 501.7 | 502.1 | ++++ |
| 46 | CH | (tetrahydropyridine-2H-triazole) | 443.6 | 444.6 | ++++ |
| 47 | CH | (tetrahydropyridine-1H-triazole) | 443.6 | 444.6 | ++++ |
| 48 | CH | (piperidine-2-carboxylic acid ethyl ester) | 450.6 | 451.3 | ++++ |

TABLE 4-continued

| Example (Ex.) # | A | R | MW | MS (MH)+ | Human β3 agonist functional activity |
|---|---|---|---|---|---|
| 49 | CH | (1-(3-methyl-1,2,4-oxadiazol-5-yl)piperidin-2-yl) | 460.6 | 461.4 | +++++ |
| 50 | CH | (1-(thiazol-2-yl)piperidin-2-yl) | 461.6 | 462.3 | ++++ |
| 51 | CH | (1-(1-methyl-1H-imidazol-2-yl)piperidin-2-yl) | 458.6 | 459.4 | ++++ |
| 52 | CH | (2-methyl-4,5,6,7-tetrahydrothiazolo[5,4-c]pyridin-5-yl) | 447.6 | 448.4 | ++++ |
| 53 | CH | (4,5,6,7-tetrahydroisoxazolo[4,3-c]pyridin-5-yl, 3-oxo) | 433.5 | 434.3 | +++++ |
| 54 | CH | (4,5,6,7-tetrahydroisoxazolo[5,4-c]pyridin-6-yl, 3-oxo) | 433.5 | 434.3 | ++++ |
| 55 | CH | (4,5,6,7-tetrahydroisoxazolo[4,3-c]pyridin-5-yl) | 417.5 | 418.3 | ++++ |

TABLE 4-continued
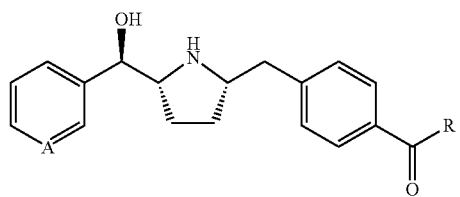
| Example (Ex.) # | A | R | MW | MS (MH)+ | Human β3 agonist functional activity |
|---|---|---|---|---|---|
| 56 | CH | | 468.6 | 469.3 | ++ |
| 57 | N | | 469.6 | 470.1 | ++ |
| 58 | CH | | 469.6 | 470.2 | +++ |
| 59 | N | | 485.6 | 486.2 | +++ |
| 60 | CH | | 458.6 | 459.2 | +++ |
| 61 | CH | | 458.6 | 459.2 | ++++ |
| 62 | CH | | 458.6 | 459.2 | ++++ |

TABLE 4-continued

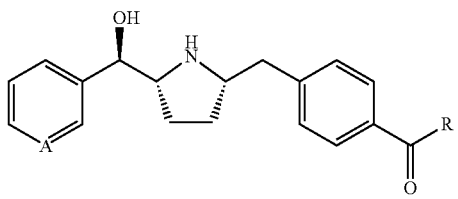

| Example (Ex.) # | A | R | MW | MS (MH)+ | Human β3 agonist functional activity |
|---|---|---|---|---|---|
| 63 | CH | ![structure] | 472.6 | 473.4 | ++ | less than 1 nM (+);
1-9.9 nM (++);
10-99.9 nM (+++);
100-999 nM (++++); and
greater than 999 nM but less than 3000 nM (+++++).

Example 64

(R)-phenyl[(2R,5S)-5-(4-{[4-(1H-pyrazol-1-yl)-piperidin-1-yl]carbonyl}benzyl)pyrrolidine-2-yl]methanol (Ex. 64)

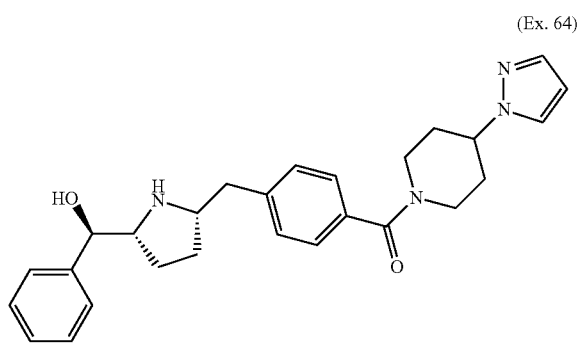 [SMILES: O=C(c1ccc(C[C@@H]2CC[C@H]([C@H](O)c3ccccc3)N2)cc1)N1CCC(n2cccn2)CC1]

(Ex. 64)

Step A: Tert-butyl (2R,5S)-2-[(R)-hydroxy(phenyl)methyl]-5-(4-{[5-(1H-pyrazol-1-yl)piperidin-1-yl]carbonyl}benzyl)pyrrolidine-1-carboxylate

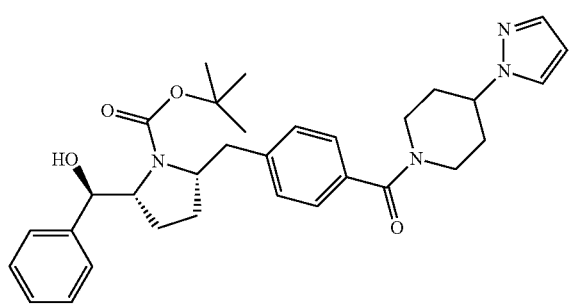 [SMILES: CC(C)(C)OC(=O)N1[C@H](Cc2ccc(C(=O)N3CCC(n4cccn4)CC3)cc2)CC[C@@H]1[C@H](O)c1ccccc1]

To a solution of 4-{((2S,5R)-1-(tert-butoxycarbonyl)-5-[(R)-hydroxy(phenyl)methyl]pyrrolidin-2-yl)methyl}benzoic acid (82 mg, 0.2 mmol) and 4-(1H-pyrazol-1-yl)piperidine (30 mg, 0.2 mmol) in 1.5 mL anhydrous DMF was added a 0.5 M solution of HOAt in DMF (0.4 mL, 0.2 mmol) followed by EDC (78 mg, 0.4 mmol) and DIEA (70 µL, 0.4 mmol). The resulting mixture was stirred at RT under nitrogen atmosphere for 16 h. The mixture was washed with water and extracted with dichloromethane (2×5 mL). The organics were combined, dried over sodium sulfate, filtered and concentrated in vacuum. The residue was purified by preparative TLC plate (1000 uM) eluting with 5% MeOH in dichloromethane to afford the title compound (88 mg, 81%). ESI-MS calculated for $C_{32}H_{40}N_4O_4$: Exact Mass: 544.30. Found 545.30 (MH)+ and 567.28 (MNa)+.

Step B: (R)-phenyl[(2R,5S)-5-(4-{[4-(1H-pyrazol-1-yl)-piperidin-1-yl]carbonyl}benzyl)pyrrolidine-2-yl]methanol (Ex. 64)

The title compound from Step A above (85 mg, 0.16 mmol) was dissolved in 4 M HCl in dioxane plus 10% water (v/v) (2 mL) and stirred at RT for 2 h. The product was concentrated under reduced pressure and dried under high vacuum to give the title compound. ESI-MS calculated for $C_{27}H_{32}N_4O_2$: Exact Mass: 444.25. Found 445.24.

Using the Biological Assays as described above, the human β3 functional activity was determined to be between 10 to 99.9 nM.

Example 65

(R)-[(2R,5S)-5-(4-{[4-(1H-pyrazol-1-yl)-piperidin-1-yl]carbonyl}benzyl)pyrrolidine-2-yl](pyridin-3-yl)methanol (Ex. 65)

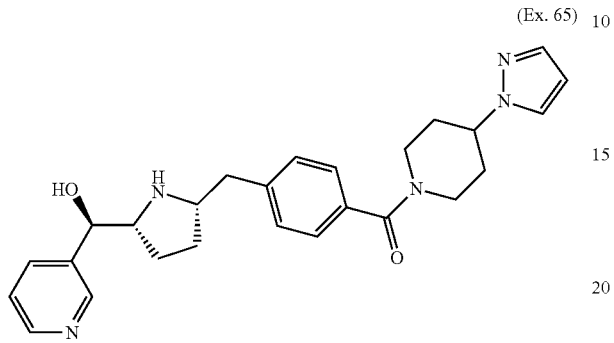
(Ex. 65)

Step A: Tert-butyl (2R,5S)-2-[(R)-hydroxy(pyridin-3-yl)methyl]-5-(4-{[5-(1H-pyrazol-1-yl)piperidin-1-yl]carbonyl}benzyl)pyrrolidine-1-carboxylate

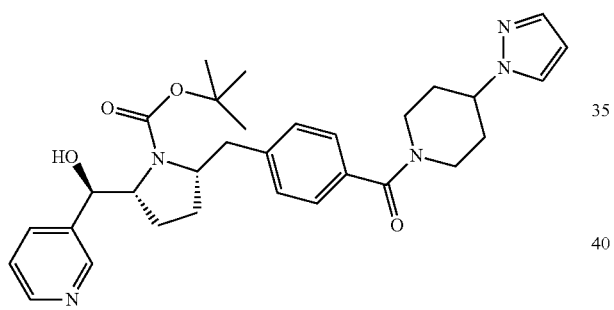

To a solution of 4-{((2S,5R)-1-(tert-butoxycarbonyl)-5-[(R)-hydroxy(pyridin-3-yl)methyl]pyrrolidin-2-yl)methyl}benzoic acid (i-4, 40 mg, 0.1 mmol) and 4-(1H-pyrazol-1-yl)piperidine (15 mg, 0.1 mmol) in 1.0 mL anhydrous DMF was added a 0.5 M solution of HOAt in DMF (0.2 mL, 0.1 mmol) followed by EDC (40 mg, 0.2 mmol) and DIEA (35 µL, 0.2 mmol). The resulting mixture was stirred at RT under nitrogen atmosphere for 16 h. The mixture was washed with water and extracted with dichloromethane (2×5 mL). The organics were combined, dried over sodium sulfate, filtered and concentrated in vacuum. The residue was purified by preparative TLC plate (1000 uM) eluting with 10% MeOH in dichloromethane to afford the title compound (38 mg, 75%). ESI-MS calculated for $C_{31}H_{39}N_5O_4$: Exact Mass: 545.30. Found 546.30 $(MH)^+$ and 568.28 $(MNa)^+$.

Step B: (R)-phenyl[(2R,5S)-5-(4-{[4-(1H-pyrazol-1-yl)-piperidin-1-yl]carbonyl}benzyl)pyrrolidine-2-yl]methanol (Ex. 65)

The title compound from Step A above (38 mg, 0.15 mmol) was dissolved in 4 M HCl in dioxane plus 10% water (v/v) (2 mL) and stirred at RT for 2 h. The product was concentrated under reduced pressure and dried under high vacuum to give the title compound. ESI-MS calculated for $C_{26}H_{31}N_5O_2$: Exact Mass: 445.25. Found 446.24.

Using the Biological Assays as described above, the human Beta-3 functional activity was determined to be between 100 to 999 nM.

Example 66

(R)-phenyl[(2R,5S)-5-(4-{[4-(1,3-thiazol-4-yl)-piperidin-1-yl]carbonyl}benzyl)pyrrolidine-2-yl]methanol (Ex. 66)

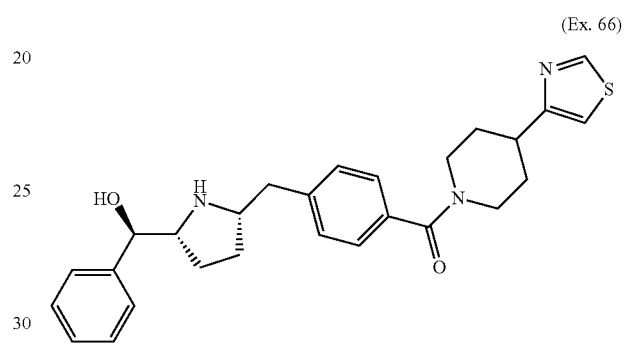
(Ex. 66)

Step A: Tert-butyl (2R,5S)-2-[(R)-hydroxy(phenyl)methyl]-5-(4-{[5-(1,3-thiazol-4-yl)piperidin-1-yl]carbonyl}benzyl)pyrrolidine-1-carboxylate

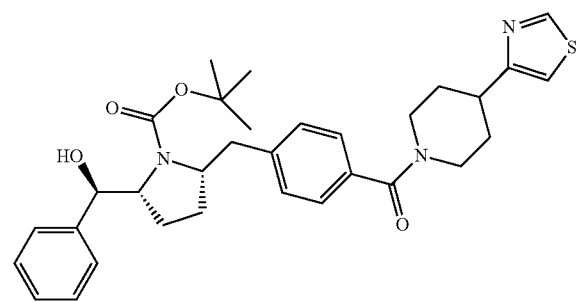 [SMILES: CC(C)(C)OC(=O)N1[C@H](Cc2ccc(C(=O)N3CCC(c4cscn4)CC3)cc2)CC[C@@H]1[C@H](O)c1ccccc1]

To a solution of 4-{((2s,5R)-1-(tert-butoxycarbonyl)-5-[(R)-hydroxy(phenyl)methyl]pyrrolidin-2-yl)methyl}benzoic acid (82 mg, 0.2 mmol) and 4-(1,3-thiazol-4-yl)piperidine (30 mg, 0.2 mmol) in 1.5 mL anhydrous DMF was added a 0.5 M solution of HOAt in DMF (0.4 mL, 0.2 mmol) followed by EDC (78 mg, 0.4 mmol) and DIEA (70 µL, 0.4 mmol). The resulting mixture was stirred at RT under nitrogen atmosphere for 16 h. The mixture was washed with water and extracted with dichloromethane (2×5 mL). The organics were combined, dried over sodium sulfate, filtered and concentrated in vacuum. The residue was purified by preparative TLC plate (1000 uM) eluting with 5% MeOH in dichloromethane to afford the product (91 mg, 88%). ESI-MS calculated for $C_{32}H_{39}N_3O_4S$: Exact Mass: 561.27. Found 562.28 $(MH)^+$ and 584.28 $(MNa)^+$.

Step B: (R)-phenyl[(2R,5S)-5-(4-{[4-(1,3-thiazol-4-yl)-piperidin-1-yl]carbonyl}benzyl)pyrrolidine-2-yl]methanol (Ex. 66)

The title compound from Step A above (90 mg, 0.18 mmol) was dissolved in 4 M HCl in dioxane plus 10% water (v/v) (2 mL) and stirred at RT for 2 h. The product was concentrated under reduced pressure and dried under high vacuum to give the title compound. ESI-MS calculated for $C_{27}H_{31}N_3O_2S$: Exact Mass: 461.21. Found 462.24.

Using the Biological Assays as described above, the human β3 functional activity was determined to be between 10 to 99.9 nM.

Examples 67-168

Ex. 67 Ex. 168

Using procedures similar to those described above, Examples 67-168 were prepared from the appropriate starting materials.

Using the Beta-3 agonist in vitro functional assay described above the human Beta-3 agonist functional activity of each compound was determined and shown in Table 5 as the following ranges:

TABLE 5

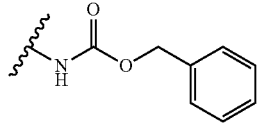 [SMILES: *NC(=O)OCc1ccccc1]

| Example (Ex.) # | A | R | MW | MS (MH)+ | Human β3 agonist functional activity |
|---|---|---|---|---|---|
| 67 | CH | H | 378.5 | 378.9 | ++++ |
| 68 | CH | 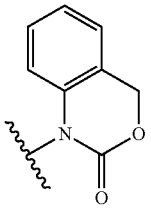 [SMILES: *N1C(=O)OCc2ccccc21] | 527.7 | 528.3 | +++ |
| 69 | CH | 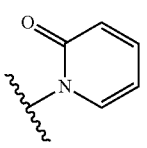 [SMILES: *n1ccccc1=O] | 525.7 | 526.9 | ++ |
| 70 | CH | 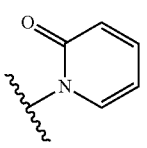 [SMILES: *n1ccccc1=O] | 471.6 | 472.2 | ++++ |

TABLE 5-continued

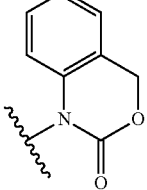

| Example (Ex.) # | A | R | MW | MS (MH)+ | Human β3 agonist functional activity |
|---|---|---|---|---|---|
| 71 | N | 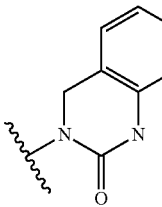 | 526.6 | 527.3 | ++ |
| 72 | CH | 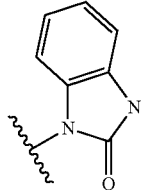 [SMILES: *n1c(=O)[nH]c2ccccc21] | 524.7 | 525.4 | ++++ |
| 73 | CH | 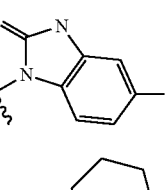 | 529.6 | 530.4 | +++ |
| 74 | CH | 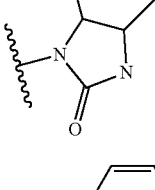 | 510.6 | 511.2 | ++++ |
| 75 | CH | 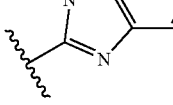 | 545.1 | 545.3 | ++++ |
| 76 | CH | 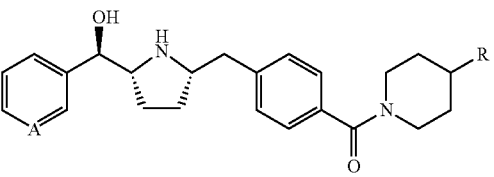 | 516.7 | 517.3 | +++ |
| 77 | CH | 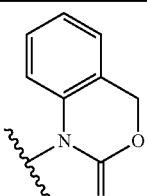 | 494.6 | 495.4 | ++++ |

TABLE 5-continued

| Ex-ample (Ex.) # | A | R | MW | MS (MH)+ | Human β3 agonist functional activity |
|---|---|---|---|---|---|
| 78 | CH | benzoxazol-2-yl | 495.6 | 496.4 | ++++ |
| 79 | CH | 4-phenyl-imidazol-2-yl | 520.7 | 521.3 | ++++ |
| 80 | CH | 4-phenyl-1,2,3-triazol-1-yl | 521.7 | 522.4 | ++++ |
| 81 | CH | 5-(pyrazin-2-yl)-1,2,4-triazol-3-yl | 523.6 | 524.3 | ++++ |
| 82 | CH | 3-(pyridin-3-yl)-1,2,4-oxadiazol-5-yl | 523.6 | 524.4 | ++++ |
| 83 | CH | 3-(pyrazin-2-yl)-1,2,4-oxadiazol-5-yl | 524.6 | 525.4 | ++++ |
| 84 | CH | 4-phenyl-2-oxo-imidazol-1-yl | 536.7 | 537.4 | +++ |
| 85 | N | 4-phenyl-2-oxo-imidazol-1-yl | 537.7 | 538.3 | +++ |
| 86 | CH | 5-methyl-imidazol-1-yl | 458.6 | 459.3 | ++++ |
| 87 | N | 5-methyl-imidazol-1-yl | 459.6 | 460.3 | ++++ |
| 88 | CH | 4-methoxycarbonyl-thiazol-2-yl | 519.7 | 520.5 | +++ |
| 89 | CH | 5-methyl-1,2,4-thiadiazol-3-yl | 476.7 | 477.2 | ++++ |
| 90 | CH | pyrazol-1-yl | 444.6 | 445.3 | +++ |
| 91 | CH | 1,2,4-triazol-1-yl | 445.6 | 446.3 | ++++ |
| 92 | CH | 1,2,4-triazol-1-yl | 445.6 | 446.3 | +++ |
| 93 | CH | 1,2,3-triazol-1-yl | 445.6 | 446.3 | ++++ |
| 94 | N | 1,2,3-triazol-2-yl | 446.6 | 447.3 | ++++ |
| 95 | CH | 4-methyl-1,2,3-triazol-1-yl | 459.6 | 460.2 | +++ |

TABLE 5-continued

Structure: (pyridyl/phenyl with OH)-CH(OH)-[pyrrolidine-NH]-CH2-(phenyl)-C(O)-N(piperidine-R)

| Example (Ex.) # | A | R | MW | MS (MH)+ | Human β3 agonist functional activity |
|---|---|---|---|---|---|
| 96 | CH | 1-methyl-5-triazolyl | 459.6 | 460.4 | ++++ |
| 97 | CH | 1-methyl-1,2,3-triazol-4-yl | 459.6 | 460.3 | ++++ |
| 98 | CH | 4-methyl-1,2,4-triazol-3-yl | 459.6 | 460.3 | ++++ |
| 99 | CH | 5-amino-1,3,4-oxadiazol-2-yl | 461.6 | 462.1 | +++ |
| 100 | CH | 1H-tetrazol-1-yl | 446.6 | 447.3 | +++ |
| 101 | CH | 5-methyl-tetrazol-1-yl | 460.6 | 461.3 | ++ |
| 102 | CH | tetrazol-1-yl | 446.6 | 447.3 | ++ |
| 103 | N | tetrazol-1-yl | 447.5 | 447.3 | +++ |
| 104 | CH | 5-methyl-tetrazol-1-yl | 460.6 | 461.3 | ++++ |
| 105 | CH | tetrazol-5-yl | 446.6 | 447.2 | +++ |
| 106 | CH | 2-methyl-tetrazol-5-yl | 460.6 | 461.2 | +++ |
| 107 | CH | 2-isopropyl-tetrazol-5-yl | 488.6 | 489.2 | +++ |
| 108 | CH | 1-methyl-tetrazol-5-yl | 460.6 | 461.2 | ++ |
| 109 | CH | 1-isopropyl-tetrazol-5-yl | 488.6 | 489.2 | ++ |
| 110 | CH | 1-cyclopropyl-tetrazol-5-yl | 486.6 | 487.2 | + |
| 111 | CH | 2-(methoxycarbonyl)phenyl | 512.7 | 513.3 | +++ |
| 112 | CH | 6-fluoropyridin-2-yl | 473.6 | 474.2 | +++ |
| 113 | N | 6-fluoropyridin-2-yl | 474.6 | 475.1 | +++ |

TABLE 5-continued
| Example (Ex.) # | A | R | MW | MS (MH)+ | Human β3 agonist functional activity |
|---|---|---|---|---|---|
| 114 | CH | 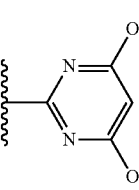 | 456.6 | 457.3 | ++++ |
| 115 | CH | 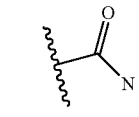 | 516.6 | 517.3 | ++++ |
| 116 | CH | 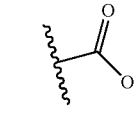 | 421.5 | 422.4 | ++++ |
| 117 | CH | 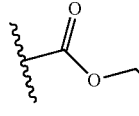 | 422.5 | 423.6 | ++++ |
| 118 | CH | 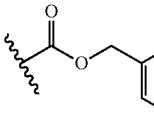 | 450.6 | 451.3 | +++ |
| 119 | CH | 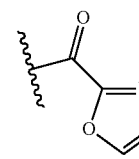 | 512.7 | 513.3 | +++ |
| 120 | CH | 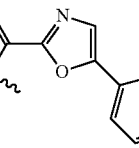 | 473.6 | 474.4 | +++ |
| 121 | CH | 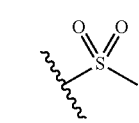 | 568.7 | 569.5 | ++ |
| 122 | CH | 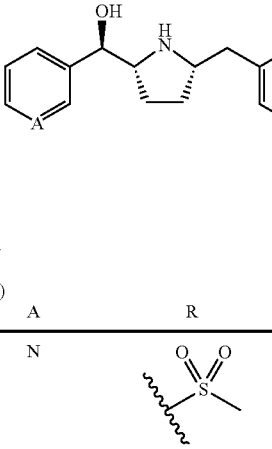 | 456.6 | 457.3 | +++ |
TABLE 5-continued
| Example (Ex.) # | A | R | MW | MS (MH)+ | Human β3 agonist functional activity |
|---|---|---|---|---|---|
| 123 | N | 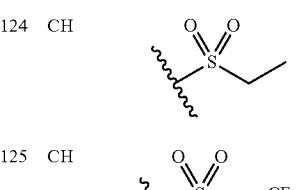 | 457.6 | 458.2 | ++++ |
| 124 | CH | 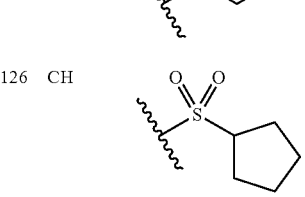 | 470.6 | 471.0 | ++ |
| 125 | CH | 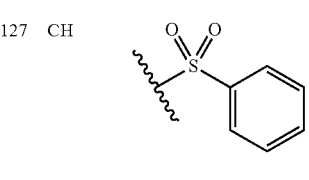 | 524.6 | 525.0 | +++ |
| 126 | CH | 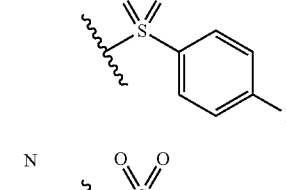 | 510.7 | 511.1 | +++ |
| 127 | CH | 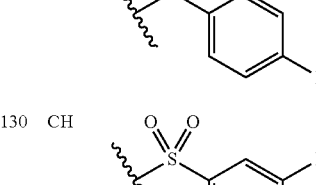 | 518.7 | 519.1 | +++ |
| 128 | CH | 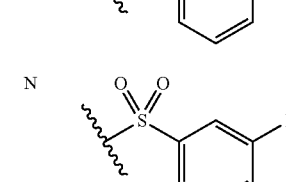 | 536.7 | 537.3 | +++ |
| 129 | N |  | 537.7 | 538.2 | ++++ |
| 130 | CH | | 536.7 | 537.3 | ++ |
| 131 | N | | 537.7 | 538.2 | ++++ |

TABLE 5-continued
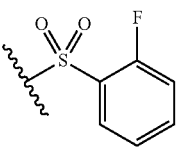 [SMILES: *S(=O)(=O)c1ccccc1F]
| Example (Ex.) # | A | R | MW | MS (MH)+ | Human β3 agonist functional activity |
|---|---|---|---|---|---|
| 132 | CH | 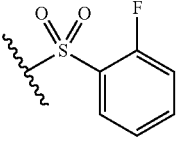 [SMILES: *S(=O)(=O)c1ccccc1F] | 536.7 | 537.3 | ++ |
| 133 | N | 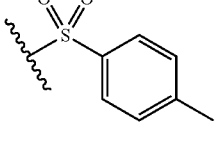 | 537.7 | 538.2 | +++ |
| 134 | CH | 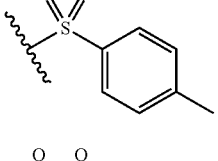 | 532.7 | 533.1 | ++ |
| 135 | N | 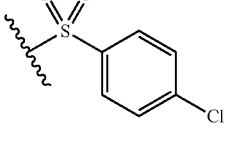 | 533.7 | 534.4 | ++++ |
| 136 | CH | 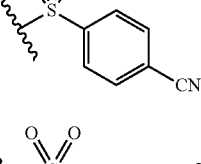 | 553.1 | 553.2 | +++ |
| 137 | CH | 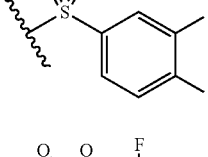 | 543.7 | 544.3 | +++ |
| 138 | CH | 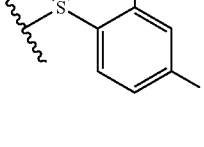 | 554.7 | 555.4 | +++ |
| 139 | CH | 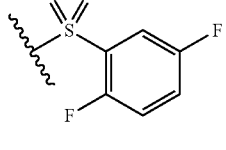 | 554.7 | 555.4 | +++ |
| 140 | CH | 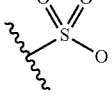 | 554.7 | 555.4 | +++ |
| 141 | CH | 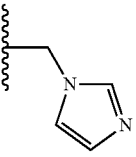 [SMILES: *Cn1ccnc1] | 458.6 | 459.2 | +++ |
| 142 | CH | 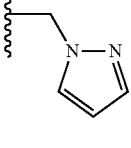 | 458.6 | 459.5 | ++++ |
| 143 | CH | 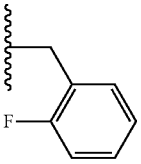 [SMILES: *Cc1ccccc1F] | 458.6 | 459.4 | +++ |
| 144 | CH | 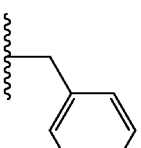 | 486.6 | 487.4 | +++ |
| 145 | CH | 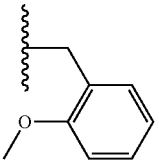 [SMILES: *Cc1ccccc1OC] | 486.6 | 487.4 | +++ |
| 146 | CH |  | 498.7 | 498.6 | +++ |

TABLE 5-continued

| Example (Ex.) # | A | R | MW | MS (MH)+ | Human β3 agonist functional activity |
|---|---|---|---|---|---|
| 147 | CH | (3-F, 4-OMe benzyl) | 516.7 | 517.6 | +++ |
| 148 | CH | (pyridazin-3(2H)-onyl-methyl) | 486.6 | 487.2 | +++ |
| 149 | CH | (pyrimidin-4(3H)-onyl-methyl) | 486.6 | 487.4 | ++++ |
| 150 | CH | (pyrimidin-2(1H)-onyl-methyl) | 486.6 | 487.4 | ++++ |
| 151 | CH | (pyrazin-2(1H)-onyl-methyl) | 486.6 | 487.4 | +++ |
| 152 | CH | (pyridin-2-yloxy) | 471.6 | 471.9 | +++ |
| 153 | CH | (5-methylpyrimidin-4-yloxy) | 486.6 | 487.0 | ++++ |
| 154 | CH | (2-methylpyrimidin-4-yloxy) | 486.6 | 487.0 | ++++ |
| 155 | CH | (6-chloropyrazin-2-yloxy) | 507.0 | 506.9, 508.9 | ++++ |
| 156 | CH | (2-methylsulfonylphenoxy) | 548.7 | 549.0 | +++ |
| 157 | CH | (2-(N-methylcarbamoyl)phenoxy) | 527.7 | 528.0 | ++++ |
| 158 | CH | (5-(N,N-dimethylcarbamoyl)isoxazol-3-yloxy) | 532.6 | 533.0 | ++++ |
| 159 | CH | (5-methoxycarbonylisoxazol-3-yloxy) | 519.6 | 520.2 | ++++ |
| 160 | CH | (5-carboxyisoxazol-3-yloxy) | 505.6 | 506.2 | ++++ |

TABLE 5-continued

| Ex-ample (Ex.) # | A | R | MW | MS (MH)+ | Human β3 agonist functional activity |
|---|---|---|---|---|---|
| 161 | CH | pyrazinyl-O-CH2- | 486.6 | 487.4 | +++ |
| 162 | CH | pyrimidinyl-O-CH2- | 486.6 | 487.4 | +++ |
| 163 | CH | pyridin-2-yl-CH2-O- | 485.6 | 486.0 | ++++ |
| 164 | CH | 1-(pyridin-2-yl)ethyl | 483.7 | 484.1 | +++ |
| 165 | CH | 1-(pyridazin-3(2H)-on-2-yl)ethyl | 500.7 | 501.4 | +++ |
| 166 | CH | 1-(pyrimidin-4(3H)-on-3-yl)ethyl | 500.7 | 501.4 | +++ |
| 167 | CH | 1-(pyrimidin-4-yloxy)ethyl | 500.7 | 501.4 | ++++ |

TABLE 5-continued

| Ex-ample (Ex.) # | A | R | MW | MS (MH)+ | Human β3 agonist functional activity |
|---|---|---|---|---|---|
| 168 | CH | (pyridin-2-yl)(hydroxy)methyl | 485.6 | 486.0 | +++ | less than 1 nM (+);
1-9.9 nM (++);
10-99.9 nM (+++);
100-999 nM (++++); and
greater than 999 nM but less than 3000 nM (+++++).

Example 169

(R)-phenyl[(2R,5S)-5-(4-{[(1R,5S,6r)-6-(1H-tetraol-1-yl)-3-azabicyclo[3.1.0]hex-3yl]carbonyl}benzyl)pyrrolidine-2-yl]methanol (Ex. 169)

(Ex. 169)

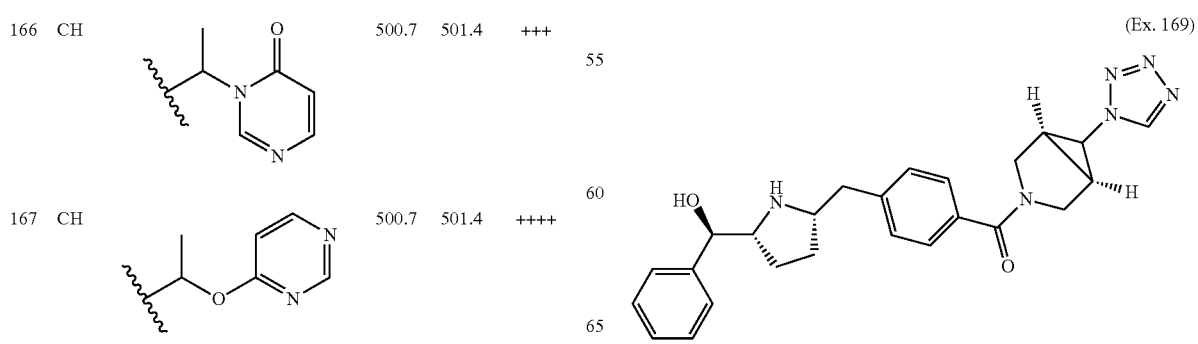

Step A: Tert-butyl (2R,5S)-2-[(R)-hydroxy(phenyl)methyl]-5-(4-{[(1R,5S,6r)-6-(1H-tetrazol-yl)-3-azabicyclo[3.1.0]hex-3-yl]carbonyl}benzyl)pyrrolidine-1-carboxylate

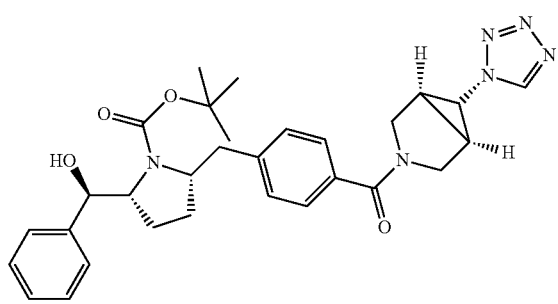

To a solution of 4-{((2S,5R)-1-(tert-butoxycarbonyl)-5-[(R)-hydroxy(phenyl)methyl]pyrrolidin-2-yl)methyl}benzoic acid (2.82 g, 6.85 mmol) and 6-(1H-tetrazol-1-yl)-3-azabicyclo[3.1.0]hexane (1.29 g, 6.85 mmol) in 15 mL anhydrous DMF was added HATU (2.61 g, 6.85 mmol) followed by TEA (2.1 mL, 20.56 mmol). The resulting mixture was stirred at RT under nitrogen atmosphere for 3 h. The mixture was washed with water and extracted with ethyl acetate (2×200 mL). The organics were washed with brine, separated, dried over sodium sulfate, filtered and concentrated under vacuum. The residue was purified by Biotage MPLC (silica gel 40+ column) eluting with 3% MeOH in dichloromethane to afford the title compound (3.62 g, 96%). ESI-MS calculated for $C_{30}H_{36}N_6O_4$: Exact Mass: 544.64. Found 545.64 $(MH)^+$ and 567.64 $(MNa)^+$.

Step B: (R)-phenyl[(2R,5S)-5-(4-{[(1R,5S,6r)-6-(1H-tetrazol-1-yl)-3-azabicyclo[3.1.0]hex-3-yl]carboxyl}benzyl)pyrrolidine-2-yl]methanol (Ex. 169)

To a solution of the title compound from Step A above (850 mg, 1.56 mmol) in dichloromethane (15 mL) was added TFA (3 mL) and the resulting solution stirred at RT for 40 min. The volatiles were removed under vacuum and the residue dissolved in ethyl acetate (150 mL). The solution was washed with sodium bicarbonate (40 mL), dried over sodium sulfate, filtered, and then concentrated to dryness under vacuum to afford the title compound (463 mg, 67%) as its free base form. ESI-MS calculated for $C_{25}H_{28}N_6O_2$: Exact Mass: 444.53. Found 445.54.

Using the Biological Assays as described above, the human 133 functional activity was determined to be between 1 to 9.9 nM.

Example 170

(R)-[(2R,5S)-5-(4-{[(1R,5S,6r)-6-(1,3,4-oxadiazol-2-yl)-3-azabicyclo[3.1.0]hex-3-yl]carbonyl}benzyl)pyrrolidin-2-yl]phenyl)methanol (Ex. 170)

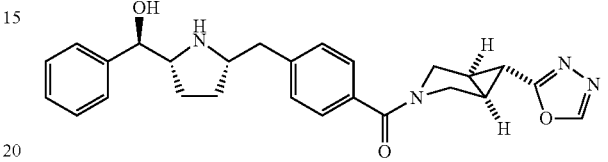

(Ex. 170)

Step A: tert-butyl (2R,5S)-2-[(R)-hydroxy(phenyl)methyl]-5-(4-{[(1R,5S,6r)-6-(1,3,4-oxadiazol-2-yl)-3-azabicyclo[3.1.0]hex-3-yl]carbonyl}benzyl)pyrrolidine-1-carboxylate

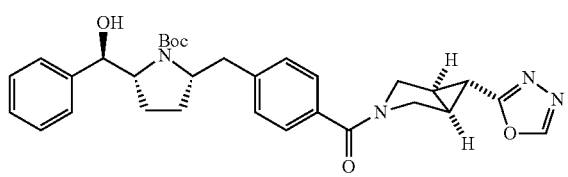

100 mg (0.40 mmol) tert-butyl (1R,5S,6r)-6-(1,3,4-oxadiazol-2-yl)-3-azabicyclo[3.1.0]hexane-3-carboxylate was added to 1 ml 4 M HCl in 1,4-dioxane. The solution was stirred for 1 h. It was concentrated under reduced pressure to give 72 mg of (1R,5S,6r)-6-(1,3,4-oxadiazol-2-yl)-3-azabicyclo[3.1.0]hexane as white solid which was used without further purification. LC/MS 151.2 (M+1)

To a solution of 30 mg (0.07 mmol) 4-({(2S,5R)-1-(tert-butoxycarbonyl)-5-[(R)-hydroxy(phenyl)methyl]pyrrolidin-2-yl}methyl)benzoic acid (i-1) in 1 ml anhydrous N,N-dimethylformamide at ambient temperature was added 20 mg (0.1 mmol) of (1R,5S,6r)-6-(1,3,4-oxadiazol-2-yl)-3-azabicyclo[3.1.0]hexane from above, followed by 20 mg (0.1 mmol) EDCl, 15 mg (0.10 mmol) HOBt, and 0.070 ml (0.35 mmol) N,N-diisopropylethylamine. The solution was stirred for 2 h. It was then filtered and purified by reverse-phase HPLC (TMC Pro-Pac C18; 35-100% 0.1% trifluoroacetic acid in acetonitrile/0.1% trifluoroacetic acid in water gradient). The pure fractions were lyophilized overnight to give 30 mg (70%) of the title compound as a white solid. LC/MS 545.3 (M+1).

Step B: (R)-[(2R,5S)-5-(4-{[(1R,5S,6r)-6-(1,3,4-oxadiazol-2-yl)-3-azabicyclo[3.1.0]hex-3-yl]carbonyl}benzyl)pyrrolidin-2-yl](phenyl)methanol (Ex. 170)

To a solution of 20 mg (0.1 mmol) of the title compound from Step A above in 1 ml anhydrous dichloromethane at ambient temperature was added 0.3 ml trifluoroacetic acid.

The solution was stirred for 1 h. It was then evaporated and purified by reverse-phase HPLC (TMC Pro-Pac C18; 5-65% 0.1% trifluoroacetic acid in acetonitrile/0.1% trifluoroacetic acid in water gradient). The pure fractions were lyophilized overnight to give 20 mg (80%) of the title compound as a white solid. LC/MS 445.3 (M+1).

Using the Beta-3 agonist in vitro functional assay described above the human Beta-3 agonist functional activity was determined to be between 1 to 9.9 nM.

Examples 171-238

Ex. 171-Ex. 238

Using procedures similar to those described above, Examples 171-235 were prepared from the appropriate starting materials.

Using the Beta-3 agonist in vitro functional assay described above the human Beta-3 agonist functional activity of each compound was determined and shown in Tables 6 and 7 as the following ranges:

TABLE 6

| Example (Ex.) # | A | R | MW | MS (MH)+ | Human β3 agonist functional activity |
|---|---|---|---|---|---|
| 171 | CH | —NH₂ | 391.5 | 392.3 | ++++ |
| 172 | CH | —CO₂H | 420.5 | 421.1 | ++ |
| 173 | CH | —CONH₂ | 419.5 | 20.3 | ++ |
| 174 | CH | —CN | 401.5 | 402.2 | ++++ |
| 175 | CH | —CH₂OH | 406.5 | 407.3 | +++ |
| 176 | CH | (ethyl ester) | 448.6 | 449.1 | + |
| 177 | N | (ethyl ester) | 449.6 | 450.3 | ++ |
| 178 | CH | (N-ethyl amide) | 447.6 | 448.3 | +++ |
| 179 | CH | (N-methyl, N-ethyl amide) | 461.6 | 462.4 | ++++ |
| 180 | CH | (pyrrolidinyl amide) | 473.6 | 474.4 | ++++ |
| 181 | CH | (oxazole) | 443.6 | 444.2 | +++ |
| 182 | CH | (5-methyl oxazole) | 457.6 | 458.2 | ++ |
| 183 | N | (5-methyl oxazole) | 458.6 | 459.2 | +++ |
| 184 | CH | (4-methyl oxazole) | 457.6 | 458.2 | +++ |
| 185 | N | (oxadiazole) | 445.5 | 446.2 | ++ |
| 186 | CH | (5-methyl oxadiazole) | 458.6 | 459.2 | ++ |
| 187 | CH | (5-ethyl oxadiazole) | 472.6 | 472.3 | ++ |
| 188 | CH | (methyl-oxadiazole-CH₂OH) | 474.6 | 475.3 | ++ |
| 189 | CH | (oxadiazole-C(CH₃)₂OH) | 502.6 | 503.3 | +++ |

TABLE 6-continued
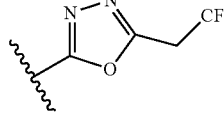
| Example (Ex.) # | A | R | MW | MS (MH)+ | Human β3 agonist functional activity |
|---|---|---|---|---|---|
| 190 | CH | 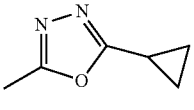 | 526.6 | 527.2 | ++ |
| 191 | CH | 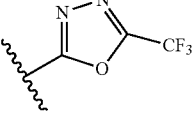 | 484.6 | 485.3 | ++ |
| 192 | CH | 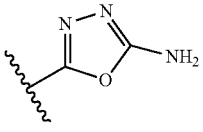 [SMILES: *c1nnc(N)o1] | 512.5 | 513.2 | +++ |
| 193 | CH | 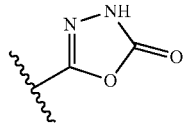 | 459.6 | 460.0 | ++ |
| 194 | CH | 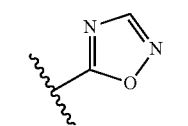 | 460.5 | 461.0 | +++ |
| 195 | CH | 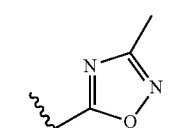 | 444.5 | 445.3 | ++ |
| 196 | CH | 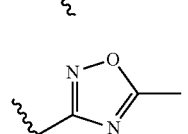 | 458.6 | 459.0 | +++ |
| 197 | CH | 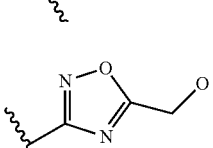 | 458.6 | 459.0 | ++ |
| 198 | CH | 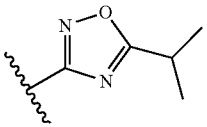 [SMILES: *c1noc(C(C)C)n1] | 474.6 | 475.0 | ++ |
TABLE 6-continued
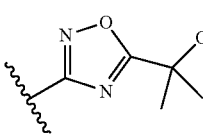
| Example (Ex.) # | A | R | MW | MS (MH)+ | Human β3 agonist functional activity |
|---|---|---|---|---|---|
| 199 | CH | 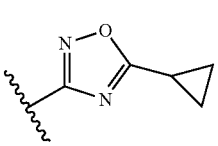 [SMILES: *c1noc(C2CC2)n1] | 486.6 | 487.1 | +++ |
| 200 | CH | 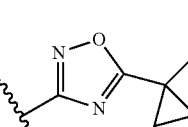 | 502.6 | 503.1 | +++ |
| 201 | CH | 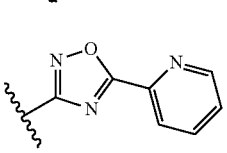 | 484.6 | 485.2 | ++ |
| 202 | CH | 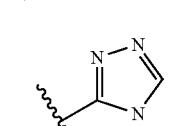 | 500.6 | 501.1 | ++ |
| 203 | CH | 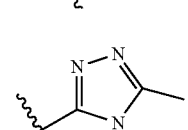 | 521.6 | 522.1 | ++ |
| 204 | CH | 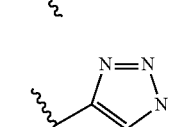 | 443.6 | 444.2 | +++ |
| 205 | CH | 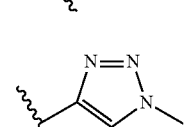 | 457.6 | 457.3 | ++++ |
| 206 | CH | | 443.6 | 444.1 | ++ |
| 207 | CH | | 457.6 | 457.1 | +++ |

TABLE 6-continued

[Structure shown with OH, pyridine ring labeled A, cyclopentane linker, benzene, carbonyl, bicyclic amine with R substituent]

| Example (Ex.) # | A | R | MW | MS (MH)+ | Human β3 agonist functional activity |
|---|---|---|---|---|---|
| 208 | CH | 2-isopropyl-triazolyl | 485.6 | 486.1 | +++ |
| 209 | CH | 1-isopropyl-triazolyl | 485.6 | 486.2 | +++ |
| 210 | CH | methyl-thiadiazolyl | 474.6 | 475.2 | +++ |
| 211 | CH | tetrazolyl | 444.5 | 445.0 | ++ |
| 212 | CH | 1-methyl-tetrazolyl | 458.6 | 459.1 | +++ |
| 213 | CH | 1-isopropyl-tetrazolyl | 486.6 | 487.2 | ++ |
| 214 | CH | 2-methyl-tetrazolyl | 458.6 | 459.1 | ++ |
| 215 | CH | 2-isopropyl-tetrazolyl | 486.6 | 487.2 | ++ |
| 216 | CH | methyl-tetrazolyl | 458.6 | 459.3 | ++++ |

TABLE 6-continued

[Same core structure]

| Example (Ex.) # | A | R | MW | MS (MH)+ | Human β3 agonist functional activity |
|---|---|---|---|---|---|
| 217 | CH | CH2-pyrazolyl | 456.6 | 457.0 | +++ |
| 218 | CH | CH2-triazolyl | 457.6 | 458.2 | ++++ |
| 219 | CH | CH2-triazolyl | 457.6 | 458.0 | +++ |
| 220 | CH | CH2-triazolyl | 457.6 | 458.0 | ++++ |
| 221 | CH | CH2-tetrazolyl | 458.6 | 459.0 | +++ |
| 222 | CH | CH2-tetrazolyl | 458.6 | 459.0 | +++ |
| 223 | CH | CH(CH3)-pyrazolyl | 470.6 | 471.1 | ++ |
| 224 | CH | CH(CH3)-triazolyl | 471.6 | 472.1 | +++ |

TABLE 6-continued

| Example (Ex.) # | A | R | MW | MS (MH)+ | Human β3 agonist functional activity |
|---|---|---|---|---|---|
| 225 | CH | (1H-1,2,3-triazol-1-yl)ethyl | 471.6 | 472.1 | ++++ |
| 226 | CH | (1H-1,2,4-triazol-1-yl)ethyl | 471.6 | 472.1 | ++++ |
| 227 | CH | (1H-tetrazol-1-yl)isopropyl | 472.6 | 473.1 | +++ |
| 228 | CH | (1H-tetrazol-1-yl)ethyl | 472.6 | 473.1 | +++ | less than 1 nM (+);
1-9.9 nM (++);
10-99.9 nM (+++);
100-999 nM (++++); and
greater than 999 nM but less than 3000 nM (+++++).

TABLE 7

| Example (Ex.) # | A | R | MW | MS (MH)+ | Human β3 agonist functional activity |
|---|---|---|---|---|---|
| 229 | CH | benzyl 3-azabicyclo ester | 510.6 | 511.4 | + |
| 230 | CH | ethyl 3-azabicyclo[3.1.0]hexane carboxylate | 448.6 | 449.4 | +++ |

TABLE 7-continued
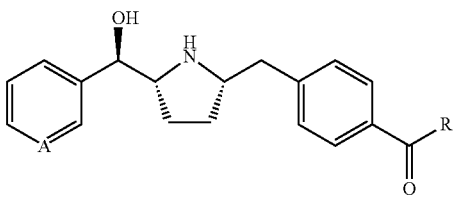
| Example (Ex.) # | A | R | MW | MS (MH)+ | Human β3 agonist functional activity |
|---|---|---|---|---|---|
| 231 | CH | 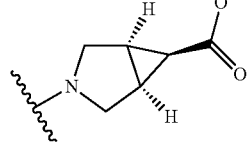 | 420.5 | 421.3 | ++++ |
| 232 | CH | 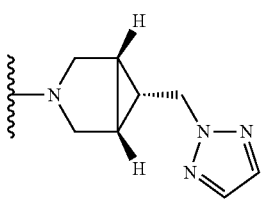 [SMILES: *N1C[C@@H]2[C@H](C1)[C@@H]2Cn1nccn1] | 457.6 | 458.0 | ++++ |
| 233 | CH | 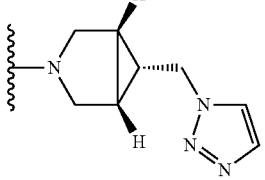 | 457.6 | 458.0 | ++++ |
| 234 | CH | 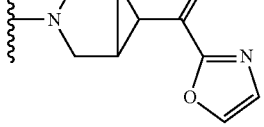 | 471.6 | 472.4 | +++ |
| 235 | CH | 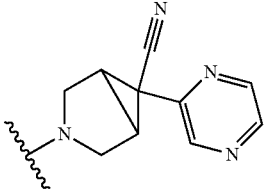 [SMILES: *N1CC2C(C1)C2(C#N)c1cnccn1] | 479.6 | 480.0 | +++ |
| 236 | CH | 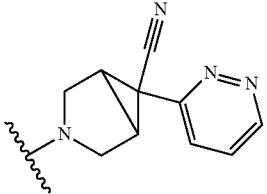 [SMILES: *N1CC2C(C1)C2(C#N)c1cccnn1] | 479.6 | 480.0 | +++ |

TABLE 7-continued

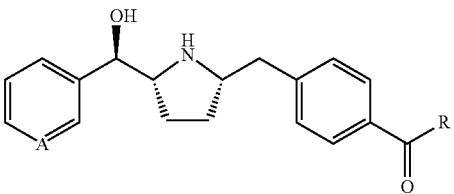

| Example (Ex.) # | A | R | MW | MS (MH)+ | Human β3 agonist functional activity |
|---|---|---|---|---|---|
| 237 | CH | (structure) | 479.6 | 480.0 | +++ |
| 238 | CH | (structure) | 478.6 | 479.0 | +++ |

Example 239

8-[4-({(2S,5R)-5-[(R)-hydroxy(phenyl)methyl]pyrrolidin-2-yl}methyl)benzoyl]-2-oxa-8-azaspiro[4.5]decan-1-one (Ex. 239)

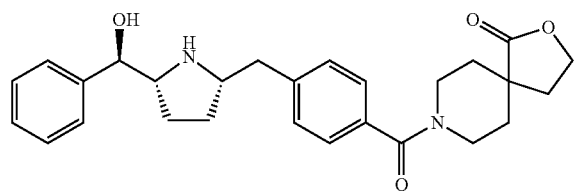 [SMILES: O=C(c1ccc(C[C@@H]2CC[C@H]([C@H](O)c3ccccc3)N2)cc1)N1CCC2(CCOC2=O)CC1]

Step A: tert-butyl (2R,5S)-2-[(R)-hydroxy(phenyl)methyl]-5-{4-[(1-oxo-2-oxa-8-azaspiro[4.5]dec-8-yl)carbonyl]benzyl}pyrrolidine-1-carboxylate

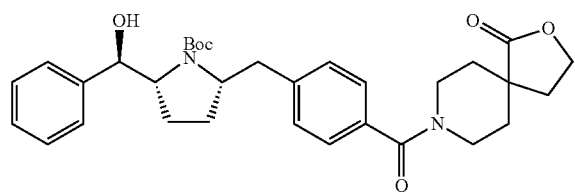 [SMILES: CC(C)(C)OC(=O)N1[C@H](Cc2ccc(C(=O)N3CCC4(CCOC4=O)CC3)cc2)CC[C@@H]1[C@H](O)c1ccccc1]

To a solution of 30 mg (0.07 mmol) 4-({(2S,5R)-1-(tert-butoxycarbonyl)-5-[(R)-hydroxy(phenyl)methyl]pyrrolidin-2-yl}methyl)benzoic acid (i-1) in 1 ml anhydrous DMF at ambient temperature was added 20 mg (0.1 mmol) 2-oxa-8-azaspiro[4.5]decan-1-one, followed by 20 mg (0.1 mmol) EDCl, 15 mg (0.10 mmol) HOBt, and 0.070 ml (0.35 mmol) diisopropylethylamine. The solution was stirred for 2 h. It was then filtered and purified by reverse-phase HPLC (TMC Pro-Pac C18; 35-100% 0.1% trifluoroacetic acid in acetonitrile/0.1% trifluoroacetic acid in water gradient). The pure fractions were lyophilized overnight to give 28 mg (70%) of the title compound as a white solid. LC/MS 549.2 (M+1).

Step B: 8-[4-({(2S,5R)-5-[(R)-hydroxy(phenyl)methyl]pyrrolidin-2-yl}methyl)benzoyl]-2-oxa-8-azaspiro[4.5]decan-1-one (Ex. 239)

To a solution of 28 mg (0.05 mmol) of the title compound from Step A above in 1 ml anhydrous dichloromethane at ambient temperature was added 0.3 ml trifluoroacetic acid. The solution was stirred for 1 h. It was then evaporated and purified by reverse-phase HPLC (TMC Pro-Pac C18; 5-65% 0.1% trifluoroacetic acid in acetonitrile/0.1% trifluoroacetic acid in water gradient). The pure fractions were lyophilized overnight to give 18 mg (80%) of the title compound as a white solid. LC/MS 449.2 (M+1). $^1$H NMR (DMSO): δ 7.27-7.32 (m, 8H), 7.19-7.22 (m, 1H), δ 5.15 (bs, 1H), δ 4.28 (t, J=6.8 Hz, 2H), δ 4.23 (d, J=7.2 Hz, 1H), δ 4.20 (bs, 1H), δ 3.60 (bs, 1H), δ 3.27 (t, J=7.0 Hz, 1H), δ 3.21 (m, 2H), δ 3.11 (q, J=7.1 Hz, 1H), δ 2.71 (qd, J=13.1, 6.8 Hz, 2H), δ 2.23 (s, 2H), δ 1.52-1.65 (m, 5H), δ 1.38-1.44 (m, 1H), δ 1.28-1.34 (m, 2H).

Using the Beta-3 agonist in vitro functional assay described above the human Beta-3 agonist functional activity was determined to be between 1 to 9.9 nM.

Examples 240-340

Ex. 240-Ex. 340

Using procedures similar to those described above, Examples 240-340 were prepared from the appropriate starting materials.

Using the Beta-3 agonist in vitro functional assay described above the human Beta-3 agonist functional activity of each compound was determined and shown in Table 8 as the following ranges:

TABLE 8

| Example (Ex.) # | A | R | MW | MS (MH)$^+$ | Human β3 agonist functional activity |
|---|---|---|---|---|---|
| 240 | CH | | 554.7 | 555.4 | +++ |
| 241 | CH | | 498.6 | 499.4 | ++++ |
| 242 | CH | | 522.7 | 523.0 | +++ |
| 243 | CH | | 460.6 | 461.2 | ++++ |
| 244 | CH | | 474.6 | 475.3 | ++++ |

TABLE 8-continued

| Example (Ex.) # | A | R | MW | MS (MH)+ | Human β3 agonist functional activity |
|---|---|---|---|---|---|
| 245 | CH | (4-benzyl-4-hydroxypiperidin-1-yl) | 484.6 | 485.4 | +++ |
| 246 | CH | (4-hydroxy-4-(4-methylbenzyl)piperidin-1-yl) | 498.7 | 499.5 | +++ |
| 247 | N | (4-(4-methoxyphenyl)-4-((pivalamidomethyl))piperidin-1-yl) | 598.8 | 599.4 | ++++ |
| 248 | CH | (4-phenyl-4-(3-(N,N-dipropylamino)-3-oxopropyl)piperidin-1-yl) | 595.8 | 596.1 | ++++ |
| 249 | CH | (4-cyclohexyl-4-(5-methyl-1,3,4-oxadiazol-2-yl)piperidin-1-yl) | 542.7 | 543.0 | ++++ |

TABLE 8-continued
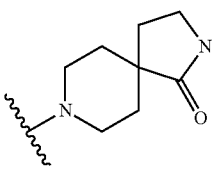 [SMILES: *N1CCC2(CCNC2=O)CC1]
| Example (Ex.) # | A | R | MW | MS (MH)+ | Human β3 agonist functional activity |
|---|---|---|---|---|---|
| 250 | CH | 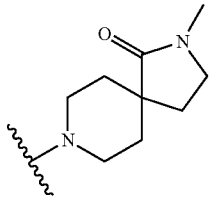 [SMILES: *N1CCC2(CC1)CCN(C)C2=O] | 447.6 | 448.4 | +++ |
| 251 | CH | 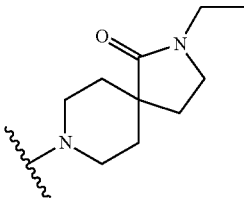 [SMILES: *N1CCC2(CC1)CCN(CC)C2=O] | 461.6 | 462.2 | ++++ |
| 252 | CH | 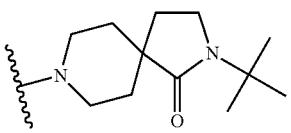 [SMILES: *N1CCC2(CC1)CCN(C(C)(C)C)C2=O] | 475.6 | 476.4 | ++++ |
| 253 | N | 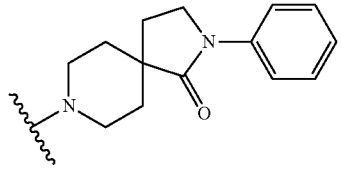 [SMILES: *N1CCC2(CC1)CCN(c1ccccc1)C2=O] | 504.7 | 505.4 | ++++ |
| 254 | CH | 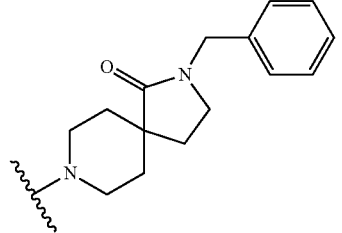 [SMILES: *N1CCC2(CC1)CCN(Cc1ccccc1)C2=O] | 523.7 | 524.4 | ++++ |
| 255 | CH | | 537.7 | 538.4 | ++ |

TABLE 8-continued

| Example (Ex.) # | A | R | MW | MS (MH)+ | Human β3 agonist functional activity |
|---|---|---|---|---|---|
| 256 | CH | | 461.6 | 462.4 | ++++ |
| 257 | CH | | 475.6 | 476.4 | ++++ |
| 258 | CH | | 448.6 | 449.4 | +++ |
| 259 | N | | 525.7 | 526.4 | ++ |
| 260 | CH | | 524.7 | 525.2 | + |
| 261 | CH | | 523.7 | 524.4 | + |

TABLE 8-continued
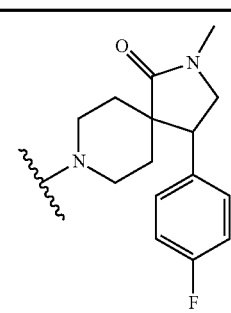
| Example (Ex.) # | A | R | MW | MS (MH)+ | Human β3 agonist functional activity |
|---|---|---|---|---|---|
| 262 | CH | 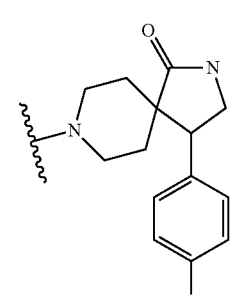 | 555.7 | 556.5 | + |
| 263 | CH | 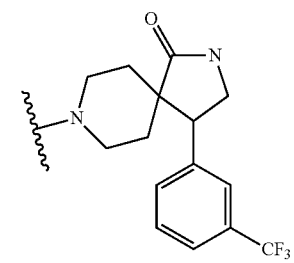 [SMILES: *N1CCC2(CC1)C(=O)NCC2c1cccc(C(F)(F)F)c1] | 591.7 | 592.5 | + |
| 264 | CH | 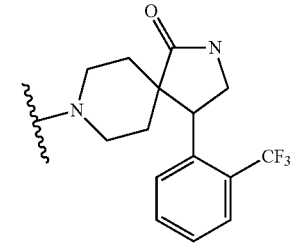 | 591.7 | 592.4 | + |
| 265 | CH | | 591.7 | 592.4 | ++ |

TABLE 8-continued
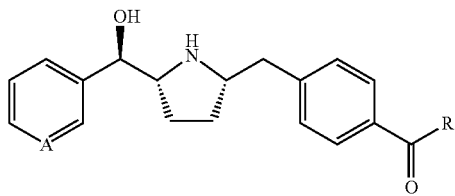
| Example (Ex.) # | A | R | MW | MS (MH)+ | Human β3 agonist functional activity |
|---|---|---|---|---|---|
| 266 | CH | | 524.7 | 525.4 | ++ |
| 267 | CH | | 462.6 | 463.4 | +++ |
| 268 | N | | 463.5 | 464.4 | +++ |
| 269 | CH | | 552.7 | 553.4 | +++ |
| 270 | N | | 553.7 | 554.3 | +++ |
| 271 | CH | | 449.5 | 450.3 | ++++ |

TABLE 8-continued
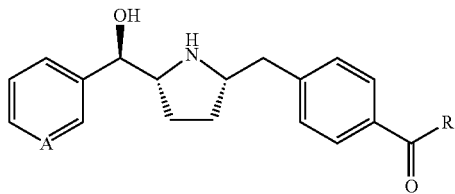
| Example (Ex.) # | A | R | MW | MS (MH)+ | Human β3 agonist functional activity |
|---|---|---|---|---|---|
| 272 | CH | 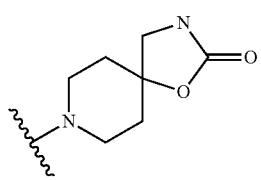 [SMILES: *N1CCC2(CC1)CNC(=O)O2] | 449.5 | 450.3 | ++++ |
| 273 | CH | 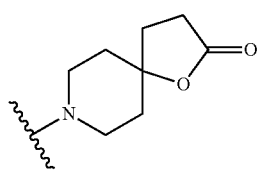 [SMILES: *N1CCC2(CCC(=O)O2)CC1] | 448.6 | 449.3 | +++ |
| 274 | CH | 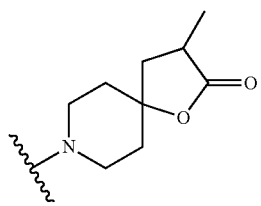 [SMILES: *N1CCC2(CC1)CC(C)C(=O)O2] | 462.6 | 463.1 | +++ |
| 275 | CH | 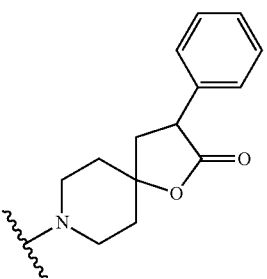 [SMILES: *N1CCC2(CC1)CC(c1ccccc1)C(=O)O2] | 524.6 | 525.2 | +++ |
| 276 | CH | 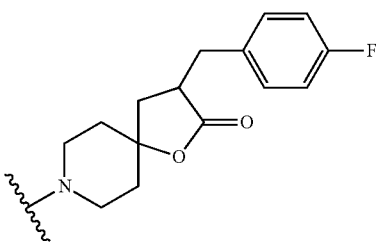 [SMILES: *N1CCC2(CC1)CC(Cc1ccc(F)cc1)C(=O)O2] | 556.6 | 557.4 | ++ |

TABLE 8-continued
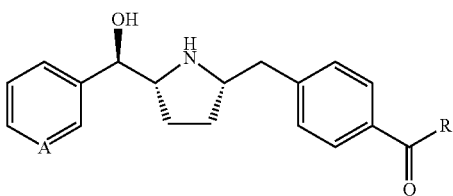
| Example (Ex.) # | A | R | MW | MS (MH)+ | Human β3 agonist functional activity |
|---|---|---|---|---|---|
| 277 | N | 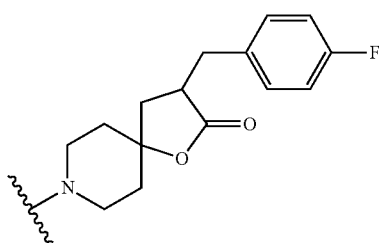 [SMILES: *N1CCC2(CC1)CC(Cc1ccc(F)cc1)C(=O)O2] | 557.7 | 558.3 | ++ |
| 278 | CH | 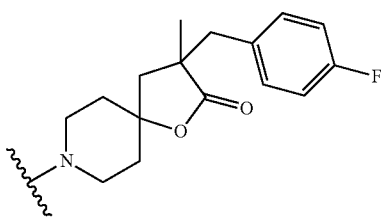 [SMILES: *N1CCC2(CC1)CC(C)(Cc1ccc(F)cc1)C(=O)O2] | 570.7 | 571.1 | + |
| 279 | CH | 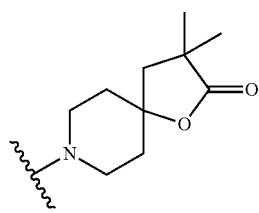 [SMILES: *N1CCC2(CC1)CC(C)(C)C(=O)O2] | 476.6 | 477.4 | +++ |
| 280 | CH | 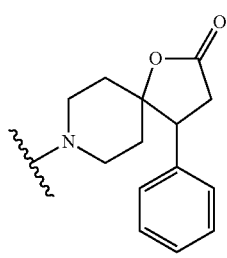 [SMILES: *N1CCC2(CC1)OC(=O)CC2c1ccccc1] | 524.7 | 525.4 | ++ |
| 281 | CH | 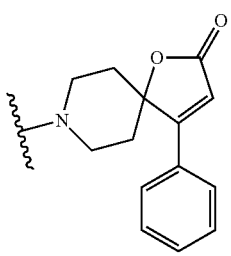 [SMILES: *N1CCC2(CC1)OC(=O)C=C2c1ccccc1] | 522.7 | 523.0 | ++ |

TABLE 8-continued
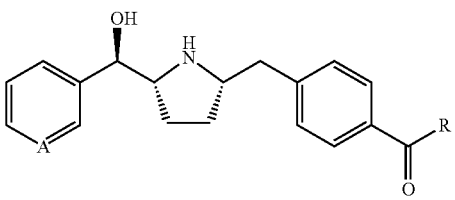
| Example (Ex.) # | A | R | MW | MS (MH)+ | Human β3 agonist functional activity |
|---|---|---|---|---|---|
| 282 | CH | 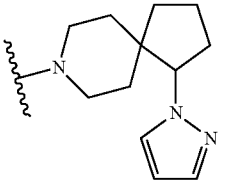 [SMILES: *N1CCC2(CCCC2n2cccn2)CC1] | 498.7 | 499.4 | ++++ |
| 283 | CH | 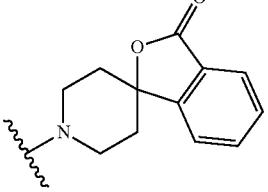 | 496.6 | 497.4 | +++ |
| 284 | N | 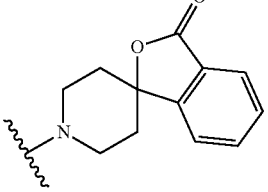 | 497.6 | 498.3 | ++ |
| 285 | CH | 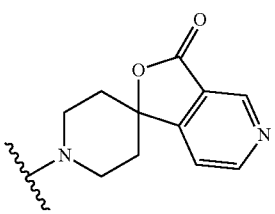 [SMILES: *N1CCC2(CC1)OC(=O)c1cnccc12] | 497.6 | 498.3 | +++ |
| 286 | CH | 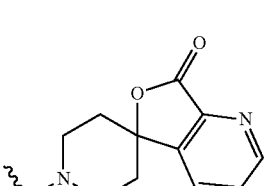 | 497.6 | 498.3 | +++ |
| 287 | CH | 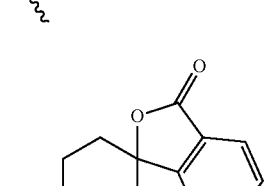 | 497.6 | 498.3 | +++ |

TABLE 8-continued

| Example (Ex.) # | A | R | MW | MS (MH)+ | Human β3 agonist functional activity |
|---|---|---|---|---|---|
| 288 | CH | (spiro-piperidine fused furo[3,2-b]pyridinone with methoxy) | 527.6 | 528.2 | +++ |
| 289 | CH | (spiro-piperidine fused furo-thiazolone) | 503.6 | 504.1 | +++ |
| 290 | CH | (spiro-piperidine benzofuranone) | 496.6 | 497.4 | +++ |
| 291 | CH | (spiro-piperidine γ-butyrolactone) | 448.6 | 449.4 | ++ |
| 292 | N | (spiro-piperidine γ-butyrolactone) | 449.6 | | +++ |
| 293 | CH | (spiro-piperidine dimethyl γ-butyrolactone) | 476.6 | 477.4 | ++ |

TABLE 8-continued
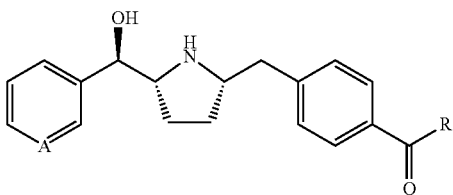
| Example (Ex.) # | A | R | MW | MS (MH)+ | Human β3 agonist functional activity |
|---|---|---|---|---|---|
| 294 | N | | 477.6 | 478.1 | ++ |
| 295 | NO | | 493.6 | 494.3 | ++++ |
| 296 | CH | | 462.6 | 463.2 | ++ |
| 297 | CH | | 476.6 | 477.5 | ++ |
| 298 | CH | | 476.6 | 477.3 | ++ |
| 299 | CH | | 495.6 | 496.4 | +++ |

TABLE 8-continued
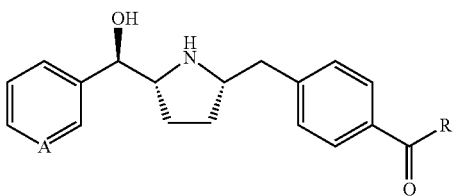
| Example (Ex.) # | A | R | MW | MS (MH)+ | Human β3 agonist functional activity |
|---|---|---|---|---|---|
| 300 | CH | | 509.7 | 510.4 | +++ |
| 301 | N | | 499.7 | 500.2 | ++++ |
| 302 | CH | | 530.7 | 531.1 | +++ |
| 303 | CH | | 484.6 | 485.0 | +++ |
| 304 | CH | | 468.6 | 469.0 | ++++ |
| 305 | CH | | 433.6 | 434.4 | ++++ |
| 306 | CH | | 433.6 | 434.1 | ++ |

TABLE 8-continued

| Example (Ex.) # | A | R | MW | MS (MH)+ | Human β3 agonist functional activity |
|---|---|---|---|---|---|
| 307 | CH | (1-oxa-8-azaspiro[4.5]decan-8-yl) | 434.6 | 435.0 | +++ |
| 308 | CH | (3-cyclopropyl-spiro[isobenzofuran-1,4'-piperidine]) | 522.7 | 523.0 | +++ |
| 309 | CH | (3-methylsulfonyl-spiro[isobenzofuran-1,4'-piperidine]) | 559.7 | 560.0 | +++ |
| 310 | CH | (3-(4-fluorophenyl)-1-oxa-8-azaspiro[4.5]decan-8-yl) | 528.7 | 529.2 | ++++ |
| 311 | CH | (2-oxa-8-azaspiro[4.5]decan-8-yl) | 434.6 | 435.0 | ++++ |
| 312 | CH | (3,3-dimethyl-1-oxa-8-azaspiro[4.5]decan-8-yl) | 462.6 | 463.2 | ++++ |

TABLE 8-continued

| Example (Ex.) # | A | R | MW | MS (MH)+ | Human β3 agonist functional activity |
|---|---|---|---|---|---|
| 313 | CH | (2,2-dimethyl-4-oxo-1-oxa-8-azaspiro[4.5]decane) | 478.6 | 479.1 | ++++ |
| 314 | CH | (1-hydroxy-2-azaspiro[4.5]decane derivative) | 448.6 | 449.0 | ++++ |
| 315 | CH | (1-imino-2-azaspiro[4.5]decane derivative) | 447.6 | 448.1 | ++++ |
| 316 | CH | (1-oxo-8-azaspiro[4.5]decane) | 446.6 | 447.2 | ++ |
| 317 | CH | (1-(hydroxyimino)-8-azaspiro[4.5]decane) | 461.6 | 462.1 | +++ |
| 318 | CH | (1-(methoxyimino)-8-azaspiro[4.5]decane) | 475.6 | 476.1 | ++++ |
| 319 | CH | (1,1-difluoro-8-azaspiro[4.5]decane) | 468.6 | 467.1 | +++ |

TABLE 8-continued
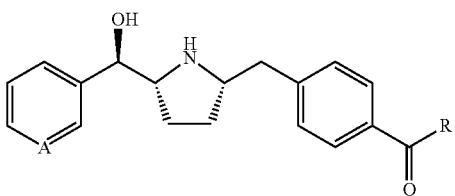
| Example (Ex.) # | A | R | MW | MS (MH)+ | Human β3 agonist functional activity |
|---|---|---|---|---|---|
| 320 | CH | | 538.7 | 539.4 | +++ |
| 321 | CH | | 470.6 | 471.3 | ++++ |
| 322 | CH | | 471.6 | 472.4 | +++ |
| 323 | CH | | 510.6 | 511.4 | +++ |
| 324 | CH | | 582.7 | 583.1 | +++ |
| 325 | CH | | 578.7 | 579.1 | +++ |

TABLE 8-continued
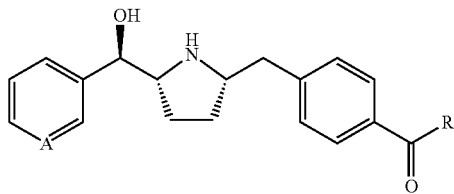
| Example (Ex.) # | A | R | MW | MS (MH)+ | Human β3 agonist functional activity |
|---|---|---|---|---|---|
| 326 | CH | 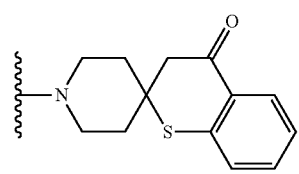 [SMILES: *N1CCC2(CC1)CC(=O)c1ccccc1S2] | 526.7 | 527.0 | ++ |
| 327 | N | 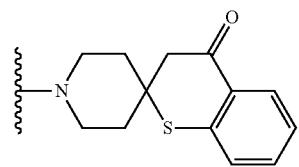 | 527.7 | 528.2 | +++ |
| 328 | CH | 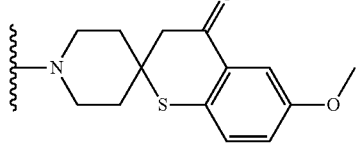 | 556.7 | 557.1 | ++ |
| 329 | N | 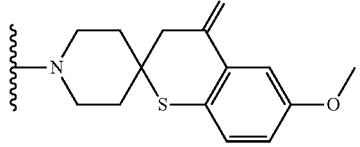 | 557.7 | 558.3 | +++ |
| 330 | CH | 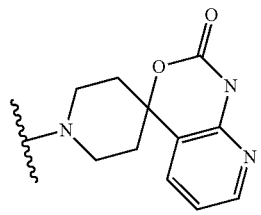 [SMILES: *N1CCC2(CC1)OC(=O)Nc1ncccc12] | 512.6 | 513.0 | +++ |
| 331 | N | 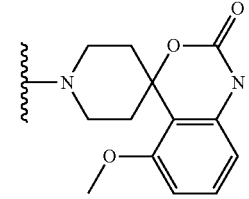 [SMILES: *N1CCC2(CC1)OC(=O)Nc1cccc(OC)c12] | 542.6 | 543.3 | +++ |

TABLE 8-continued
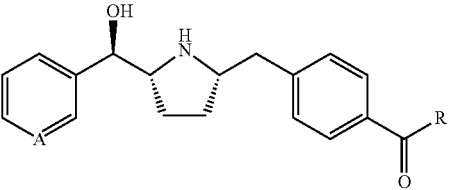
| Example (Ex.) # | A | R | MW | MS (MH)+ | Human β3 agonist functional activity |
|---|---|---|---|---|---|
| 332 | CH | 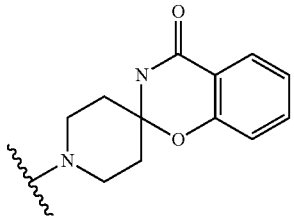 [SMILES: *N1CCC2(CC1)NC(=O)c1ccccc1O2] | 511.6 | 512.4 | +++ |
| 333 | CH | 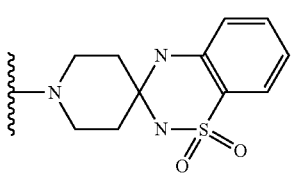 | 510.6 | 511.1 | ++ |
| 334 | CH | 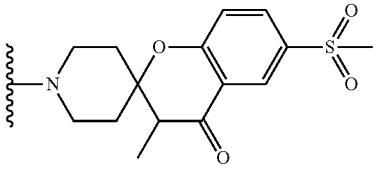 [SMILES: *N1CCC2(CC1)Oc1ccc(S(C)(=O)=O)cc1C(=O)C2C] | 546.7 | 547.0 | ++ |
| 335 | CH | 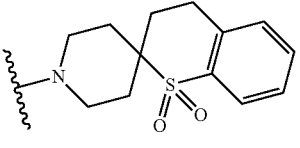 [SMILES: *N1CCC2(CCc3ccccc3S2(=O)=O)CC1] | 602.8 | 603.1 | +++ |
| 336 | CH | 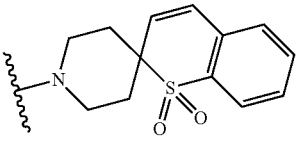 [SMILES: *N1CCC2(C=Cc3ccccc3S2(=O)=O)CC1] | 544.7 | 545.0 | ++ |
| 337 | CH | 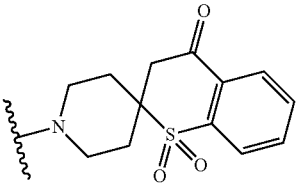 [SMILES: *N1CCC2(CC1)CC(=O)c1ccccc1S2(=O)=O] | 542.7 | 543.0 | ++ |
| 338 | CH |  | 558.7 | 559.2 | ++ |

TABLE 8-continued

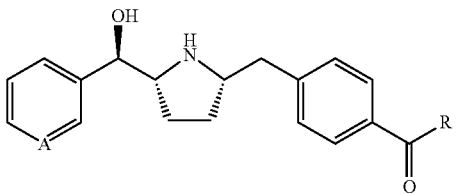

| Example (Ex.) # | A | R | MW | MS (MH)+ | Human β3 agonist functional activity |
|---|---|---|---|---|---|
| 339 | CH | (structure: spiro piperidine-thiochromanone S,S-dioxide with methoxy) | 588.7 | 589.2 | ++ |
| 340 | CH | (structure: spiro piperidine-thienothiopyranone S,S-dioxide) | 564.7 | 564.9 | ++ | less than 1 nM (+);
1-9.9 nM (++);
10-99.9 nM (+++);
100-999 nM (++++); and
greater than 999 nM but less than 3000 nM (+++++).

Example 341

(R)-Phenyl[(2R,5S)-5-(4-{[4-(pyridin-2-ylmethyl)piperazin-1-yl]carbonyl}benzyl)pyrrolidin-2-yl]methanol (Ex. 341)

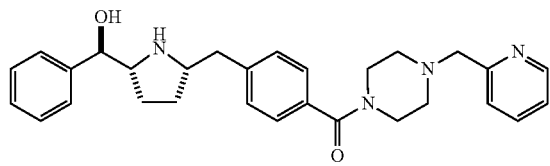

Step A: Tert-butyl (2R,5S)-2-[(R)-hydroxy(phenyl)methyl]-5-(4-{[4-(pyridin-2-ylmethyl)piperazin-1-yl]carbonyl}benzyl)pyrrolidine-1-carboxylate To a solution of 0.018 g (0.102 mmol) of (1-(pyridine-2-ylmethyl)piperazine and 0.035 g (0.085 mmol) of 4-({(2S,5R)-1-(tert-butoxycarbonyl)-5-[(R)-hydroxy(phenyl)methyl]pyrrolidin-2-yl}methyl)benzoic acid in 2 mL of N,N-dimethylformamide was added 0.074 mL (0.425 mmol) of N,N-diisopropylethylamine and 0.065 g (0.170 mmol) of HATU. The resulting mixture was stirred under an atmosphere of nitrogen for 3 h and then purified directly by reverse-phase HPLC (TMC Pro-Pac C18; 10-100% 0.1% trifluoroacetic acid in acetonitrile/0.1% trifluoroacetic acid in water gradient). LC/MS: m/z (ES) 571.2 (MH)+.

Step B: (R)-Phenyl[(2R,5S)-5-(4-{[4-(pyridin-2-ylmethyl)piperazin-1-yl]carbonyl}benzyl)pyrrolidin-2-yl]methanol (Ex. 341)

A solution of 0.038 g (0.067 mmol) of the title compound from Step A above in 1 mL dichloromethane and 1 mL trifluoroacetic acid was stirred at ambient temperature for 1 h. All volatiles were removed in vacuo and the crude light brown residue was purified directly by reverse-phase HPLC to afford the title compound (TMC Pro-Pac C18; 10-100% 0.1% trifluoroacetic acid in acetonitrile/0.1% trifluoroacetic acid in water gradient). $^1$H-NMR (500 MHz, CD$_4$O) δ 8.70 (d, J=4.9 Hz, 1H), 7.99-7.98 (m, 1H), 7.59 (d, J=7.8 Hz, 1H), 7.53-7.34 (m, 10H), 4.76 (d, J=8.8 Hz, 1H), 4.51 (s, 2H), 4.10-3.81 (m, 6H), 3.42-3.39 (m, 4H), 3.33-3.08 (m, 2H), 2.10-2.00 (m, 1H), 1.86-1.75 (m, 3H). LC/MS: m/z (ES) 471.3 (MH)+, 493.3 (MNa)+.

Using the Beta-3 agonist in vitro functional assay described above the human Beta-3 agonist functional activity of this Example was determined to be between 10 to 99.9 nM.

Examples 342-431

Ex. 342-Ex. 431

Using procedures similar to those described above, Examples 342-431 were prepared from the appropriate starting materials.

Using the Beta-3 agonist in vitro functional assay described above the human Beta-3 agonist functional activity of each compound was determined and shown in Table 9 as the following ranges:

TABLE 9

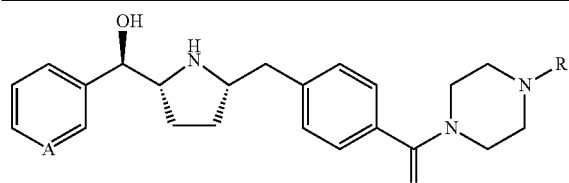

| Ex- ample (Ex.) # | A | R | MW | MS (MH)+ | Human β3 agonist functional activity |
|---|---|---|---|---|---|
| 342 | CH | H | 379.5 | 379.1 | ++++ |
| 343 | CH | (acetyl) | 421.5 | 422.4 | ++++ |
| 344 | CH | (ethyl ester) | 451.6 | 452.3 | ++++ |
| 345 | CH | (methylsulfonyl) | 457.6 | 458.1 | ++++ |
| 346 | CH | (phenylsulfonyl) | 519.7 | 520 | +++ |
| 347 | CH | (benzoyl) | 483.6 | 484.4 | ++++ |
| 348 | CH | (pyridine-2-carbonyl) | 484.6 | 485.1 | +++ |
| 349 | CH | (furan-2-carbonyl) | 473.6 | 474.2 | ++++ |
| 350 | CH | (2-carboxyphenyl) | 499.6 | 500.2 | ++++ |

TABLE 9-continued

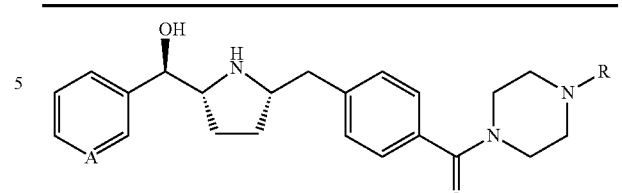

| Ex- ample (Ex.) # | A | R | MW | MS (MH)+ | Human β3 agonist functional activity |
|---|---|---|---|---|---|
| 351 | CH | (2-methoxycarbonylphenyl) | 513.6 | 514.3 | +++ |
| 352 | CH | (4-fluorophenyl) | 473.6 | 474.1 | ++++ |
| 353 | CH | (benzo[1,3]dioxol-5-yl) | 499.6 | 500.2 | ++++ |
| 354 | CH | (2,3-dihydrobenzo[1,4]dioxin-6-yl) | 513.6 | 514.4 | ++++ |
| 355 | CH | (pyridin-2-yl) | 456.6 | 457.1 | ++++ |
| 356 | CH | (pyridin-4-yl) | 456.6 | 457.2 | ++++ |
| 357 | CH | (3-fluoropyridin-2-yl) | 474.6 | 475.1 | ++++ |

TABLE 9-continued
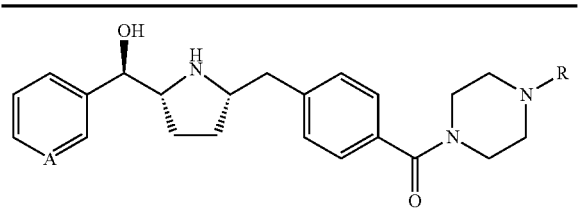
| Example (Ex.) # | A | R | MW | MS (MH)+ | Human β3 agonist functional activity |
|---|---|---|---|---|---|
| 358 | CH | 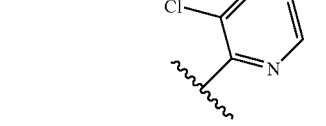 | 491.0 | 492.1 | +++ |
| 359 | CH | 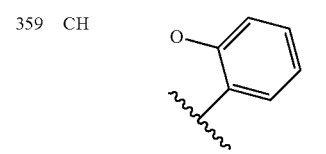 | 471.6 | 472.1 | +++ |
| 360 | CH | 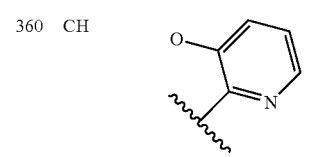 | 472.6 | 473.1 | +++ |
| 361 | CH | 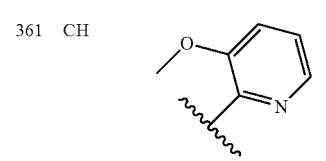 | 486.6 | 487.1 | +++ |
| 362 | CH | 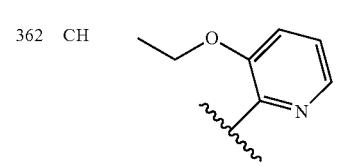 | 500.6 | 501.2 | +++ |
| 363 | CH | 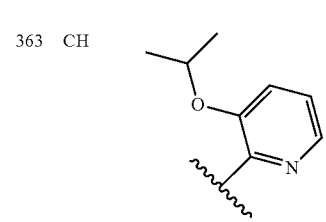 | 514.7 | 515.2 | +++ |
| 364 | CH | 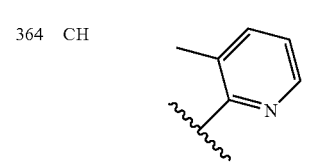 | 470.6 | 471.1 | +++ |
TABLE 9-continued
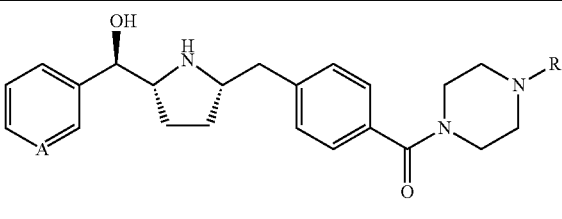
| Example (Ex.) # | A | R | MW | MS (MH)+ | Human β3 agonist functional activity |
|---|---|---|---|---|---|
| 365 | CH | 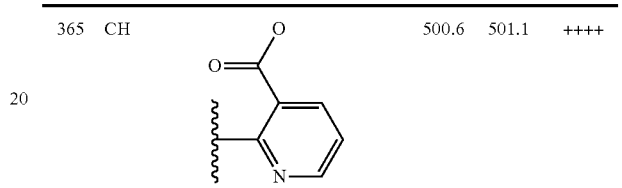 | 500.6 | 501.1 | ++++ |
| 366 | CH | 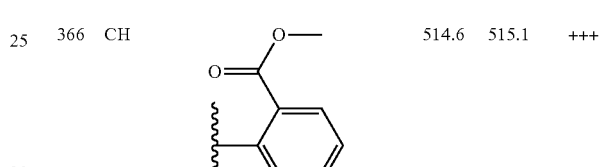 | 514.6 | 515.1 | +++ |
| 367 | CH | 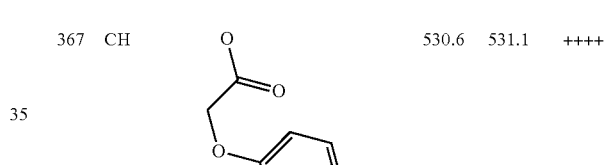 | 530.6 | 531.1 | ++++ |
| 368 | CH | 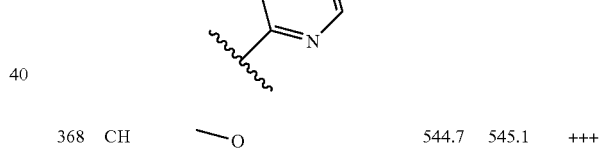 | 544.7 | 545.1 | +++ |
| 369 | CH | 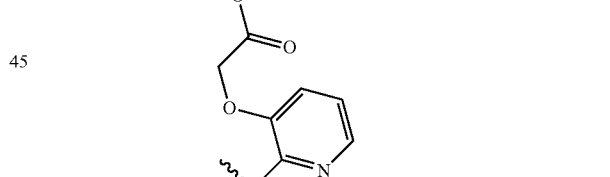 | 550.7 | 551.2 | +++ |
| 370 | CH | 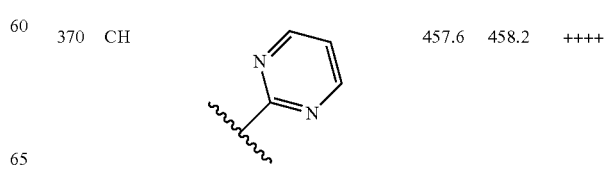 | 457.6 | 458.2 | ++++ |

TABLE 9-continued
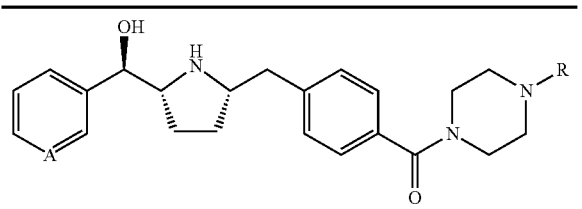
| Example (Ex.) # | A | R | MW | MS (MH)+ | Human β3 agonist functional activity |
|---|---|---|---|---|---|
| 371 | CH | 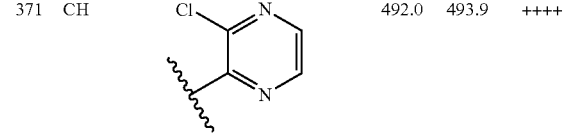 | 492.0 | 493.9 | ++++ |
| 372 | CH | 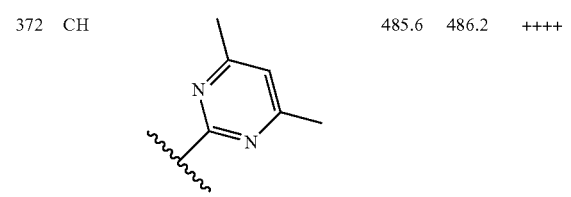 | 485.6 | 486.2 | ++++ |
| 373 | CH | 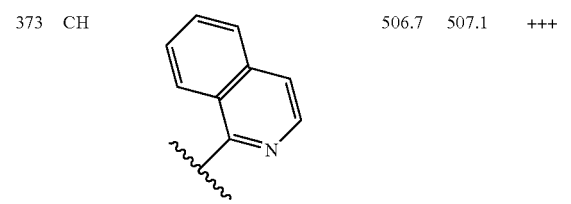 | 506.7 | 507.1 | +++ |
| 374 | CH | 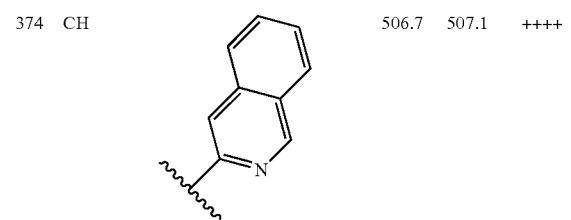 | 506.7 | 507.1 | ++++ |
| 375 | CH | 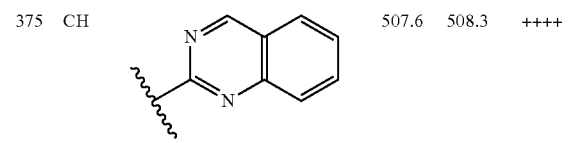 | 507.6 | 508.3 | ++++ |
| 376 | CH | 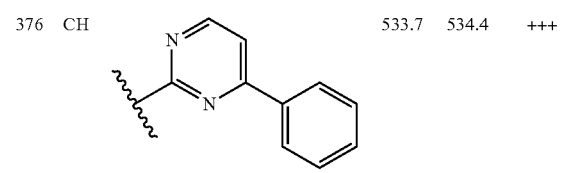 | 533.7 | 534.4 | +++ |
| 377 | N | 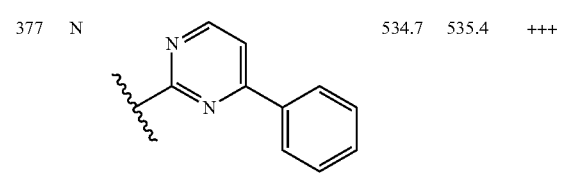 | 534.7 | 535.4 | +++ |
TABLE 9-continued
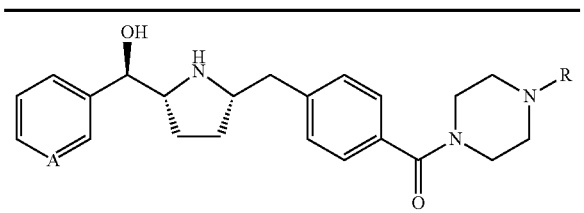
| Example (Ex.) # | A | R | MW | MS (MH)+ | Human β3 agonist functional activity |
|---|---|---|---|---|---|
| 378 | CH | 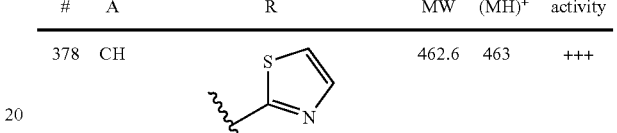 | 462.6 | 463 | +++ |
| 379 | N | 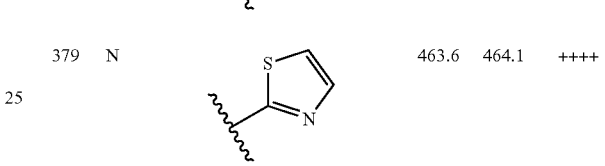 | 463.6 | 464.1 | ++++ |
| 380 | CH | 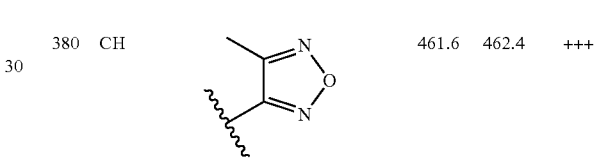 | 461.6 | 462.4 | +++ |
| 381 | CH | 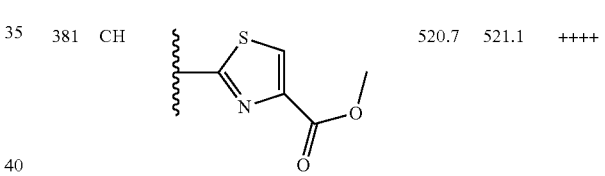 | 520.7 | 521.1 | ++++ |
| 382 | CH | 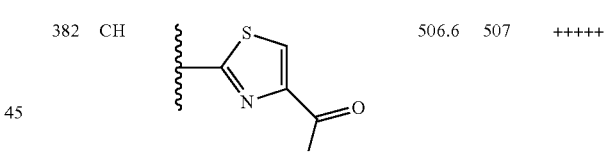 | 506.6 | 507 | +++++ |
| 383 | CH | 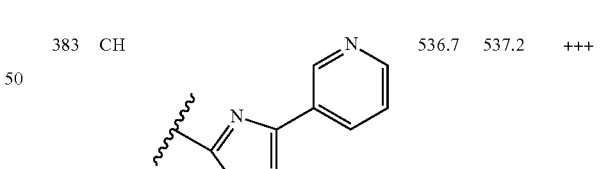 | 536.7 | 537.2 | +++ |
| 384 | CH | 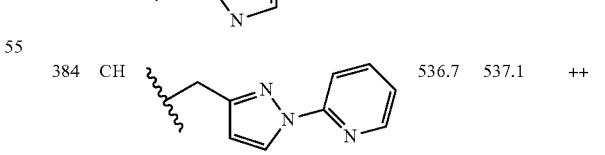 | 536.7 | 537.1 | ++ |
| 385 | CH | 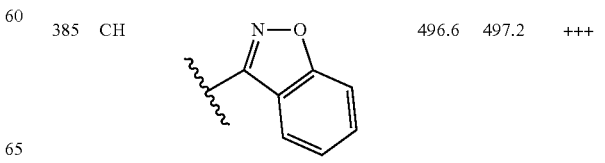 | 496.6 | 497.2 | +++ |

TABLE 9-continued
| Example (Ex.) # | A | R | MW | MS (MH)+ | Human β3 agonist functional activity |
|---|---|---|---|---|---|
| 386 | CH | 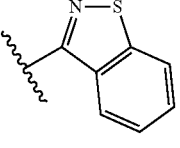 [SMILES: *c1nsc2ccccc12] | 512.7 | 513 | +++ |
| 387 | CH | 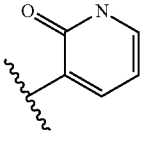 | 472.6 | 473.3 | +++ |
| 388 | CH | 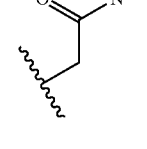 | 436.6 | 437.1 | ++++ |
| 389 | CH | 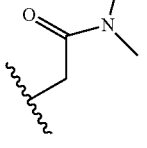 | 464.6 | 465.2 | ++++ |
| 390 | CH | 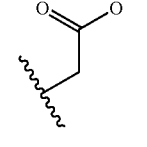 | 437.5 | 438.1 | ++++ |
| 391 | CH | 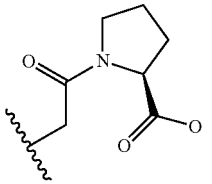 [SMILES: *CC(=O)N1CCC[C@H]1C(=O)O] | 534.7 | 535.2 | ++++ |
| 392 | CH | 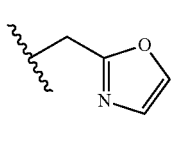 [SMILES: *Cc1ncco1] | 460.6 | 461 | +++ |
| 393 | CH | 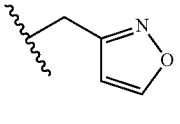 [SMILES: *Cc1ccon1] | 460.6 | 461.1 | +++ |
| 394 | CH | 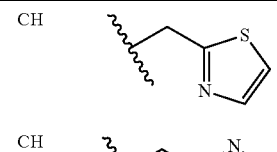 | 476.6 | 477.1 | +++ |
| 395 | CH | 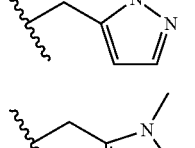 | 459.6 | 460 | +++ |
| 396 | CH | 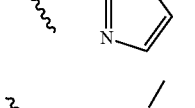 | 473.6 | 474.3 | ++++ |
| 397 | CH | 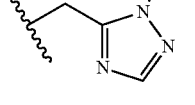 | 474.6 | 475.1 | +++ |
| 398 | CH | 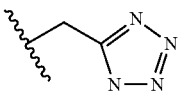 | 461.6 | 462.1 | +++ |
| 399 | CH | 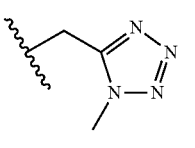 [SMILES: *Cc1nnnn1C] | 475.6 | 476.2 | +++ |
| 400 | CH | 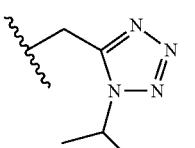 | 503.7 | 504.2 | +++ |
| 401 | CH | 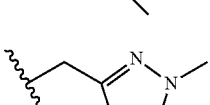 | 475.6 | 476.2 | +++ |
| 402 | CH | 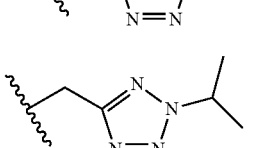 | 503.7 | 504.2 | +++ |
| 403 | CH | 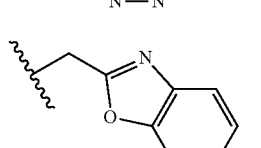 | 510.6 | 511.3 | ++ |

TABLE 9-continued
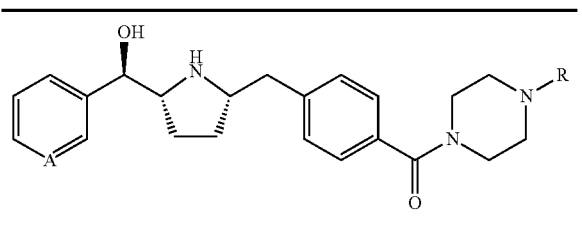
| Example (Ex.) # | A | R | MW | MS (MH)+ | Human β3 agonist functional activity |
|---|---|---|---|---|---|
| 404 | CH | 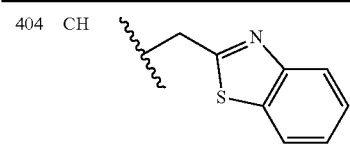 | 526.7 | 527.3 | +++ |
| 405 | CH | 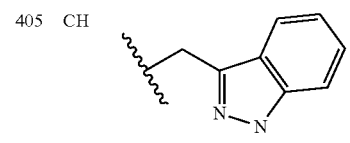 | 509.7 | 510.2 | ++ |
| 406 | CH | 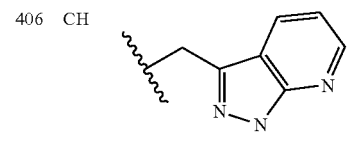 | 510.6 | 511.1 | +++ |
| 407 | CH | 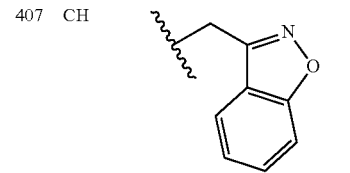 | 510.6 | 511.1 | ++ |
| 408 | CH | 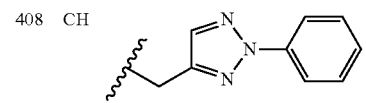 | 536.7 | 537.2 | ++ |
| 409 | CH | 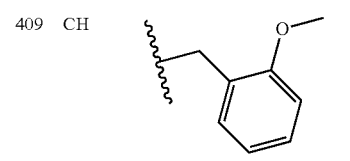 | 499.7 | 500.1 | +++ |
| 410 | CH | 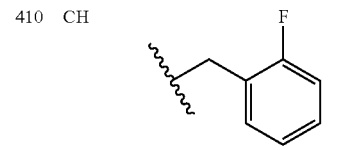 | 487.6 | 488.2 | +++ |
| 411 | CH | 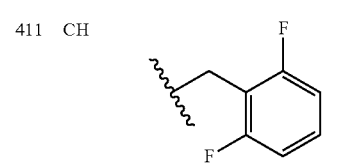 | 505.6 | 506.2 | ++ |
TABLE 9-continued
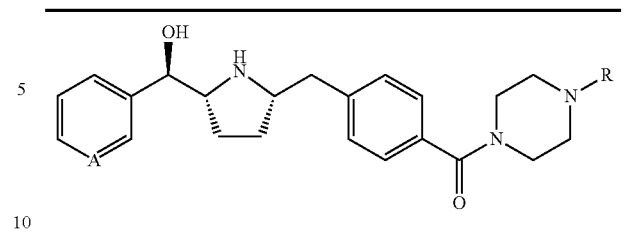
| Example (Ex.) # | A | R | MW | MS (MH)+ | Human β3 agonist functional activity |
|---|---|---|---|---|---|
| 412 | CH | 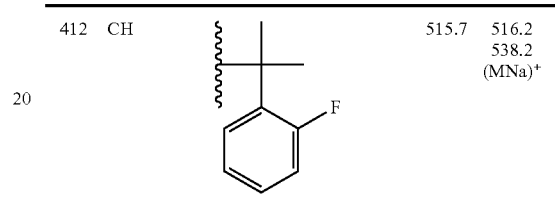 | 515.7 | 516.2 538.2 (MNa)+ | ++ |
| 413 | CH | 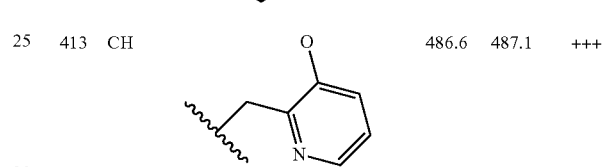 | 486.6 | 487.1 | +++ |
| 414 | CH | 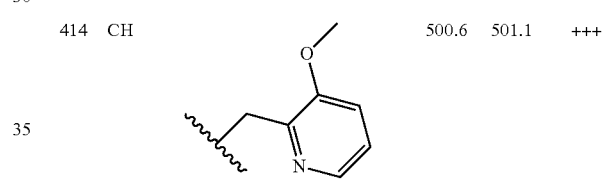 | 500.6 | 501.1 | +++ |
| 415 | CH | 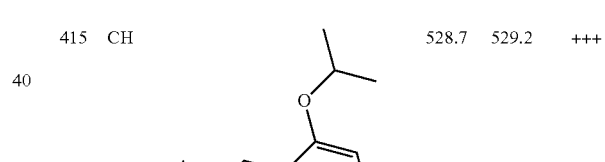 | 528.7 | 529.2 | +++ |
| 416 | CH | 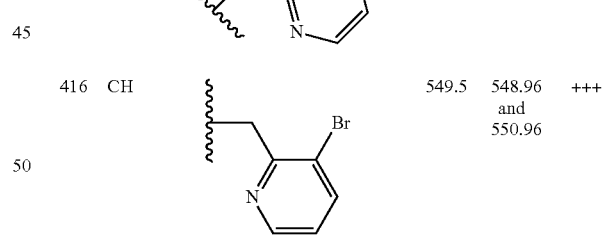 | 549.5 | 548.96 and 550.96 | +++ |
| 417 | CH | 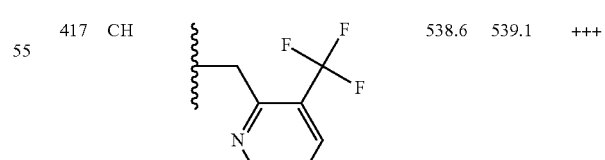 | 538.6 | 539.1 | +++ |
| 418 | CH | 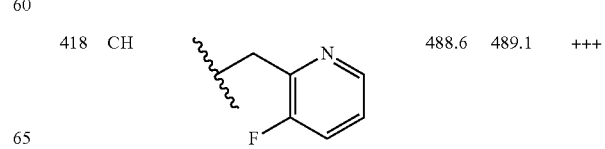 | 488.6 | 489.1 | +++ |

TABLE 9-continued
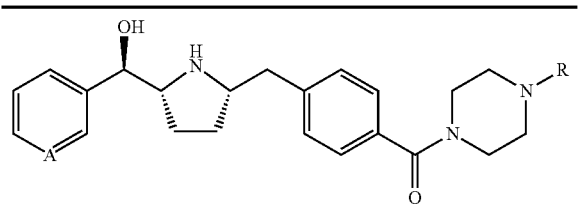
| Example (Ex.) # | A | R | MW | MS (MH)+ | Human β3 agonist functional activity |
|---|---|---|---|---|---|
| 419 | CH | 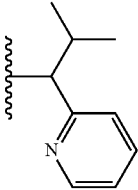 [SMILES: *C(c1ccccn1)C(C)C] | 512.7 | 513.2 | +++ |
| 420 | CH | 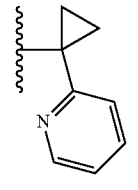 | 496.7 | 497.2 | ++++ |
| 421 | CH | 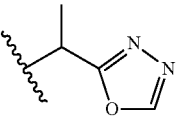 [SMILES: *C(C)c1nnco1] | 475.6 | 476.1 | +++ |
| 422 | CH | 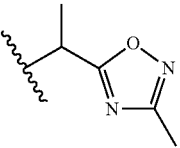 [SMILES: *C(C)c1nc(C)no1] | 489.6 | 490.1 | +++ |
| 423 | CH | 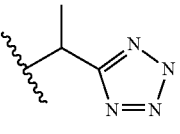 [SMILES: *C(C)c1nn[nH]n1] | 475.6 | 476.2 | +++ |
| 424 | CH | 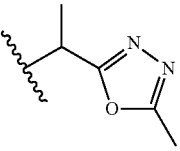 [SMILES: *C(C)c1nnc(C)o1] | 489.6 | 490.1 | ++++ |
| 425 | CH | 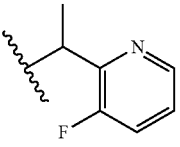 [SMILES: *C(C)c1ncccc1F] | 502.6 | 503.1 | +++ |
| 426 | CH | 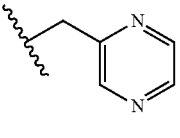 [SMILES: *Cc1cnccn1] | 471.6 | 472.2 | +++ |
TABLE 9-continued
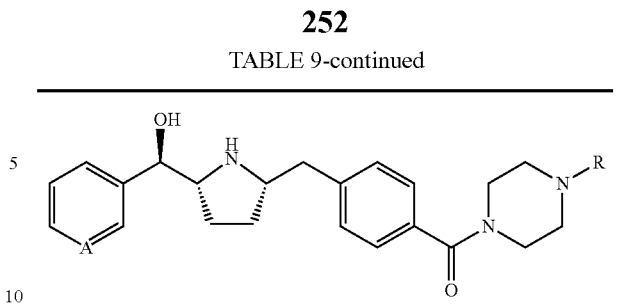
| Example (Ex.) # | A | R | MW | MS (MH)+ | Human β3 agonist functional activity |
|---|---|---|---|---|---|
| 427 | CH | 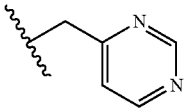 | 471.6 | 472.2 | +++ |
| 428 | CH | 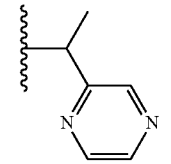 [SMILES: *C(C)c1cnccn1] | 485.6 | 486.04 | +++ |
| 429 | CH | 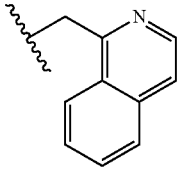 [SMILES: *Cc1nccc2ccccc12] | 520.7 | 521.3 | +++ |
| 430 | CH | 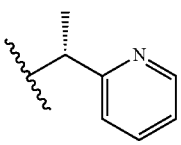 [SMILES: *[C@H](C)c1ccccn1] | 484.6 | 485.2 | ++ |
| 431 | CH | 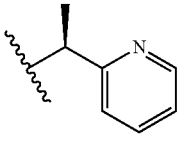 [SMILES: *[C@@H](C)c1ccccn1] | 484.6 | 485.2 | +++ |
less than 1 nM (+);
1-9.9 nM (++);
10-99.9 nM (+++);
100-999 nM (++++); and
greater than 999 nM but less than 3000 nM (+++++).

Example 432

(R)-{(2R,5S)-5-[4-({4-{2-(3,3,-Difluoropyrrolidin-1-yl)-1-methyl-2-oxoethyl]piperazine-1-yl}carbonyl)benzyl}pyrrolidin-2-yl)(phenyl)methanol, TFA salt (Ex. 432)

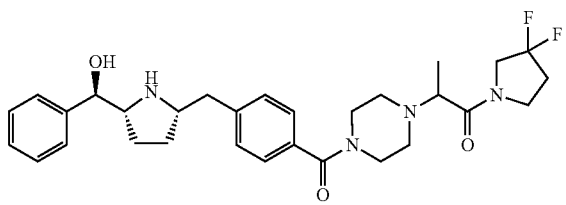 [SMILES: CC(C(=O)N1CCC(F)(F)C1)N1CCN(C(=O)c2ccc(C[C@@H]3CC[C@H]([C@H](O)c4ccccc4)N3)cc2)CC1]

Step A: tert-Butyl-(2S,5R)-2-[4-({4-[2-(3,3-difluoropyrrolidin-1-yl)-1-methyl-2-oxoethyl]piperazin-1-yl}carbonyl)benzyl-]-5-[(R)-hydroxyl(phenyl)methyl]pyrrolidine-1-carboxylate

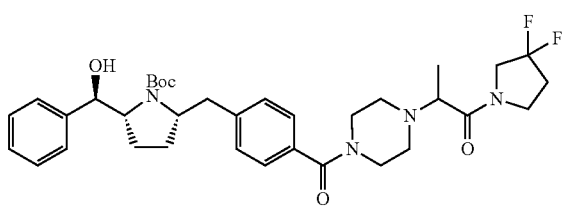 [SMILES: CC(C(=O)N1CCC(F)(F)C1)N1CCN(C(=O)c2ccc(C[C@@H]3CC[C@H]([C@H](O)c4ccccc4)N3C(=O)OC(C)(C)C)cc2)CC1]

To a stirred solution of 12 mg (0.049 mmol) of 4-(2-(3,3-Difluoropyrrolidin-1-yl)-1-methyl-2-oxoethyl)piperazine (TEA salt), and 20 mg (0.049 mmol) of 4-({(2S,5R)-1-(tert-butoxycarbonyl)-5-[(R)-hydroxy(phenyl)methyl]pyrrolidin-2-yl}methyl)benzoic acid (i-1) in 1 mL anhydrous N,N-dimethylformamide under nitrogen atmosphere was added 0.042 mL (0.24 mmol) of N,N-diisopropylethylamine and 37 mg (0.097 mmol) of 2-(1H-7-azabezotriazole-1-yl)-1,1,3,3,-tetramethyl uranium hexafluoro phosphate methanium. The resulting reaction mixture was stirred at ambient temperature overnight. The reaction was purified by reverse-phase HPLC (TMC Pro-Pac C18; 10-100% 0.1% trifluoroacetic acid in acetonitrile/0.1% trifluoroacetic acid in water gradient) to give 23 mg of the title compound. LC/MS: (M+1)=641.2.

Step B: (R)-{(2-R,5S)-5-[4-({4-{2-(3,3-Difluoropyrrolidin-1-yl)-1-methyl-2-oxoethyl]piperazine-1-yl}carbonyl)benzyl}pyrrolidin-2-yl)(phenyl)methanol, TFA salt (Ex. 432)

A solution of 23 mg of the title compound from Step A above in 1 mL dichloromethane and 1 mL trifluoroacetic acid was stirred at ambient temperature for 1 h. All volatiles were removed in vacuo. The reaction was purified by reverse-phase HPLC (TMC Pro-Pac C18; 10-100% 0.1% trifluoroacetic acid in acetonitrile/0.1% trifluoroacetic acid in water gradient) to give 15 mg of the title compound. LC/MS: (M+1) 541.2. $^1$H NMR (500 MHz, CD$_3$OD) δ: 7.78 (s, 1H), 7.35-7.47 (m, 7H), 6.53 (s, 1H), 4-67-4.86 (m, 3H), 3.06-3.84 (m, 8H), 1.38-2.80 (m, 6H)

Using the Beta-3 agonist in vitro functional assay described above the human Beta-3 agonist functional activity was determined to be between 10-99.9 nM.

Examples 433-523

Ex. 433-Ex. 523

Using procedures similar to those described above, Examples 433-523 were prepared from the appropriate starting materials.

Using the Beta-3 agonist in vitro functional assay described above the human Beta-3 agonist functional activity of each compound was determined and shown in Table 10 as the following ranges:

TABLE 10

| Example | R | MW | MS (MH)$^+$ | Human β3 agonist functional activity |
|---|---|---|---|---|
| 433 | —OH | 451.6 | 452.1 | ++ |
| 434 | —OMe | 465.6 | 466.1 | ++ |
| 435 | –N(Me) | 464.6 | 465.3 | +++ |
| 436 | –N(Et) | 478.6 | 479.3 | ++++ |

TABLE 10-continued
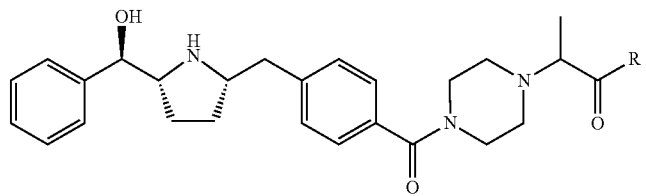
| Example | R | MW | MS (MH)+ | Human β3 agonist functional activity |
|---|---|---|---|---|
| 437 | ⤳N(iPr) | 492.7 | 493.3 | ++++ |
| 438 | ⤳N-CH2CH2CH(CH3)2 | 520.7 | 521.4 | ++++ |
| 439 | ⤳N-C(CH3)2CH2CH3 | 520.7 | 521.4 | ++ |
| 440 | ⤳N-CH(CH3)CH2CH3 | 506.7 | 507.3 | +++ |
| 441 | ⤳N-CH(CH3)CH(CH3)2 | 520.7 | 521.4 | +++ |
| 442 | ⤳N-CH2CH2OCH3 | 508.7 | 509.3 | ++++ |
| 443 | ⤳N-CH2C(CH3)2-O | 522.7 | 523.3 | +++ |
| 444 | ⤳N-C(CH3)2CH2OH | 522.7 | 523.3 | ++++ |
| 445 | ⤳NH-CH2C(O)N | 507.6 | 508.3 | ++++ |
| 446 | ⤳NH-CH(CH3)CH2OCH3 | 522.7 | 523.3 | +++ |
| 447 | ⤳N-CH2-cyclopropyl | 504.7 | 505.3 | +++ |
| 448 | ⤳N-CH2CH2-cyclopropyl | 518.7 | 519.3 | +++ |

TABLE 10-continued

| Example | R | MW | MS (MH)+ | Human β3 agonist functional activity |
|---|---|---|---|---|
| 449 | N-CH2-(1-oxaspiro cyclopropane) | 520.7 | 521.3 | +++ |
| 450 | N-CH2-(2,2-dimethylcyclopropyl) | 532.7 | 533.4 | +++ |
| 451 | N-CH(cyclopropyl)2 | 544.7 | 545.3 | +++ |
| 452 | N-CH2-cyclobutyl | 518.7 | 519.3 | ++ |
| 453 | N-CH2-(1-methylcyclobutyl) | 532.7 | 533.3 | ++ |
| 454 | N-CH2-(3-isopropylcyclobutyl) | 560.8 | 561.4 | +++ |
| 455 | N-CH2-(tetrahydrofuran-2-yl) | 534.7 | 535.3 | +++ |
| 456 | N-cyclopentyl | 518.7 | 519.3 | +++ |
| 457 | N-(tetrahydrofuran-3-yl) | 520.7 | 521.3 | +++ |

TABLE 10-continued
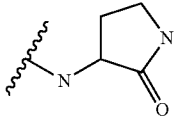 [SMILES: *NC1CCNC1=O]
| Example | R | MW | MS (MH)+ | Human β3 agonist functional activity |
|---|---|---|---|---|
| 458 | 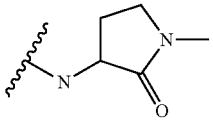 [SMILES: *NC1CCN(C)C1=O] | 533.7 | 534.3 | ++++ |
| 459 | 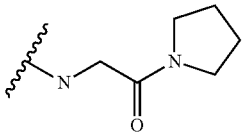 [SMILES: *NCC(=O)N1CCCC1] | 547.7 | 548.3 | + |
| 460 | 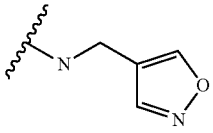 [SMILES: *NCc1cnoc1] | 561.7 | 562.3 | +++ |
| 461 | 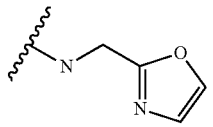 [SMILES: *NCc1ncco1] | 531.7 | 532.3 | +++ |
| 462 | 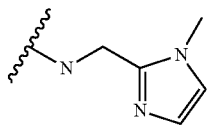 [SMILES: *NCc1nccn1C] | 531.7 | 532.3 | +++ |
| 463 | 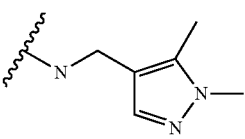 [SMILES: *NCc1cnn(C)c1C] | 544.7 | 545.3 | ++++ |
| 464 | 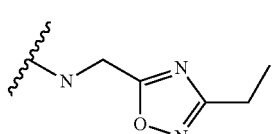 | 558.7 | 559.4 | +++ |
| 465 | 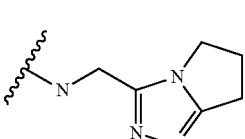 | 560.7 | 561.3 | +++ |
| 466 |  | 571.7 | 572.3 | ++++ |

TABLE 10-continued
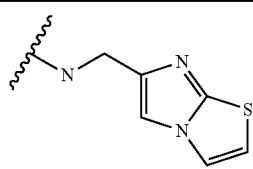
| Example | R | MW | MS (MH)+ | Human β3 agonist functional activity |
|---|---|---|---|---|
| 467 | 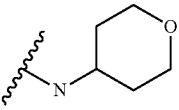 | 586.8 | 587.3 | +++ |
| 468 | 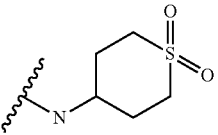 | 534.7 | 535.3 | ++++ |
| 469 | 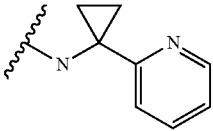 [SMILES: *NC1(c2ccccn2)CC1] | 582.8 | 583.3 | +++ |
| 470 | 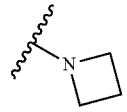 | 567.7 | 568.3 | +++ |
| 471 | 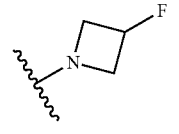 [SMILES: *N1CC(F)C1] | 490.7 | 491.3 | ++ |
| 472 | 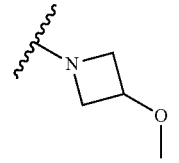 [SMILES: *N1CC(OC)C1] | 508.6 | 509.1 | ++ |
| 473 | 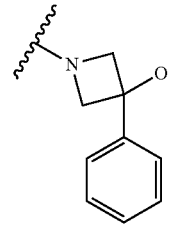 [SMILES: *N1CC(O)(c2ccccc2)C1] | 520.7 | 521.3 | +++ |
| 474 | | 582.7 | 583.3 | ++ |

TABLE 10-continued
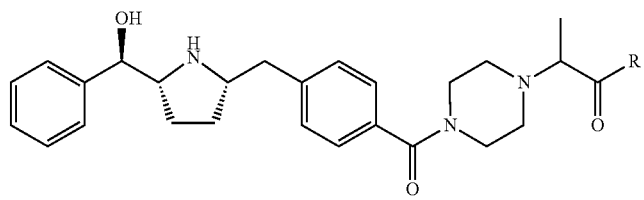
| Example | R | MW | MS (MH)+ | Human β3 agonist functional activity |
|---|---|---|---|---|
| 475 | | 522.7 | 523.2 | ++ |
| 476 | | 540.7 | 541.3 | +++ |
| 477 | | 520.7 | 521.3 | ++++ |
| 478 | | 547.7 | 548.3 | ++++ |
| 479 | | 532.7 | 533.4 | +++ |
| 480 | | 518.7 | 519.3 | +++ |
| 481 | | 522.7 | 523.3 | ++++ |
| 482 | | 553.7 | 554.4 | +++ |

TABLE 10-continued

| Example | R | MW | MS (MH)+ | Human β3 agonist functional activity |
|---|---|---|---|---|
| 483 | 5,7-dihydropyrrolo[3,4-d]pyrimidin-6-yl | 554.7 | 555.3 | ++++ |
| 484 | piperidin-1-yl | 519.3 | 518.7 | +++ |
| 485 | 2-methylpiperidin-1-yl | 532.7 | 533.4 | +++ |
| 486 | 3-methylpiperidin-1-yl | 532.7 | 533.4 | +++ |
| 487 | 3-(trifluoromethyl)piperidin-1-yl | 586.7 | 587.3 | ++ |
| 488 | 4-methylpiperidin-1-yl | 532.7 | 533.4 | ++++ |
| 489 | 4-oxopiperidin-1-yl | 534.7 | 535.3 | +++ |
| 490 | 4-(hydroxymethyl)piperidin-1-yl | 548.7 | 549.3 | +++ |

TABLE 10-continued
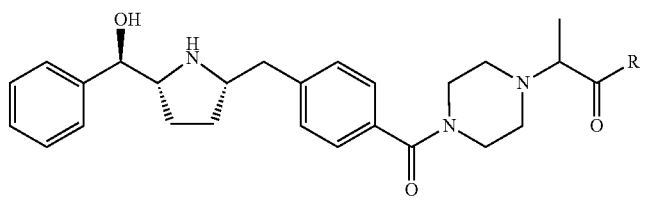
| Example | R | MW | MS (MH)+ | Human β3 agonist functional activity |
|---|---|---|---|---|
| 491 | N-piperidine-F | 536.7 | 537.3 | +++ |
| 492 | tetrahydropyridine | 516.7 | 517.3 | +++ |
| 493 | spiro cyclopropane piperidine | 544.7 | 545.3 | +++ |
| 494 | 4-cyclopropylpiperidine | 558.8 | 559.4 | +++ |
| 495 | oxetane spiro piperidine | 560.7 | 561.3 | +++ |
| 496 | spiro cyclobutane piperidine | 558.8 | 559.4 | +++ |
| 497 | oxolane spiro piperidine | 574.8 | 575.4 | +++ |

TABLE 10-continued
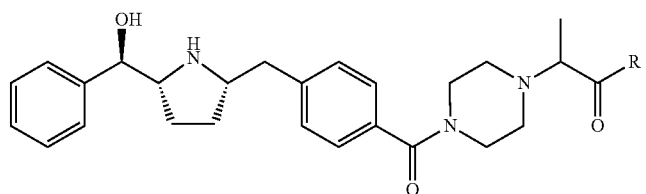
| Example | R | MW | MS (MH)+ | Human β3 agonist functional activity |
|---|---|---|---|---|
| 498 | | 588.8 | 589.4 | +++ |
| 499 | | 520.7 | 521.3 | ++++ |
| 500 | | 532.7 | 533.3 | +++ |
| 501 | | 530.7 | 531.4 | ++++ |
| 502 | | 556.7 | 557.3 | +++ |
| 503 | | 557.7 | 558.3 | +++ |
| 504 | | 571.7 | 572.3 | ++ |

TABLE 10-continued
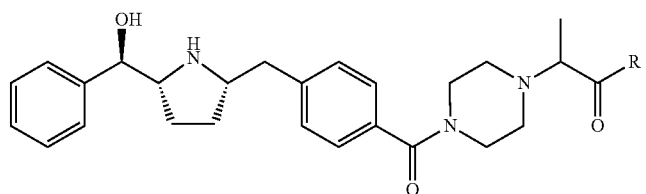
| Example | R | MW | MS (MH)+ | Human β3 agonist functional activity |
|---|---|---|---|---|
| 505 | (N-linked 2-cyclopropyl-4,5,6,7-tetrahydrothiazolo-pyridine) | 613.8 | 614.3 | + |
| 506 | (tetrahydro-2,7-naphthyridine) | 567.7 | 568.3 | +++ |
| 507 | (tetrahydro-1,6-naphthyridine) | 567.7 | 568.4 | +++ |
| 508 | (tetrahydro-2,6-naphthyridine) | 567.7 | 568.3 | +++ |
| 509 | (7-fluoro-tetrahydroisoquinoline) | 584.7 | 585.3 | ++ |
| 510 | (7-chloro-tetrahydroisoquinoline) | 601.2 | 601.3 | ++ |

TABLE 10-continued
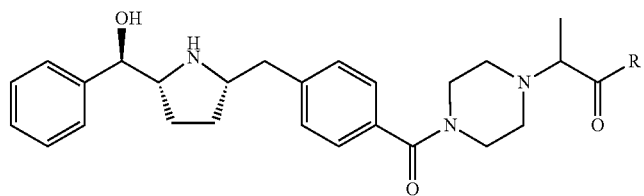
| Example | R | MW | MS (MH)+ | Human β3 agonist functional activity |
|---|---|---|---|---|
| 511 | (azepan-1-yl) | 532.7 | 533.3 | ++++ |
| 512 | (N-methyl-N-((4-methyl-1,2,5-oxadiazol-3-yl)methyl)amino) | 560.7 | 561.3 | +++ |
| 513 | (N,N-dimethylamino) | 478.6 | 479.3 | ++ |
| 514 | (N-butyl-N-methylamino) | 520.7 | 521.4 | +++ |
| 515 | (N-ethyl-N-isopropylamino) | 520.7 | 521.4 | +++ |
| 516 | (N,N-diethylamino) | 506.7 | 507.3 | ++++ |
| 517 | (N-tert-butyl-N-methylamino) | 520.7 | 521.4 | ++++ |
| 518 | (N-isobutyl-N-methylamino) | 520.7 | 521.4 | ++++ |
| 519 | (N-(2-methoxyethyl)-N-methylamino) | 508.7 | 509.3 | ++++ |

TABLE 10-continued

[Structure with OH, phenyl, pyrrolidine, benzyl, piperazine carbonyl, and R group]

| Example | R | MW | MS (MH)+ | Human β3 agonist functional activity |
|---------|---|-----|----------|--------------------------------------|
| 520 | [N-ethyl-N-(2-hydroxyethyl)amino group] | 522.7 | 523.3 | +++ |
| 521 | [N-methyl-N-(2-cyanoethyl)amino group] | 517.7 | 518.3 | +++ |
| 522 | [N,N-dicyclopropylamino group] | 530.7 | 531.4 | +++ |
| 523 | [N-methyl-N-(dicyclopropylmethyl)amino group] | 558.8 | 559.4 | +++ | less than 1 nM (+);
1-9.9 nM (++);
10-99.9 nM (+++);
100-999 nM (++++); and
greater than 999 nM but less than 3000 nM (+++++).

Example 524

(R)-phenyl[(2R,5S)-5-(4-{[10-(pyridin-2-ylmethyl)-9,10-diazatricyclo[4.2.1.1²,⁵]dec-9-yl]carbonyl}benzyl)pyrrolidin-2-yl]methanol (Ex. 524)

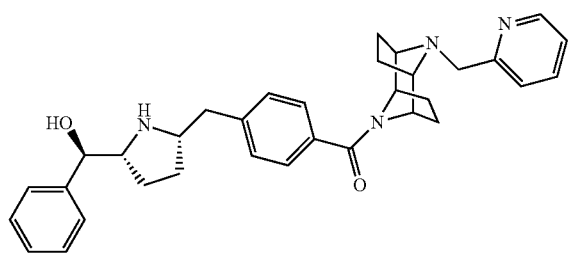 [SMILES: O=C(c1ccc(C[C@@H]2CC[C@H]([C@H](O)c3ccccc3)N2)cc1)N1C2CCC1C1CCC2N1Cc1ccccn1]

Step A: Tert-butyl (1R,2R,5S,6S)-10-(pyridin-2-ylmethyl)-9,10-diazatricyclo[4.2.1.1.²,⁵]decane-9-carboxylate

[Structure of tert-butyl carbamate with diazatricyclodecane and pyridylmethyl group]

To a solution of tert-butyl (1R,2R,5S,6S)-9,10-diazatricyclo[4.2.1.1.²,⁵]decane-9-carboxylate (100 mg, 0.54 mmol) and 2-(bromomethyl)piperidine (209 mg, 1.58 mmol) in DMF (5.0 mL) was added solid potassium carbonate (87 mg, 0.54 mmol) and the resulting mixture heated to 60° C. overnight. The mixture was cooled and poured into water. The mixture was extracted with ethyl acetate (3×25 mL) and the organics combined, dried, filtered and concentrate. The residue was purified via preparative TLC plate (2×1000 μM) eluting with 2.5% methanol in dichloromethane to afford the title compound (88 mg, 61%). ESI-MS calculated for $C_{19}H_{27}N_3O_2$: Exact Mass: 329.21. Found 330.30.

Step B: (1R,2R,5S,6S)-9-(pyridin-2-ylmethyl)-9,10-diazatricyclo[4.2.1.1.$^{2,5}$]decane

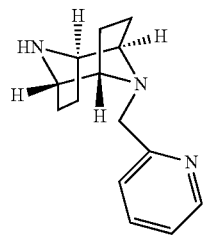 [SMILES: c1ccc(CN2[C@@H]3CC[C@H]2[C@@H]2CC[C@H]3N2)nc1]

The title compound from Step A above (80 mg, 0.24 mmol was dissolved in 4 M HCl in dioxane plus 10% water (v/v) (2 mL) and stirred at RT for 2 h. The mixture was concentrated under reduced pressure and dried under high vacuum to give (R)-phenyl[(2R,5S)-5-(4-{[4-(1,3-thiazol-4-yl)-piperidin-1-yl]carbonyl}benzyl)pyrrolidine-2-yl]methanol. ESI-MS calculated for $C_{14}H_{19}N_3$: Exact Mass: 229.29. Found 230.24.

Step C: Tert-butyl (2R,5S)-2-[(R)-hydroxy(phenyl)methyl]-5-(4-{[10-(pyridin-2-ylmethyl)-9,10-diazatricyclo[4.2.1.1$^{2,5}$]dec-9-yl]carbonyl}benzyl)pyrrolidine-1-carboxylate

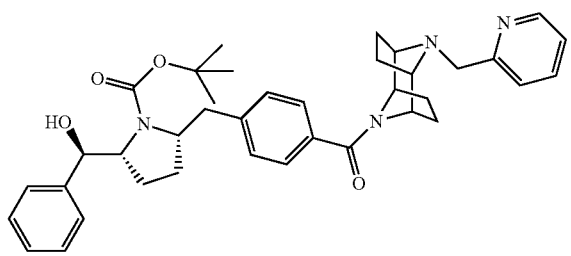 [SMILES: CC(C)(C)OC(=O)N1[C@H](Cc2ccc(C(=O)N3C4CCC3C3CCC4N3Cc3ccccn3)cc2)CC[C@@H]1[C@H](O)c1ccccc1]

To a solution of 4-{((2s,5R)-1-(tert-butoxycarbonyl)-5-[(R)-hydroxy(phenyl)methyl]pyrrolidin-2-yl)methyl}benzoic acid (50 mg, 0.13 mmol) and the title compound from Step B above (37 mg, 0.13 mmol) in 1.5 mL anhydrous DMF was added a 0.5 M solution of HOAt in DMF (0.24 mL, 0.13 mmol) followed by EDC (46 mg, 0.26 mmol) and DIEA (17 μL, 0.13 mmol). The resulting mixture was stirred at RT under nitrogen atmosphere for 16 h. The mixture was washed with water and extracted with dichloromethane (2×5 mL). The organics were combined, dried over sodium sulfate, filtered and concentrated in vacuum. The residue was purified by preparative TLC plate (1000 uM) eluting with 5% MeOH in dichloromethane to afforded the product (32 mg, 42%). ESI-MS calculated for $C_{38}H_{46}N_4O_4$: Exact Mass: 622.35. Found 623.38 (MH)$^+$ and 645.33 (MNa)$^+$.

Step D: (R)-phenyl[(2R,5S)-5-(4-{[10-(pyridin-2-ylmethyl)-9,10-diazatricyclo[4.2.1.1$^{2,5}$]dec-9-yl]carbonyl}benzyl)pyrrolidin-2-yl]methanol (Ex. 524)

The title compound from Step C above (30 mg, 0.06 mmol was dissolved in 4 M HCl in dioxane plus 10% water (v/v) (2 mL) and stirred at RT for 2 h. The mixture was concentrated under reduced pressure and dried under high vacuum to give the title compound. ESI-MS calculated for both is $C_{33}H_{36}N_4O_2$: Exact Mass: 522.32. Found 523.30.

Using the Biological Assays as described above, the human β3 functional activity was determined to be between 10 to 99.9 nM.

Example 525

(R)-phenyl[(2R,5S)-5-(4-{[10-[(1R)-1-pyridin-2-ylethyl)]-9,10-diazatricyclo[4.2.1.1$^{2,5}$]dec-9-yl]carbonyl}benzyl)pyrrolidin-2-yl]methanol (Ex. 525)

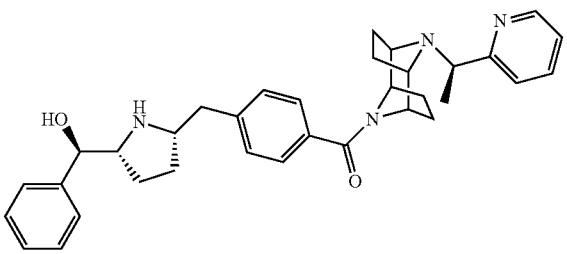 [SMILES: C[C@H](c1ccccn1)N1C2CCC1C1CCC2N1C(=O)c1ccc(C[C@@H]2CC[C@H]([C@H](O)c3ccccc3)N2)cc1]

Step A: (1R)-1-pyridin-2-ylethyl methanesulfonate

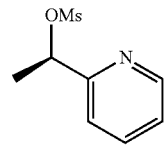

To a solution of (1R)-1-pyridin-2-ylethanol (250 mg, 2.03 mmol) and DMAP (496 mg, 4.06 mmol) in DCM (8 mL) was added MsCl (190 μL, 2.44 mmol) at 0° C. The mixture was stirred for 10 min at the same temperature and for an additional hour at RT. The mixture was quenched with ice water and extracted with ethyl acetate (2×15 mL). The organic layer was washed with water and brine, dried over sodium sulfate, filtered, and concentrated under vacuum. The residue oil was purified via prep-plate purification (1000 μM) eluting with 60% ethyl acetate in hexane to afford the product (310 mg, 76%).

Step B: Tert-butyl (1R,2R,5S,6S)-10-[(1R)-1-pyridin-2-ylethyl)]-9,10-diazatricyclo[4.2.1.1.$^{2,5}$]decane-9-carboxylate

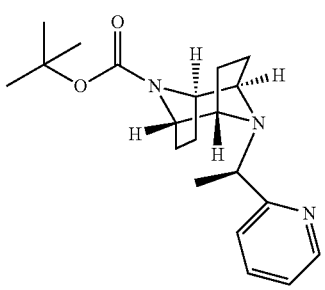 [SMILES: C[C@H](c1ccccn1)N1[C@@H]2CC[C@H]1[C@@H]1CC[C@H]2N1C(=O)OC(C)(C)C]

To a solution of tert-butyl (1R,2R,5S,6S)-9,10-diazatricyclo[4.2.1.1.$^{2,5}$]decane-9-carboxylate (100 mg, 0.54 mmol) and the title compound from Step A above (209 mg, 1.58 mmol) in DMF (5.0 mL) was added solid potassium carbonate (87 mg, 0.54 mmol) and the resulting mixture heated to 60° C. overnight. The mixture was cooled and poured into water. The mixture was extracted with ethyl acetate (3×25 mL) and the organics combined, dried, filtered and concentrated. The residue was purified via preparative TLC plate (2×1000 μM) eluting with 2.5% methanol in dichloromethane to afford the title compound (88 mg, 61%). ESI-MS calculated for $C_{20}H_{29}N_3O_2$: Exact Mass: 343.21. Found 344.30.

Step C: (1R,2R,5S,6S)-9-[(1R)-1-pyridin-2-ylethyl)-9,10-diazatricyclo[4.2.1.1.$^{2,5}$]decane

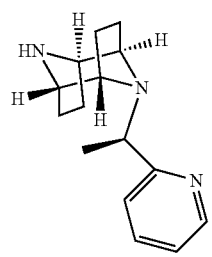 [SMILES: C[C@H](c1ccccn1)N1[C@@H]2CC[C@H]1[C@@H]1CC[C@H]2N1]

The title compound from Step B above (80 mg, 0.24 mmol) was dissolved in 4 M HCl in dioxane plus 10% water (v/v) (2 mL) and stirred at RT for 2 h. The mixture was concentrated under reduced pressure and dried under high vacuum to give ((1R,2R,5S,6S)-9-[(1R)-1-pyridin-2-ylethyl)-9,10-diazatricyclo[4.2.1.1.$^{2,5}$]decane. ESI-MS calculated for $C_{15}H_{21}N_3$: Exact Mass: 243.17. Found 244.18.

Step D: Tert-butyl (2R,5S)-2-[(R)-hydroxy(phenyl)methyl]-5-(4-{[10-pyridin-2-ylmethyl)-9,10-diazatricyclo[4.2.1.1$^{2,5}$]dec-9-yl]carbonyl}benzyl)pyrrolidine-1-carboxylate

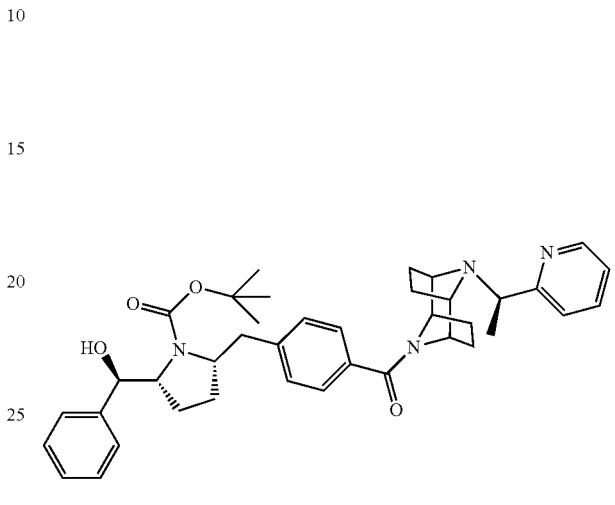

To a solution of 4-{((2S,5R)-1-(tert-butoxycarbonyl)-5-[(R)-hydroxy(phenyl)methyl]pyrrolidin-2-yl) methyl}benzoic acid (50 mg, 0.13 mmol) and the title compound from Step C above (37 mg, 0.13 mmol) in 1.5 mL anhydrous DMF was added a 0.5 M solution of HOAt in DMF (0.24 mL, 0.13 mmol) followed by EDC (46 mg, 0.26 mmol) and DIEA (17 μL, 0.13 mmol). The resulting mixture was stirred at RT under nitrogen atmosphere for 16 h. The mixture was washed with water and extracted with dichloromethane (2×5 mL). The organics were combined, dried over sodium sulfate, filtered and concentrated in vacuum. The residue was purified by preparative TLC plate (1000 uM) eluting with 5% MeOH in dichloromethane to afforded the product (32 mg, 42%). ESI-MS calculated for $C_{39}H_{48}N_4O_4$: Exact Mass: 636.35. Found 637.38 (MH)$^+$ and 659.33 (MNa)$^+$.

Step E: (R)-phenyl[(2R,5S)-5-(4-{[10-(pyridin-2-ylmethyl)-9,10-diazatricyclo[4.2.1.1$^{2,5}$]dec-9-yl]carbonyl}benzyl)pyrrolidin-2-yl]methanol (Ex. 525)

The title compound from Step D above (30 mg, 0.06 mmol) was dissolved in 4 M HCl in dioxane plus 10% water (v/v) (2 mL) and stirred at RT for 2 h. The product was concentrated under reduced pressure and dried under high vacuum to give the title compound. ESI-MS calculated for both is $C_{34}H_{40}N_4O_2$: Exact Mass: 536.32. Found 537.30.

Using the Biological Assays as described above, the human β3 functional activity was determined to be between 10 to 99.9 nM.

Example 526

(R)-phenyl[(2R,5S)-5-(4-{[10-(pyridin-2-ylmethyl)-9,10-diazatricyclo[4.2.1.1$^{2,5}$]dec-9-yl]carbonyl}benzyl)pyrrolidin-2-yl]methanol (Ex. 526)

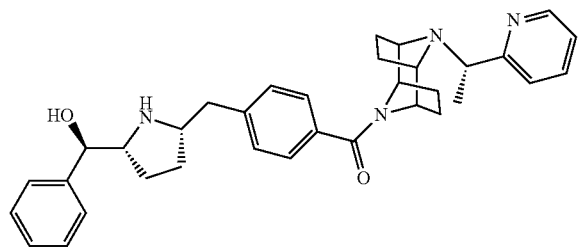 [SMILES: C[C@@H](c1ccccn1)N1C2CCC1C1CCC2N1C(=O)c1ccc(C[C@@H]2CC[C@H]([C@H](O)c3ccccc3)N2)cc1]

The title compound was prepared according to the procedure outlined above for Ex. 525, replacing (1R)-1-pyridine-2-ylethanol with (1S)-1-pyridine-2-ylethanol in Step B. ESI-MS calculated for both is $C_{34}H_{40}N_4O_2$: Exact Mass: 536.32. Found 537.30.

Using the Biological Assays as described above, the human β3 functional activity was determined to be between 10 to 99.9 nM.

Examples 527-552

Ex. 527-Ex. 552

Using procedures similar to those described above, Examples 527-552 were prepared from the appropriate starting materials.

Using the Beta-3 agonist in vitro functional assay described above the human Beta-3 agonist functional activity of each compound was determined and shown in Table 11 as the following ranges:

TABLE 11

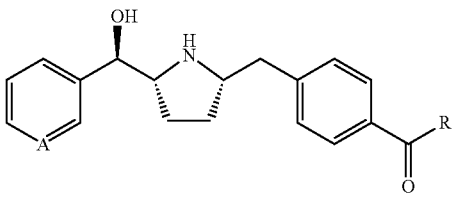

| Example (Ex.) # | A | R | MW | MS (MH)+ | Human β3 agonist functional activity |
|---|---|---|---|---|---|
| 527 | CH | | 484.7 | 485.2 | +++ |
| 528 | CH | | 484.7 | 485.2 | +++ |
| 529 | CH | | 484.7 | 485.2 | ++++ |
| 530 | CH | | 484.7 | 485.2 | +++ |

TABLE 11-continued
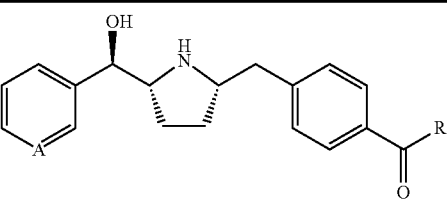
| Example (Ex.) # | A | R | MW | MS (MH)+ | Human β3 agonist functional activity |
|---|---|---|---|---|---|
| 531 | CH | (piperazine-methyl-benzoxazole) | 524.7 | 525.3 | +++ |
| 532 | CH | (piperazine-methyl-indazole) | 523.7 | 524.3 | +++ |
| 533 | CH | (dimethylpiperazine-methyl-pyridine) | 498.7 | 499.3 | ++++ |
| 534 | CH | (diazabicyclic-methyl-pyridine) | 482.6 | 483.3 | ++++ |
| 535 | CH | (diazabicyclic-methyl-pyridine) | 496.7 | 497.3 | ++++ |
| 536 | CH | (diazabicyclic-methyl-pyridine) | 496.7 | 497.3 | ++++ |
| 537 | CH | (diazabicyclic-ethyl-pyridine) | 496.7 | 497.3 | ++++ |

TABLE 11-continued

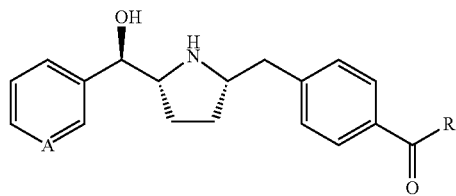

| Example (Ex.) # | A | R | MW | MS (MH)+ | Human β3 agonist functional activity |
|---|---|---|---|---|---|
| 538 | CH | *bicyclic diamine with 2-pyridyl ethyl* | 496.7 | 497.3 | ++++ |
| 539 | CH | *bicyclic diamine with 2-pyridyl ethyl* | 510.7 | 511.4 | +++ |
| 540 | CH | *bicyclic diamine with 2-pyridyl ethyl* | 510.7 | 511.4 | ++++ |
| 541 | CH | *bicyclic diamine with 2-pyridyl ethyl* | 510.7 | 511.5 | ++++ |
| 542 | CH | *bicyclic diamine with 2-pyridyl ethyl* | 510.7 | 511.4 | ++++ |
| 543 | CH | *bicyclic diamine with thiazole* | 488.7 | 489.2 | +++ |
| 544 | CH | *bicyclic diamine with thiazole* | 474.6 | 475.2 | +++++ |

TABLE 11-continued
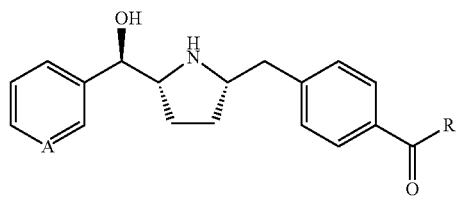
| Example (Ex.) # | A | R | MW | MS (MH)+ | Human β3 agonist functional activity |
|---|---|---|---|---|---|
| 545 | CH | 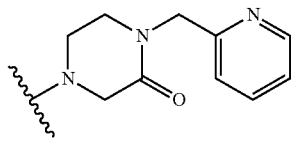 [SMILES: *N1CCN(Cc2ccccn2)C(=O)C1] | 484.6 | 485.1 | ++++ |
| 546 | CH | 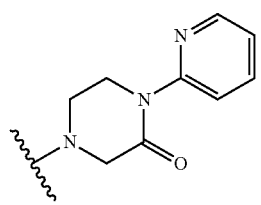 [SMILES: *N1CCN(c2ccccn2)C(=O)C1] | 470.6 | 471.1 | ++++ |
| 547 | CH | 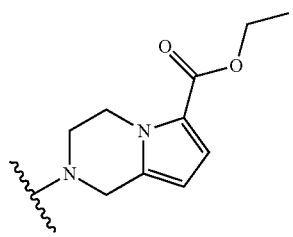 [SMILES: *N1CCn2c(ccc2C(=O)OCC)C1] | 489.6 | 490.4 | ++++ |
| 548 | CH | 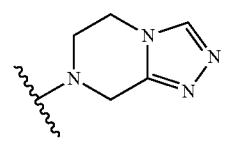 [SMILES: *N1CCn2cnnc2C1] | 417.5 | 418.4 | ++++ |
| 549 | CH | 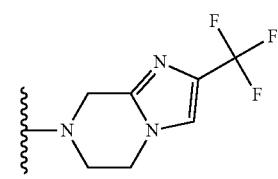 [SMILES: *N1CCn2cc(C(F)(F)F)nc2C1] | 484.5 | 484.2 | ++++ |
| 550 | CH | 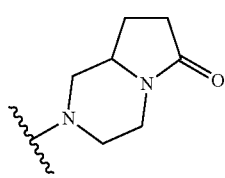 [SMILES: *N1CCN2C(=O)CCC2C1] | 433.6 | 434.1 | ++++ |
| 551 | CH | 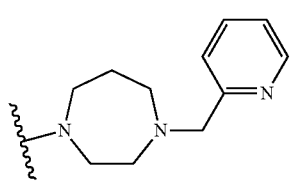 [SMILES: *N1CCCN(Cc2ccccn2)CC1] | 484.6 | 485.1 | +++ |

TABLE 11-continued

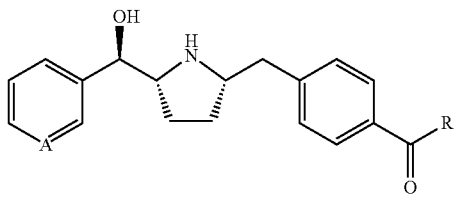

| Example (Ex.) # | A | R | MW | MS (MH)+ | Human β3 agonist functional activity |
|---|---|---|---|---|---|
| 552 | CH | 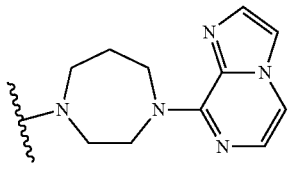 [SMILES: *N1CCCN(c2nccn3ccnc23)CC1] | 510.6 | 511.2 | ++ | less than 1 nM (+);
1-9.9 nM (++);
10-99.9 nM (+++);
100-999 nM (++++); and
greater than 999 nM but less than 3000 nM (+++++).

Example 553 and 554

(3R) 3-Cyclopropyl-8-[4-((2S,5R)-5-[(R)-hydroxy(phenyl)methyl]pyrrolidin-2-yl}methyl)benzoyl]-2-oxa-8-azaspiro[4,5]decan-1-one (Ex. 553) and (3S) 3-Cyclopropyl-8-[4-((2S,5R)-5-[(R)-hydroxy(phenyl)methyl]pyrrolidin-2-yl}methyl)benzoyl]-2-oxa-8-azaspiro[4.5]decan-1-one (Ex. 554)

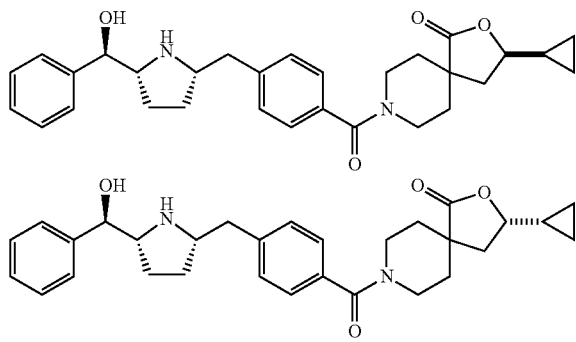

Step A: Tert-butyl(2S,5R)-2-{4-[(3-cyclopropyl-1-oxo-2-oxa-8-azaspiro[4.5]dec-8-yl)carbonyl]-benzyl}-5-[(R)-hydroxy(phenyl)methyl]pyrrolidine-1-carboxylate

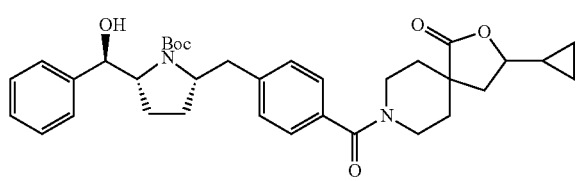 [SMILES: CC(C)(C)OC(=O)N1[C@H](Cc2ccc(C(=O)N3CCC4(CC3)CC(C3CC3)OC4=O)cc2)CC[C@@H]1[C@H](O)c1ccccc1]

To a solution of 0.20 g (0.68 mmol) tert-butyl-3-cyclopropyl-1-oxo-2-oxa-8-azaspiro[4.5]decane-8-carboxylate was added 1 ml 4 M HCl in 1,4-dioxane. The solution was stirred for 1 h. It was concentrated under reduced pressure to give 0.15 g (96%) white solid which was used without further purification. LC/MS 196.2 (M+1).

To a solution of 0.16 g (0.39 mmol) of 4-({(2S,5R)-1-(tert-butoxycarbonyl)-5-[(R)-hydroxy(phenyl)methyl]pyrrolidin-2-yl}methyl)benzoic acid (i-1) in 2 ml anhydrous DMF at ambient temperature was added 0.14 g (0.58 mmol) 3-cyclopropyl-2-oxa-8-azaspiro[4.5]decan-1-one from the above, followed by 0.12 g (0.58 mmol) EDCl, 0.08 g (0.58 mmol) HOBt, and 0.34 ml (1.94 mmol) N,N-diisopropylethylamine. The solution was stirred for 2 h at ambient temperature. The solution was poured into water (20 ml) and extracted with ethyl acetate (2×20 ml). The combined organic layers were extracted with brine (20 ml). It was dried over magnesium sulfate and concentrated. The residue was purified using a Biotage Horizon® system (50-100% ethyl acetate/hexanes mixture) to give 0.135 g of the title compounds as a mixture of diastereomers in a 50:50 ratio. The two diastereomers were separated by chiral HPLC employing a Daicel CHIRAL-PAK® OD® column (eluent: 40% IPA in Heptane). The first eluting diastereomer was designated as Isomer 1 and is colorless solid (0.030 g, 16%). LC/MS 589.3 (M+1). The second eluting diastereomer was designated as Isomer 2 and is a colorless solid (0.025 g, 13%). LC/MS 589.3 (M+1).

Step B: (3R) 3-Cyclopropyl-8-[4-((2S,5R)-5-[(R)-hydroxy(phenyl)methyl]pyrrolidin-2-yl}-methyl)benzoyl]-2-oxa-8-azaspiro[4.5]decan-1-one (Ex. 553) and (3S) 3-Cyclopropyl-8-[4-((2S,5R)-5-[(R)-hydroxy(phenyl)methyl]pyrrolidin-2-yl}methyl)benzoyl]-2-oxa-8-azaspiro[4.5]decan-1-one (Ex. 553)

To a solution of 30 mg (0.05 mmol) Isomer I from step A above in 1 ml anhydrous dichloromethane at ambient temperature was added 0.3 ml trifluoroacetic acid. The solution was stirred for 1 h. It was then evaporated and purified by reverse-phase HPLC (TMC Pro-Pac C18; 5-65% 0.1% trifluoroacetic acid in acetonitrile/0.1% trifluoroacetic acid in water gradient). The pure fractions were lyophilized overnight to give 20 mg (80%) of either (3R) 3-cyclopropyl-8-[4-((2S,5R)-5-[(R)-hydroxy(phenyl)methyl]pyrrolidin-2- yl}methyl)benzoyl]-2-oxa-8-azaspiro[4.5]decan-1-one or (3S) 3-cyclopropyl-8-[4-((2S,5R)-5-[(R)-hydroxy(phenyl)methyl]pyrrolidin-2-yl}methyl)benzoyl]-2-oxa-8-azaspiro[4.5]decan-1-one as a white solid. LC/MS 489.3 (M+1).

The same procedure was used for the deprotection of Isomer 2 from Step A above to give 15 mg (71%) of either (3R) 3-cyclopropyl-8-[4-((2S,5R)-5-[(R)-hydroxy(phenyl)methyl]pyrrolidin-2-yl}methyl)benzoyl]-2-oxa-8-azaspiro[4.5]decan-1-one or (3S) 3-cyclopropyl-8-[4-((2S,5R)-5-[(R)-hydroxy(phenyl)methyl]pyrrolidin-2-yl}methyl)benzoyl]-2-oxa-8-azaspiro[4.5]decan-1-one. LC/MS 489.3 (M+1).

Using the Biological Assays as described above, the human β3 functional activities of Ex. 553 and Ex. 554 were determined to be between 1-9.9 nM.

Examples 555-608

Ex. 555-Ex. 608

Using similar procedures described above, the examples in Table 12 were prepared.

The conditions for the separation of the diastereomers are designated as follows:

Separation Method A: Daicel CHIRALPAK® AD® column eluting with an IPA in Heptane mixture or ethanol in Hexanes mixture.

Separation Method B: Daicel CHIRALCEL® OD® column eluting with an IPA or ethanol in Heptane mixture.

Separation Method C: Pirkle (R,R)-Whelk-O® column eluting with an IPA in Heptane mixture.

Separation Method D: Daicel CHIRALCEL® OJ® column eluting with SFC conditions eluting with $CO_2$/methanol.

Separation Method E: Daicel CHIRALPAK® AD® or CHIRALPAK® AD-H column under SFC conditions eluting with $CO_2$/methanol or $CO_2$/IPA.

Separation Method F: Single enantiomers of the amines were used in the preparation of these derivatives.

Using the Biological Assays described above, the human β3 functional activity of each compound was determined and shown in Table 12 as the following ranges:

TABLE 12

| Example | A | Separation Method | Isomer | R | MW | MS (MH)+ | Human β3 agonist functional activity |
|---------|---|-------------------|--------|---|------|----------|--------------------------------------|
| 555     | N | A                 | 1      |   | 542.7 | 543.3   | ++                                   |
| 556     | N | A                 | 2      |   | 542.7 | 543.3   | ++                                   |

TABLE 12-continued
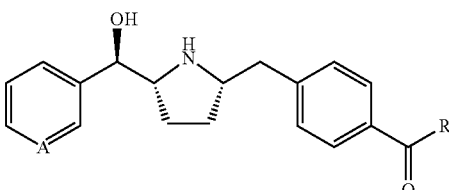
| Example | A | Separation Method | Isomer | R | MW | MS (MH)+ | Human β3 agonist functional activity |
|---|---|---|---|---|---|---|---|
| 557 | CH | F | 1 | 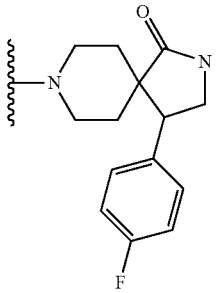 [SMILES: *N1CCC2(CC1)C(=O)NCC2c1ccc(F)cc1] | 541.7 | 542.4 | ++ |
| 558 | CH | F | 2 | 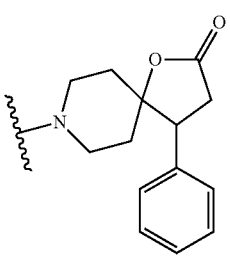 [SMILES: *N1CCC2(CC1)OC(=O)CC2c1ccccc1] | 541.7 | 542.4 | + |
| 559 | N | A | 1 | 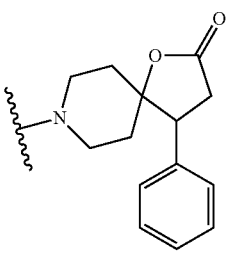 [SMILES: *N1CCC2(CC1)OC(=O)CC2c1ccccc1] | 525.7 | 526.4 | ++++ |
| 560 | N | A | 2 | 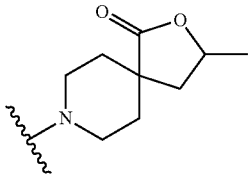 [SMILES: *N1CCC2(CC1)CC(C)OC2=O] | 525.7 | 526.4 | ++ |
| 561 | CH | B | 1 | | 462.6 | 463.2 | ++ |

TABLE 12-continued
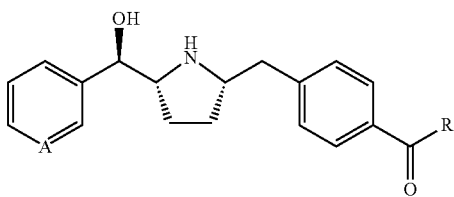
| Example | A | Separation Method | Isomer | R | MW | MS (MH)+ | Human β3 agonist functional activity |
|---|---|---|---|---|---|---|---|
| 562 | CH | B | 2 | ![] | 462.6 | 463.2 | ++ |
| 563 | CH | B | 1 | ![] | 476.6 | 477.3 | ++ |
| 564 | CH | B | 2 | ![] | 476.6 | 477.3 | ++ |
| 565 | CH | E | 1 | ![] | 516.6 | 517.2 | ++ |
| 566 | CH | E | 2 | ![] | 516.6 | 517.2 | +++ |
| 567 | CH | D | 1 | ![] | 490.6 | 491.2 | ++ |

TABLE 12-continued

| Example | A | Separation Method | Isomer | R | MW | MS (MH)+ | Human β3 agonist functional activity |
|---|---|---|---|---|---|---|---|
| 568 | CH | D | 2 | | 490.6 | 491.2 | +++ |
| 569 | CH | E | 1 | | 504.7 | 505.4 | ++ |
| 570 | CH | E | 2 | | 504.7 | 505.4 | ++ |
| 571 | CH | A | 1 | | 535.7 | 536.2 | ++ |
| 572 | CH | | 1 & 2 | | 535.7 | 536.2 | ++ |
| 573 | CH | E | 1 | | 501.7 | 502.1 | ++ |

TABLE 12-continued
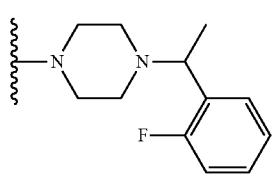 [SMILES: *N1CCN(C(C)c2ccccc2F)CC1]
| Example | A | Separation Method | Isomer | R | MW | MS (MH)+ | Human β3 agonist functional activity |
|---|---|---|---|---|---|---|---|
| 574 | CH | E | 2 | 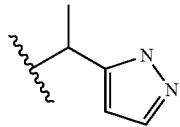 [SMILES: *C(C)c1ccn[nH]1] | 501.7 | 502.1 | +++ |
| 575 | CH | A | 1 | 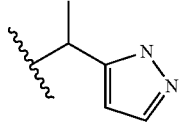 | 473.6 | 474.2 | ++ |
| 576 | CH | A | 2 | 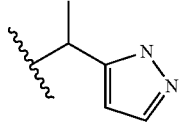 | 473.6 | 474.2 | ++ |
| 577 | CH | A | 1 | 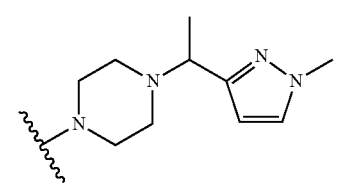 [SMILES: *N1CCN(C(C)c2ccn(C)n2)CC1] | 487.7 | 488.1 | ++ |
| 578 | CH | A | 2 | 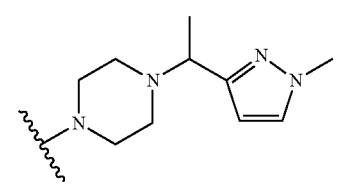 [SMILES: *N1CCN(C(C)c2ccn(C)n2)CC1] | 487.7 | 488.1 | ++++ |
| 579 | CH | A | 1 | 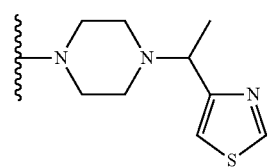 | 490.7 | 491.04 | ++ |
| 580 | CH | A | 2 | 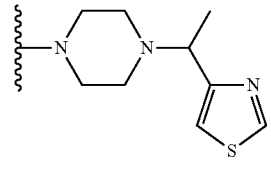 [SMILES: *N1CCN(C(C)c2cscn2)CC1] | 490.7 | 491.04 | +++ |

TABLE 12-continued
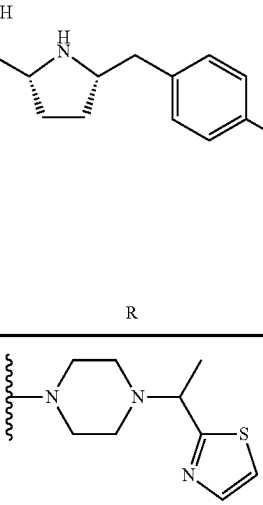
| Example | A | Separation Method | Isomer | R | MW | MS (MH)+ | Human β3 agonist functional activity |
|---|---|---|---|---|---|---|---|
| 581 | CH | B | 1 | 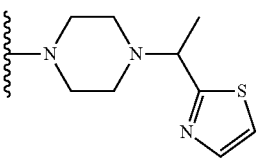 [SMILES: *N1CCN(C(C)c2nccs2)CC1] | 490.7 | 491.1 | ++ |
| 582 | CH | B | 2 | 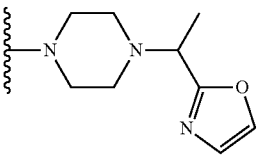 [SMILES: *N1CCN(C(C)c2ncco2)CC1] | 490.7 | 491.1 | +++ |
| 583 | CH | A | 1 | 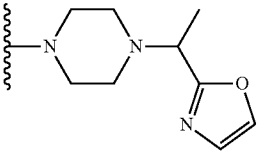 [SMILES: *N1CCN(C(C)c2ncco2)CC1] | 474.6 | 475.1 | +++ |
| 584 | CH | A | 2 | 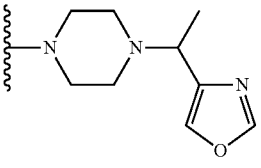 [SMILES: *N1CCN(C(C)c2cocn2)CC1] | 474.6 | 475.1 | +++ |
| 585 | CH | A | 1 | 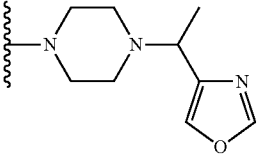 [SMILES: *N1CCN(C(C)c2cocn2)CC1] | 474.6 | 475.01 | +++ |
| 586 | CH | A | 2 | 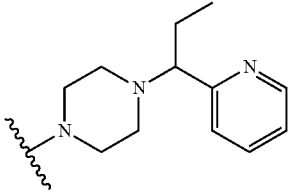 [SMILES: *N1CCN(C(CC)c2ccccn2)CC1] | 474.6 | 475.01 | +++ |
| 587 | CH | F | 1 |  | 498.7 | 499.2 | +++ |

TABLE 12-continued

| Example | A | Separation Method | Isomer | R | MW | MS (MH)+ | Human β3 agonist functional activity |
|---|---|---|---|---|---|---|---|
| 588 | CH | F | 2 | piperazine-CH(Et)-2-pyridyl | 498.7 | 499.2 | ++ |
| 589 | CH | F | 1 | piperazine-CH(cyclopropyl)-2-pyridyl | 510.7 | 511.2 | +++ |
| 590 | CH | F | 2 | piperazine-CH(cyclopropyl)-2-pyridyl | 510.7 | 511.2 | ++ |
| 591 | CH | B | 1 | piperazine-CH(Me)-3-pyridazinyl | 485.6 | 486.07 | +++ |
| 592 | CH | B | 2 | piperazine-CH(Me)-3-pyridazinyl | 485.6 | 486.07 | ++++ |
| 593 | CH | F | 1 | piperazine-CH(Me)-(3-Cl-2-pyridyl) | 519.1 | 519.08 | ++ |

TABLE 12-continued
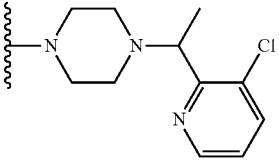
| Example | A | Separation Method | Isomer | R | MW | MS (MH)+ | Human β3 agonist functional activity |
|---|---|---|---|---|---|---|---|
| 594 | CH | F | 2 | 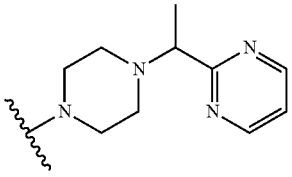 [SMILES: *N1CCN(C(C)c2ncccn2)CC1] | 519.1 | 519.08 | ++ |
| 595 | CH | B | 1 | 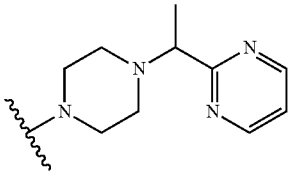 [SMILES: *N1CCN(C(C)c2ncccn2)CC1] | 485.6 | 486.2 | +++ |
| 596 | CH | B | 2 | 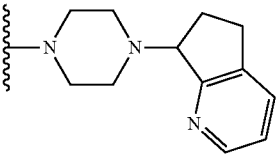 [SMILES: *N1CCN(C2CCc3cccnc32)CC1] | 485.6 | 486.2 | +++ |
| 597 | CH | F | 1 | 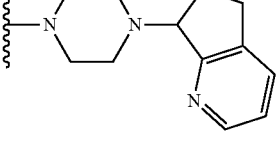 | 496.7 | 497.2 519.2 (MNa)+ | ++ |
| 598 | CH | F | 2 | 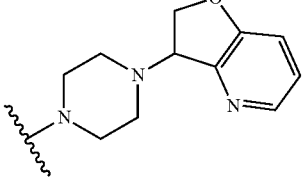 | 496.7 | 497.2 519.2 (MNa)+ | ++ |
| 599 | CH | C | 1 | 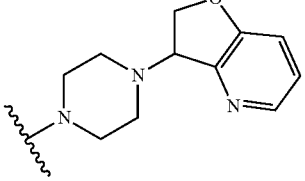 | 498.6 | 499.0 | ++ |
| 600 | CH | C | 2 | 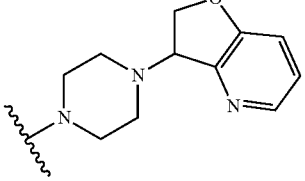 | 498.6 | 499.1 | ++ |

TABLE 12-continued
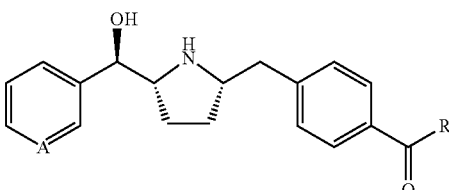
| Example | A | Separation Method | Isomer | R | MW | MS (MH)+ | Human β3 agonist functional activity |
|---|---|---|---|---|---|---|---|
| 601 | CH | F | 1 | 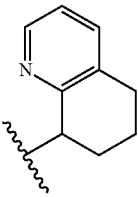 [SMILES: *C1CCCc2cccnc21] | 510.7 | 511.1 | +++ |
| 602 | CH | F | 2 | 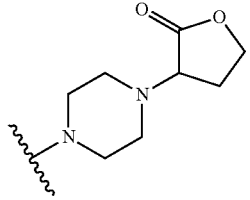 [SMILES: *N1CCN(C2CCOC2=O)CC1] | 510.7 | 511.2 | +++ |
| 603 | CH | A | 1 | 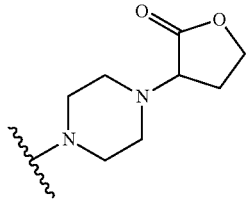 [SMILES: *N1CCN(C2CCOC2=O)CC1] | 463.6 | 464.1 | ++ |
| 604 | CH | A | 2 | 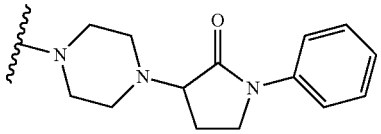 [SMILES: *N1CCN(C2CCN(c3ccccc3)C2=O)CC1] | 463.6 | 464.1 | ++ |
| 605 | CH | F | 1 | 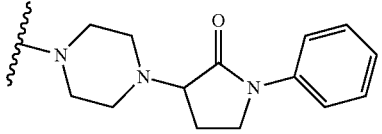 [SMILES: *N1CCN(C2CCN(c3ccccc3)C2=O)CC1] | 538.7 | 539.3 | ++ |
| 606 | CH | F | 2 | 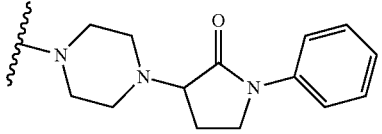 [SMILES: *N1CCN(C2CCN(c3ccccc3)C2=O)CC1] | 538.7 | 539.3 | +++ |
| 607 | CH | F | 1 | 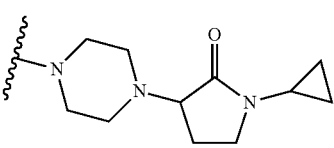 [SMILES: *N1CCN(C2CCN(C3CC3)C2=O)CC1] | 502.7 | 503.3 | ++++ |

TABLE 12-continued

[Structure: pyrrolidine with hydroxyl-substituted aryl group A and benzamide with R substituent]

| Example | A | Separation Method | Isomer | R | MW | MS (MH)+ | Human β3 agonist functional activity |
|---------|-----|---------|--------|---|-------|-------|-------|
| 608 | CH | F | 2 | [piperazine-cyclopropyl pyrrolidinone] | 502.7 | 503.3 | +++ | less than 1 nM (+);
1-9.9 nM (++);
10-99.9 nM (+++);
100-999 nM (++++); and
greater than 999 nM but less than 3000 nM (+++++).

Examples 609-610

Ex. 609-Ex. 610

Using similar procedures as described above, Examples 609-610 were prepared from the appropriate starting materials.

Using the Beta-3 agonist in vitro functional assay described above the human Beta-3 agonist functional activity of each compound was determined and shown in Table 13 as the following range: 1-9.9 nM (++).

TABLE 13

[Structure: pyrrolidine with OH, R1-substituted aryl, and aryl with R2, R3, and R-C(=O) substituents]

| Example | R¹ | R² | R³ | R | MW | MS (MH)+ | Human β3 agonist functional activities |
|---------|----|----|----|---|-------|-------|-------|
| 609 | H | Br | H | [bicyclic amine-tetrazole] | 523.4 | 525.1 | ++ |
| 610 | H | Br | H | [spiro piperidine lactone] | 527.5 | 527.1, 529.1 | ++ |

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I, or a pharmaceutically acceptable salt thereof, or a stereoisomer thereof, or a pharmaceutically acceptable salt of the stereoisomer thereof:

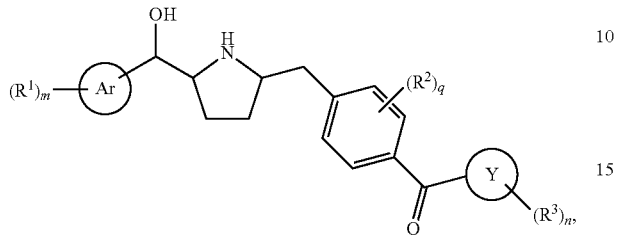

(I)

wherein:
m is 0, 1, 2, 3, 4, or 5;
n is 0, 1, 2, 3, 4, or 5;
p is 0, 1, or 2;
q is 0, 1, 2, 3, or 4;
Ar is phenyl or pyridyl;
Y is a ring system selected from the group consisting of:

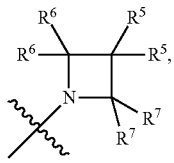

(1)

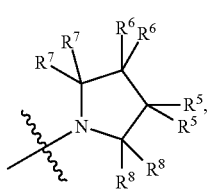

(2)

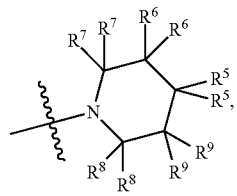

(3)

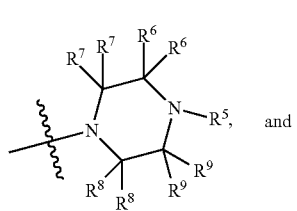

(4)

and

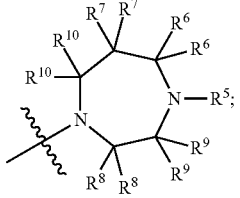

(5)

wherein $R^5$, $R^6$, $R^7$, $R^8$, $R^9$, and $R^{10}$ are each a hydrogen;
or two $R^5$ groups, two $R^6$ groups, or two $R^7$ groups, together with the carbon atom to which they are attached, form a 3- to 6-membered ring containing 0, 1, 2, or 3 hetero atoms independently selected from oxygen, sulfur, and nitrogen; wherein the 3- to 6-membered ring is optionally fused to a phenyl or a 4- to 6-membered heterocyclic ring with from 1 to 4 heteroatoms selected from oxygen, sulfur and nitrogen to form a fused ring; and wherein the 3- to 6-membered ring or the fused ring is optionally substituted with 1 to 5 $R^3$ groups;
or $R^5$ and $R^6$, $R^6$ and $R^7$, or $R^5$ and $R^9$, together with the nitrogen or carbon atoms to which they are attached, form a 5- to 6-membered ring containing 0, 1, 2, or 3 hetero atoms independently selected from oxygen and nitrogen; wherein the 5- to 6-membered ring is optionally fused to a phenyl or a 4- to 6-membered heterocyclic ring with from 1 to 4 heteroatoms selected from oxygen, sulfur and nitrogen to form a fused ring; and wherein the 5- to 6-membered ring or the fused ring is optionally substituted with 1 to 5 $R^3$ groups;
or $R^6$ and $R^9$ form a direct bond;
or $R^6$ and $R^8$ form a $C_1$-$C_4$ alkylene bridge; and wherein the alkylene bridge is optionally substituted with 1 to 3 $R^3$ groups;
or $R^6$ and $R^9$ form a $C_1$-$C_4$ alkylene bridge; and wherein the alkylene bridge is optionally substituted with 1 to 3 $R^3$ groups;
or $R^7$ and $R^8$ form a $C_1$-$C_4$ alkylene bridge; and wherein the alkylene bridge is optionally substituted with 1 to 3 $R^3$ groups;
Z is selected from the group consisting of:
(1) $C_5$-$C_{10}$ carbocyclic ring,
(2) 4- to 6-membered heterocyclic ring with from 1 to 4 heteroatoms selected from oxygen, sulfur and nitrogen,
(3) benzene ring fused to a $C_5$-$C_{10}$ carbocyclic ring,
(4) 5 or 6-membered heterocyclic ring with from 1 to 4 heteroatoms selected from oxygen, sulfur and nitrogen fused to a $C_5$-$C_{10}$ carbocyclic ring, and
(5) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen;
each occurrence of $R^1$ is independently selected from the group consisting of:
(1) $C_1$-$C_6$ alkyl optionally substituted with 1 to 5 halogen atoms,
(2) $C_3$-$C_6$ cycloalkyl,
(3) halogen,
(4) —$OR^a$,
(5) oxo,
(6) cyano, (7) —C(O)R$^a$,
(8) —C(O)NR$^a$R$^b$,
(9) —NR$^a$R$^b$,
(10) —S(O)P—C$_1$-C$_6$ alkyl, and
(11) Z optionally substituted with 1 to 5 halogen atoms;
each occurrence of R$^2$ is independently selected from the group consisting of:
  (1) halogen,
  (2) —OR$^a$, and
  (3) C$_1$-C$_6$ alkyl optionally substituted with 1 to 5 halogen atoms;
each occurrence of R$^3$ is independently selected from the group consisting of:
  (1) C$_1$-C$_6$ alkyl optionally substituted with 1 to 5 groups independently selected from:
    (a) halogen,
    (b) oxo,
    (c) cyano,
    (d) —OR$^a$,
    (e) —C(O)R$^a$,
    (f) —CO$_2$R$^a$,
    (g) —C(O)R$^C$,
    (h) —C(O)NR$^a$R$^b$,
    (i) —NR$^a$R$^b$,
    (j) —N(R$^a$)C(O)R$^a$,
    (k) —S(O)p-C$_1$-C$_6$ alkyl,
    (l) C$_3$-C$_6$ cycloalkyl optionally substituted with 1 to 5 groups independently selected from halogen, C$_1$-C$_6$ alkyl optionally substituted with 1 to 5 halogen atoms, —OR$^a$, and oxo, and
    (m) Z optionally substituted with 1 to 5 groups independently selected from halogen, C$_1$-C$_6$ alkyl optionally substituted with 1 to 5 halogen atoms, oxo, cyano, —OR$^a$, —CO$_2$R$^a$, C$_3$-C$_6$ cycloalkyl, and Z,
  (2) C$_3$-C$_6$ cycloalkyl, optionally substituted with 1 to 5 groups independently selected from halogen, C$_1$-C$_6$ alkyl optionally substituted with 1 to 5 halogen atoms, oxo, —OR$^a$, and Z optionally substituted with 1 to 5 halogen atoms,
  (3) halogen,
  (4) oxo,
  (5) cyano,
  (6) —OR$^a$,
  (7) —C(O)R$^a$,
  (8) —CO$_2$R$^a$,
  (9) —C(O)NR$^a$R$^b$,
  (10) —NR$^a$R$^b$,
  (11) —N(R$^a$)C(O)R$^a$,
  (12) —N(R$^a$)CO$_2$R$^a$,
  (13) —N(R$^a$)C(O)NR$^a$R$^b$,
  (14) =N—OR$^a$,
  (15) —S(O)$_p$—R$^a$, and
  (16) Z optionally substituted with 1 to 5 groups independently selected from
    (a) C$_1$-C$_6$ alkyl optionally substituted with 1 to 5 groups independently selected from halogen, oxo, cyano, —OR$^a$, —CO$_2$R$^a$, C$_3$-C$_6$ cycloalkyl, and Z,
    (b) C$_3$-C$_6$ cycloalkyl optionally substituted with 1 to 5 groups independently selected from halogen, C$_1$-C$_6$ alkyl optionally substituted with 1 to 5 halogen atoms, oxo, —OR$^a$, —CO$_2$R$^a$, and Z,
    (c) halogen,
    (d) nitro,
    (e) oxo,
    (f) cyano,
    (g) —OR$^a$,
    (h) —C(O)R$^a$,
    (i) —CO$_2$R$^a$,
    (j) —C(O)NR$^a$R$^b$,
    (k) —NR$^a$R$^b$,
    (l) —S(O)p-C$_1$-C$_6$ alkyl, and
    (m) Z optionally substituted with 1 to 5 groups independently selected from halogen, C$_1$-C$_6$ alkyl optionally substituted with 1 to 5 halogen atoms, oxo, cyano, —OR$^a$, —CO$_2$R$^a$, and C$_3$-C$_6$ cycloalkyl;
each occurrence of R$^a$ is independently selected from the group consisting of:
  (1) hydrogen,
  (2) C$_1$-C$_6$ alkyl optionally substituted with 1 to 5 groups independently selected from:
    (a) halogen,
    (b) cyano,
    (c) —OR$^b$,
    (d) —C(O)R$^b$,
    (e) —CO$_2$R$^b$,
    (f) —C(O)NR$^b$R$^b$,
    (g) —S(O)$_p$—C$_1$-C$_6$ alkyl;
    (h) C$_3$-C$_6$ cycloalkyl optionally substituted with 1 to 5 groups independently selected from C$_1$-C$_6$ alkyl and —OR$^b$, and
    (i) Z optionally substituted with 1 to 5 groups independently selected from halogen, C$_1$-C$_6$ alkyl optionally substituted with 1 to 5 halogen atoms, oxo, cyano, —OR$^b$, —CO$_2$R$^b$, C$_3$-C$_6$ cycloalkyl, and Z,
  (3) C$_3$-C$_6$ cycloalkyl optionally substituted with 1 to 5 groups independently selected from halogen, C$_1$-C$_6$ alkyl optionally substituted with 1 to 5 groups independently selected from halogen, oxo, —OR$^b$, and Z, and
  (4) Z optionally substituted with 1 to 5 groups independently selected from:
    (a) halogen,
    (b) nitro,
    (c) cyano,
    (d) oxo,
    (e) —OR$^b$,
    (f) —C(O)R$^b$,
    (g) —CO$_2$R$^b$,
    (h) —C(O)NR$^b$R$^b$,
    (i) —NR$^b$R$^b$,
    (j) —S(O)$_p$—C$_1$-C$_6$ alkyl,
    (k) C$_1$-C$_6$ alkyl optionally substituted with 1 to 5 groups independently selected from halogen, oxo, cyano, —OR$^b$, —CO$_2$R$^b$, C$_3$-C$_6$ cycloalkyl, and Z,
    (l) C$_3$-C$_6$ cycloalkyl, and
    (m) Z optionally substituted with 1 to 5 groups independently selected from halogen, C$_1$-C$_6$ alkyl optionally substituted with 1 to 5 halogen atoms, oxo, cyano, —OR$^b$, —CO$_2$R$^b$, and C$_3$-C$_6$ cycloalkyl;
each occurrence of R$^b$ is independently selected from the group consisting of:
  (1) hydrogen,
  (2) C$_1$-C$_6$ alkyl optionally substituted with 1 to 5 groups independently selected from halogen, C$_1$-C$_6$ alkyl optionally substituted with 1 to 5 groups independently selected from halogen, oxo, cyano, hydroxy, C$_1$-C$_6$ alkoxy, —C(O)NH$_2$, —CO$_2$H, C$_3$-C$_6$ cycloalkyl optionally substituted with 1 to 5 groups independently selected from hydroxy and C$_1$-C$_6$ alkyl, and Z optionally substituted with 1 to 5 groups independently selected from halogen, hydroxy, oxo, and $C_1$-$C_6$ alkyl, (3) $C_3$-$C_6$ cycloalkyl optionally substituted with 1 to 5 groups independently selected from halogen, $C_1$-$C_6$ alkyl optionally substituted with 1 to 5 halogen atoms, hydroxy, $C_1$-$C_6$ alkoxy, and oxo, and (4) Z optionally substituted with 1 to 5 groups independently selected from halogen, trifluoromethyl, $C_1$-$C_6$ alkyl, oxo, hydroxy, and $C_1$-$C_6$ alkoxy; and each occurrence of $R^c$ is independently selected from the group consisting of:

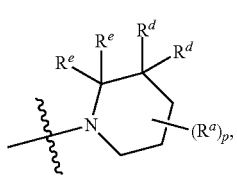

(1)

wherein $R^d$ and $R^e$ are each hydrogen or $C_1$-$C_6$ alkyl; or two $R^d$ groups or two $R^e$ groups together with the carbon atom to which they are attached form a 3- to 6-membered ring containing 0 or 1 hetero atom selected from oxygen and nitrogen; and wherein the 3- to 6-membered ring is optionally substituted with 1 to 5 $R^3$ groups;

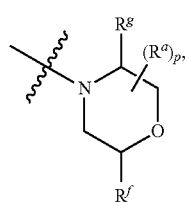

(2)

wherein $R^f$ and $R^g$ are each hydrogen or $C_1$-$C_6$ alkyl; or $R^f$ and $R^g$ form a $C_1$-$C_4$ alkylene bridge;

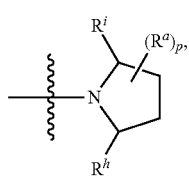

(3)

wherein $R^h$ and $R^i$ are each hydrogen or $C_1$-$C_6$ alkyl; or $R^h$ and $R^i$ form a $C_1$-$C_4$ alkylene bridge; and

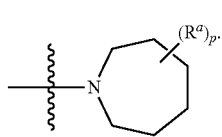

(4)

2. The compound of claim 1, wherein m is 0 and q is 0.

3. The compound of claim 2, wherein Z is selected from the group consisting of:
(1) phenyl,
(2) 4 to 6-membered heterocyclic ring with from 1 to 4 heteroatoms selected from oxygen, sulfur and nitrogen,
(3) benzene ring fused to a $C_5$-$C_{10}$ carbocyclic ring,
(4) benzene ring fused to a 5 or 6-membered heterocyclic ring with from 1 to 4 heteroatoms selected from oxygen, sulfur and nitrogen, and
(5) 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen.

4. The compound of claim 3 wherein Z is a 5-membered heterocyclic ring having one nitrogen atom and 0 to 3 additional heteroatoms independently selected from N, O and S; or a 6-membered heterocycle having 1, 2 or 3 nitrogen atoms, or 1 nitrogen atom and one oxygen or sulfur atom.

5. The compound of claim 3 wherein Z is a 5- or 6-membered heterocyclic ring with from 1 to 4 heteroatoms selected from oxygen, sulfur and nitrogen fused to a $C_5$-$C_6$ carbocyclic ring; and wherein the heterocyclic ring is a 5-membered heterocycle having one nitrogen ring atom and 0 to 3 additional heteroatoms independently selected from N, O and S, or a 6-membered heterocycle having 1, 2 or 3 ring nitrogen atoms, or 1 ring nitrogen atom and 1 ring oxygen or sulfur atom.

6. The compound of claim 3 wherein Z is a 5- or 6-membered heterocyclic ring with from 1 to 4 heteroatoms selected from oxygen, sulfur and nitrogen fused to a 5- or 6-membered heterocyclic ring with from 1 to 4 heteroatoms selected from oxygen, sulfur and nitrogen; wherein the fused ring has 2 to 5 heteroatoms, at least one of which is nitrogen.

7. The compound of claim 3 wherein Z is selected from the group consisting of thiazolyl, oxazolyl, pyridyl, dihydropyridyl, 1,2,4-triazolyl, 1,2,3-triazolyl, tetrazolyl, pyrimidinyl, dihydropyrimidinyl, tetrahydropyrimidinyl, pyrazinyl, dihydropyrazinyl, pyridazinyl, dihydropyridazinyl, pyrrolidinyl, imidazolyl, pyrazolyl, 1,2,4-oxadiazolyl, 1,2,5-oxadiazolyl,

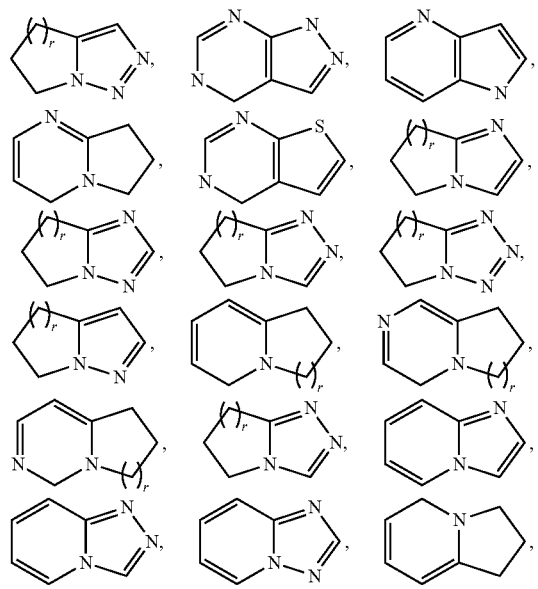

-continued

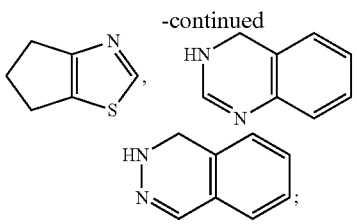

and r is 1 or 2.

8. The compound of claim 1 wherein each occurrence of $R^3$ is independently selected from the group consisting of:
(1) $C_1$-$C_6$ alkyl optionally substituted with 1 to 3 groups independently selected from:
   (a) halogen,
   (b) oxo,
   (c) —$OR^a$,
   (d) —$C(O)R^a$,
   (e) —$CO_2R^a$,
   (f) —$C(O)NR^aR^b$,
   (g) —$NR^aR^b$,
   (h) —$N(R^a)C(O)R^a$,
   (i) —$S(O)p$-$C_1$-$C_6$ alkyl,
   (j) $C_3$-$C_6$ cycloalkyl optionally substituted with 1 to 3 groups independently selected from halogen, $C_1$-$C_6$ alkyl optionally substituted with 1 to 3 halogen atoms, and —$OR^a$,
   (k) Z optionally substituted with 1 to 3 groups independently selected from halogen, $C_1$-$C_6$ alkyl optionally substituted with 1 to 3 halogen atoms, oxo, cyano, —$OR^a$, $C_3$-$C_6$ cycloalkyl, and Z,
(2) $C_3$-$C_6$ cycloalkyl, optionally substituted with 1 to 3 groups independently selected from halogen, $C_1$-$C_6$ alkyl optionally substituted with 1 to 3 halogen atoms, —$OR^a$, and Z optionally substituted with 1 to 3 halogen atoms,
(3) halogen,
(4) oxo,
(5) —$OR^a$,
(6) —$C(O)R^a$,
(7) —$CO_2R^a$,
(8) —$C(O)NR^aR^b$,
(9) —$NR^aR^b$,
(10) —$N(R^a)C(O)R^a$,
(11) —$S(O)p$-$R^a$, and
(12) Z optionally substituted with 1 to 3 groups independently selected from
   (a) $C_1$-$C_6$ alkyl optionally substituted with 1 to 3 groups independently selected from halogen, oxo, —$OR^a$, $C_3$-$C_6$ cycloalkyl, and Z,
   (b) $C_3$-$C_6$ cycloalkyl optionally substituted with 1 to 3 groups independently selected from halogen, $C_1$-$C_6$ alkyl optionally substituted with 1 to 3 halogen atoms, —$OR^a$, and Z,
   (c) halogen,
   (d) oxo,
   (e) —$OR^a$,
   (f) —$C(O)R^a$,
   (g) —$CO_2R^a$,
   (h) —$C(O)NR^aR^b$,
   (i) —$NR^aR^b$,
   (j) —$S(O)p$-$C_1$-$C_6$ alkyl, and
   (k) Z optionally substituted with 1 to 3 groups independently selected from halogen, $C_1$-$C_6$ alkyl optionally substituted with 1 to 3 halogen atoms, oxo, —$OR^a$, —$CO_2R^a$, and $C_3$-$C_6$ cycloalkyl.

9. The compound of claim 1 wherein each occurrence of $R^a$ is independently selected from the group consisting of:
(1) hydrogen,
(2) $C_1$-$C_6$ alkyl optionally substituted with 1 to 3 groups independently selected from:
   (a) halogen,
   (b) —$OR^b$,
   (c) —$C(O)R^b$,
   (d) —$C(O)NR^bR^b$,
   (e) —$S(O)_p$—$C_1$-$C_6$ alkyl;
   (f) $C_3$-$C_6$ cycloalkyl optionally substituted with 1 to 3 groups independently selected from $C_1$-$C_6$ alkyl and —$OR^b$, and
   (g) Z optionally substituted with 1 to 3 groups independently selected from halogen, $C_1$-$C_6$ alkyl optionally substituted with 1 to 3 halogen atoms, oxo, —$OR^b$, $C_3$-$C_6$ cycloalkyl, and Z,
(3) $C_3$-$C_6$ cycloalkyl optionally substituted with 1 to 3 groups independently selected from halogen, $C_1$-$C_6$ alkyl optionally substituted with 1 to 3 groups independently selected from halogen, —$OR^b$, and Z, and
(4) Z optionally substituted with 1 to 3 groups independently selected from:
   (a) halogen,
   (b) oxo,
   (c) —$OR^b$,
   (d) —$C(O)R^b$,
   (e) —$NR^bR^b$,
   (f) —$S(O)_p$—$C_1$-$C_6$ alkyl,
   (g) $C_1$-$C_6$ alkyl optionally substituted with 1 to 3 groups independently selected from halogen, oxo, —$OR^b$, $C_3$-$C_6$ cycloalkyl, and Z,
   (h) $C_3$-$C_6$ cycloalkyl, and
   (i) Z optionally substituted with 1 to 3 groups independently selected from halogen, $C_1$-$C_6$ alkyl optionally substituted with 1 to 3 halogen atoms, oxo, —$OR^b$, and $C_3$-$C_6$ cycloalkyl.

10. The compound of claim 1 having Formula Ib:

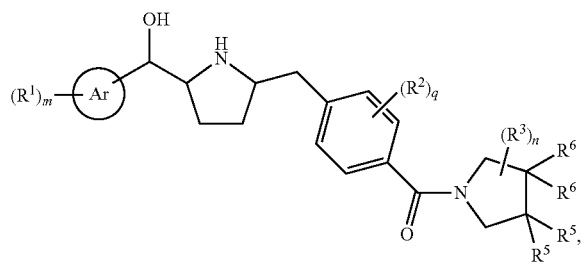

(Ib)

wherein $R^5$ and $R^6$ are each a hydrogen;
or two $R^5$ groups, together with the carbon atom to which they are attached, form a 5-membered ring containing 0 or 1 hetero atom selected from oxygen and nitrogen; and wherein the 5-membered ring is optionally substituted with 1 to 3 $R^3$ groups;
or $R^5$ and $R^6$, together with the carbon atoms to which they are attached, form a 5- to 6-membered ring containing 0, 1, 2, or 3 hetero atoms independently selected from oxygen and nitrogen; and wherein the 5- to 6-membered ring is optionally substituted with 1 to 3 $R^3$ groups.

11. The compound of claim 1 having Formula Ic:

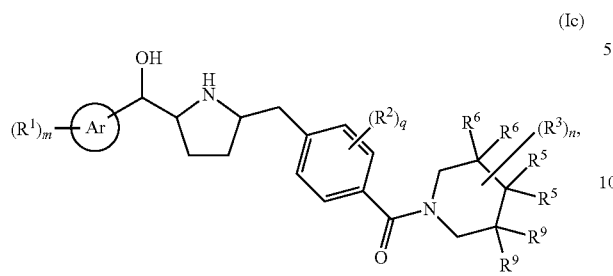

(Ic)

wherein $R^5$, $R^6$, and $R^9$ are each a hydrogen;
or two $R^5$ groups, together with the carbon atom to which they are attached, form a 4- to 6-membered ring containing 0, 1, 2, or 3 hetero atoms selected from oxygen, sulfur, and nitrogen; wherein the 4- to 6-membered ring is optionally fused to a phenyl or a 5- to 6-membered heterocyclic ring with from 1 to 4 heteroatoms selected from oxygen, sulfur and nitrogen to form a fused ring; and wherein the 4- to 6-membered ring or the fused ring is optionally substituted with 1 to 3 $R^3$ groups;
or two $R^6$ groups, together with the carbon atom to which they are attached, form a 4- to 6-membered ring containing 0, 1, 2, or 3 hetero atoms selected from oxygen, sulfur, and nitrogen; wherein the 4- to 6-membered ring is optionally fused to a phenyl or a 5- to 6-membered heterocyclic ring with from 1 to 4 heteroatoms selected from oxygen, sulfur and nitrogen to form a fused ring; and wherein the 4- to 6-membered ring or the fused ring is optionally substituted with 1 to 3 $R^3$ groups;
or $R^5$ and $R^6$, together with the carbon atoms to which they are attached, form a 5- to 6-membered ring containing 0, 1, 2, or 3 hetero atoms independently selected from oxygen and nitrogen; wherein the 5- to 6-membered ring is optionally fused to a phenyl or a 5- to 6-membered heterocyclic ring with from 1 to 4 heteroatoms selected from oxygen, sulfur and nitrogen to form a fused ring; and wherein the 5- to 6-membered ring or the fused ring is optionally substituted with 1 to 3 $R^3$ groups;
or $R^6$ and $R^9$ form a direct bond;
or $R^6$ and $R^9$ form a $C_1$-$C_4$ alkylene bridge, and wherein the alkylene bridge is optionally substituted with 1 to 2 $R^3$ groups.

12. The compound of claim 1 having Formula Id:

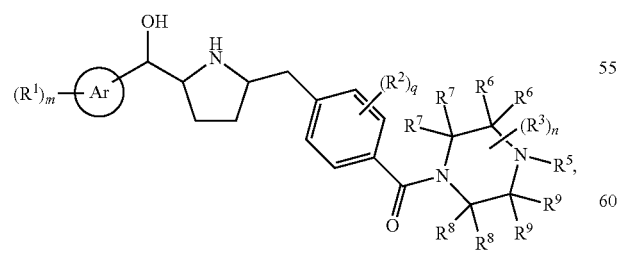

(Id)

wherein $R^5$, $R^6$, $R^7$, $R^8$, and $R^9$ are each a hydrogen;
or $R^5$ and $R^6$, together with the carbon and nitrogen atoms to which they are attached, form a 5- to 6-membered ring containing 0, 1, 2, or 3 hetero atoms independently selected from oxygen and nitrogen; and wherein the 5- to 6-membered ring is optionally substituted with 1 to 3 $R^3$ groups;
or $R^6$ and $R^8$ form a $C_1$-$C_4$ alkylene bridge, and wherein the alkylene bridge is optionally substituted with 1 to 2 $R^3$ groups;
or $R^6$ and $R^9$ form a $C_1$-$C_4$ alkylene bridge, and wherein the alkylene bridge is optionally substituted with 1 to 2 $R^3$ groups;
or $R^7$ and $R^8$ form a $C_1$-$C_4$ alkylene bridge, and wherein the alkylene bridge is optionally substituted with 1 to 2 $R^3$ groups.

13. A compound having Formula II:

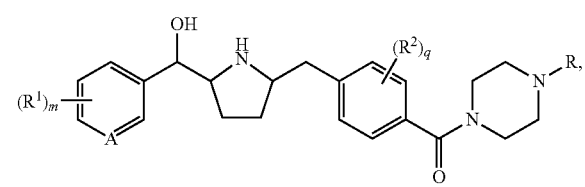

(II)

wherein m is 0, 1, 2, 3, 4, or 5;
q is 0, 1, 2, 3, or 4;
each occurrence of $R^1$ is independently selected from the group consisting of:
 (1) $C_1$-$C_4$ alkyl optionally substituted with 1 to 3 halogen atoms,
 (2) $C_3$-$C_6$ cycloalkyl,
 (3) —$OR^a$,
 (4) —$NR^aR^b$, and
 (5) halogen;
each occurrence of $R^2$ is independently selected from the group consisting of:
 (1) halogen,
 (2) —$OR^a$, and
 (3) $C_1$-$C_6$ alkyl optionally substituted with 1 to 5 halogen atoms; and
A and R are as defined in the following table:

| A | R |
|---|---|
| CH | H |
| CH | |
| CH | |
| CH | |
| CH | |

321
-continued
| A | R |
|---|---|
| CH | 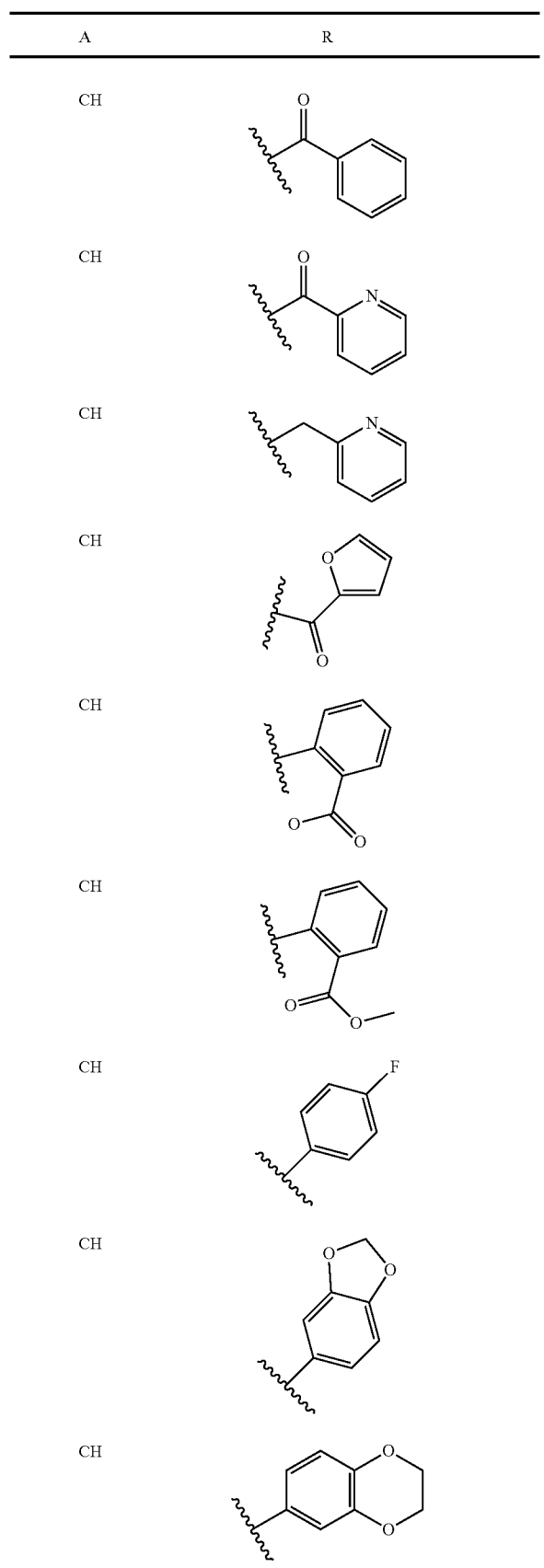 |
| CH | |
| CH | |
| CH | |
| CH | |
| CH | |
| CH | |
| CH | |
| CH | |
| CH | |
322
-continued
| A | R |
|---|---|
| CH | 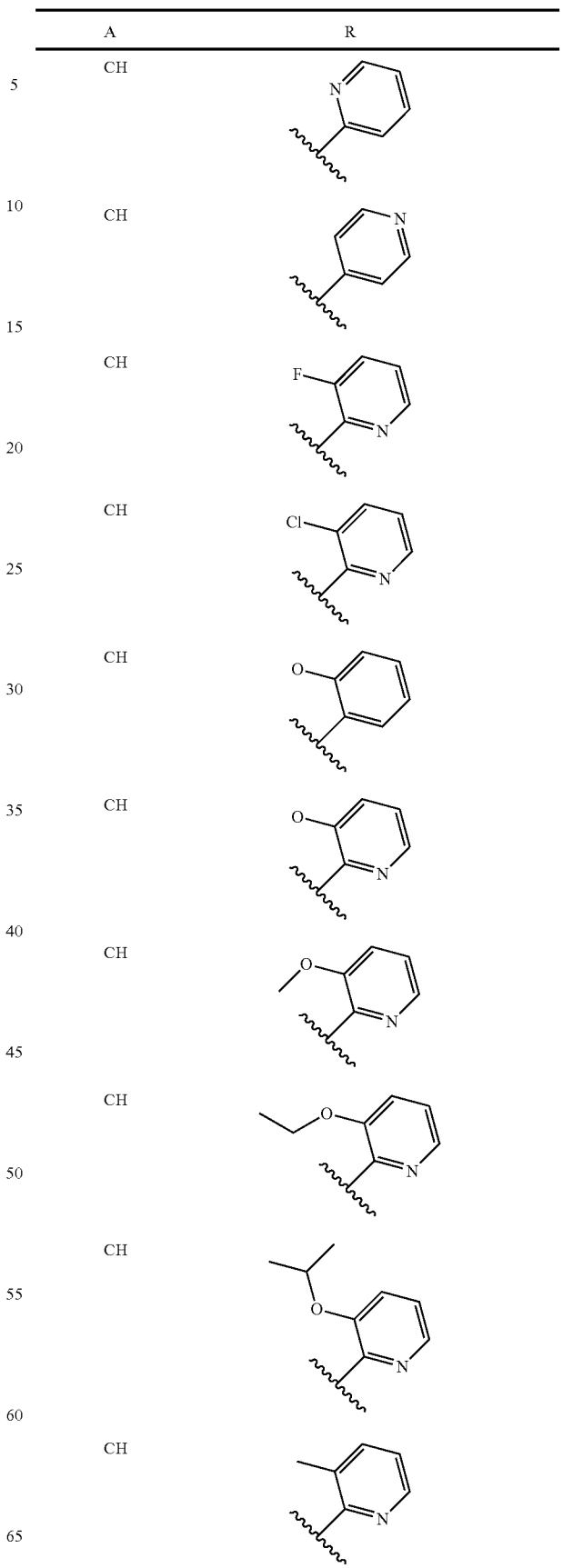 |
| CH | |
| CH | |
| CH | |
| CH | |
| CH | |
| CH | |
| CH | |
| CH | |
| CH | |

323
-continued
| A | R |
|---|---|
| CH | 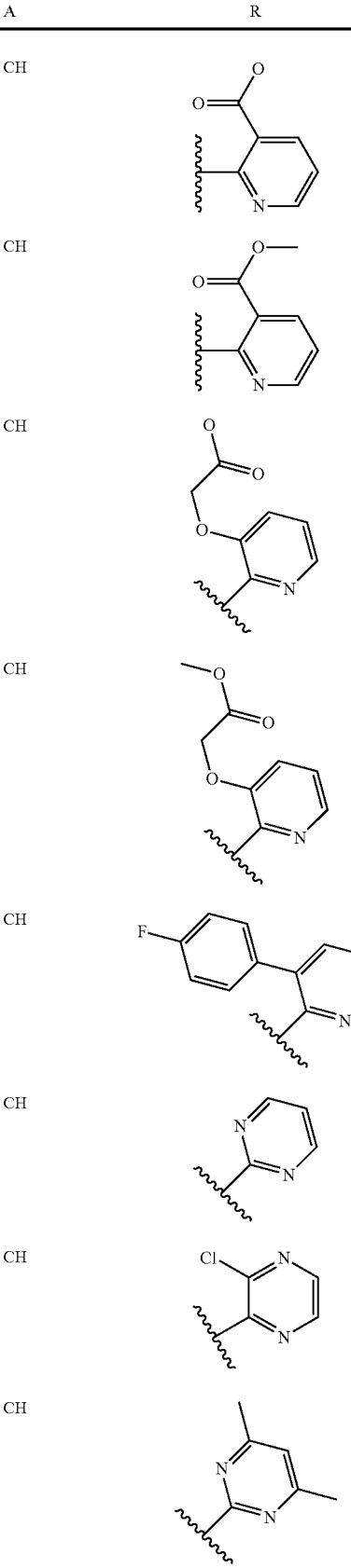 |
| CH | |
| CH | |
| CH | |
| CH | |
| CH | |
| CH | |
| CH | |
324
-continued
| A | R |
|---|---|
| CH | 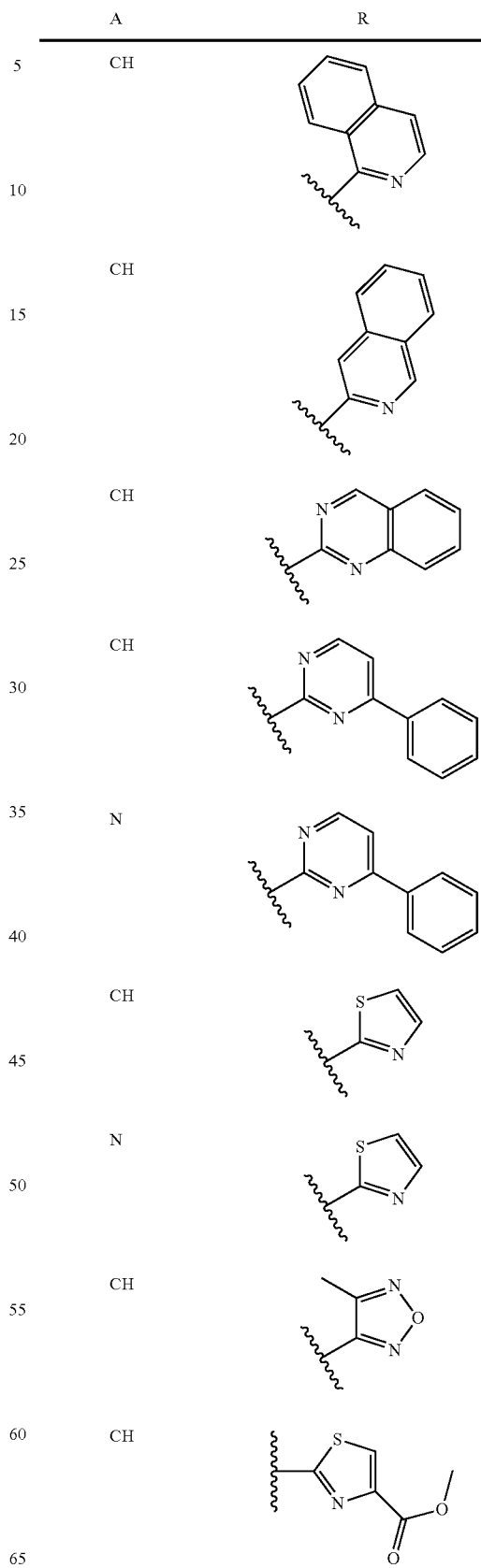 |
| CH | |
| CH | |
| CH | |
| N | |
| CH | |
| N | |
| CH | |
| CH | |

| A | R |
|---|---|
| | 325 -continued |
| CH | 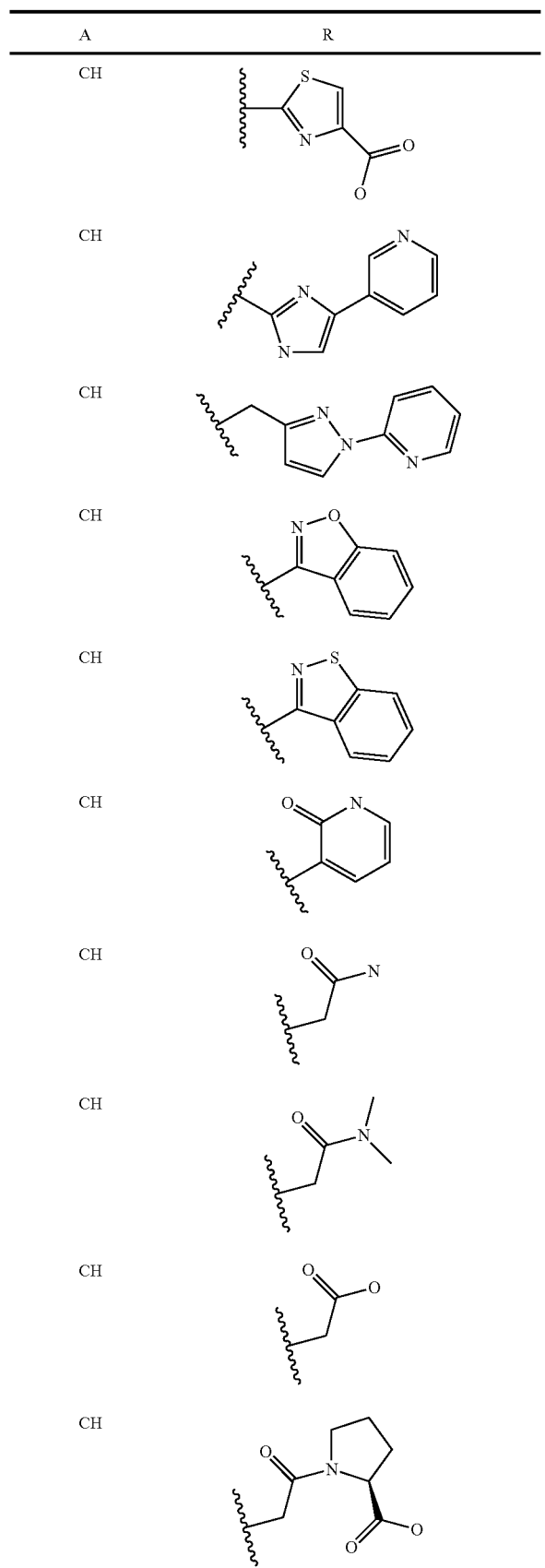 |
| A | R |
|---|---|
| | 326 -continued |
| CH | 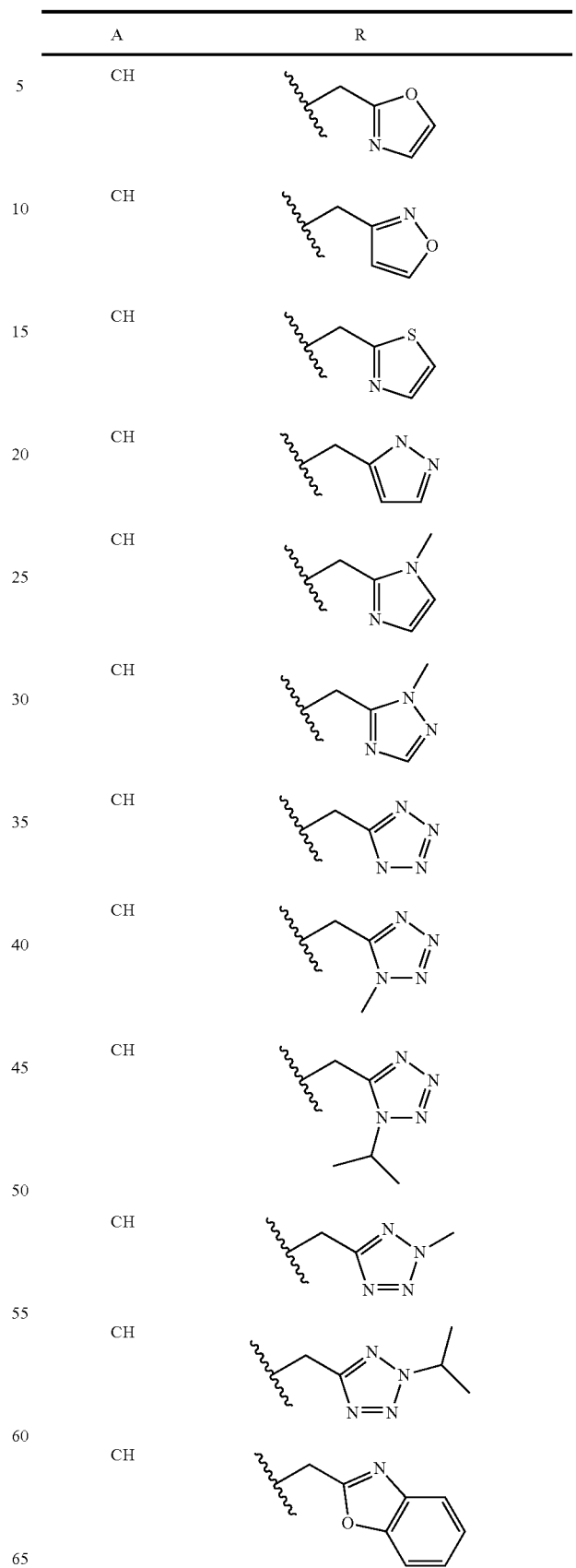 |

327
-continued
| A | R |
|---|---|
| CH | |
| CH | |
| CH | |
| CH | |
| CH | |
| CH | |
| CH | |
| CH | |
| CH | |
| CH | |
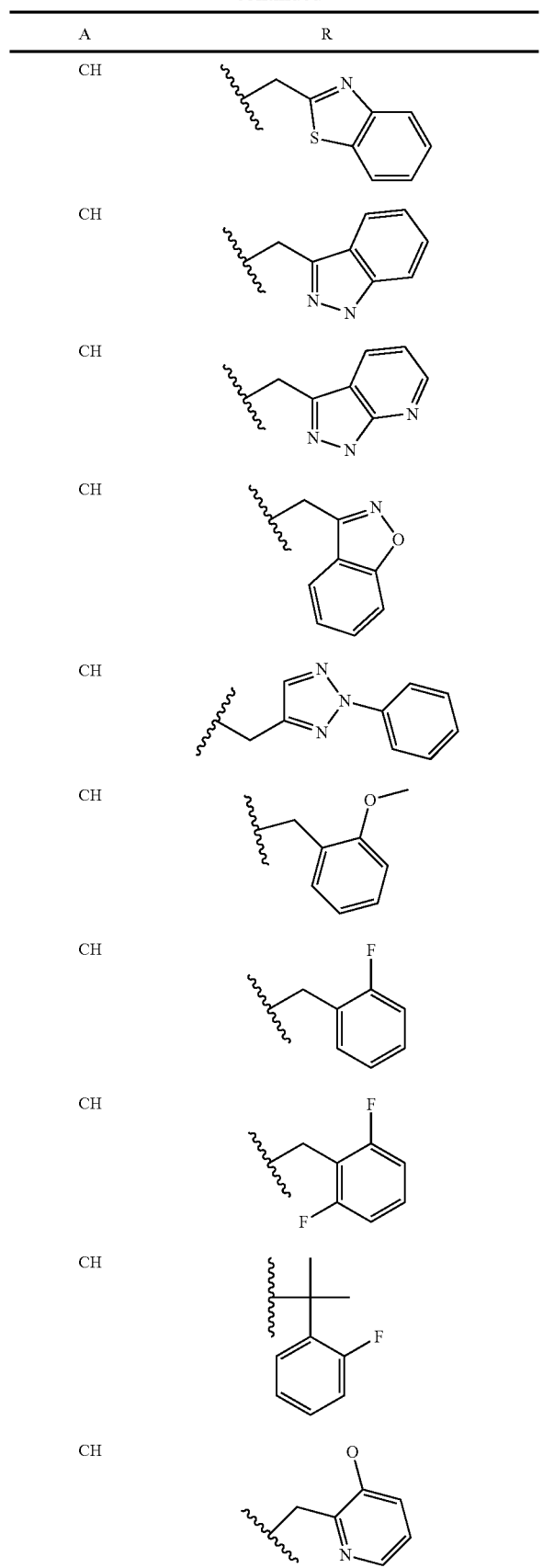
328
-continued
| A | R |
|---|---|
| CH | |
| CH | |
| CH | |
| CH | |
| CH | |
| CH | |
| CH | |
| CH | |
| CH | |
| CH | |
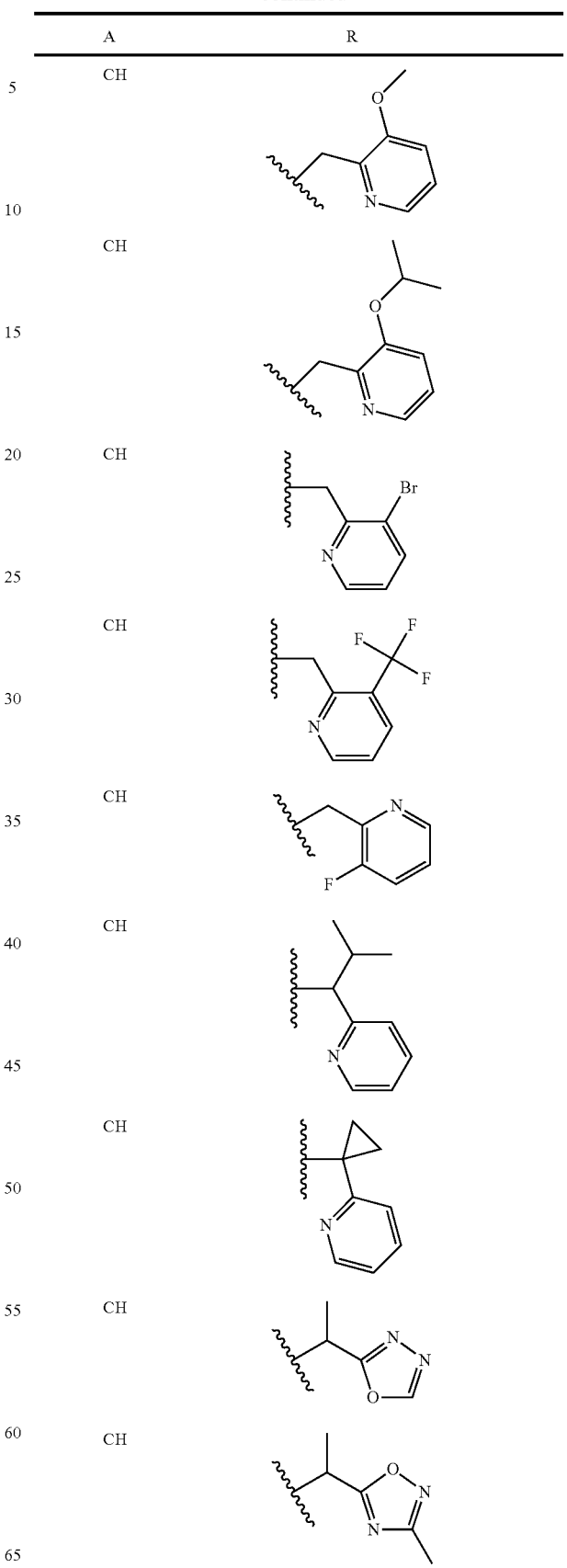

-continued
| A | R |
|---|---|
| CH | 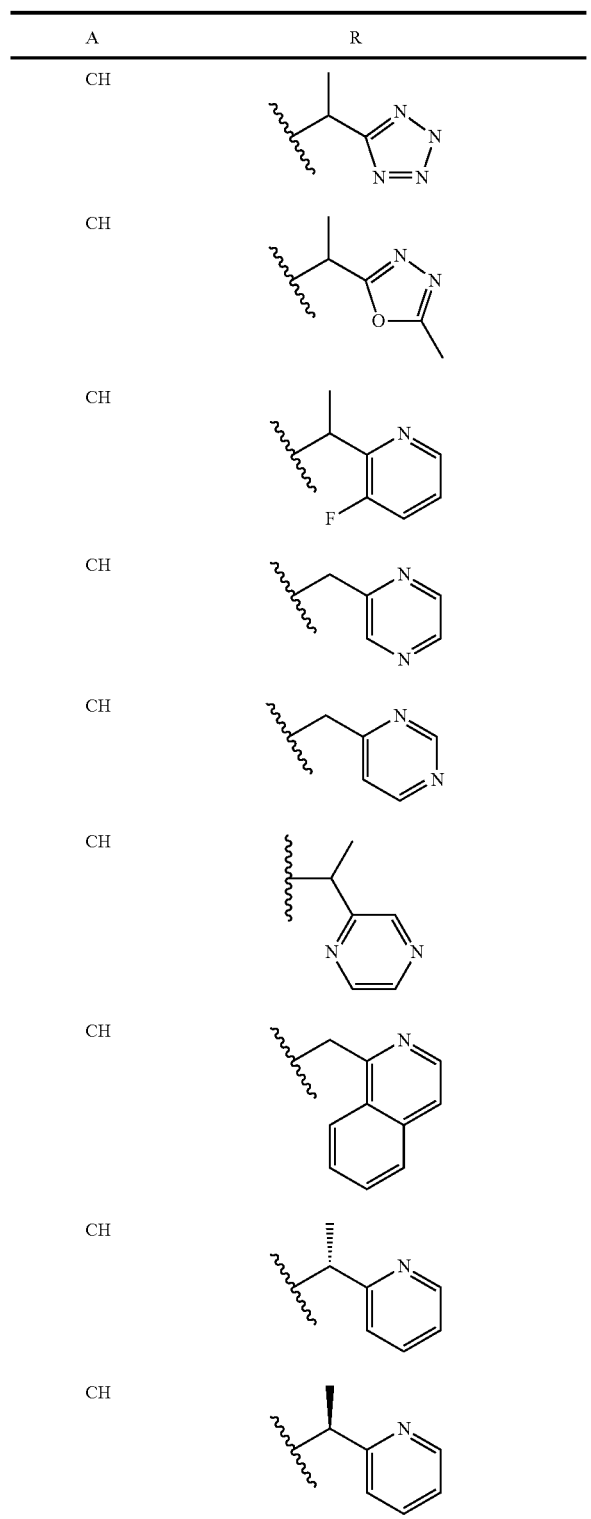 |
| CH | |
| CH | |
| CH | |
| CH | |
| CH | |
| CH | |
| CH | |
| CH | |
| CH | |
-continued
| A | R |
|---|---|
| CH | 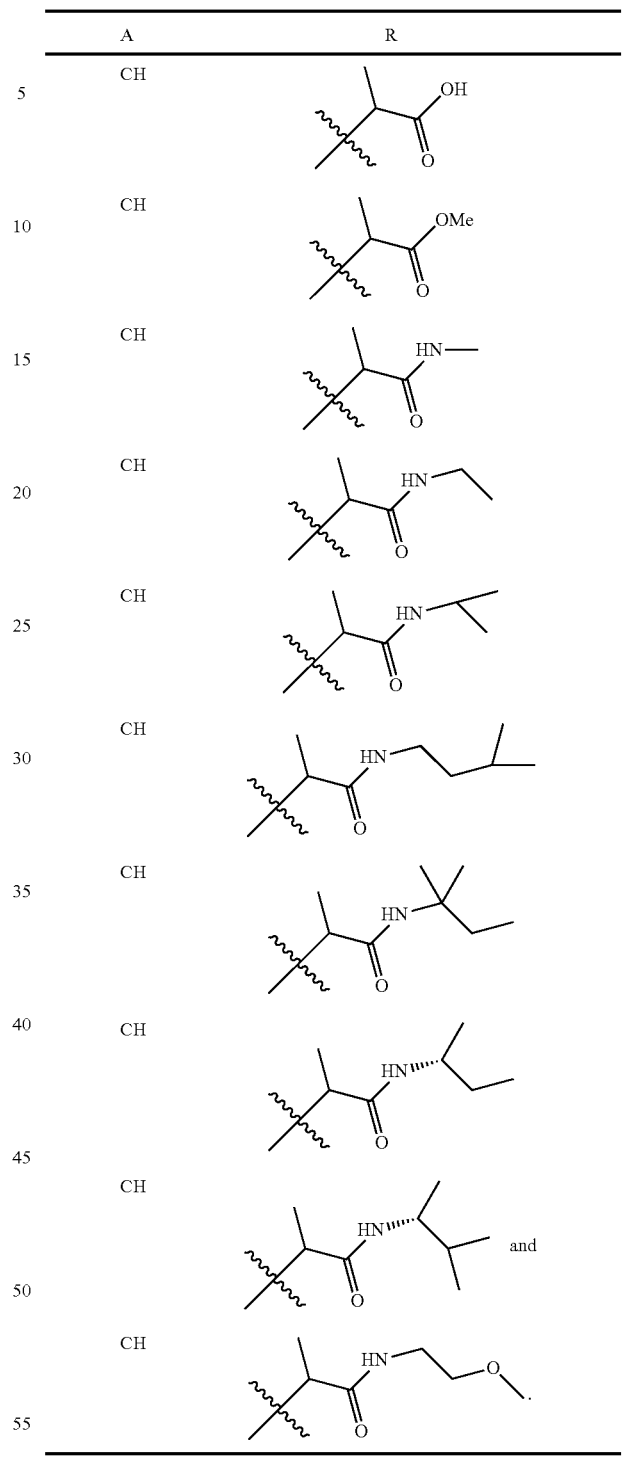 |
| CH | |
| CH | |
| CH | |
| CH | |
| CH | |
| CH | |
| CH | |
| CH | and |
| CH | . |
14. A pharmaceutical composition comprising a compound of claim 1 and a pharmaceutically acceptable carrier.
* * * * *